United States Patent
Becklund et al.

(10) Patent No.: US 12,234,297 B2
(45) Date of Patent: Feb. 25, 2025

(54) IGE BINDING PROTEINS AND USES THEREOF

(71) Applicants: Phylaxis Bioscience, LLC, Denver, CO (US); Inhibrx Biosciences, Inc., La Jolla, CA (US)

(72) Inventors: Bryan R. Becklund, San Diego, CA (US); Kyle S. Jones, San Marcos, CA (US); Andrew M. Eckles, La Jolla, CA (US); Brendan P. Eckelman, Encinitas, CA (US); Tony Dung-Ling Yao, Denver, CO (US)

(73) Assignees: Phylaxis Bioscience, LLC, Denver, CO (US); Inhibrx Biosciences, Inc., La Jolla, CA (US)

( * ) Notice: Subject to any disclaimer, the term of this patent is extended or adjusted under 35 U.S.C. 154(b) by 0 days.

(21) Appl. No.: 18/792,921

(22) Filed: Aug. 2, 2024

(65) Prior Publication Data

US 2025/0019464 A1    Jan. 16, 2025

Related U.S. Application Data

(63) Continuation of application No. PCT/US2024/037846, filed on Jul. 12, 2024.

(60) Provisional application No. 63/605,695, filed on Dec. 4, 2023, provisional application No. 63/526,570, filed on Jul. 13, 2023.

(51) Int. Cl.
*C07K 16/42* (2006.01)

(52) U.S. Cl.
CPC ...... *C07K 16/4291* (2013.01); *C07K 2317/24* (2013.01); *C07K 2317/35* (2013.01); *C07K 2317/565* (2013.01); *C07K 2317/569* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 8,084,582 B2 | 12/2011 | Dahiyat et al. |
| 8,137,670 B2 | 3/2012 | Wu et al. |
| 8,404,236 B2 | 3/2013 | Wu et al. |
| 8,435,517 B2 | 5/2013 | Desjarlais et al. |
| 8,632,775 B2 | 1/2014 | Wu et al. |
| 8,734,791 B2 | 5/2014 | Lazar et al. |
| 9,663,582 B2 | 5/2017 | Lazar et al. |
| 9,902,773 B2 | 2/2018 | Chu et al. |
| 10,183,999 B2 | 1/2019 | Lazar et al. |
| 10,556,949 B2 | 2/2020 | Igawa et al. |
| 11,673,947 B2 | 6/2023 | Igawa et al. |
| 11,827,719 B2 | 11/2023 | Saito et al. |
| 2006/0115470 A1 * | 6/2006 | Silence ............... A61P 31/16 435/327 |
| 2007/0178082 A1 | 8/2007 | Silence et al. |
| 2019/0112393 A1 | 4/2019 | Igawa et al. |
| 2019/0353661 A1 | 11/2019 | Smith |
| 2023/0122862 A1 | 4/2023 | Kuo et al. |

OTHER PUBLICATIONS

GenBank [Online] Dec. 1, 2020, retrieved from NCBI, Database accession No. QEP17171.1.
International Search Report and Written Opinion, PCT/US2024/037846, dated Nov. 26, 2024, 12 pages.
Chu, Seung Y. et al., "Reduction of Total IgE by Targeted Coengagement of IgE B-Cell Receptor and FcγRIIB with Fc-engineered Antibody," J. Allergy Clin Immunol, vol. 126, No. 4, pp. 1102-1115.
Ganesan, Latha P. et al., "FcγRIIB on Liver Sinusoidal Endothelium Clears Small Immune Complexes," J Immumol. Nov. 15, 2012; 189(10): 4981-4988. doi: 10.4049/jimmumnol.1202017.
S. J. Wigginton et al., "An Immunoglobulin E-Reactive Chimeric Human Immunoglobulin G1 Anti-Idiotype Inhibits Basophil Degranulation through Cross-linking of FceRI with FceRIIIb," Clinical and Experimental Allergy, 38, 313-319.

* cited by examiner

*Primary Examiner* — Juliet C Switzer
*Assistant Examiner* — Katherine Ann Holtzman
(74) *Attorney, Agent, or Firm* — Goodwin Procter LLP

(57) ABSTRACT

Provided herein are IgE-binding VHH domains, polypeptides, and proteins, and methods of using such IgE-binding polypeptides and proteins to modulate the biological activity of IgE.

30 Claims, 46 Drawing Sheets

Specification includes a Sequence Listing.

```
                        10        20        30        40        50        60
                        |         |         |         |         |         |
B10          EVQLVQSGGELVQAGGSLRLSCVASGLTFSSYNMGWLRQAPGKEREFVGMSGSSSTSTYYADSVK
hzB10v1      ....LE...G...P..................................................
hzB10v2      ..............................V..................S.............
hzB10v3      ..............................V.................................
hzB10v4      .............................................................E...
hzB10v5      .................................................................
hzB10v6      .................................................................
hzB10v7      ..................................................L..............
hzB10v8      ..................................................I..............
hzB10v9      ..................................................V..............
hzB10v10     .................................................................
hzB10v11     .................................................................
hzB10v12     .................................................................
hzB10v13     .............................................................E...
hzB10v14     ....LE...GE..P....................................L..............
hzB10v15     ....LE...GE..P................V..................SL..............
hzB10v16     ....LE...GE..P....................................L...........E...
hzB10v17     ....LE...GE..P....................................L...........A...
hzB10v18     ....LE...GE..P....................................L...........T...
hzB10v20     ....LE...GE..P....................................L..............
hzB10v21     ....LE...GE..P....................................L..............
hzB10v22     ....LE...GE..P....................................L..............
hzB10v23     ....LE...GE..P....................................L..............
hzB10v24     ....LE...GE..P................V...................L..............
hzB10v25     ....LE...GE..P....................................SL..............
hzB10v26     ....LE...GE..P....................................................
hzB10v27     ....LE...GE..P....................................L...........E...
hzB10v28     ....LE...GE..P....................................L...........E...
hzB10v29     ....LE...GE..P....................................L...........E...
hzB10v30     ....LE...GE..P....................................L...........E...
hzB10v31     ....LE...GE..P....................................L...........E...
hzB10v32     ....LE...GE..P................V...................L...........E...
hzB10v33     ....LE...GE..P....................................SL..........E...
hzB10v34     ....LE...GE..P................V..................SL...........E...
hzB10v37     ....LE...GE..P....................................L...........E...
hzB10v38     ....LE...GE..P....................................L...........E...
hzB10v39     ....LE...GE..P....................................L...........E...
hzB10v40     ....LE...GE..P....................................L...........E...
hzB10v41     ....LE...GE..P....................................L...........E...
hzB10v42     ....LE...GE..P....................................L...........E...
hzB10v43     ....LE...GE..P....................................L...........E...
hzB10v44     ....LE...GE..P....................................L...........E...
VH3-23       ....LE...GE..P........A...F.....A.S.V......GL.W.SAISG.GG.......E...
```

*FIG. 2A*

```
              70        80        90       100       110       120      SEQ ID
               |         |         |         |         |         |       NO:
B10       GRFTISRDNSKNTVYLQMNSLKPEDTAVYYCAARRMLSTYWSDRSWDFWGQGTQVTVKP       2
hzB10v1   ............................................................    6
hzB10v2   ............................................................    7
hzB10v3   ............................................................    8
hzB10v4   .........A...L....S..RA.....................................    9
hzB10v5   ..........................................................E.   10
hzB10v6   ..........................................................R.   11
hzB10v7   ............................................................   12
hzB10v8   ............................................................   13
hzB10v9   ............................................................   14
hzB10v10  ..................................L.....................A..   15
hzB10v11  ..................................I.........................  16
hzB10v12  ..................................V.........................  17
hzB10v13  .........A........................................A..........  18
hzB10v14  ..................................L.......................E.   19
hzB10v15  ..................................L.......................E.   20
hzB10v16  ..................................L.......................E.   21
hzB10v17  ..................................L.......................E.   22
hzB10v18  ..................................L.......................E.   23
hzB10v20  ..............L...................L.......................E.   24
hzB10v21  ....................S.............L.......................E.   25
hzB10v22  ....................R.............L.......................E.   26
hzB10v23  .....................A............L.......................E.   27
hzB10v24  ..................................L.......................E.   28
hzB10v25  ..................................L.......................E.   29
hzB10v26  ............................................................   30
hzB10v27  ....................RA............L.......................E.   31
hzB10v28  ...................S.RA...........L.......................E.   32
hzB10v29  ...................Q.RA...........L.......................E.   33
hzB10v30  ...................T.RA...........L.......................E.   34
hzB10v31  ..................T.RA............L.......................E.   35
hzB10v32  .....................RA...........L.......................E.   36
hzB10v33  .....................RA...........L.......................E.   37
hzB10v34  .....................RA...........L.......................E.   38
hzB10v37  ...................T..A...........L................L......E.   39
hzB10v38  ...................T.R.............L................L......E.  40
hzB10v39  ...................T.RA...........L................L......E.   41
hzB10v40  ........A..........T.RA...........L................L......E.   42
hzB10v41  ........Q..........T.RA...........L................L......E.   43
hzB10v42  ........S..........T.RA...........L................L......E.   44
hzB10v43  ........T..........T.RA...........L................L......E.   45
hzB10v44  .........T.........T.RA...........L................L......E.   46
VH3-23    .........A...L....S..RA.....................................   94
```

FIG. 2B

| No. | Frequency | Site | Clone | VHCDR1 (SEQ ID NO: 3) GLTFSSYNMG | R1 Screening OD450 | R1 Screening WT | Confirm OD450 Duplicate1 | Confirm OD450 Duplicate2 | WT |
|---|---|---|---|---|---|---|---|---|---|
| 1 | 1 | 2 | 2-1F11 | .I........ | 0.7545 | 0.8763 | 0.6469 | 0.6014 | 0.6254 |
| 2 | 1 |  | 2-2C3 | .V........ | 0.9138 | 0.9613 | 0.6205 | 0.6196 | 0.5814 |
| 3 | 1 | 3 | 3-1A1 | ..V....... | 0.8964 |  | 0.6066 | 0.5715 |  |
| 4 | 1 |  | 3-1B9 | ..N....... | 0.9452 | 1.0273 | 0.585 | 0.6337 |  |
| 5 | 1 |  | 3-1B10 | ..K....... | 0.9036 |  | 0.5699 | 0.5935 |  |
| 6 | 1 |  | 3-1H1 | ..I....... | 0.857 |  | 0.5672 | 0.5592 |  |
| 7 | 2 | 4 | 4-1F10 | ...Y...... | 0.7085 |  | 0.697 | 0.545 |  |
| 8 | 1 |  | 4-1F11 | ...P...... | 0.7981 |  | 0.5822 | 0.4827 |  |
| 9 | 5 |  | 4-2E2 | ...G...... | 1.0497 | 1.0306 | 0.5785 | 0.586 |  |
| 10 | 1 | 5 | 5A1 | ....K..... | 0.9143 | 0.9292 | 0.6093 | 0.5731 |  |
| 11 | 1 |  | 5A10 | ....A..... | 0.9603 |  | 0.5539 | 0.549 |  |
| 12 | 1 |  | 5C3 | ....D..... | 0.8974 |  | 0.5457 | 0.5557 |  |
| 13 | 1 |  | 5H11 | ....R..... | 0.8931 |  | 0.5449 | 0.5499 |  |
| 14 | 1 | 6 | 6A9 | .....E.... | 0.8515 | 1.0778 | 0.4751 | 0.4883 |  |
| 15 | 2 |  | 6C2 | .....Q.... | 0.8262 |  | 0.5339 | 0.5265 |  |
| 16 | 1 |  | 6E11 | .....T.... | 0.8165 |  | 0.454 | 0.4676 |  |
| 17 | 1 |  | 6F11 | .....R.... | 0.8853 |  | 0.4175 | 0.4016 |  |
| 18 | 3 |  | 6G9 | .....A.... | 0.8749 |  | 0.5559 | 0.5117 |  |
| 19 | 2 |  | 6H1 | .....P.... | 0.9082 |  | 0.4871 | 0.5301 |  |
| 20 | 2 | 8 | 8F11 | .......T.. | 0.9224 | 0.22665 | 0.5196 | 0.5587 |  |
| 21 | 2 |  | 8G10 | .......S.. | 0.9166 |  | 0.5342 | 0.5525 |  |
| 22 | 5 |  | 8H11 | .......R.. | 0.9695 |  | 0.5714 | 0.5676 |  |
| 23 | 1 | 9 | 9B1 | ........V. | 0.8787 | 0.859 | 0.4523 | 0.4539 |  |
| 24 | 1 |  | 9D1 | ........I. | 0.9053 |  | 0.4355 | 0.4424 |  |
| 25 | 3 |  | 9E8 | ........L. | 0.8968 |  | 0.5218 | 0.5388 |  |
| 26 | 1 |  | 9F1 | ........S. | 0.9211 |  | 0.4983 | 0.4672 |  |
| 27 | 1 |  | 9G9 | ........T. | 0.8865 |  | 0.5353 | 0.5236 |  |
| 28 | 1 |  | 9H9 | ........F. | 0.8803 |  | 0.4902 | 0.4999 |  |
| 29 | 2 | 10 | 10E3 | .........S | 0.8462 | 0.7817 | 0.5078 | 0.494 |  |
| 30 | 2 |  | 10G10 | .........A | 0.9664 |  | 0.4839 | 0.4793 |  |

FIG. 16D

| No. | Frequency | Site | Clone | VHCDR3 (SEQ ID NO: 74) AARRLLSTYWSDRSWDF | R1 Screening OD450 | R1 Screening WT | Confirm OD450 Duplicate1 | Confirm OD450 Duplicate2 | WT |
|---|---|---|---|---|---|---|---|---|---|
| 1 | 1 | 28 | 28H1 | .......S.......... | 0.9275 | 1.1002 | 0.4714 | 0.4922 | 0.6759 |
| 2 | 1 | 32 | 32F11 | ...........R...... | 0.9243 | 0.8958 | 0.5569 | 0.5567 | 0.5513 |
| 3 | 2 | 33 | 33-2A2 | ............K..... | 1.0106 | 1.0162 | 0.5567 | 0.5642 | |
| 4 | 1 | 33 | 33-2C4 | ............F..... | 1.0032 | | 0.5145 | 0.5235 | |
| 5 | 1 | 33 | 33-2C5 | ............H..... | 1.0108 | | 0.525 | 0.5727 | |
| 6 | 3 | 35 | 35G3 | ..............R... | 1.075 | 1.0009 | 0.5926 | 0.6117 | |
| 7 | 1 | 39 | 39C11 | ..................M... | 1.0031 | 1.0865 | 0.5624 | 0.5846 | |
| 8 | 1 | 39 | 39E11 | ..................H... | 1.0055 | | 0.5501 | 0.5339 | |
| 9 | 2 | 44 | 44A11 | ...................K | 1.1391 | 1.102 | 0.661 | 0.6545 | |
| 10 | 1 | 44 | 44C1 | ...................M | 1.0635 | | 0.5563 | 0.5374 | |

FIG. 16E

IGE BINDING PROTEINS AND USES THEREOF

CROSS-REFERENCE TO RELATED APPLICATIONS

This application is a continuation of International Application No. PCT/US2024/037846, filed on Jul. 12, 2024, which claims the benefit of and priority to U.S. Provisional Application No. 63/526,570, filed on Jul. 13, 2023 and 63/605,695, filed on Dec. 4, 2023, the entire contents of each of which are incorporated herein by reference.

SEQUENCE LISTING

This application contains a Sequence Listing which has been submitted electronically in XML format and is hereby incorporated by reference in its entirety. The XML copy, created on Jul. 25, 2024, is titled PXS-003USWOC1_SL.xml and is 144.3 kilobytes in size.

BACKGROUND

IgE, plays a role in several diseases and disorders, such as asthma and allergic diseases. For example, IgE, when cross-linked by antigen, activates mast cells and basophils, which then release allergic mediators of inflammation, such as histamines and cytokines. Xolair® (omalizumab) is the sole anti-IgE antibody that has been FDA approved to date. While this antibody does block IgE-dependent allergic reactions, Xolair does not reduce the serum concentration of IgE. Instead, this drug has been shown to increase IgE serum concentrations because the Xolair:IgE complex has a circulating half-life enhanced by the Xolair Fc. IgE has an estimated circulating half-life of about 2.5 days, likely due to the fact that IgE does not bind to FcRn, but the omalizumab:IgE complex, through the omalizumab component, now allows the complex to have a longer half-life than free IgE. See, e.g., Hu et al., *Clin. Transl. Allergy* 8:27 (2018) and Dodig et al., *Acta. Pharm.* 55:123-138 (2005). In patients who receive omalizumab, a total IgE serum concentration increase by 5- to 10-fold due to this increased complex half-life. While the omalizumab:IgE complex is "inactive", or unable to bind to FceRI when omalizumab is properly dosed, the omalizumab:IgE complexes can disassociate when the amount of free omalizumab is too low, which can occur with, for example, a missed dose. Omalizumab has a fast $K_{off}$, with much of the IgE falling off the omalizumab within 5 minutes. In patients on omalizumab, the large concentration of omalizumab:IgE complex can then be a source of free IgE and rapidly reload mast cells. FceRI is a well characterized receptor, and its hallmark is a very slow off-rate. It is estimated that FceRI:IgE complex can reside on a mast cell for a week. Withdrawal from omalizumab can therefore exacerbate already high, pathogenic levels of IgE in patients suffering with chronic allergic disorders. A therapeutic that functions to significantly reduce levels of IgE has the potential to provide superior disease control with a better safety profile. Therefore, there exists a therapeutic need for improved anti-IgE antibody treatments that reduce serum levels of IgE.

SUMMARY

The present disclosure is based, in part, on the creation of VHH domains that bind IgE and reduce IgE-mediated immune responses. IgE binds two main receptors, the high-affinity receptor FcεRI expressed primarily on mast cells and basophils, which binds IgE dimer at a 1:1 molar ratio, and a low-affinity receptor CD23 expressed primarily on mature B cells and other cell types, which binds IgE dimer at a 2:1 molar ratio. The VHH domains of the present disclosure blocks IgE from binding to FcεR1A, thereby suppressing FcεR1A-mediated signaling and downstream activation of mast cells and basophils. The VHH domain, when provided at an approximately equimolar to excess amount relative to IgE, also blocks CD23 binding to IgE.

Importantly, the VHH domains of the present disclosure do not bind or binds very poorly to an existing complex of IgE and FcεR1A. In contrast, IgE026, another VHH that binds soluble IgE and blocks it from binding to FceRI, can also bind IgE already bound to FceRI. It is contemplated that a complex of IgE dimer and a bivalent or multivalent VHH-containing protein (e.g., VHH-Fc) could form a larger complex as a result of crosslinking. For example, a first IgE dimer can bind a first polypeptide of a VHH-Fc dimer, which uses a second polypeptide to bind a first subunit of a second IgE dimer, which in turn can recruit another VHH-Fc using its second subunit, thereby forming a linear chain of alternating IgE and VHH-Fc. The chain is likely to have the propensity to circularize at a certain lengths depending on the concentration of both IgE and the VHH-Fc. A significant safety issue can occur when an antibody or VHH-Fc fusion protein (bivalent or multivalent) binds to the preformed FceRI:IgE complex, in which the IgE is a dimer of two subunits. The antibody or VHH-Fc fusion protein can then bind an adjacent FceRI:IgE complex, resulting in a cross-linking event which could cause mast cell and/or basophil degranulation and anaphylaxis. Another scenario where anaphylaxis could occur is when the antibody or VHH-Fc fusion protein can form a stable heterotrimer complex of FceRI: IgE: antibody or FceRI:IgE: VHH-Fc. Since the antibody or VHH-Fc has an Fc region that can interact with Fcgamma receptors (FcγRs), neighboring FcγR-expressing cells can interact with the heterotrimers on the basophils or mast cells in trans, resulting in activation of the basophils or mast cells and anaphylaxis. The VHH domains of the present disclosure, which are unable to bind a complex of IgE and FcεR1A, cannot mediate these forms of crosslinking. As a result, these VHH domains in bivalent or multivalent formats are expected to have improved safety profile.

It is also contemplated that the VHH domains of the present disclosure, when present in a bivalent or multivalent format, may crosslink with membrane-bound IgE dimer to form a bigger complex. When the bivalent or multivalent VHH domain construct includes an Fc domain with a mutation(s) which enhance the Fc binding to FcγRIIB (a.k.a. CD32b), CD32b on the surface of the IgE-expressing B cells is recruited to the B cell receptor complex, with the CDR portion of the VHH-Fc binding to the membrane-bound IgE and the Fc portion of the VHH-Fc recruiting CD32b to the BCR. The recruitment of CD32b to BCR results in inhibition of B cell receptor signaling, because C32b is an inhibitory FcγR. This negative feedback regulation may in turn reduce IgE production from the IgE class-switched B cells only. In addition, CD32b expressed on liver sinusoidal endothelial cells may mediate internalization and degradation of IgE: VHH-Fc complexes, resulting in clearance of soluble IgE from circulation. Exemplary Fc mutations that increase binding to FcγRIIB include S267E and L328F ("SELF" mutations), under EU numbering, in a human Fc region.

The VHH domains and proteins comprising such VHH domains are useful for treating IgE-associated diseases and disorders, such as allergy. They are particularly suitable for subcutaneous administration. It is known that volume of administration is often a limiting factor in the subcutaneous route of administration. Given their greater solubility in aqueous solutions and lower molecular weight than traditional antibodies, VHH-Fc proteins, at the same concentration, can be at a 2-fold higher molar concentration than a conventional antibody (conventional antibody is about 150 kDa whereas a VHH-Fc is about 80 kDa). This feature, combined with the ability to rapidly remove IgE from circulation and reduce IgE production and the low off-rate for IgE binding (see, e.g., Examples 3 and 13 below), renders the VHH-Fc proteins of the present disclosure particularly suitable for administration (e.g., by the subcutaneous route) at a reduced frequency, thereby enhancing patient compliance. Given that it is critical to maintain some amount of drug in a patient to prevent the development of detectable circulating IgE, which than can arm a mast cell, compliance may be an important component of efficacy for anti-IgE therapy.

Relatedly, the VHH-Fc proteins of the present disclosure may reduce healthcare cost, given their potentially lower dosing frequency. Furthermore, compared to traditional antibodies that include a heavy chain and a light chain, VHH-Fc proteins do not include two or more different polypeptide sequences. This allows easier and more economical manufacture of VHH-Fc proteins at large scales due to higher titer production in conventional production cell lines.

Accordingly, provided herein are IgE binding VHH domains, polypeptides, proteins, and methods of using IgE binding VHH domains, polypeptides, and proteins for medical treatments. For example, the VHH domains, polypeptides, and proteins disclosed here are useful to reduce IgE levels (such that mast cells no longer have IgE on their surface) and/or to treat allergies such as food allergies, environmental allergies, venom allergies, and/or companion animal allergies. In some embodiments, an IgE binding polypeptide comprises at least one VHH domain. Some embodiments are provided below.

In one aspect, the present disclosure provides a VHH domain that binds IgE (e.g., human IgE), comprising a complementarity determining region 1 (CDR1), a complementarity determining region 2 (CDR2), and a complementarity determining region 3 (CDR3) of a VHH that comprises the amino acid sequences of SEQ ID NO: 119. In some embodiments, the VHH domain comprises a CDR1, a CDR2, and a CDR3 of a VHH that comprises the amino acid sequences of SEQ ID NO: 47.

In some embodiments of the above aspect, the CDR1 comprises the amino acid sequence of SEQ ID NO: 3; the CDR2 comprises the amino acid sequence of SEQ ID NO: 58; and the CDR3 comprises the amino acid sequence of SEQ ID NO: 63, under the AbM definition. In some embodiments of the above aspect, the CDR1 comprises the amino acid sequence of SEQ ID NO: 3; the CDR2 comprises the amino acid sequence of SEQ ID NO: 48, 4, 49, 50, or 102; and the CDR3 comprises the amino acid sequence of SEQ ID NO: 51, 5, 52, 53, or 103. In some embodiments of the above aspect, the CDR1 comprises the amino acid sequence of SEQ ID NO: 3, the CDR2 comprises the amino acid sequence of SEQ ID NO: 48, and the CDR3 comprises the amino acid sequence of SEQ ID NO: 51. In some embodiments, the CDR1 comprises the amino acid sequence of SEQ ID NO: 3, the CDR2 comprises the amino acid sequence of SEQ ID NO: 102, and the CDR3 comprises the amino acid sequence of SEQ ID NO: 103.

In some embodiments of the above aspect, the CDR1 comprises the amino acid sequence of SEQ ID NO: 54; the CDR2 comprises the amino acid sequence of SEQ ID NO: 59; and the CDR3 comprises the amino acid sequence of SEQ ID NO: 64, under the Chothia definition. In some embodiments of the above aspect, the CDR1 comprises the amino acid sequence of SEQ ID NO: 54, the CDR2 comprises the amino acid sequence of SEQ ID NO: 59, and the CDR3 comprises the amino acid sequence of SEQ ID NO: 71.

In some embodiments of the above aspect, the CDR1 comprises the amino acid sequence of SEQ ID NO: 55; the CDR2 comprises the amino acid sequence of SEQ ID NO: 60; and the CDR3 comprises the amino acid sequence of SEQ ID NO: 65, under the Kabat definition. In some embodiments of the above aspect, the CDR1 comprises the amino acid sequence of SEQ ID NO: 55, the CDR2 comprises the amino acid sequence of SEQ ID NO: 68, and the CDR3 comprises the amino acid sequence of SEQ ID NO: 72.

In some embodiments of the above aspect, the CDR1 comprises the amino acid sequence of SEQ ID NO: 56; the CDR2 comprises the amino acid sequence of SEQ ID NO: 61; and the CDR3 comprises the amino acid sequence of SEQ ID NO: 66, under the Contact definition. In some embodiments of the above aspect, the CDR1 comprises the amino acid sequence of SEQ ID NO: 56, the CDR2 comprises the amino acid sequence of SEQ ID NO: 69, and the CDR3 comprises the amino acid sequence of SEQ ID NO: 73.

In some embodiments of the above aspect, the CDR1 comprises the amino acid sequence of SEQ ID NO: 57; the CDR2 comprises the amino acid sequence of SEQ ID NO: 62; and the CDR3 comprises the amino acid sequence of SEQ ID NO: 67, under the IMGT definition. In some embodiments of the above aspect, the CDR1 comprises the amino acid sequence of SEQ ID NO: 57, the CDR2 comprises the amino acid sequence of SEQ ID NO: 70, and the CDR3 comprises the amino acid sequence of SEQ ID NO: 74.

In one aspect, the present disclosure provides a VHH domain that binds IgE, comprising a paratope comprising 1, 2, 3, 4, 5, 6, 7, or 8 of amino acids 26, 27, 32, 99, 100, 105, 106, and 110 of SEQ ID NO: 42. In some embodiments, the paratope comprises amino acids 26, 27, 32, 99, 100, 105, 106, and 110 of SEQ ID NO: 42. In some embodiments, the paratope further comprises amino acids 29, 35, 52, 97, 98, 103, 107, 111, and 112 of SEQ ID NO: 42.

In another aspect, the present disclosure provides a VHH domain that binds IgE, comprising a CDR1 that comprises the amino acid sequence of SEQ ID NO: 115 and a CDR3 that comprises the amino acid sequence of SEQ ID NO: 116. It is understood that although the VHH domain can also comprise a CDR2, the sequence of the CDR2 need not be specified given that it has minimal to no interaction with IgE. In some embodiments, the CDR1 comprises the amino acid sequence of SEQ ID NO: 114. In some embodiments, the CDR3 comprises the amino acid sequence of SEQ ID NO: 118. In some embodiments, the CDR3 comprises the amino acid sequence of SEQ ID NO: 117.

In some embodiments of any one of the foregoing aspects, the VHH domain comprises glutamate (E), aspartate (D), lysine (K), or arginine (R) at position 11 according to Kabat numbering. In some embodiments the VHH domain comprises glutamate (E), arginine (R), or aspartate (D) at position 112 according to Kabat numbering. In some embodiments the VHH domain comprises leucine (L) at position 108 according to Kabat numbering.

In some embodiments the VHH domain is humanized.

In some embodiments the VHH domain comprises the amino acid sequence of SEQ ID NO: 47.

In some embodiments the VHH domain comprises an amino acid sequence at least 85%, at least 90%, at least 95%, at least 96%, at least 97%, at least 98% or at least 99% identical to an amino acid sequence selected from SEQ ID NOs: 2, 6-46, and 101. In some embodiments the VHH domain comprises an amino acid sequence selected from SEQ ID NOs: 2, 6-46, and 101.

In some embodiments the VHH domain comprises an amino acid sequence at least 85%, at least 90%, at least 95%, at least 96%, at least 97%, at least 98% or at least 99% identical to the amino acid sequence of SEQ ID NO: 42. In some embodiments the VHH domain comprises the amino acid sequence of SEQ ID NO: 42.

In some embodiments the VHH domain comprises an amino acid sequence at least 85%, at least 90%, at least 95%, at least 96%, at least 97%, at least 98% or at least 99% identical to the amino acid sequence of SEQ ID NO: 101. In some embodiments the VHH domain comprises the amino acid sequence of SEQ ID NO: 101.

In some embodiments, the VHH domain binds human IgE. In some embodiments the human IgE comprises the amino acid sequence of SEQ ID NO: 1.

In some embodiments, the VHH domain inhibits binding of IgE to FcεR1A. In some embodiments, the VHH domain does not bind a complex of human IgE and FcεR1A.

In some embodiments, the VHH domain does not bind cynomolgus monkey IgE. In some embodiments the VHH domain does not bind IgA, IgM, or IgG2.

In another aspect, the present disclosure provides a polypeptide comprising a first VHH domain disclosed herein. In some embodiments, the polypeptide further comprises a second VHH domain disclosed herein. In some embodiments, the polypeptide further comprises a third VHH domain discloses herein. In some embodiments, the VHH domains in the polypeptide comprise the same CDR1, CDR2, and CDR3 amino acid sequences. In some embodiments, the VHH domains in the polypeptide comprise the same VHH amino acid sequence. In some embodiments, the polypeptide comprises one single VHH domain.

In some embodiments, the polypeptide further comprises an Fc region, such as a human IgG1 Fc region. In some embodiments, the Fc region comprises one or more substitutions selected from G236D, S267E and L328F, numbered according to the EU index as in Kabat. In some embodiments, the Fc region comprises substitutions S267E and L328F, numbered according to the EU index as in Kabat. In some embodiments, Fc region comprises the amino acid sequence of SEQ ID NO: 79, 75, 76, 80, 81, or 82.

In some embodiments of any of the applicable aspects above, the polypeptide comprises the amino acid sequence of SEQ ID NO: 86, 85, 92, or 93.

In some embodiments of any of the applicable aspects above, the polypeptide consists of the amino acid sequence of SEQ ID NO: 86, 85, 92, or 93.

The present disclosure also provides a protein comprising two or more polypeptides disclosed herein that form a dimer under physiological conditions. In some embodiments, the dimer is a homodimer, optionally consisting of two polypeptides.

In some embodiments, the polypeptide or protein inhibits binding of IgE to FCER1A. In some embodiments, the polypeptide or protein does not bind an IgE:FCER1A complex.

In some embodiments, polypeptide or protein reduces IgE production in a subject's blood to a greater extent than an isotype antibody. In some embodiments, the polypeptide or protein inhibits degranulation of mast cells or basophils to a greater extent than an isotype antibody. In some embodiments, the polypeptide or protein inhibits activation of mast cells or basophils to a greater extent than an isotype antibody. In some embodiments, the polypeptide or protein does not induce antigen-independent mast cell or basophil activation.

In some embodiments, wherein the polypeptide or protein binds IgE with a $K_D$ of less than or equal to about 5 nM, 4 nM, 3 nM, 2 nM, or 1 nM, as measured by surface plasmon resonance (SPR) assay. In some embodiments, the KD is measured using a polypeptide or protein that includes two copies of the VHH domain (e.g., a dimer of VHH-Fc polypeptides) and a native human IgE dimer.

The present disclosure also provides an immunoconjugate comprising a polypeptide or protein disclosed herein.

The present disclosure also provides a pharmaceutical composition comprising a polypeptide disclosed herein or an immunoconjugate disclosed herein, and a pharmaceutically acceptable carrier.

In addition, the present disclosure provides an isolated nucleic acid that encodes a polypeptide disclosed herein, a vector comprising the nucleic acid, a host cell comprising the nucleic acid or the vector, and a host cell that expresses the polypeptide or protein.

The present disclosure also provides a method of producing a polypeptide or protein disclosed herein, comprising incubating the host cell under conditions for expression of the polypeptide or protein. The method can further comprise isolating the polypeptide or protein.

Another aspect of the present disclosure provides a method of reducing IgE levels in a subject, the method comprising administering to a subject in need thereof a polypeptide, a protein, an immunoconjugate, or a pharmaceutical composition disclosed herein.

Another aspect of the present disclosure provides a method of treating an allergy, the method comprising administering to a subject in need thereof a polypeptide, protein, an immunoconjugate, or a pharmaceutical composition disclosed herein. The subject may have a food allergy, an environmental allergy, a companion animal allergy, and/or a venom allergy.

BRIEF DESCRIPTION OF THE FIGURES

FIGS. 2A-2B show an alignment of the parental B10 VHH amino acid sequence (SEQ ID NO: 2) with humanized variants (SEQ ID NOs: 6-46) and the human heavy chain germline sequence "VH3-23" (SEQ ID NO: 94). Residues identical to B10 are indicated with a dot, and residues that differ are shown. The CDRs (AbM definition) are bolded and underlined.

FIGS. 3A and 3C show binding to human IgE, FIG. 3B shows binding to cynomolgous monkey IgE, FIG. 3D shows binding to human IgA, FIG. 3E shows binding to human IgG2, FIG. 3F shows binding to human IgM, FIG.

3G shows binding to mouse IgE, FIG. 3H shows binding to rat IgE, FIG. 3I shows binding to human IgD, FIG. 3J shows binding to pig IgE, and FIG. 3K shows binding to dog IgE.

FIG. 16A), CDR2 (SEQ ID NO: 68; FIG. 16B), and CDR3 (SEQ ID NO: 74; FIG. 16C) to bind IgE-coated ELISA plates. For each residue site at least 96 clones were tested. Each rectangle represents an individual clone tested and contains an OD value. Rectangles are colored by relative binding affinity as indicated by the inset scale. Site numbering for each residue tested is indicated by the inset table. Positions where changes led to complete loss of binding are indicated with a "*", positions where changes led to almost complete loss of binding are indicated by "^", and positions where changes led to partial loss of binding are indicated by "!. " FIGS. 16D and 16E are tables showing specific mutations in CDR1 and CDR3, respectively, in hzB10v40 that retained binding to IgE.

DETAILED DESCRIPTION

Figure 1A:
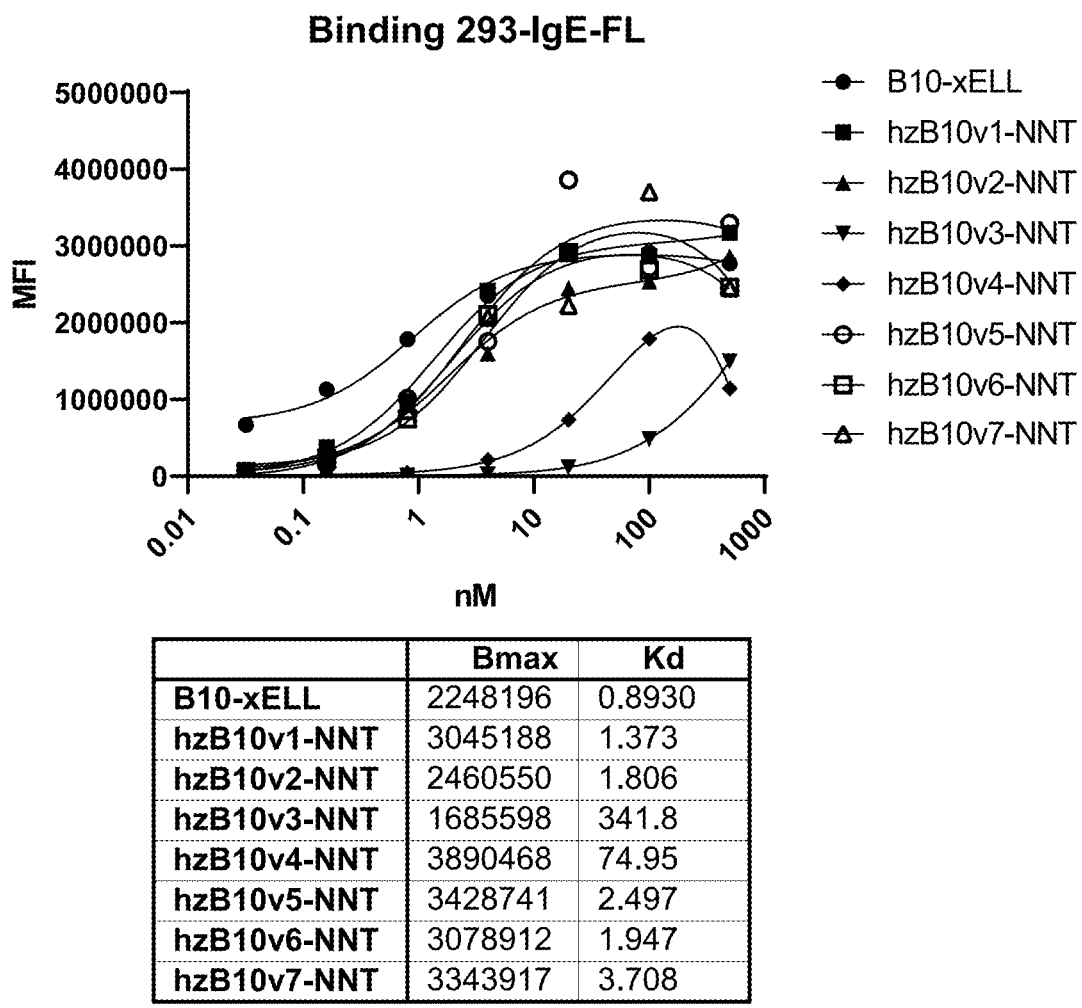
FIGS. 1A-1G show the median fluorescence intensity of parental anti-human IgE-B10 and humanized variants thereof formatted as monomeric VHH-hIgG1 fusions binding to human IgE-expressing 293 cells as determined by binding of an Alexa Fluor® 647 conjugated anti-human IgG Fcγ fragment-specific secondary antibody using flow cytometry. The Bmax and Kd values for each curve are provided.
Figure 1B:
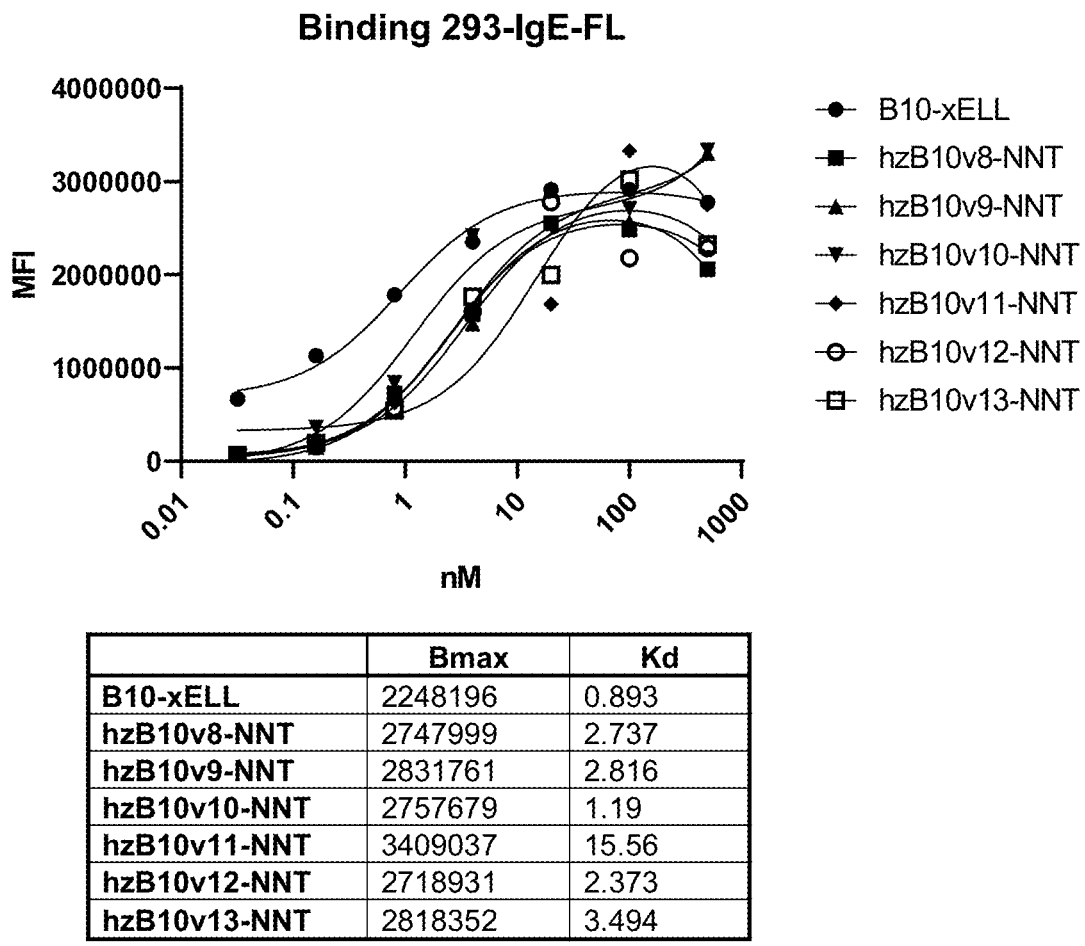
Figure 1C:
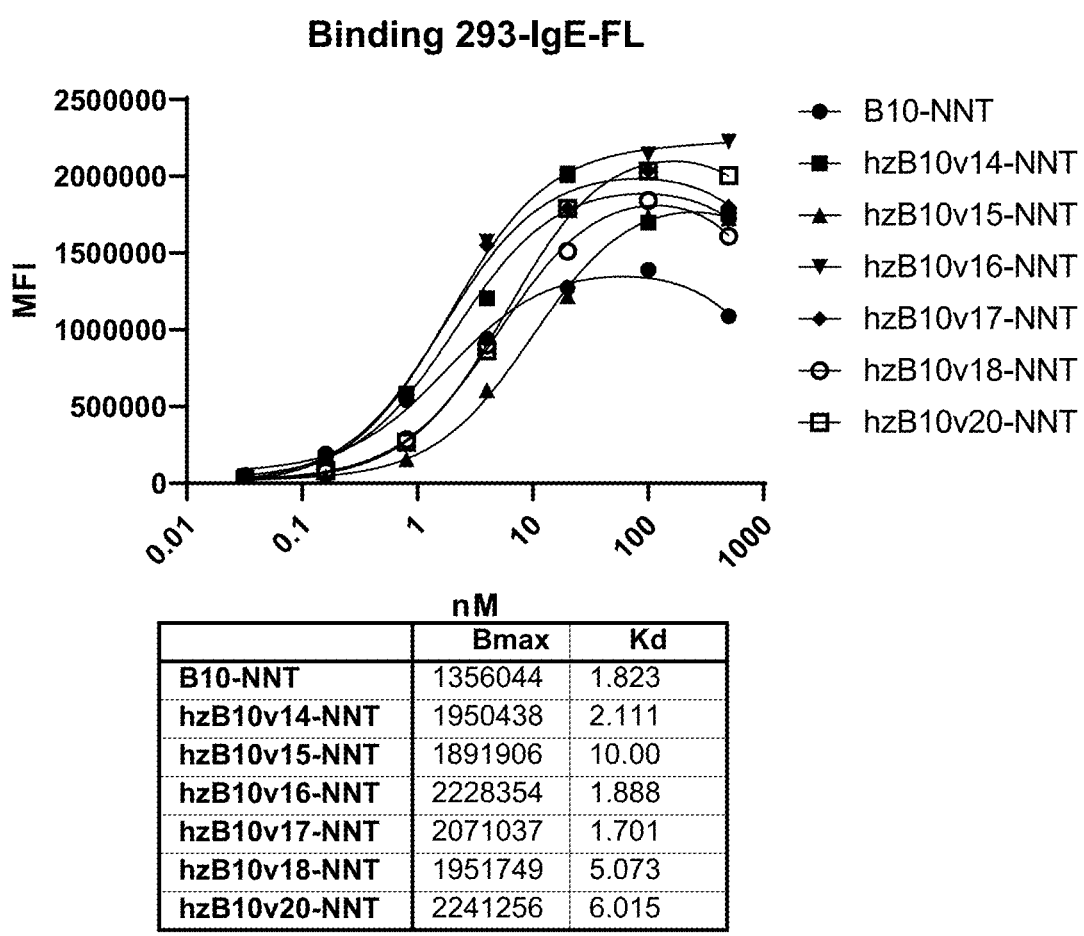
Figure 1D:
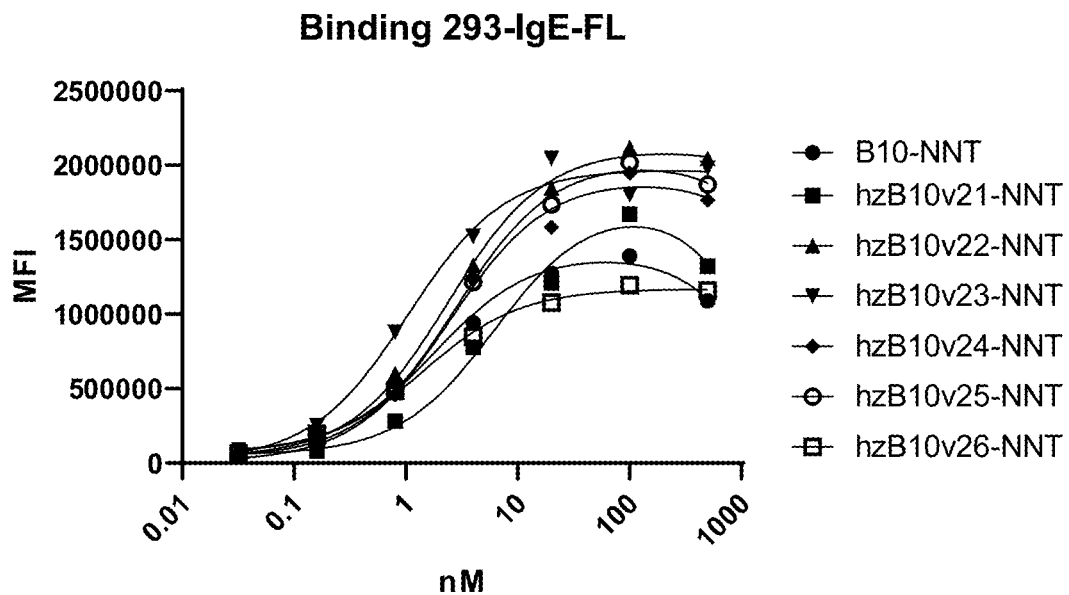
Figure 1E:
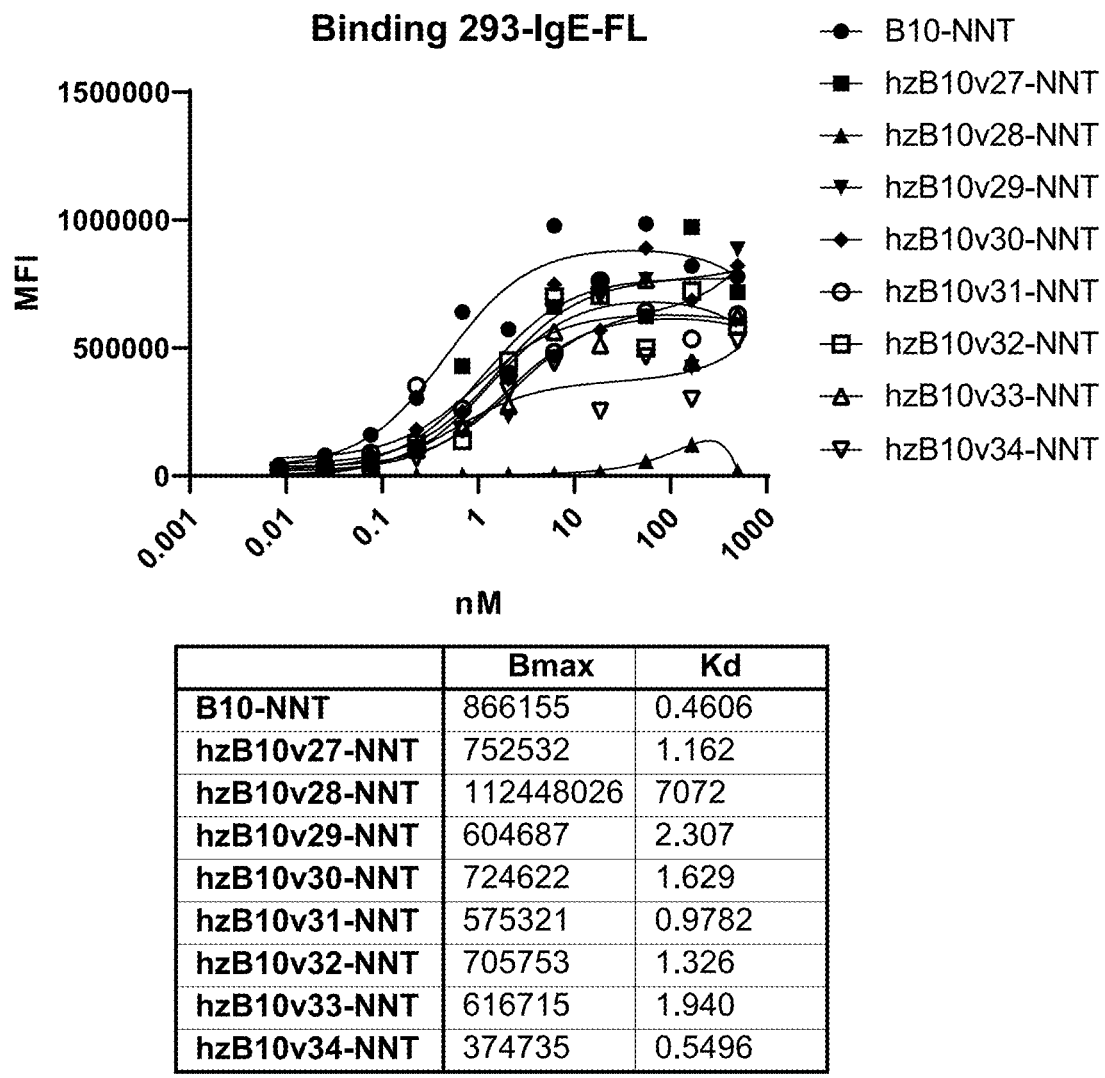
Figure 1F:
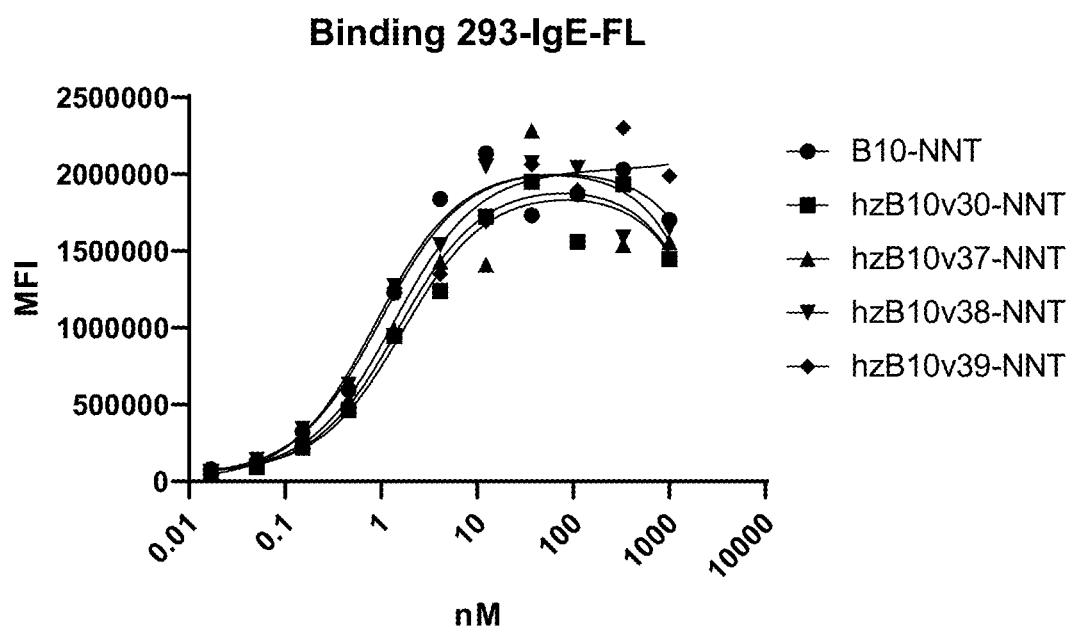
Figure 1G:
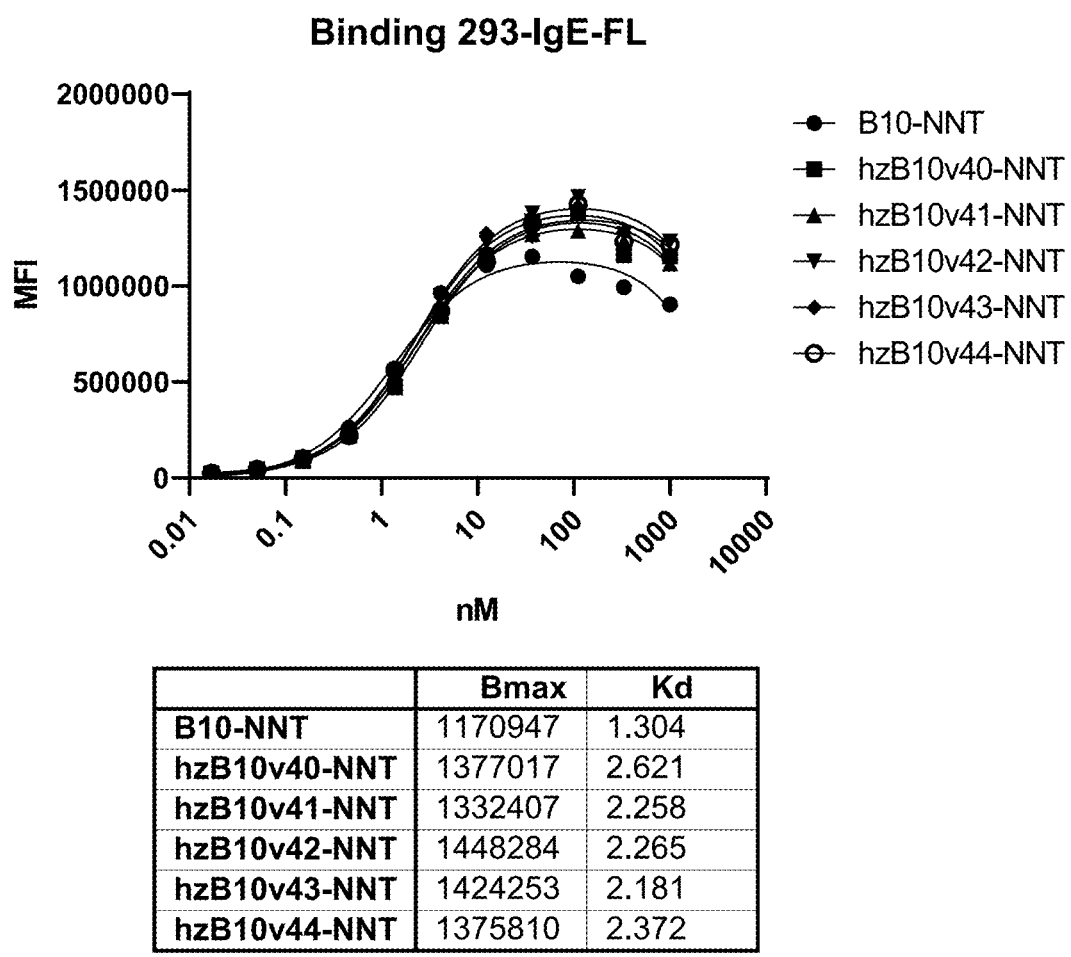

Embodiments provided herein relate to IgE binding polypeptides and their use in various methods of treating IgE related diseases or disorders, such as IgE-mediated allergies.

Definitions and Various Embodiments

The section headings used herein are for organizational purposes only and are not to be construed as limiting the subject matter described.

All references cited herein, including patent applications, patent publications, and GenBank accession numbers are herein incorporated by reference, as if each individual reference were specifically and individually indicated to be incorporated by reference in its entirety.

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J.B. Lippincott Company, 1993); and updated versions thereof.

Unless otherwise defined, scientific and technical terms used in connection with the present disclosure shall have the meanings that are commonly understood by those of ordinary skill in the art. Further, unless otherwise required by context or expressly indicated, singular terms shall include pluralities and plural terms shall include the singular. For any conflict in definitions between various sources or references, the definition provided herein will control.

In general, the numbering of the residues in the variable regions of an immunoglobulin is that of the Kabat numbing system while the numbering of residues in the constant regions of an immunoglobulin is that of the EU index, both numbering scheme are provided in Kabat et al., *Sequences of Proteins of Immunological Interest*, 5th Ed. Public Health Service, National Institutes of Health, Bethesda, Md. (1991). The "EU index as in Kabat" refers to the residue numbering of the human IgG1 EU antibody.

It is understood that embodiments of the invention described herein include "comprising," "consisting," and/or "consisting essentially of" embodiments. As used herein, the singular form "a", "an", and "the" includes plural references unless indicated otherwise. Use of the term "or" herein is not meant to imply that alternatives are mutually exclusive.

In this application, the use of "or" means "and/or" unless expressly stated or understood by one skilled in the art. In the context of a multiple dependent claim, the use of "or" refers back to more than one preceding independent or dependent claim.

The phrase "reference sample", "reference cell", or "reference tissue", denote a sample with at least one known characteristic that can be used as a comparison to a sample with at least one unknown characteristic. In some embodiments, a reference sample can be used as a positive or negative indicator. A reference sample can be used to establish a level of protein and/or mRNA that is present in, for example, healthy tissue, in contrast to a level of protein and/or mRNA present in the sample with unknown characteristics. In some embodiments, the reference sample comes from the same subject, but is from a different part of the subject than that being tested. In some embodiments, the reference sample is from a tissue area surrounding or adjacent to the cancer. In some embodiments, the reference sample is not from the subject being tested, but is a sample from a subject known to have, or not to have, a disorder in question (for example, an IgE related disorder). In some embodiments, the reference sample is from the same subject, but from a point in time before the subject developed the disorder. In some embodiments, the reference sample is from the same or a different subject. When a negative reference sample is used for comparison, the level of expression or amount of the molecule in question in the negative reference sample will indicate a level at which one of skill in the art will appreciate, given the present disclosure, that there is no and/or a low level of the molecule. When a positive reference sample is used for comparison, the level of expression or amount of the molecule in question in the positive reference sample will indicate a level at which one of skill in the art will appreciate, given the present disclosure, that there is a level of the molecule. The terms "benefit", "clinical benefit", "responsiveness", and "therapeutic responsiveness" as used herein in the context of benefiting from or responding to administration of a therapeutic agent, can be measured by assessing various endpoints, e.g., inhibition, to some extent, of disease progression, including slowing down and complete arrest; reduction in the number of disease episodes and/or symptoms; reduction in lesion size; inhibition (that is, reduction, slowing down or complete stopping) of disease cell infiltration into adjacent peripheral organs and/or tissues; inhibition (that is, reduction, slowing down or complete stopping) of disease spread; relief, to some extent, of one or more symptoms associated with the disorder; increase in the length of disease-free presentation following treatment, for example, progression-free survival; increased overall survival; higher response rate; and/or decreased mortality at a given point of time following treatment. A subject or cancer that is "non-responsive" or "fails to respond" is one that has failed to meet the above noted qualifications to be "responsive".

The terms "nucleic acid molecule", "nucleic acid" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides comprised in the nucleic acid molecule or polynucleotide.

The term "polypeptide" refers to a polymer of amino acid residues, and is not limited to a minimum length. Such polymers of amino acid residues may contain natural or non-natural amino acid residues, and include, but are not limited to, peptides, oligopeptides, dimers, trimers, and multimers of amino acid residues. Both full-length polypeptides and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" can include modifications, such as deletions, additions, and substitutions (generally conservative in nature), to the native sequence, as long as it maintains the desired activity. These modifications may be deliberate, as through site-directed mutagenesis, or may be accidental, such as through mutations of hosts which produce the proteins or errors due to PCR amplification.

The term "protein" refers to a macromolecule comprising one or more polypeptides. For example, a protein can be a multimer (e.g., dimer, trimer, or tetramer) formed by a plurality of the same or different polypeptides.

"IgE" as used herein refers to any native, mature IgE that results from processing of an IgE precursor in a cell. The term includes IgE from any mammalian source, including primates (e.g., humans and cynomolgus or rhesus monkeys) and rodents (e.g., mice and rats), unless otherwise indicated. A nonlimiting exemplary human IgE constant region amino acid sequence is shown, e.g., in GenBank accession no. AAB59424.1. See SEQ ID NO. 1.

"FCER1A" as used herein refers to any native, Fc fragment of IgE receptor Ia that binds IgE. The term includes FCER1A from any mammalian source, including primates (e.g., humans and cynomolgus or rhesus monkeys) and rodents (e.g., mice and rats), unless otherwise indicated. A nonlimiting exemplary human FCER1A precursor amino acid sequence is shown, e.g., in GenBank accession no. NP_001374209.1. See SEQ ID NO. 90.

The term "specifically binds" to an antigen or epitope is a term that is well understood in the art, and methods to determine such specific binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. A single-domain antibody (sdAb) or VHH-containing polypeptide "specifically binds" or "preferentially binds" to a target if it binds with greater affinity, avidity, more readily, and/or with greater duration than it binds to other substances. For example, a sdAb or VHH-containing polypeptide that specifically or preferentially binds to an IgE epitope is a sdAb or VHH-containing polypeptide that binds this epitope with greater affinity, avidity, more readily, and/or with greater duration than it binds to other IgE epitopes or non-IgE epitopes. It is also understood by reading this definition that; for example, a sdAb or VHH-containing polypeptide that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "Specificity" refers to the ability of a binding protein to selectively bind an antigen.

The terms "inhibition" or "inhibit" refer to a decrease, cessation, or suppression of any phenotypic characteristic or to the decrease, cessation, or suppression in the incidence, degree, or likelihood of that characteristic. To "reduce" or "inhibit" is to decrease, reduce, suppress, or arrest an activity, function, amount, abundance, or rate of increase as compared to a reference. In some embodiments, by "reduce" or "inhibit" is meant the ability to cause an overall decrease of 10% or greater. In some embodiments, by "reduce" or "inhibit" is meant the ability to cause an overall decrease of 50% or greater. In some embodiments, by "reduce" or "inhibit" is meant the ability to cause an overall decrease of 75%, 85%, 90%, 95%, or greater. In some embodiments, the amount noted above is inhibited or decreased over a period of time, relative to a control over the same period of time. It is understood that an inhibition of the rate of increase of IgE refers to a decrease in the rate of IgE level increase with or without a concurrent decrease in absolute IgE levels. An inhibition of the activity of IgE refers to a decrease in an activity of IgE, such as activation of mast cells and basophils and activation and differentiation of B cells. In some embodiments, "inhibit" refers to a decrease in a IgE activity compared to the IgE activity in the absence of the modulator. An inhibition of IgE level includes decrease of IgE levels, such as decrease of serum IgE levels, and/or decrease of IgE expression.

As used herein, the term "epitope" refers to a site on a target molecule (for example, an antigen, such as a protein, nucleic acid, carbohydrate or lipid) to which an antigen-binding molecule (for example, a sdAb or VHH-containing polypeptide) binds. Epitopes often include a chemically active surface grouping of molecules such as amino acids, polypeptides or sugar side chains and have specific three-dimensional structural characteristics as well as specific charge characteristics. Epitopes can be formed both from contiguous and/or juxtaposed noncontiguous residues (for example, amino acids, nucleotides, sugars, lipid moiety) of the target molecule. Epitopes formed from contiguous residues (for example, amino acids, nucleotides, sugars, lipid moiety) typically are retained on exposure to denaturing solvents whereas epitopes formed by tertiary folding typically are lost on treatment with denaturing solvents. An epitope may include but is not limited to at least 3, at least 5 or 8-10 residues (for example, amino acids or nucleotides). In some embodiments, an epitope is less than 20 residues (for example, amino acids or nucleotides) in length, less than 15 residues or less than 12 residues. Two antibodies may bind the same epitope within an antigen if they exhibit competitive binding for the antigen. In some embodiments, an epitope can be identified by a certain minimal distance to a CDR residue on the antigen-binding molecule. In some embodiments, an epitope can be identified by the above distance, and further limited to those residues involved in a bond (for example, a hydrogen bond) between a residue of the antigen-binding molecule and an antigen residue. An epitope can be identified by various scans as well, for example an alanine or arginine scan can indicate one or more residues that the antigen-binding molecule can interact with. Unless explicitly denoted, a set of residues as an epitope does not exclude other residues from being part of the epitope for a particular antigen-binding molecule. Rather, the presence of such a set designates a minimal series (or set of species) of epitopes. Thus, in some embodiments, a set of residues identified as an epitope designates a minimal epitope of relevance for the antigen, rather than an exclusive list of residues for an epitope on an antigen.

A "nonlinear epitope" or "conformational epitope" comprises noncontiguous polypeptides, amino acids and/or sugars within the antigenic protein to which an antigen-binding molecule specific to the epitope binds. In some embodiments, at least one of the residues will be noncontiguous with the other noted residues of the epitope; however, one or more of the residues can also be contiguous with the other residues.

A "linear epitope" comprises contiguous polypeptides, amino acids and/or sugars within the antigenic protein to which an antigen-binding molecule specific to the epitope binds. It is noted that, in some embodiments, not every one of the residues within the linear epitope need be directly bound (or involved in a bond) by the antigen-binding molecule. In some embodiments, linear epitopes can be from immunizations with a peptide that effectively consisted of the sequence of the linear epitope, or from structural sections of a protein that are relatively isolated from the remainder of the protein (such that the antigen-binding molecule can interact, at least primarily), just with that sequence section.

The term "antibody" is used in the broadest sense and encompass various polypeptides that comprise antibody-like antigen-binding domains, including but not limited to conventional antibodies (typically comprising at least one heavy chain and at least one light chain), single-domain antibodies (sdAbs, comprising at least one VHH domain and optionally an Fc region), VHH-containing polypeptides (polypeptides comprising at least one VHH domain), and fragments of any of the foregoing so long as they exhibit the desired antigen-binding activity. In some embodiments, an antibody comprises a dimerization domain. Such dimerization domains include, but are not limited to, heavy chain constant domain CH1, which typically pairs with a light chain constant domain, CL, to form a heterodimer, and Fc regions (comprising hinge, CH2, and CH3, where the hinge and/or CH3 mediate dimerization).

The term antibody also includes, but is not limited to, chimeric antibodies, humanized antibodies, and antibodies of various species such as camelid (including llama), shark, mouse, human, cynomolgus monkey, etc.

The term "antigen-binding domain" as used herein refers to a portion of an antibody sufficient to bind antigen. In some embodiments, an antigen binding domain of a conventional antibody comprises three heavy chain CDRs and three light chain CDRs. Thus, in some embodiments, an antigen binding domain comprises a heavy chain variable region comprising CDR1-FR2-CDR2-FR3-CDR3, and any portions of FR1 and/or FR4 required to maintain binding to antigen, and a light chain variable region comprising CDR1-FR2-CDR2-FR3-CDR3, and any portions of FR1 and/or FR4 required to maintain binding to antigen. In some embodiments, an antigen-binding domain of an sdAb or VHH-containing polypeptide comprises three CDRs of a VHH domain. Thus, in some embodiments, an antigen binding domain of an sdAb or VHH-containing polypeptide comprises a VHH domain comprising CDR1-FR2-CDR2-FR3-CDR3, and any portions of FR1 and/or FR4 required to maintain binding to antigen.

The term "VHH" or "VHH domain" or "VHH antigen-binding domain" as used herein refers to the antigen-binding portion (e.g., one or more of the CDRs) of a single-domain antibody, such as a camelid antibody. In some embodiments, a VHH comprises three CDRs and four framework regions, designated FR1, CDR1, FR2, CDR2, FR3, CDR3, and FR4. In some embodiments, a VHH may be truncated at the N-terminus or C-terminus such that it comprises only a partial FR1 and/or FR4, or lacks one or both of those framework regions, so long as the VHH substantially maintains antigen binding and specificity.

The terms "single domain antibody" and "sdAb" are used interchangeably herein to refer to an antibody comprising at least one monomeric domain, such as a VHH domain, or a VNAR domain (from a shark antibody) without a light chain, and an Fc region. In some embodiments, an sdAb is a dimer of two polypeptides wherein each polypeptide comprises at least one VHH domain and an Fc region. As used herein, the terms "single domain antibody" and "sdAb" encompass polypeptides that comprise multiple VHH domains, such as a polypeptide having the structure $VHH_1$-$VHH_2$-Fc or $VHH_1$-$VHH_2$-$VHH_3$-Fc, wherein $VHH_1$, $VHH_2$, and $VHH_3$ may be the same or different.

The term "VHH-containing polypeptide" refers to a polypeptide that comprises at least one VHH domain. In some embodiments, a VHH polypeptide comprises two, three, or four or more VHH domains, wherein each VHH domain may be the same or different. In some embodiments, a VHH-containing polypeptide comprises an Fc region. In some such embodiments, the VHH-containing polypeptide may be referred to as an sdAb. Further, in some such embodiments, the VHH polypeptide may form a dimer. Nonlimiting structures of VHH-containing polypeptides, which are also sdAbs, include $VHH_1$-Fc, $VHH_1$-$VHH_2$-Fc, and $VHH_1$-$VHH_2$-$VHH_3$-Fc, wherein $VHH_1$, $VHH_2$, and $VHH_3$ may be the same or different. In some embodiments of such structures, one VHH may be connected to another VHH by a linker, or one VHH may be connected to the Fc region by a linker. In some such embodiments, the linker comprises 1-20 amino acids, preferably 1-20 amino acids predominantly composed of glycine and, optionally, serine. In some embodiments, when a VHH-containing polypeptide comprises an Fc, it forms a dimer. Thus, the structure $VHH_1$-$VHH_2$-Fc, if it forms a dimer, is considered to be tetravalent (i.e., the dimer has four VHH domains). Similarly, the structure $VHH_1$-$VHH_2$-$VHH_3$-Fc, if it forms a dimer, is considered to be hexavalent (i.e., the dimer has six VHH domains). In some embodiments a VHH-containing polypeptide comprising an Fc region forms a homodimer, e.g., through association of the hinge of the Fc regions.

The term "monoclonal antibody" refers to an antibody (including an sdAb or VHH-containing polypeptide) of a substantially homogeneous population of antibodies, that is, the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. Thus, a sample of monoclonal antibodies can bind to the same epitope on the antigen. The modifier "monoclonal" indicates the character of the antibody as being obtained from a substantially homogeneous population of antibodies, and is not to be construed as requiring production of the antibody by any particular method. For example, the monoclonal antibodies may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

The term "CDR" denotes a complementarity determining region as defined by at least one manner of identification to one of skill in the art. In some embodiments, CDRs can be defined in accordance with any of the Chothia numbering schemes (see Chothia and Lesk, J Mol Biol, 1987, 196:901-917), the Kabat numbering scheme (see Kabat et al., 1992, Sequences of Proteins of Immunological Interest, DIANE Publishing: 2719), a combination of Kabat and Chothia, the AbM definition (see Whitelegg & Rees, Protein Eng. 2000, 13:819-824; Whitelegg & Rees, Methods Mol Biol. 2004, 248:51-91), the IMGT definition (see Lefranc, (1999) The Immunologist, 7, 132-136), and/or the contact definition (see MacCallum et al., J. Mol. Biol. 1996, 262:732-745). A VHH comprises three CDRs, designated CDR1, CDR2, and CDR3.

The term "heavy chain constant region" as used herein refers to a region comprising at least three heavy chain constant domains, CH1, hinge, CH2, and CH3. Of course, non-function-altering deletions and alterations within the domains are encompassed within the scope of the term "heavy chain constant region," unless designated otherwise. Nonlimiting exemplary heavy chain constant regions include γ, δ, and α. Nonlimiting exemplary heavy chain constant regions also include δ and μ. Each heavy constant region corresponds to an antibody isotype. For example, an antibody comprising a γ constant region is an IgG antibody, an antibody comprising a δ constant region is an IgD antibody, and an antibody comprising an α constant region is an IgA antibody. Further, an antibody comprising a μ constant region is an IgM antibody, and an antibody comprising an δ constant region is an IgE antibody. Certain isotypes can be further subdivided into subclasses. For example, IgG antibodies include, but are not limited to, IgG1 (comprising a $γ_1$ constant region), IgG2 (comprising a $γ_2$ constant region), IgG3 (comprising a $γ_3$ constant region), and IgG4 (comprising a $γ_4$ constant region) antibodies; IgA antibodies include, but are not limited to, IgA1 (comprising an $α_1$ constant region) and IgA2 (comprising an $α_2$ constant region) antibodies; and IgM antibodies include, but are not limited to, IgM1 and IgM2.

An "Fc region" as used herein refers to a portion of a heavy chain constant region comprising CH2 and CH3. In some embodiments, an Fc region comprises a hinge, CH2, and CH3. In various embodiments, when an Fc region comprises a hinge, the hinge and/or CH3 mediate dimerization between two Fc-containing polypeptides. An Fc region may be of any antibody heavy chain constant region isotype discussed herein. In some embodiments, an Fc region is an IgG1, IgG2, IgG3, or IgG4. In some embodiments the Fc region lacks the C-terminal lysine. In some embodiments, the C-terminal amino acid of the Fc region is an amino acid other than lysine.

An "acceptor human framework" as used herein is a framework comprising the amino acid sequence of a heavy chain variable domain ($V_H$) framework derived from a human immunoglobulin framework or a human consensus framework, as discussed herein. An acceptor human framework derived from a human immunoglobulin framework or a human consensus framework can comprise the same amino acid sequence thereof, or it can contain amino acid sequence changes. In some embodiments, the number of amino acid changes are fewer than 10, or fewer than 9, or fewer than 8, or fewer than 7, or fewer than 6, or fewer than 5, or fewer than 4, or fewer than 3, across all of the human frameworks in a single antigen binding domain, such as a VHH.

"Affinity" refers to the strength of the sum total of noncovalent interactions between a single binding site of a molecule (for example, an antibody, such as an sdAb, or VHH-containing polypeptide) and its binding partner (for example, an antigen). The affinity or the apparent affinity of a molecule X for its partner Y can generally be represented by the dissociation constant ($K_d$) or the $K_{d\text{-}apparent}$, respectively. Affinity can be measured by common methods known in the art (such as, for example, ELISA $K_d$, KinExA, flow cytometry, and/or surface plasmon resonance devices), including those described herein. Such methods include, but are not limited to, methods involving BIAcore®, Octet®, or flow cytometry. In some embodiments, a VHH containing polypeptide binds to IgE with a $K_D$ of less than or equal to about 1 nM, 0.8 nM, 0.6 nM, 0.4 nM, or 0.2 nM as measured by ELISA. In some embodiments, a VHH containing polypeptide binds to IgE with a $K_D$ of less than or equal to about 5 nM, 4 nM, 3 nM, 2 nM, 1.5, 1 nM, 0.8 nM, or 0.6 nM, as measured by surface plasmon resonance (SPR).

The term "$K_d$", as used herein, refers to the equilibrium dissociation constant of an antigen-binding molecule/antigen interaction. When the term "$K_d$" is used herein, it includes $K_d$ and $K_{d\text{-}apparent}$.

In some embodiments, the $K_d$ of the antigen-binding molecule is measured by flow cytometry using an antigen-expressing cell line and fitting the mean fluorescence measured at each antibody concentration to a non-linear one-site binding equation (Prism Software graphpad). In some such embodiments, the $K_d$ is $K_{d\text{-}apparent}$.

The term "biological activity" refers to any one or more biological properties of a molecule (whether present naturally as found in vivo, or provided or enabled by recombinant means).

An "agonist" or "activating" antibody is one that increases and/or activates a biological activity of the target antigen. In some embodiments, the agonist antibody binds to an antigen and increases its biologically activity by at least about 20%, 40%, 60%, 80%, 85% or more.

An "antagonist", a "blocking" or "neutralizing" antibody is one that inhibits a biological activity of the target antigen. In some embodiments, a neutralizing antibody binds to an antigen and reduces its biologically activity by at least about 20%, 40%, 60%, 80%, 85% 90%, 95%, 99% or more.

An "affinity matured" sdAb or VHH-containing polypeptide refers to a sdAb or VHH-containing polypeptide with one or more alterations in one or more CDRs compared to a parent sdAb or VHH-containing polypeptide that does not possess such alterations, such alterations resulting in an improvement in the affinity of the sdAb or VHH-containing polypeptide for antigen.

A "humanized VHH" as used herein refers to a VHH in which one or more framework regions have been substantially replaced with human framework regions. In some instances, certain framework region (FR) residues of the human immunoglobulin are replaced by corresponding non-human residues. Furthermore, the humanized VHH can comprise residues that are found neither in the original VHH nor in the human framework sequences, but are included to further refine and optimize sdAb VHH-containing polypeptide performance. In some embodiments, a humanized sdAb or VHH-containing polypeptide comprises a human Fc region. As will be appreciated, a humanized sequence can be identified by its primary sequence and does not necessarily denote the process by which the antibody was created.

An "effector-positive Fc region" possesses an "effector function" of a native sequence Fc region. Exemplary "effector functions" include Fc receptor binding; C1q binding and complement dependent cytotoxicity (CDC); Fc receptor binding; antibody-dependent cell-mediated cytotoxicity (ADCC); phagocytosis; down regulation of cell surface receptors (for example B-cell receptor); and B-cell activation, etc. Such effector functions generally require the Fc region to be combined with a binding domain (for example, an antibody variable domain) and can be assessed using various assays.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification. In some embodiments, a "variant Fc region" comprises an amino acid sequence which differs from that of a native sequence Fc region by virtue of at least one amino acid modification, yet retains at least one effector function of the native sequence Fc region. In some embodiments, the variant Fc region has at least one amino acid substitution compared to a native sequence Fc region or to the Fc region of a parent polypeptide, for example, from about one to about ten amino acid substitutions, and preferably, from about one to about five amino acid substitutions in a native sequence Fc region or in the Fc region of the parent polypeptide. In some embodiments, the variant Fc region herein will possess at least about 80% sequence identity with a native sequence Fc region and/or with an Fc region of a parent polypeptide, at least about 90% sequence identity therewith, at least about 95%, at least about 96%, at least about 97%, at least about 98%, or at least about 99% sequence identity therewith.

"Fc receptor" or "FcR" describes a receptor that binds to the Fc region of an antibody. In some embodiments, an FcγR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (See, for example, Daeron, *Annu. Rev. Immunol.* 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. For example, the term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, for example, Ghetie and Ward, *Immunol. Today* 18 (12): 592-598 (1997); Ghetie et al., *Nature Biotechnology,* 15(7): 637-640 (1997); Hinton et al., *J. Biol. Chem.* 279 (8): 6213-6216 (2004); WO 2004/92219 (Hinton et al.).

The term "substantially similar" or "substantially the same," as used herein, denotes a sufficiently high degree of similarity between two or more numeric values such that one of skill in the art would consider the difference between the two or more values to be of little or no biological and/or statistical significance within the context of the biological characteristic measured by said value. In some embodiments the two or more substantially similar values differ by no more than about any one of 5%, 10%, 15%, 20%, 25%, or 50%.

A polypeptide "variant" means a biologically active polypeptide having at least about 80% amino acid sequence identity with the native sequence polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, or deleted, at the N- or C-terminus of the polypeptide. In some embodiments, a variant will have at least about 80% amino acid sequence identity. In some embodiments, a variant will have at least about 90% amino acid sequence identity. In some embodiments, a variant will have at least about 95% amino acid sequence identity with the native sequence polypeptide.

As used herein, "percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGA-LIGN™ (DNASTAR) software. Those skilled in the art can determine appropriate parameters for measuring alignment, including any algorithms needed to achieve maximal alignment over the full length of the sequences being compared.

An amino acid substitution may include but are not limited to the replacement of one amino acid in a polypeptide with another amino acid. Exemplary substitutions are shown in Table 1. Amino acid substitutions may be introduced into a polypeptide of interest and the products screened for a desired activity, for example, retained/improved antigen binding, decreased immunogenicity, or improved ADCC or CDC.

TABLE 1

| Original Residue | Exemplary Substitutions |
| --- | --- |
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "vector" is used to describe a polynucleotide that can be engineered to contain a cloned polynucleotide or polynucleotides that can be propagated in a host cell. A vector can include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that can be used in colorimetric assays, for example, B-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6® cells (Crucell), and 293 and CHO cells, and their derivatives, such as 293-6E, CHO-DG44, CHO-K1, CHO-S, and CHO-DS cells. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) a provided herein.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, for example, in the case of an RNA polynucleotide. Thus, a DNA polynucleotide that is contained in a vector inside a host cell may be referred to as "isolated".

The terms "individual" and "subject" are used interchangeably herein to refer to an animal; for example, a mammal. In some embodiments, methods of treating mammals, including, but not limited to, humans, rodents, simians, felines, canines, equines, bovines, porcines, ovines, caprines, mammalian laboratory animals, mammalian farm animals, mammalian sport animals, and mammalian pets, are provided. In some examples, an "individual" or "subject" refers to an individual or subject in need of treatment for a disease or disorder. In some embodiments, the subject to receive the treatment can be a patient, designating the fact that the subject has been identified as having a disorder of relevance to the treatment, or being at adequate risk of contracting the disorder.

A "disease" or "disorder" as used herein refers to a condition where treatment is needed and/or desired.

In some embodiments, an "increase" or "decrease" refers to a statistically significant increase or decrease, respectively. As will be clear to the skilled person, "modulating" can also involve effecting a change (which can either be an increase or a decrease) in affinity, avidity, specificity and/or selectivity of a target or antigen, for one or more of its ligands, binding partners, partners for association into a homomultimeric or heteromultimeric form, or substrates; effecting a change (which can either be an increase or a decrease) in the sensitivity of the target or antigen for one or more conditions in the medium or surroundings in which the target or antigen is present (such as pH, ion strength, the presence of co-factors, etc.); and/or cellular proliferation or cytokine production, compared to the same conditions but without the presence of a test agent. This can be determined in any suitable manner and/or using any suitable assay known per se or described herein, depending on the target involved.

As used herein, "an immune response" is meant to encompass cellular and/or humoral immune responses that are sufficient to inhibit or prevent onset or ameliorate the symptoms of disease (for example, cancer or cancer metastasis). "An immune response" can encompass aspects of both the innate and adaptive immune systems.

As used herein, "treatment" is an approach for obtaining beneficial or desired clinical results. "Treatment" as used herein, covers any administration or application of a therapeutic for disease in a mammal, including a human. For purposes of this disclosure, beneficial or desired clinical results include, but are not limited to, any one or more of: alleviation of one or more symptoms, diminishment of extent of disease, preventing exacerbation of disease, preventing or delaying recurrence of disease, delay or slowing of disease progression, amelioration of the disease state, inhibiting the disease or progression of the disease, and inhibiting or slowing the disease or its progression. Also encompassed by "treatment" is a reduction of pathological consequence of a disease. The methods provided herein contemplate any one or more of these aspects of treatment. In-line with the above, the term treatment does not require one-hundred percent removal of all aspects of the disorder.

"Ameliorating" means a lessening or improvement of one or more symptoms as compared to not administering a therapeutic agent. "Ameliorating" also includes shortening or reduction in duration of a symptom.

The term "biological sample" means a quantity of a substance from a living thing or formerly living thing. Such substances include, but are not limited to, blood, (for example, whole blood), plasma, serum, bronchoalveolar lavage fluid, sputum, nasal lavage fluid, urine, amniotic fluid, synovial fluid, endothelial cells, leukocytes, monocytes, other cells, organs, tissues, bone marrow, lymph nodes and spleen.

The term "control" or "reference" in the context of an experiment or comparison, refers to a composition known to not contain an analyte ("negative control") or to contain an analyte ("positive control"). A positive control can comprise a known concentration of analyte. A control or reference may also refer to a control agent known to lack the activity of an agent being tested, such as an antibody.

"Preventing," as used herein, includes providing prophylaxis with respect to the occurrence or recurrence of a disease in a subject that may be predisposed to the disease but has not yet been diagnosed with the disease. Unless otherwise specified, the terms "reduce", "inhibit", or "prevent" do not denote or require complete prevention over all time, but just over the time period being measured.

A "therapeutically effective amount" of a substance/molecule, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A therapeutically effective amount may be delivered in one or more administrations. A therapeutically effective amount refers to an amount effective, at dosages and for periods of time necessary, to achieve the desired therapeutic and/or prophylactic result.

The terms "pharmaceutical formulation" and "pharmaceutical composition" are used interchangeably and refer to a preparation which is in such form as to permit the biological activity of the active ingredient(s) to be effective, and which contains no additional components which are unacceptably toxic to a subject to which the formulation would be administered. Such formulations may be sterile.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and are compatible with other ingredients of the formulation. The pharmaceutically acceptable carrier is appropriate for the formulation employed.

Administration "in combination with" one or more further therapeutic agents includes simultaneous (concurrent) and sequential administration in any order.

The term "concurrently" is used herein to refer to administration of two or more therapeutic agents, where at least part of the administration overlaps in time, or where the administration of one therapeutic agent falls within a short period of time relative to administration of the other therapeutic agent, or wherein the therapeutic effects of both agents overlap for at least a period of time.

The term "sequentially" is used herein to refer to administration of two or more therapeutic agents that does not overlap in time, or wherein the therapeutic effects of the agents do not overlap.

As used herein, "in conjunction with" refers to administration of one treatment modality in addition to another treatment modality. As such, "in conjunction with" refers to administration of one treatment modality before, during, or after administration of the other treatment modality to the individual.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (for example, a package or container) or kit comprising at least one reagent, for example, a medicament for treatment of a disease or disorder (for example, cancer), or a probe for specifically detecting a biomarker described herein. In some embodiments, the manufacture or kit is promoted, distributed, or sold as a unit for performing the methods described herein.

The terms "label" and "detectable label" mean a moiety attached, for example, to an antibody or antigen to render a reaction (for example, binding) between the members of the specific binding pair, detectable. The labeled member of the specific binding pair is referred to as "detectably labeled." Thus, the term "labeled binding protein" refers to a protein with a label incorporated that provides for the identification of the binding protein. In some embodiments, the label is a detectable marker that can produce a signal that is detectable by visual or instrumental means, for example, incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Examples of labels for polypeptides include, but are not limited to, the following: radioisotopes or radionuclides (for example, $^{3}$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm); chromogens, fluorescent labels (for example, FITC, rhodamine, lanthanide phosphors), enzymatic labels (for example, horseradish peroxidase, luciferase, alkaline phosphatase); chemiluminescent markers; biotinyl groups; predetermined polypeptide epitopes recognized by a secondary reporter (for example, leucine zipper pair sequences, binding sites for secondary antibodies, metal binding domains, epitope tags); and magnetic agents, such as gadolinium chelates. Representative examples of labels commonly employed for immunoassays include moieties that produce light, for example, acridinium compounds, and moieties that produce fluorescence, for example, fluorescein. In this regard, the moiety itself may not be detectably labeled but may become detectable upon reaction with yet another moiety.

Exemplary IgE Binding Polypeptides and Proteins

IgE binding polypeptides and proteins are provided herein. In various embodiments, the IgE binding polypeptides or proteins comprise at least one VHH domain that binds IgE. In some embodiments, the IgE is human IgE (e.g., having an amino acid sequence set forth in SEQ ID NO: 1). In some embodiments, an IgE binding polypeptide or protein is specific for IgE and does not bind to IgG, IgM, or IgA.

In some embodiments, an IgE binding polypeptide or protein blocks binding of IgE to FCER1A. In some embodiments, the IgE binding polypeptide or protein inhibits activation, such as activation of mast cells or basophils. In some embodiments, the IgE binding polypeptide or protein inhibits activation of mast cells or basophils to a greater extent than an isotype antibody. In some embodiments, the IgE binding polypeptide or protein inhibits degranulation, such as degranulation of mast cells or basophils, for example, with an IC50 below 5 or 10 nM (e.g., 0.1-10 nM, 0.2-10 nM, 0.5-10 nM, 1-10 nM, 0.1-5 nM, 0.2-5 nM, 0.5-5 nM, or 1-5 nM). An exemplary method of assessing impact on basophil degranulation is described in Example 8 herein.

In some embodiments, an IgE binding polypeptide provided herein comprises one, two, three, four, five, six, seven, or eight VHH domains that bind IgE. In some embodiments, an IgE binding polypeptide provided herein comprises one, two, three, or four VHH domains that bind IgE. IgE binding polypeptides may comprise one or more VHH domains that bind one or more target proteins other than IgE. Such polypeptides may be referred to as "multispecific" polypeptides.

In some embodiments, an IgE binding polypeptide comprises at least one VHH domain that binds IgE and a multimerization domain. Such polypeptides can form multimers that include a plurality of the VHH domains. In some embodiments, an IgE binding polypeptide comprises at least one VHH domain that binds IgE and an Fc region (e.g., an IgG Fc region). In some embodiments, an IgE binding polypeptide provided herein comprises one, two, three, or four VHH domains and an Fc region. In some embodiments, an Fc region mediates dimerization of the IgE binding polypeptide at physiological conditions such that a dimer is formed that doubles the number of IgE binding sites in the protein. For example, an IgE binding polypeptide comprising three VHH domains that bind IgE and an Fc region is trivalent as a monomer, but at physiological conditions, the Fc region may mediate dimerization, to form an IgE binding protein as a hexavalent dimer under such conditions. In various embodiments, an Fc region included in an IgE binding polypeptide is a human Fc region (e.g., a human IgG1 or IgG4 Fc region), or is derived from a human Fc region. In some embodiments the Fc region lacks the C-terminal lysine. In some embodiments, the C-terminal amino acid of the Fc region is an amino acid other than lysine.

In some embodiments, an Fc region included in an IgE binding polypeptide is a Fc region that binds FcγRIIb (a.k.a. CD32b), for example, has an increased binding affinity to FcγRIIb than a wild-type human IgG1 Fc region. In some embodiments, the Fc region comprises one or more of the mutations, G236D, S267E and L328F, numbered according to the EU index as in Kabat. In some embodiments, an Fc region included in an IgE binding polypeptide is a human Fc region comprising the "SELF" mutations S267E and L328F. In some embodiments, an Fc region included in an IgE binding polypeptide is a human Fc region comprising the "DSELF" mutations G236D, S267E and L328F. In some embodiments, an Fc region included in an IgE binding polypeptide is a human Fc region comprising the "xELL" mutations that delete E233, L234, and L235. In some such embodiments, the Fc region can be an IgG1 isotype, such as a human IgG1. In some embodiments, the Fc region is a human IgG1 Fc region variant, such as any human IgG1 Fc region variant described herein. In some such embodiments, the Fc region comprises "SELF" mutations (S267E, L328F), as in SEQ ID NOs: 79 and 80. In some such embodiments, the Fc region comprises "DSELF" mutations (G236D, S267E, L328F), as in SEQ ID NOs: 81 and 82. In some such embodiments, the Fc region comprises "xELL" mutations (deletion of E233, L234, and L235), as in SEQ ID NOs: 77 and 78. Such Fc regions, when engaged to IgE-producing B cells, can inhibit the activity (e.g., IgE production activity) of the B cells. Accordingly, in some embodiments, the IgE binding polypeptide or protein reduces IgE production in a subject's blood to a greater extent than an isotype antibody. For example, in some embodiments, the IgE binding polypeptide or protein, at a concentration of 1 nM, reduces IgE production in a subject's blood by at least 20%, 30%, 40%, 50%, or 60% than an isotype antibody. in some embodiments, the IgE binding polypeptide or protein, at a concentration of 10 nM, reduces IgE production in a subject's blood by at least 20%, 30%, 40%, 50%, 60%, 70%, 80%, 90%, or 95% than an isotype antibody. An exemplary method of assessing impact on IgE production is described in Example 12 herein. In some embodiments, an IgE binding polypeptide or protein depletes IgE levels in vivo. In some such embodiments, the IgE binding polypeptide or protein does not change IgG, IgM, or IgA levels in vivo.

In some embodiments, the VHH domain does not bind a complex of human IgE and FcεR1A. Accordingly, a polypeptide or protein comprising the VHH domain (e.g., one that includes an Fc domain) does not induce antigen-independent mast cell or basophil activation.

In some embodiments, the Fc region included in an IgE binding polypeptide is derived from a human Fc region and comprises mutations designed for heterodimerization.

Fc regions that can be used in an IgE binding polypeptide include Fc regions comprising the amino acid sequences of SEQ ID NOs: 75, 76, 77, 78, 79, 80, 81, or 82.

In some embodiments, an IgE binding polypeptide comprises at least two VHH domains, wherein a first VHH domain binds a first epitope of IgE and a second VHH domain binds a second epitope of IgE. When the IgE binding polypeptide comprises a VHH domain that binds a first epitope of IgE and a VHH domain that binds a second epitope of IgE, the IgE binding polypeptide may be referred to as "biepitopic", "biparatopic" or "bispecific." In some embodiments, an IgE binding polypeptide comprises at least two VHH domains, wherein a first VHH domain binds IgE and a second VHH domain binds an antigen other than IgE. Such polypeptides may be referred to as "bispecific" or "multispecific."

In some embodiments of the polypeptides, adjacent portions of an IgE binding polypeptide, such as a first VHH and a second VHH or a VHH and an Fc region, may be connected to one another by a linker. In some such embodiments, the linker comprises 1-20, 1-12, 1-8, or 1-4 amino acids, preferably predominantly composed of glycine and, optionally, serine. A non-limiting example of such linker is GGGG (SEQ ID NO: 91).

IgE Binding VHH Domains

Non-limiting exemplary VHH domains that bind IgE are provided in Table 2A, the CDR sequences according to the AbM definition are shown. CDR sequences according to the indicated CDR definition are shown in Table 2B (consensus) and Table 2C (hzB10v37-hzB10v44). The sequences for the indicated VHH are shown in the Table of Certain Sequences herein. A polypeptide name that begins with "hz" indicates that it is a humanized version of the corresponding parental polypeptide, and a polypeptide name that ends with "con" represents a consensus sequence.

TABLE 2A

VHH domains that binds IgE - CDRs according to the AbM definition are shown

| Clone name | CDR1 | SEQ ID NO | CDR2 | SEQ ID NO | CDR3 | SEQ ID NO | VHH SEQ ID NO |
|---|---|---|---|---|---|---|---|
| B10 | GLTFSSYNMG | 3 | MSGSSSTSTY | 4 | RRMLSTYWSDRSWDF | 5 | 2 |
| B10 Humanized Variants | | | | | | | |
| hzB10v1 | GLTFSSYNMG | 3 | MSGSSSTSTY | 4 | RRMLSTYWSDRSWDF | 5 | 6 |
| hzB10v2 | GLTFSSYNMG | 3 | MSGSSSTSTY | 4 | RRMLSTYWSDRSWDF | 5 | 7 |
| hzB10v3 | GLTFSSYNMG | 3 | MSGSSSTSTY | 4 | RRMLSTYWSDRSWDF | 5 | 8 |
| hzB10v4 | GLTFSSYNMG | 3 | MSGSSSTSTY | 4 | RRMLSTYWSDRSWDF | 5 | 9 |
| hzB10v5 | GLTFSSYNMG | 3 | MSGSSSTSTY | 4 | RRMLSTYWSDRSWDF | 5 | 10 |
| hzB10v6 | GLTFSSYNMG | 3 | MSGSSSTSTY | 4 | RRMLSTYWSDRSWDF | 5 | 11 |
| hzB10v7 | GLTFSSYNMG | 3 | LSGSSSTSTY | 48 | RRMLSTYWSDRSWDF | 5 | 12 |

TABLE 2A-continued

VHH domains that binds IgE - CDRs according to the AbM definition are shown

| Clone name | CDR1 | SEQ ID NO | CDR2 | SEQ ID NO | CDR3 | SEQ ID NO | VHH SEQ ID NO |
|---|---|---|---|---|---|---|---|
| hzB10v8 | GLTFSSYNMG | 3 | ISGSSSTSTY | 49 | RRMLSTYWSDRSWDF | 5 | 13 |
| hzB10v9 | GLTFSSYNMG | 3 | VSGSSSTSTY | 50 | RRMLSTYWSDRSWDF | 5 | 14 |
| hzB10v10 | GLTFSSYNMG | 3 | MSGSSSTSTY | 4 | RRLLSTYWSDRSWDF | 51 | 15 |
| hzB10v11 | GLTFSSYNMG | 3 | MSGSSSTSTY | 4 | RRILSTYWSDRSWDF | 52 | 16 |
| hzB10v12 | GLTFSSYNMG | 3 | MSGSSSTSTY | 4 | RRVLSTYWSDRSWDF | 53 | 17 |
| hzB10v13 | GLTFSSYNMG | 3 | MSGSSSTSTY | 4 | RRMLSTYWSDRSWDF | 5 | 18 |
| hzB10v14 | GLTFSSYNMG | 3 | LSGSSSTSTY | 48 | RRLLSTYWSDRSWDF | 51 | 19 |
| hzB10v15 | GLTFSSYNMG | 3 | LSGSSSTSTY | 48 | RRLLSTYWSDRSWDF | 51 | 20 |
| hzB10v16 | GLTFSSYNMG | 3 | LSGSSSTSTY | 48 | RRLLSTYWSDRSWDF | 51 | 21 |
| hzB10v17 | GLTFSSYNMG | 3 | LSGSSSTSTY | 48 | RRLLSTYWSDRSWDF | 51 | 22 |
| hzB10v18 | GLTFSSYNMG | 3 | LSGSSSTSTY | 48 | RRLLSTYWSDRSWDF | 51 | 23 |
| hzB10v20 | GLTFSSYNMG | 3 | LSGSSSTSTY | 48 | RRLLSTYWSDRSWDF | 51 | 24 |
| hzB10v21 | GLTFSSYNMG | 3 | LSGSSSTSTY | 48 | RRLLSTYWSDRSWDF | 51 | 25 |
| hzB10v22 | GLTFSSYNMG | 3 | LSGSSSTSTY | 48 | RRLLSTYWSDRSWDF | 51 | 26 |
| hzB10v23 | GLTFSSYNMG | 3 | LSGSSSTSTY | 48 | RRLLSTYWSDRSWDF | 51 | 27 |
| hzB10v24 | GLTFSSYNMG | 3 | LSGSSSTSTY | 48 | RRLLSTYWSDRSWDF | 51 | 28 |
| hzB10v25 | GLTFSSYNMG | 3 | LSGSSSTSTY | 48 | RRLLSTYWSDRSWDF | 51 | 29 |
| hzB10v26 | GLTFSSYNMG | 3 | MSGSSSTSTY | 4 | RRMLSTYWSDRSWDF | 5 | 30 |
| hzB10v27 | GLTFSSYNMG | 3 | LSGSSSTSTY | 48 | RRLLSTYWSDRSWDF | 51 | 31 |
| hzB10v28 | GLTFSSYNMG | 3 | LSGSSSTSTY | 48 | RRLLSTYWSDRSWDF | 51 | 32 |
| hzB10v29 | GLTFSSYNMG | 3 | LSGSSSTSTY | 48 | RRLLSTYWSDRSWDF | 51 | 33 |
| hzB10v30 | GLTFSSYNMG | 3 | LSGSSSTSTY | 48 | RRLLSTYWSDRSWDF | 51 | 34 |
| hzB10v31 | GLTFSSYNMG | 3 | LSGSSSTSTY | 48 | RRLLSTYWSDRSWDF | 51 | 35 |
| hzB10v32 | GLTFSSYNMG | 3 | LSGSSSTSTY | 48 | RRLLSTYWSDRSWDF | 51 | 36 |
| hzB10v33 | GLTFSSYNMG | 3 | LSGSSSTSTY | 48 | RRLLSTYWSDRSWDF | 51 | 37 |
| hzB10v34 | GLTFSSYNMG | 3 | LSGSSSTSTY | 48 | RRLLSTYWSDRSWDF | 51 | 38 |
| hzB10v37 | GLTFSSYNMG | 3 | LSGSSSTSTY | 48 | RRLLSTYWSDRSWDF | 51 | 39 |
| hzB10v38 | GLTFSSYNMG | 3 | LSGSSSTSTY | 48 | RRLLSTYWSDRSWDF | 51 | 40 |
| hzB10v39 | GLTFSSYNMG | 3 | LSGSSSTSTY | 48 | RRLLSTYWSDRSWDF | 51 | 41 |
| hzB10v40 | GLTFSSYNMG | 3 | LSGSSSTSTY | 48 | RRLLSTYWSDRSWDF | 51 | 42 |
| hzB10v40.52 | GLTFSSYNMG | 3 | LSGVSSTSTY | 102 | RRLLSTYWSHRSWDF | 103 | 101 |
| hzB10v41 | GLTFSSYNMG | 3 | LSGSSSTSTY | 48 | RRLLSTYWSDRSWDF | 51 | 43 |
| hzB10v42 | GLTFSSYNMG | 3 | LSGSSSTSTY | 48 | RRLLSTYWSDRSWDF | 51 | 44 |
| hzB10v43 | GLTFSSYNMG | 3 | LSGSSSTSTY | 48 | RRLLSTYWSDRSWDF | 51 | 45 |
| hzB10v44 | GLTFSSYNMG | 3 | LSGSSSTSTY | 48 | RRLLSTYWSDRSWDF | 51 | 46 |

TABLE 2A-continued

VHH domains that binds IgE - CDRs according to the AbM definition are shown

| Clone name | CDR1 | SEQ ID NO | CDR2 | SEQ ID NO | CDR3 | SEQ ID NO | VHH SEQ ID NO |
|---|---|---|---|---|---|---|---|
| hzB10con | GLTFSSYNMG | 3 | XSGSSSTSTY | 58 | RRXLSTYWSDRSWDF | 63 | 47 |
| hzB10con-1 | GLTFSSYNMG | 3 | X$_1$SGX$_2$SSTSTY | 104 | RRX$_1$LSTYWSX$_2$RSWDF | 109 | 119 |

TABLE 2B

CDRs of consensus VHH according to the indicated definition

| Region | Definition | Sequence Fragment | SEQ ID NO |
|---|---|---|---|
| CDR1 | AbM | GLTFSSYNMG | 3 |
| | Chothia | GLTFSSY--- | 54 |
| | Kabat | -----SYNMG | 55 |
| | Contact | ----SSYNMG | 56 |
| | IMGT | -LTFSSYN-- | 57 |
| CDR2 | AbM | ---XSGSSSTSTY------ | 58 |
| | Chothia | -----GSSSTS-------- | 59 |
| | Kabat | ---X$_1$SGSSSTSTYYAX$_2$X$_3$VKG | 60 |
| | Contact | FVX$_1$X$_2$SGSSSTSTY------ | 61 |
| | IMGT | ----SGSSSTST-------- | 62 |
| CDR2 (con-1) | AbM | ---X$_1$SGX$_2$SSTSTY------ | 104 |
| | Chothia | -----GXSSTS-------- | 105 |
| | Kabat | ---X$_1$SGX$_2$SSTSTYYAX$_3$X$_4$VKG | 106 |
| | Contact | FVX$_1$X$_2$SGX$_3$SSTSTY------ | 107 |
| | IMGT | ----SGXSSTST-------- | 108 |
| CDR3 | AbM | --RRXLSTYWSDRSWDF | 63 |
| | Chothia | --RRXLSTYWSDRSWDF | 64 |
| | Kabat | --RRXLSTYWSDRSWDF | 65 |
| | Contact | AARRXLSTYWSDRSWD- | 66 |
| | IMGT | AARRXLSTYWSDRSWDF | 67 |
| CDR3 (con-1) | AbM | --RRX$_1$LSTYWSX$_2$RSWDF | 109 |
| | Chothia | --RRX$_1$LSTYWSX$_2$RSWDF | 109 |
| | Kabat | --RRX$_1$LSTYWSX$_2$RSWDF | 109 |
| | Contact | AARRX$_1$LSTYWSX$_2$RSWD- | 110 |
| | IMGT | AARRX$_1$LSTYWSX$_2$RSWDF | 111 |

TABLE 2C

CDRs of hzB10v37 to hzB10v44 according to the indicated definition

| Region | Definition | Sequence Fragment | SEQ ID NO |
|---|---|---|---|
| CDR1 | AbM | GLTFSSYNMG | 3 |
| | Chothia | GLTFSSY--- | 54 |
| | Kabat | -----SYNMG | 55 |
| | Contact | ----SSYNMG | 56 |
| | IMGT | -LTFSSYN-- | 57 |
| CDR2 | AbM | ---LSGSSSTSTY------ | 48 |
| | Chothia | -----GSSSTS-------- | 59 |
| | Kabat | ---LSGSSSTSTYYAESVKG | 68 |
| | Contact | FVGLSGSSSTSTY------ | 69 |
| | IMGT | ----SGSSSTST-------- | 70 |
| CDR3 | AbM | --RRLLSTYWSDRSWDF | 51 |
| | Chothia | --RRLLSTYWSDRSWDF | 71 |
| | Kabat | --RRLLSTYWSDRSWDF | 72 |
| | Contact | AARRLLSTYWSDRSWD- | 73 |
| | IMGT | AARRLLSTYWSDRSWDF | 74 |

TABLE 2D consensus CDR1 and CDR3 of hzB10v40 variants

| Region | Definition | Sequence Fragment | SEQ ID NO |
|---|---|---|---|
| CDR1 | AbM | GX$_1$X$_2$X$_3$X$_4$X$_5$YX$_6$X$_7$X$_8$ | 114 |
| | Chothia | GX$_1$X$_2$X$_3$X$_4$X$_5$Y | 115 |
| CDR3 | AbM, Chothia, Kabat | RRX$_1$X$_2$SX$_3$YWSX$_4$RSWDX$_5$ | 116 |
| | Contact | X$_1$ARRX$_2$X$_3$SX$_4$YWSX$_5$RSWD | 118 |
| | IMGT | X$_1$ARRX$_2$X$_3$SX$_4$YWSX$_5$RSWDX$_6$ | 117 |

In various embodiments, the IgE binding polypeptides herein comprise at least one VHH domain that binds IgE and comprises the CDR1 sequence of SEQ ID NO: 3; a CDR2 sequence selected from SEQ ID NOs: 4, 48-50, and 102; and a CDR3 sequence selected from SEQ ID NOs: 5, 51-53, and 103. In some embodiments, the VHH domain comprises the CDR1, CDR2, and CDR3 sequences, under any CDR system (e.g., AbM, Chothia, Kabat, Contact, IMGT, etc.), of any one of the VHHs listed in Table 2A above. Although the CDR sequences of every VHH under every CDR definition are not provided in the Sequence Listing, they can be identified by methods known in the art, e.g., using the AbYsis server (www.abysis.org/abysis/). Additionally, the CDR sequences of a given VHH domain under a Chothia, Kabat, Contact, or IMGT definition can be identified by aligning the VHH amino acid sequences with a reference sequence (e.g., hzB10v37 to hzB10v44) and isolating the regions corresponding to the CDRs of the reference sequence under the same CDR definition. In some embodiments, the VHH domain comprises the CDR1, CDR2, and CDR3 sequences of SEQ ID NOs: 3, 48, and 51. In some embodiments, the VHH domain comprises the CDR1, CDR2, and CDR3 sequences of SEQ ID NOs: 3, 102, and 103. In some embodiments, the VHH domain comprises the CDR1, CDR2, and CDR3 sequences of SEQ ID NOs: 3, 4, and 5. In some embodiments, the VHH domain comprises the CDR1, CDR2, and CDR3 sequences of SEQ ID NOs: 3, 48, and 5. In some embodiments, the VHH domain comprises the CDR1, CDR2, and CDR3 sequences of SEQ ID NOs: 3, 49, and 5. In some embodiments, the VHH domain comprises the CDR1, CDR2, and CDR3 sequences of SEQ ID NOs: 3, 50, and 5. In some embodiments, the VHH domain comprises the CDR1, CDR2, and CDR3 sequences of SEQ ID NOs: 3, 4, and 51. In some embodiments, the VHH domain comprises the CDR1, CDR2, and CDR3 sequences of SEQ ID NOs: 3, 4, and 52. In some embodiments, the VHH domain comprises the CDR1, CDR2, and CDR3 sequences of SEQ ID NOs: 3, 4, and 53. In some embodiments, the VHH domain comprises the CDR1, CDR2, and CDR3 sequences of SEQ ID NOs: 3, 48, and 52. In some embodiments, the VHH domain comprises the CDR1, CDR2, and CDR3 sequences of SEQ ID NOs: 3, 48, and 53. In some embodiments, the VHH domain comprises the CDR1, CDR2, and CDR3 sequences of SEQ ID NOs: 3, 49, and 51. In some embodiments, the VHH domain comprises the CDR1, CDR2, and CDR3 sequences of SEQ ID NOs: 3, 49, and 52. In some embodiments, the VHH domain comprises the CDR1, CDR2, and CDR3 sequences of SEQ ID NOs: 3, 49, and 53. In some embodiments, the VHH domain comprises the CDR1, CDR2, and CDR3 sequences of SEQ ID NOs: 3, 50, and 51. In some embodiments, the VHH domain comprises the CDR1, CDR2, and CDR3 sequences of SEQ ID NOs: 3, 50, and 52. In some embodiments, the VHH domain comprises the CDR1, CDR2, and CDR3 sequences of SEQ ID NOs: 3, 50, and 53. In various embodiments, the VHH domain is humanized.

In some embodiments, the VHH domain comprises the CDR2 sequence XSGSSSTSTY, wherein X is leucine (L), isoleucine (I), valine (V) or methionine (M) (SEQ ID NO: 58). In some embodiments, the VHH domain comprises the CDR3 sequence RRXLSTYWSDRSWDF, wherein X is leucine (L), isoleucine (I), valine (V) or methionine (M) (SEQ ID NO: 63). In some embodiments, the VHH domain comprises the CDR1, CDR2, and CDR3 sequences of SEQ ID NOs: 3, 58, and 63.

In some embodiments, the VHH domain comprises the CDR2 sequence $X_1SGX_2SSTSTY$, wherein: $X_1$ is leucine (L), isoleucine (1), valine (V) or methionine (M); and $X_2$ is serine(S) or valine (V) (SEQ ID NO. 104). In some embodiments, the VHH domain comprises the CDR3 sequence $RRX_1LSTYWSX_2RSWDF$, wherein: $X_1$ is leucine (L), isoleucine (I), valine (V) or methionine (M), and $X_2$ is aspartate (D) or histidine (H) (SEQ ID NO. 109). In some embodiments, the VHH domain comprises the CDR1, CDR2, and CDR3 sequences of SEQ ID NOs: 3, 104, and 109.

In some embodiments, an IgE binding polypeptide provided herein comprises one to three CDRs of a VHH domain selected from SEQ ID NOs: 2, 6-47, 101, and 119. In some embodiments, an IgE binding polypeptide provided herein comprises two to three CDRs of a VHH domain selected from SEQ ID NOs: 2, 6-47, 101, and 119. In some embodiments, an IgE binding polypeptide provided herein comprises three CDRs of a VHH domain selected from SEQ ID NOs: 2, 6-47, 101, and 119. In some embodiments, the VHH domain comprises a CDR1 sequence selected from SEQ ID NOs: 3 and 54-57; a CDR2 sequence selected from SEQ ID NOs: 4, 48-50, 58-62, 68-70, and 102; and a CDR3 sequence selected from SEQ ID NOs: 5, 51-53, 63-67, 71-74, and 103. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, an IgE binding polypeptide provided herein comprises CDR1 and CDR3 sequences of a VHH domain selected from SEQ ID NOs: 2, 6-47, 101, and 119. In some embodiments, the VHH domain comprises a CDR1 sequence selected from SEQ ID NOs: 3 and 54-57; and a CDR3 sequence selected from SEQ ID NOs: 5, 51-53, 63-67, 71-74, and 103. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, an IgE binding polypeptide provided herein comprises (a) a CDR1 comprising the amino acid sequence of $GX_1X_2X_3X_4X_5YX_6X_7X_8$, wherein $X_1$ is L, I, or V; $X_2$ is T, V, N, K, or I; $X_3$ is F, Y, P, or G; $X_4$ is S, K, A, D, or R; $X_5$ is S, E, Q, T, R, A, or P; $X_6$ is N, T, S, or R; $X_7$ is M, V, I, L, S, T, or F; and $X_8$ is G, S, or A (SEQ ID NO: 114); or $GX_1X_2X_3X_4X_5Y$, wherein $X_1$ is L, I, or V; $X_2$ is T, V, N, K, or I; $X_3$ is F, Y, P, or G; $X_4$ is S, K, A, D, or R; and $X_5$ is S, E, Q, T, R, A, or P (SEQ ID NO: 115), and (b) a CDR3 comprising the amino acid sequence of SEQ ID NO: 116, 117, or 118. In some embodiments, the CDR1 and CDR3 comprise the amino acid sequences of 114 and 116; 114 and 117; 114 and 118; 115 and 116; 115 and 117; or 115 and 118, respectively. Some of the CDR1 and CDR3 pairs are identified under different CDR definitions. Notwithstanding, such matches are selected to cover all the invariant positions in the three CDRs, according to the paratope mapping results described in Example 11 below.

In some embodiments, a VHH domain or an IgE binding polypeptide provided herein comprises CDRs having at least about 85%, at least 90%, at least 95%, at least 96%, at least 97%, at least 98%, or at least 99% identity with a CDR1, CDR2, or CDR3 of SEQ ID NOs: 3, 4, 5, 48-74, or 102-111. In some embodiments, the CDR1 is selected from SEQ ID NOs: 3 and 54-57 with up to 1, 2, 3, 4, or 5 amino acid substitutions. In some embodiments, the CDR2 is selected from SEQ ID NOs: 4, 48-50, 58-62, 68-70, 102, and 104-108 with up to 1, 2, 3, 4, 5, 6, 7, or 8 amino acid substitutions. In some embodiments, the CDR3 is selected from SEQ ID NOs: 5, 51-53, 63-67, 71-74, 103, and 109-111 with up to 1, 2, 3, 4, 5, 6, 7, or 8 amino acid substitutions. In some aspects, the amino acid substitutions are conservative amino acid substitutions. In some embodiments, the IgE binding polypeptides described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining IgE binding polypeptides.

In some embodiments, a VHH domain of the present disclosure comprises a paratope that comprises amino acid 26 and/or 32 of SEQ ID NO: 42, i.e., amino acids 1 and/or 7 (G and/or Y, respectively) of the CDR1 sequence of hzB10v40 under AbM definition. In some embodiments, the VHH domain comprises a paratope that comprises amino acid 26 and 32 of SEQ ID NO: 42. In some embodiments, a VHH domain of the present disclosure comprises a paratope comprising 1, 2, 3, 4, 5, 6, 7, or 8 of amino acids 26, 27, 32, 99, 100, 105, 106, and 110 of SEQ ID NO: 42, i.e., amino acids 1, 2, and 7 (G, L, and Y, respectively) of the CDR1 sequence, and amino acids 1, 2, 7, 8, and 12 (R, R, Y, W, and S, respectively) of the CDR3 sequence, each under AbM definition. In some embodiments, the VHH domain comprises a paratope comprising amino acids 26, 27, 32, 99, 100, 105, 106, and 110 of SEQ ID NO: 42. In some embodiments, a VHH domain of the present disclosure comprises a paratope comprising 1, 2, 3, 4, 5, 6, 7, 8, 9, 10, 11, 12, 13, 14, 15, 16, or 17 of amino acids 26, 27, 29, 32, 35, 52, 97, 98, 99, 100, 103, 105, 106, 107, 110, 111, and 112 of SEQ ID NO: 42, i.e., amino acids 1, 2, 4, 7, and 10 (G, L, F, Y, and G, respectively) of the CDR1 sequence and amino acid 3 (G) of the CDR2 sequence of hzB10v40 under AbM definition, and amino acids 1, 2, 3, 4, 7, 9, 10, 11, 14, 15, and 16 (A, A, R, R, S, Y, W, S, S, W, and D, respectively) of hzB10v40 under Contact definition. In some embodiments, the VHH domain comprises a paratope comprising 1, 2, 3, 4, 5, 6, 7, 8, 9, 10, 11, 12, 13, 14, 15, 16, or 17 of amino acids 26, 27, 29, 32, 35, 52, 97, 98, 99, 100, 103, 105, 106, 107, 110, 111, and 112 of SEQ ID NO: 42. The amino acid positions in this paragraph refer to the positions in the respective sequences by mere counting, which is not necessarily identical with the positions under Kabat or Chothia numbering system. In some embodiments, the VHH domain having the specified paratope comprises an amino acid sequence at least 80%, at least 85%, at least 90%, at least 95%, at least 96%, at least 97%, at least 98%, or at least 99% identical to SEQ ID NO: 42.

In some embodiments, a VHH domain that binds IgE comprises a glutamate (E), aspartate (D), lysine (K), or arginine (R) at position 11 according to Kabat numbering. In certain embodiments the VHH domain may comprise a modification at Leu 11 within framework 1. For example, the VHH domain may comprise Leu11Glu (L11E), Leu11Asp (L11D), Leu11Arg (L11R) or Leu11Lys (L11K), wherein the numbering is according to Kabat numbering. In some embodiments, a VHH domain that binds IgE comprises a leucine (L) at position 108 and/or, a glutamate (E), arginine (R), or aspartate (D) at position 112 according to Kabat numbering. In certain embodiments the VHH domain may comprise a modification of one or more of Gln 108 and Lys 112 within framework 4. For example, the VHH domain may comprise Gln 108Leu (Q108L), Lys112Glu (K112E), Lys112Arg (K112R), or Lys112Asp (K112D), wherein the numbering is according to Kabat numbering. It will be understood that Kabat positions 11, 108 and 112 correspond to residues 11, 119 and 123, respectively of SEQ ID NO: 2. In some embodiments, a VHH domain that binds IgE comprises a C-terminal extension of one or more glycine residues. In some embodiments, a VHH domain that binds IgE comprises a modification at Leu 11 and a modification at Lys 112. In some embodiments, a VHH domain that binds IgE comprises a modification at Leu 11 a modification at Gln 108 and a modification at Lys 112. In some such embodiments, the VHH domain comprises an amino acid sequence that is at least 85%, at least 90%, at least 95%, at least 96%, at least 97%, at least 98%, or at least 99% identical to an amino acid sequence selected from SEQ ID NOs: 2, and 6-46. In some embodiments, a VHH domain that binds IgE comprises an amino acid sequence selected from SEQ ID NOs: 2, and 6-46. In some embodiments, the VHH domain that binds IgE comprises the amino acid sequence that is at least 85%, at least 90%, at least 95%, at least 96%, at least 97%, at least 98%, or at least 99% identical to SEQ ID NO: 42. In some embodiments, a VHH domain that binds IgE comprises the amino acid sequence of SEQ ID NO: 42. In some embodiments, a VHH domain that binds IgE comprises an amino acid sequence set forth in SEQ ID NO: 119. In some embodiments, a VHH domain that binds IgE comprises an amino acid sequence set forth in SEQ ID NO: 47.

In some embodiments, a VHH domain of the present disclosure competes with ligelizumab for binding IgE. In some embodiments, a VHH domain of the present disclosure competes with 8D6 (UB-221) for binding IgE.

In some embodiments, a VHH domain of the present disclosure does not compete with omalizumab for binding IgE. In some embodiments, the VHH domain binds a different epitope of IgE than omalizumab. It is understood that XmAb7195, a traditional antibody that binds IgE and includes an Fc region with SELF mutations, causes thrombocytopenia when administered at high doses, potentially due to binding to an unknown antigen on platelets. Without wishing to be bound by theory, it is contemplated that the VHH domain of the present disclosure, by binding a different epitope, is unlikely to cause the same adverse effect, either alone or fused to an Fc domain (e.g., an Fc domain with SELF mutations).

In various embodiments, an IgE binding polypeptide comprises one, two, three, or four VHH domains that bind IgE.

In some embodiments, a VHH domain that binds IgE is humanized. Humanized antibodies (such as sdAbs or VHH-containing polypeptides) are useful as therapeutic molecules because humanized antibodies reduce or eliminate the human immune response to non-human antibodies, which can result in an immune response to an antibody therapeutic, and decreased effectiveness of the therapeutic. Generally, a humanized antibody comprises one or more variable domains in which CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (for example, the antibody from which the CDR residues are derived), for example, to restore or improve antibody specificity or affinity.

Humanized antibodies and methods of making them are reviewed, for example, in Almagro and Fransson, (2008) *Front. Biosci.* 13:1619-1633, and are further described, for example, in Riechmann et al., (1988) *Nature* 332:323-329; Queen et al., (1989) *Proc. Natl Acad. Sci. USA* 86:10029-10033; U.S. Pat. Nos. 5,821,337, 7,527,791, 6,982,321, and 7,087,409; Kashmiri et al., (2005) *Methods* 36:25-34; Padlan, (1991) *Mol. Immunol.* 28:489-498 (describing "resurfacing"); Dall'Acqua et al., (2005) *Methods* 36:43-60 (describing "FR shuffling"); and Osbourn et al., (2005) *Methods* 36:61-68 and Klimka et al., (2000) *Br. J. Cancer,* 83:252-260 (describing the "guided selection" approach to FR shuffling).

Human framework regions that can be used for humanization include but are not limited to: framework regions selected using the "best-fit" method (see, for example, Sims et al. (1993) *J. Immunol.* 151:2296); framework regions derived from the consensus sequence of human antibodies of a particular subgroup of heavy chain variable regions (see, for example, Carter et al. (1992) *Proc. Natl. Acad. Sci. USA,* 89:4285; and Presta et al. (1993) *J. Immunol,* 151:2623); human mature (somatically mutated) framework regions or human germline framework regions (see, for example, Almagro and Fransson, (2008) *Front. Biosci.* 13:1619-1633); and framework regions derived from screening FR libraries (see, for example, Baca et al., (1997) *J. Biol. Chem.* 272:10678-10684 and Rosok et al., (1996) *J. Biol. Chem.* 271:22611-22618). Typically, the FR regions of a VHH are replaced with human FR regions to make a humanized VHH. In some embodiments, certain FR residues of the human FR are replaced in order to improve one or more properties of the humanized VHH. VHH domains with such replaced residues are still referred to herein as "humanized."

In some embodiments, an IgE binding polypeptide comprises at least one VHH domain described herein fused to an Fc region. In various embodiments, an Fc region included in an IgE binding polypeptide is a human Fc region, or is derived from a human Fc region. In some embodiments, an Fc region included in an IgE binding polypeptide is a human Fc region, and comprises one or more of the mutations, G236D, S267E and L328F. In some embodiments, an IgE binding polypeptide includes a human Fc region, and comprises the "SELF" mutations S267E and L328F. In some embodiments, an IgE binding polypeptide includes a human Fc region, and comprises the "DSELF" mutations G236D, S267E and L328F. In some such embodiments, the Fc region can be a human IgG isotype, such as a human IgG1. In some embodiments, the Fc region included in an IgE binding polypeptide is derived from a human Fc region and comprises mutations designed for heterodimerization. Fc regions that can be used in an IgE binding polypeptide include Fc regions comprising the amino acid sequences of SEQ ID NOs: 75-83.

In some embodiments, an IgE binding polypeptide comprises at least one VHH domain described herein fused to an Fc region comprising the sequence of SEQ ID NO: 79 or 80. In some embodiments, an IgE binding polypeptide comprises at least one VHH domain described herein fused to an Fc region comprising the sequence of SEQ ID NO: 81 or 82. In some embodiments, an IgE binding polypeptide comprises at least one VHH domain described herein fused to an Fc region via a linker. In some embodiments the linker comprises the sequence of SEQ ID NO: 91.

In some embodiments, an IgE binding polypeptide comprises the amino acid sequence of SEQ ID NO: 85 or 92. In some embodiments, an IgE binding polypeptide consists of the amino acid sequence of SEQ ID NO: 85 or 92. In some embodiments, an IgE binding polypeptide comprises the amino acid sequence of SEQ ID NO: 86 or 93. In some embodiments, an IgE binding polypeptide consists of the amino acid sequence of SEQ ID NO: 86 or 93. In some embodiments, an IgE binding polypeptide comprises the amino acid sequence of SEQ ID NO: 112 or 113. In some embodiments, an IgE binding polypeptide consists of the amino acid sequence of SEQ ID NO: 112 or 113.

In some embodiments, an IgE binding polypeptide comprises means for binding human IgE, optionally binding human IgE in the region(s) of human IgE bound by hzB10v40-IgG1 (e.g., as described in the Examples below). In some embodiments, the means binds human IgE Fc region. In some embodiments, the means is a single domain (e.g., VHH) means for binding human IgE. In some embodiments, the IgE binding polypeptide further comprises an Fc region, such as a human Fc region or one derived from a human Fc region. In some embodiments, the IgE binding polypeptide comprises a human Fc region, and comprises one or more of the mutations, G236D, S267E and L328F. In some embodiments, an IgE binding polypeptide includes a human Fc region, and comprises the "SELF" mutations S267E and L328F. In some embodiments, an IgE binding polypeptide includes a human Fc region, and comprises the "DSELF" mutations G236D, S267E and L328F. In some such embodiments, the Fc region can be a human IgG isotype, such as a human IgG1. In some embodiments, the Fc region included in an IgE binding polypeptide is derived from a human Fc region and comprises mutations designed for heterodimerization. Fc regions that can be used in an IgE binding polypeptide include Fc regions comprising the amino acid sequences of SEQ ID NOs: 75-83. In some embodiments, the means for binding IgE includes the anti-IgE antibodies and antigen-binding fragments thereof described herein, optionally excluding cx-Oma. In some embodiments, the IgE binding polypeptide comprising means for binding human IgE is multivalent.

Polypeptide and Protein Expression and Production

Nucleic acid molecules comprising polynucleotides that encode an IgE binding polypeptide or protein are provided. In some embodiments, the nucleic acid molecule may also encode a leader sequence that directs secretion of the IgE binding polypeptide or protein, which leader sequence is typically cleaved such that it is not present in the secreted polypeptide or protein. The leader sequence may be a native heavy chain (or VHH) leader sequence, or may be another heterologous leader sequence.

Nucleic acid molecules can be constructed using recombinant DNA techniques conventional in the art. In some embodiments, a nucleic acid molecule is an expression vector that is suitable for expression in a selected host cell.

Vectors comprising nucleic acids that encode the IgE binding polypeptides and proteins described herein are provided. Such vectors include, but are not limited to, DNA vectors, phage vectors, viral vectors, retroviral vectors, etc. In some embodiments, a vector is selected that is optimized for expression of polypeptides or proteins in a desired cell type, such as CHO or CHO-derived cells, or in NSO cells. Exemplary such vectors are described, for example, in Running Deer et al., *Biotechnol. Prog.* 20:880-889 (2004).

In some embodiments, an IgE binding polypeptide or protein may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides and proteins include, but are not limited to, COS cells, including COS 7 cells; 293 cells, including 293-6E cells; CHO cells, including CHO-S, DG44. Lec13 CHO cells, and FUT8 CHO cells; PER.C6R cells (Crucell); and NSO cells. In some embodiments, the IgE binding polypeptides or proteins may be expressed in yeast. See, e.g., U.S. Publication No. US 2006/0270045 A1. In some embodiments, a particular eukaryotic host cell is selected based on its ability to make desired post-translational modifications to the polypeptide or protein. For example, in some embodiments, CHO cells produce polypeptides or proteins that have a higher level of sialylation than the same polypeptide or protein produced in HEK 293 cells.

Introduction of one or more nucleic acids (such as vectors) into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, for example, in Sambrook et al., Molecular Cloning, A Laboratory Manual, 3rd ed. Cold Spring Harbor Laboratory Press (2001). Nucleic acids may be transiently or stably transfected in the desired host cells, according to any suitable method.

Host cells comprising any of the nucleic acids or vectors described herein are also provided. In some embodiments, a host cell that expresses an IgE binding polypeptide or protein described herein is provided. The IgE binding polypeptides or proteins expressed in host cells can be purified by any suitable method. Such methods include, but are not limited to, the use of affinity matrices or hydrophobic interaction chromatography. Suitable affinity ligands include the RORI ECD and agents that bind Fc regions. For example, a Protein A, Protein G, Protein A/G, or an antibody affinity column may be used to bind the Fc region and to purify an IgE binding polypeptide or protein that comprises an Fc region. Hydrophobic interactive chromatography, for example, a butyl or phenyl column, may also be suitable for purifying some polypeptides or proteins such as antibodies. Ion exchange chromatography (for example anion exchange chromatography and/or cation exchange chromatography) may also be suitable for purifying some polypeptides or proteins such as antibodies. Mixed-mode chromatography (for example reversed phase/anion exchange, reversed phase/cation exchange, hydrophilic interaction/anion exchange, hydrophilic interaction/cation exchange, etc.) may also be suitable for purifying some polypeptides or proteins such as antibodies. Many methods of purifying polypeptides or proteins are known in the art.

In some embodiments, the IgE binding polypeptide or protein is produced in a cell-free system. Nonlimiting exemplary cell-free systems are described, for example, in Sitaraman et al., *Methods Mol. Biol.* 498:229-44 (2009); Spirin, *Trends Biotechnol.* 22:538-45 (2004); Endo et al., *Biotechnol. Adv.* 21:695-713 (2003).

In some embodiments, IgE binding polypeptides or proteins prepared by the methods described above are provided. In some embodiments, the IgE binding polypeptide or protein is prepared in a host cell. In some embodiments, the IgE binding polypeptide or protein is prepared in a cell-free system. In some embodiments, the IgE binding polypeptide is purified. In some embodiments, a cell culture media comprising an IgE binding polypeptide or protein is provided.

In some embodiments, compositions comprising antibodies prepared by the methods described above are provided. In some embodiments, the composition comprises an IgE binding polypeptide or protein prepared in a host cell. In some embodiments, the composition comprises an IgE binding polypeptide or protein prepared in a cell-free system. In some embodiments, the composition comprises a purified IgE binding polypeptide or protein.

Exemplary Methods of Treating Diseases Using IgE Binding Polypeptides or Proteins In some embodiments, methods of treating disease in an individual comprising administering an IgE binding polypeptide or protein are provided. In some embodiments, methods for treating a disease associated with IgE. Such diseases include allergies such as food allergies (such as, for example, peanut, sesame, milk, egg, fish, or tree nut allergy), environmental allergies (such as, for example, dust mite, pollen, mold, or latex allergy), allergies to companion animals (such as, for example, cat, dog, gird, horse, or cow allergy), and venom allergies (such as, for example, bee, wasp, or spider allergy). In some embodiments, methods for treating allergic disorders are provided. In some embodiments, methods for reducing IgE are provided. The method comprises administering to the individual an effective amount of an IgE binding polypeptide or protein provided herein. In some embodiments, the IgE binding polypeptide or protein blocks binding of IgE to FCER1A. In some embodiments, the IgE binding polypeptide or protein inhibits activation or degranulation and thus the allergic response. In some such embodiments, the IgE binding polypeptide or protein depletes IgE.

In some embodiments, the IgE binding polypeptide or protein is linked to an additional agent, such as an additional therapeutic agent, to form an immunoconjugate.

In some embodiments, the methods of treatment may be in humans or animals. In some embodiments, methods of treating humans are provided.

The IgE binding polypeptides and proteins can be administered as needed to subjects. Determination of the frequency of administration can be made by persons skilled in the art, such as an attending physician based on considerations of the condition being treated, age of the subject being treated, severity of the condition being treated, general state of health of the subject being treated and the like. In some embodiments, an effective dose of an IgE binding polypeptide or protein is administered to a subject one or more times. In some embodiments, an effective dose of an IgE binding polypeptide or protein is administered to the subject daily, semiweekly, weekly, every two weeks, once a month, etc. An effective dose of an IgE binding polypeptide or protein is administered to the subject at least once. In some embodiments, the effective dose of an IgE binding polypeptide or protein may be administered multiple times.

In some embodiments, pharmaceutical compositions are administered in an amount effective for treating a disease associated with IgE. The therapeutically effective amount is typically dependent on the weight of the subject being treated, his or her physical or health condition, the extensiveness of the condition to be treated, or the age of the subject being treated.

In some embodiments, IgE binding polypeptides and proteins can be administered in vivo by various routes, including, but not limited to, intravenous, intra-arterial, parenteral, intraperitoneal or subcutaneous. The appropriate formulation and route of administration may be selected according to the intended application.

Pharmaceutical Compositions

In some embodiments, compositions comprising IgE binding polypeptides or proteins are provided in formulations with a wide variety of pharmaceutically acceptable carriers (see, for example, Gennaro, Remington: The Science and Practice of Pharmacy with Facts and Comparisons: Drugfacts Plus, 20th ed. (2003); Ansel et al., Pharmaceutical Dosage Forms and Drug Delivery Systems, $7^{th}$ ed., Lippencott Williams and Wilkins (2004); Kibbe et al., Handbook of Pharmaceutical Excipients, $3^{rd}$ ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available.

Combination Therapy

IgE binding polypeptides and proteins of the present disclosure can be administered alone or in combination with other modes of treatment, such as an additional therapeutic agent. The IgE binding polypeptide or protein can be provided before, substantially contemporaneous with, or after the one or more other modes of treatment (i.e., concurrently or sequentially).

Nonlimiting Exemplary Methods of Diagnosis

In some embodiments, the methods described herein are useful for evaluating a subject and/or a specimen from a subject. In some embodiments, evaluation is one or more of diagnosis, prognosis, and/or response to treatment.

In some embodiments, the methods described herein comprise evaluating a presence, absence, or level of a protein or other molecule, for example, IgE, histamine, β-tryptase or other allergic mediators. In some embodiments, the methods described herein comprise evaluating a presence, absence, or level of expression of a nucleic acid. The compositions described herein may be used for these measurements. For example, in some embodiments, the methods described herein comprise contacting a sample, serum, or cells from a sample with a therapeutic agent as described herein.

Kits

Also provided are articles of manufacture and kits that include any of the IgE binding polypeptides or proteins as described herein, and suitable packaging. In some embodiments, the invention includes a kit with (i) an IgE binding polypeptide, and (ii) instructions for using the kit to administer the IgE binding polypeptide to an individual.

Suitable packaging for compositions, such as pharmaceutical compositions, comprising polypeptides or proteins described herein are known in the art, and include, for example, vials (e.g., sealed vials), vessels, ampules, bottles, jars, flexible packaging (e.g., sealed Mylar or plastic bags), and the like. These articles of manufacture may further be sterilized and/or sealed. Also provided are unit dosage forms comprising the compositions described herein. These unit dosage forms can be stored in a suitable packaging in single or multiple unit dosages and may also be further sterilized and sealed. Instructions supplied in the kits of the invention are typically written instructions on a label or package insert (e.g., a paper sheet included in the kit), but machine-readable instructions (e.g., instructions carried on a magnetic or optical storage disk) are also acceptable. The instructions relating to the use of the antibodies generally include information as to dosage, dosing schedule, and route of administration for the intended treatment or industrial use.

The containers may be unit doses, bulk packages (e.g., multi-dose packages) or sub-unit doses. For example, kits may also be provided that contain sufficient dosages of polypeptides or proteins disclosed herein to provide effective treatment for an individual for an extended period. Kits may also include multiple unit doses of polypeptides or proteins and instructions for use and packaged in quantities sufficient for storage and use in pharmacies, for example, hospital pharmacies and compounding pharmacies.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Development of Non-Activating IgE Binding Polypeptides

Single domain antibodies (sdAbs) targeting IgE were generated via immunization of llamas and/or alpacas with human IgE produced in vitro from a monoclonal hybridoma and purified by protein L (Thermo Fisher Catalog #DIAHE1-01). Following the development of specific anti-IgE antibody titers, llama/alpaca peripheral blood mononuclear cells (PBMCs) were isolated from 500 mL of blood from the immunized animal and total mRNA was isolated using the Qiagen RNeasy Maxi Kit and subsequently converted to first strand cDNA using Thermo Superscript IV Reverse Transcriptase and oligo-dT priming. VHH sequences were specifically amplified via PCR using the cDNA as template and cloned into a yeast surface display vector as VHH-Fc-AGA2 fusion proteins.

Yeast libraries displaying the VHH-Fc-AGA2 fusion proteins were enriched for sdAbs that bind IgE and blocked binding of IgE to FCER1A using recombinant forms of human IgE and FCER1A via magnetic bead isolation followed by fluorescence activated cell sorting (FACS). Sorted yeast were plated out and isolated colonies were picked into 96-well blocks and an induction of yeast cell surface expression of VHH-Fc-AGA2 fusion protein was conducted. Biotinylated recombinant human IgE or irrelevant biotinylated protein (IgE negative) were directly applied to induced yeast, washed, treated with fluorophore labelled streptavidin, and analyzed by 96-well flow cytometry.

Nucleic acid sequences encoding VHHs that bound to biotinylated recombinant human IgE and not to irrelevant biotinylated protein were cloned in-frame with a human Fc xELL encoding region into mammalian expression vectors, and expressed by transient transfection in HEK293 Freestyle cells (293 cells) or CHO cells using polyethylenimine. Supernatant was collected after 3-7 days, secreted recombinant protein was purified by protein A chromatography, and concentration was calculated from the absorbance at 280 nm and extinction coefficient.

Anti-IgE sdAb B10 was selected for humanization because of its high binding affinity to soluble IgE and effective blocking of IgE binding to FCER1A, the IgE receptor. In addition, B10 exhibited low binding to IgE:FCER1A complexes. Various humanized forms of sdAb B10 were generated based on human heavy chain frameworks $V_H3$-23. Several rounds of humanization were performed to reduce potential immunogenicity and optimize manufacturability. Certain mutations were tested, for example, in CDR2 and CDR3 as well as each of the framework regions. Binding of parental B10 formatted as a dimeric VHH hIgG1-Fc fusion proteins using the dimerizing Fc xELL, and parental B10 and humanized variants and humanized versions thereof formatted as monomeric VHH-hIgG1-Fc fusion proteins using a non-dimerizing human IgG1 Fc variant region lacking a hinge and comprising mutations in the CH3 domain Fc NNT (SEQ ID NO: 83) was assessed by Flow cytometry. 293 cells were transiently transfected with a plasmid that encoded the CH2-4 constant domains of human IgE linked to a transmembrane protein for cell surface expression with coexpression of citrine in the same vector. First, 25 µg of DNA was added to Opti-MEM Reduced Serum Medium (Gibco) mixed with 75 µL of 40 kDa Polyethylenimine (PEI) for a final concentration of 1 µg DNA and 2.5 µg PEI per mL of culture volume. The plasmid DNA was allowed to pre-complex with PEI for 15 minutes before transferring the mixture to 25 mL of 293 cells in a shake flask at a density of $2\times10^6$ cells/mL. The flasks were incubated at 37° C. shaking, 250 rpm, with 8% $CO_2$ overnight for validation of IgE expression as well as analysis of VHH-hIgG1-Fc fusion protein binding the following day. 293 cells transiently transfected with the constant domain CH2-4-IgE plasmids were centrifuged and resuspended in FACS buffer to a count of 1×10⁶ cells/mL. Next, 50 μL of cells were transferred to wells of a round-bottom 96-well assay plate for a total of 50,000 293 cells per well. In a separate 96-well plate, monomeric VHH-hIgG1-Fc fusion proteins were titrated 1:5 in a 8-point dilution series starting at 1 μM in FACS Buffer with the 8$^{th}$ point containing no antibody. 50 μL from each antibody dilution was added to wells containing 50 μL of FACS Buffer with transfected 293 cells which produced a 2-fold dilution of the antibody concentrations from the dilution series resulting in a 500 nM final, starting concentration of the test article titration. The test articles and 293 cells were incubated together at 4° C. for 30 minutes. Next, the 96-well plates were centrifuged at 400×g for 5 minutes and the FACS buffer containing unbound antibody was decanted. Cells were washed 1× with 150 μl 4° C. FACS Buffer. Then, 100 μL of Alexa Fluor® 647 AffiniPure Donkey Anti-Human IgG Fcγ fragment specific diluted 1:10,000 in FACS Buffer was added to the cell pellet. The cells were incubated with the fluorophore conjugated detection antibody at 4° C. for 20 minutes. 293 cells were then centrifuged and washed once as described above. Cell pellets were resuspended in 30 μL FACS Buffer and analyzed on an iQue Screener Plus flow cytometer (Sartorius, IntelliCyt) with a 1 second sip time and 1 second void time. Mean fluorescent intensity was calculated using iQue onboard software gating on GFP+ or citrine+ cells.

The data was plotted and analyzed using GraphPad Prism analysis software. The apparent affinity of the observed binding interaction (Kd in nM) was determined using the One Site—total analysis formula Y=Bmax*X/(Kd+X)+NS*X+Background, where Bmax is the maximum specific binding in the same units as Y, Kd is the equilibrium dissociation constant, in the same units as X (this is the concentration needed to achieve a half-maximum binding at equilibrium) and NS is the slope of nonspecific binding in Y units divided by X units. Background was the amount of nonspecific signal with no added antibody. The background percent was calculated by dividing the background divided by Bmax as calculated by the curve fitting model and multiplied by 100.

The binding curves, Bmax, and Kd values for the humanized B10 VHH fusion proteins are shown in FIGS. 1A-1G. No binding was observed to untransfected cells (data not shown).

FIGS. 2A-2B show an alignment of the parental B10 VHH with the humanized forms of B10 (hzB10v1-v18, v20-v34, v37-v44), and the human heavy chain acceptor sequence "VH3-23." The sequences are also provided in the Table of Certain Sequences. The partially humanized variant hzB10v14 was selected for initial studies. The further optimized and more fully humanized variant hzB10v40 was selected for further analysis as it was the most human VHH that retained high affinity to IgE having been successfully engineered to remove a number of potential deamination and oxidation sites that were present in the parent and other humanized variants.

Example 2: Binding of Polypeptides to IgE and Other Immunoglobulin Isotypes

Binding of a bivalent IgE binding polypeptide comprising the hzB10v14 VHH domain described in Example 1 to human, and cynomolgus monkey IgE was assessed by ELISA. The IgE binding polypeptide comprised the hzB10v14 VHH domain, a linker composed of glycine amino acids (SEQ ID NO: 91), and a human IgG1 Fc region variant comprising G236D, S267E and L328F substitutions (SEQ ID NO: 81, "DSELF"), the Fc region will drive the formation of homodimers. The full hzB10v14 VHH domain polypeptide with DSELF IgG1 Fc region is shown in SEQ ID NO: 84 ("cx12739"). Binding of an IgE binding polypeptide comprising a humanized version of the previously described IgE026 VHH (see e.g., WO 2012/175740) fused to a human IgG1 Fc region variant comprising S267E and L328F substitutions (SEQ ID NO: 89, "SELF") ("cx10759," SEQ ID NO: 89) and a conventional full length anti-IgE antibody, comprising a heavy chain and a light chain, and including the IgG1 SELF Fc region ("cx10710," SEQ ID NOs: 87 and 88) were also assayed as comparative IgE binders. Commercial human IgE (AbCam, Cat. No. Ab65866), was used. In place of commercial cynomolgus monkey IgE, a chimeric cynomolgus monkey IgE was generated by fusing recombinant CH1-4 constant domains from the *Macaca fascicularis* IgE (GenBank accession number EHH62331.1), and the heavy and light variable domains from a mouse monoclonal anti-hapten dinitrophenol IgE.

Immunoglobulin E from the indicated species was immobilized on plates at 1 μg/mL in DPBS overnight at 4° C. Plates were washed to remove unbound IgE. All washes were completed using a plate washer using DPBS containing 0.05% supplemental Tween-20 ("DPBST") with three washes per wash cycle. After washing, wells were blocked with 150 μL of DPBS containing 3% bovine serum albumin and incubated, shaking at 600 rpm (1.5 mm orbit) for two hours at room temperature and then washed.

An 11 point titration of each anti-IgE antibody was performed in DPBST, starting from 250 nM, then diluting 1:4 across the plate. DPBST alone was used as a negative control. 100 μL of the diluted antibodies were applied in duplicate at each concentration and incubated for one hour at room temperature, with shaking as above. Plates were washed and bound antibodies were detected by adding 100 μL of HRP conjugated goat anti-human Fc gamma specific polyclonal antibody at 100 ng/mL DPBST to each well for 30 minutes at room temperature, shaking as above. Plates were washed and HRP signal was developed by adding 100 μL of TMB substrate at room temperature and incubating for 5 minutes with shaking at 600 rpm. Sample optical densities was then read at 650 nm on a Molecular Devices Emax plate reader. Data was analyzed using Prism 9 (GraphPad Software, LLC). The apparent affinity of the observed binding interaction (Kd in nM) was determined using the One Site as described above. The background signal ("2°") due to secondary and detection antibody binding was included in the plotted data for reference.

Figure 3A:
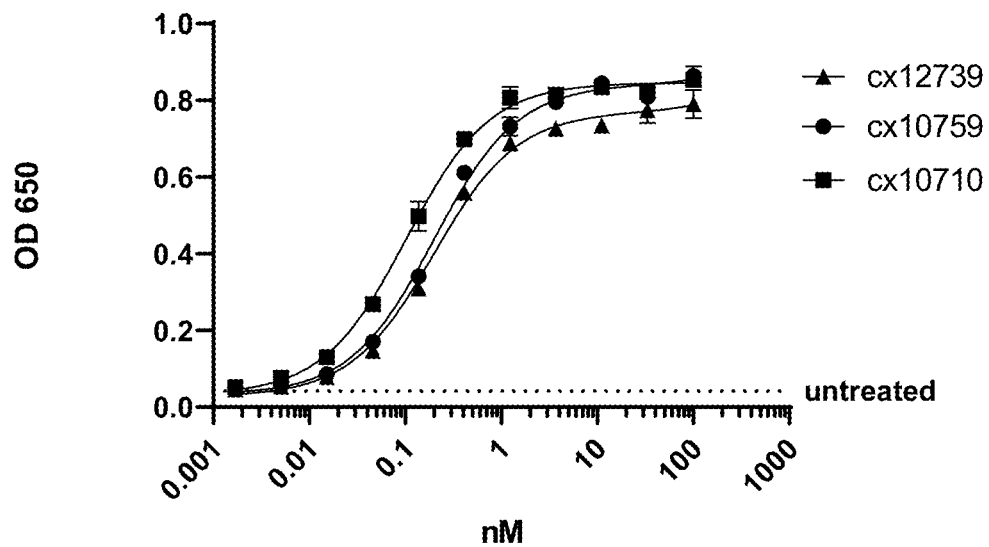
FIGS. 3A-3K show binding of the indicated anti-IgE antibodies to IgE from various species and other human immunoglobulin isotypes, by ELISA as described in Example 2.
Figure 3B:
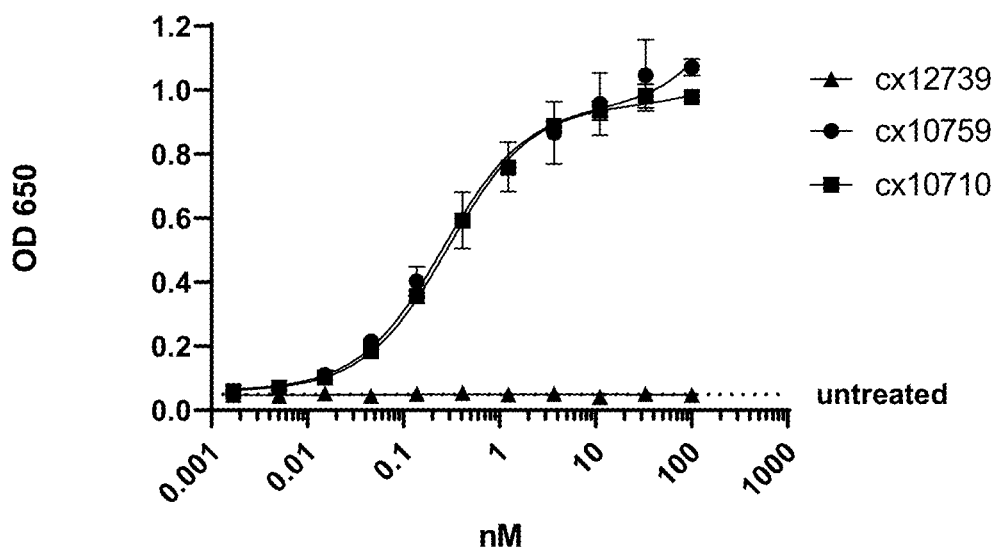

As shown in FIGS. 3A-3B and Table 3 below, all the antibodies showed titratable binding to human IgE, however the single domain antibody comprising hzB10v14 (cx12739; SEQ ID NO. 84) did not bind cynomolgus IgE indicating that it binds a unique epitope. The affinity constants from this study are shown in Table 3.

TABLE 3

| Antibody | Apparent $K_d$ (nM); (95% Confidence Interval) | Bmax (OD 650 nm) | SEQ ID NO(s) |
|---|---|---|---|
| Human IgE | | | |
| hzB10v14-DSELF (cx12739) | 0.1971 (0.1664-0.2334) | 0.7418 (0.7129-0.7707) | 84 |
| cx10759, comprising IgG1 SELF Fc | 0.1983 (0.7803-0.8376) | 0.8089 (0.7803-0.8376) | 89 |
| cx10710, comprising IgG1 SELF Fc | 0.1024 (0.08933-0.1174) | 0.8142 (0.7893-0.8391) | 87, 88 |
| Cynomolgus Monkey IgE | | | |
| hzB10v14-DSELF (cx12739) | no binding | no binding | 84 |
| cx10759, comprising IgG1 SELF Fc | 0.2546 (0.1641-0.3962) | 0.8861 (0.8079-0.9648) | 89 |
| cx10710, comprising IgG1 SELF Fc | 0.2880 (0.2537-0.3269) | 0.8955 (0.8712-0.9198) | 87, 88 |

In a further study, binding of a bivalent IgE binding polypeptides comprising the hzB10v40 VHH domain described in Example 1 to human (AbCam, Cat. No. Ab65866), rat IgE (LS Bio, Cat. No. LS-G37860), mouse IgE (Millipore, Cat. No. D8406), human IgA (Athensresearch, 16-16-090701), human IgG2 (Athensresearch, 16-16-090707-2), and human IgM (Novus, NBP1-97056) was assessed by ELISA essentially as described above. In a further study, binding of the anti-IgE antibody designated cx13054 to human IgE (AbCam, Cat. No. Ab65866), cyno IgE (generated in house), rat IgE (LS Bio, Cat. No. LS-G37860), mouse IgE (Millipore, Cat. No. D8406), dog IgE (Fortis Life Science, Cat. No. P115), pig IgE (Abbexa, Cat. No. abx652112), human IgA (Athensresearch, 16-16-090701), human IgG2 (Athensresearch, 16-16-090707-2), human IgM (Novus, NBP1-97056), Human IgD (AbCam, Cat. No. Ab91022) was assessed by ELISA essentially as described above. An IgE binding polypeptide, designated "cx13032" (SEQ ID NO: 85), comprises the hzB10v40 VHH domain, a linker composed of glycine amino acids (SEQ ID NO: 91), and the IgG1 DSELF Fc region. Another IgE binding polypeptide, designated "cx13054" (SEQ ID NO: 89), comprises the hzB10v40 VHH domain, a linker composed of glycine amino acids (SEQ ID NO: 91), and the IgG1 SELF Fc region. The binding of the anti-IgE comparator molecules cx10759 and cx10710 was also examined in this study. The background signal due to secondary and detection antibody binding is indicated by the dashed line.

Figure 3C:
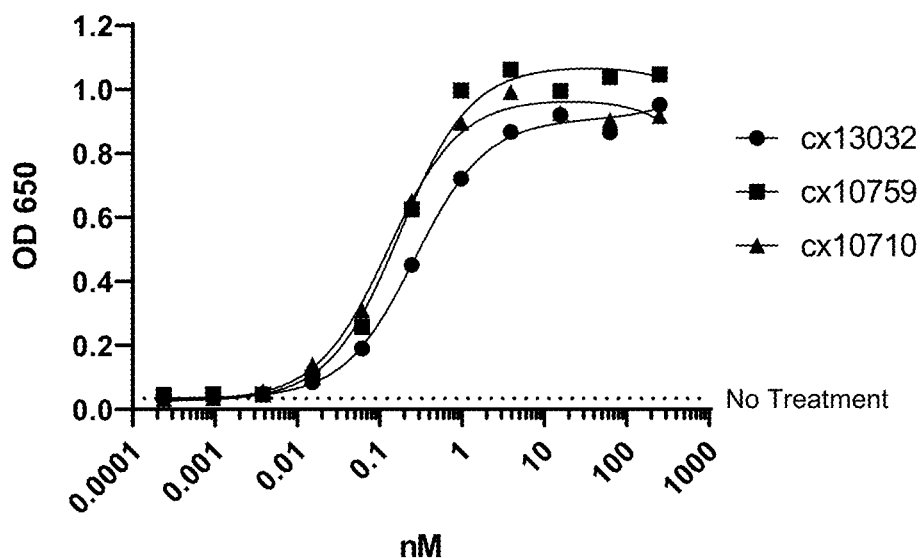
Figure 3D:
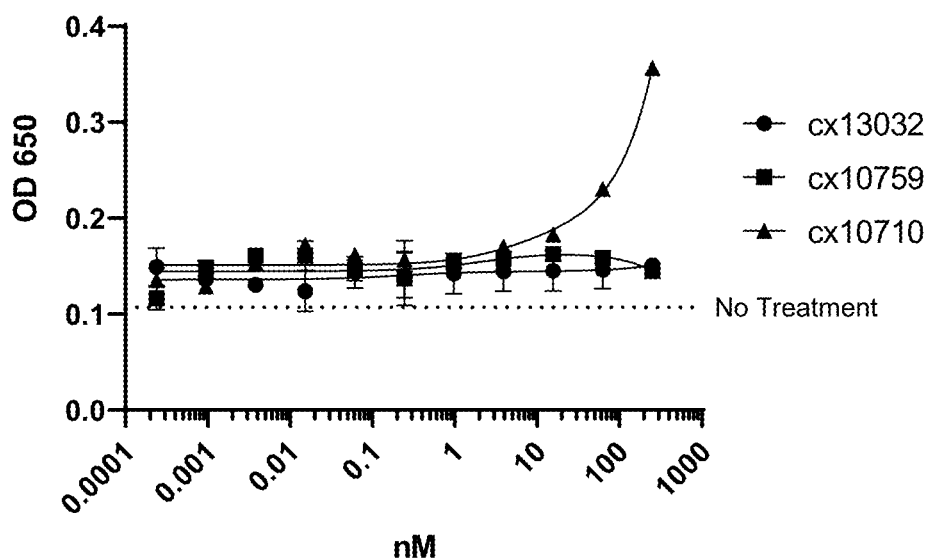
Figure 3E:
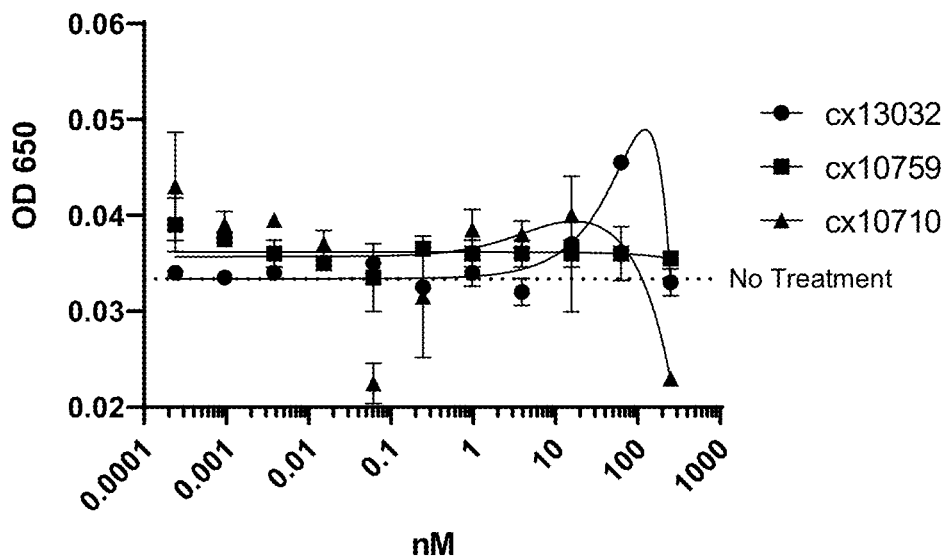
Figure 3F:
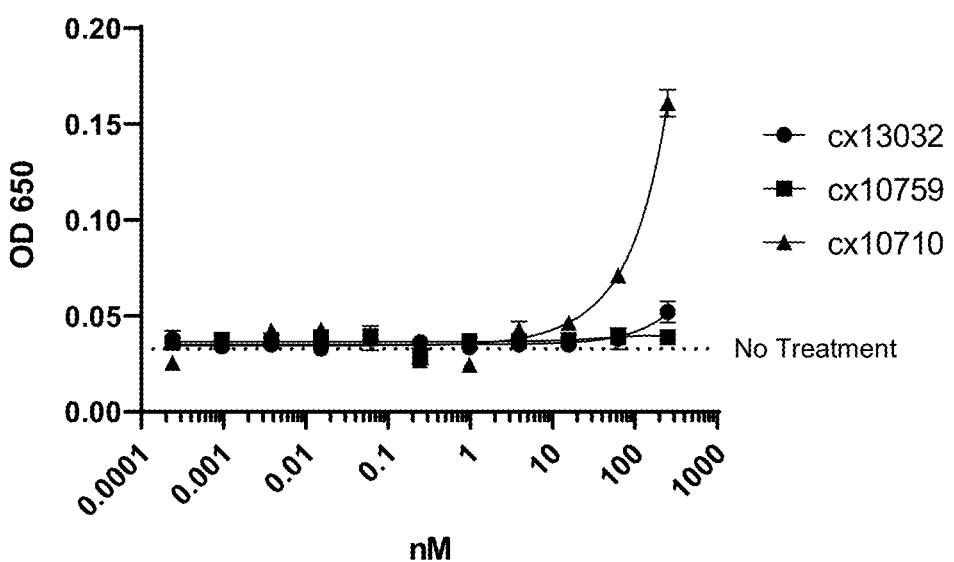
Figure 3G:
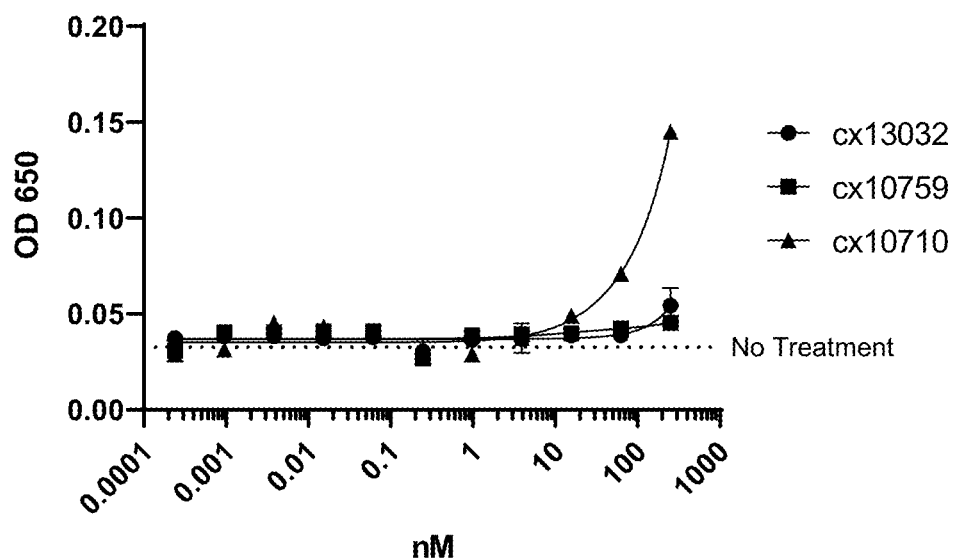
Figure 3H:
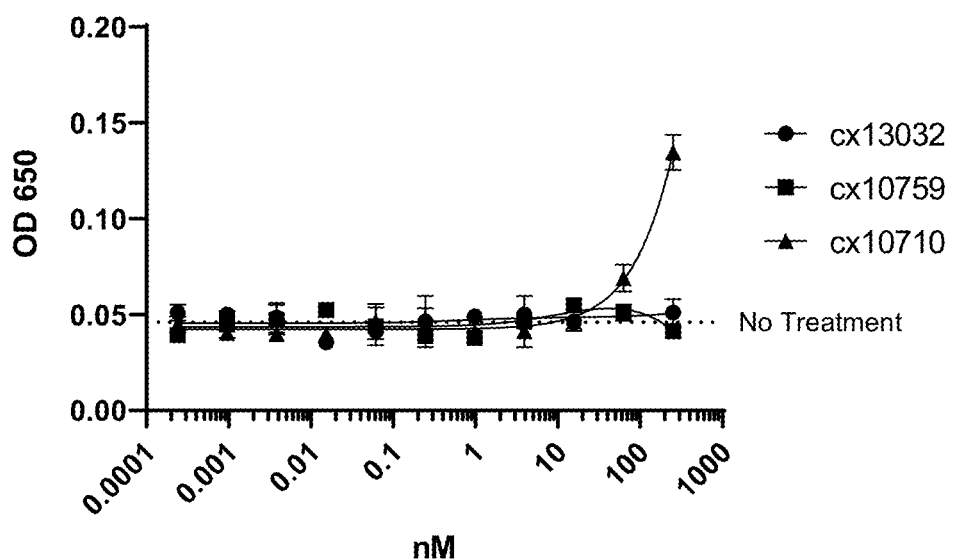
Figure 3I:
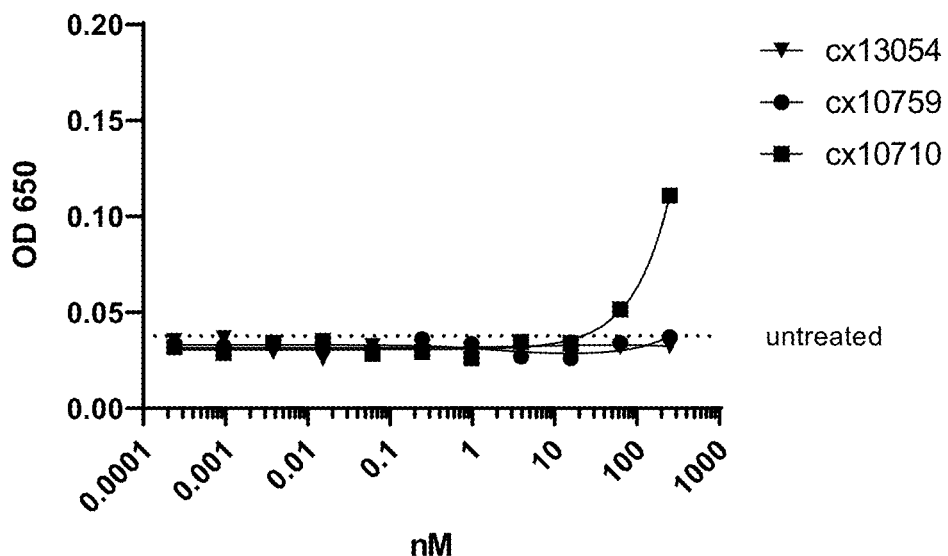
Figure 3J:
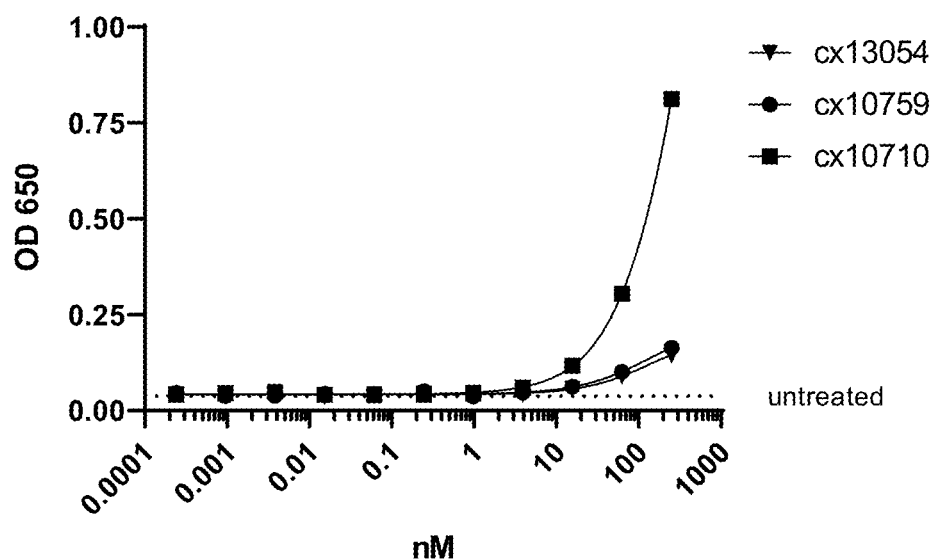
Figure 3K:
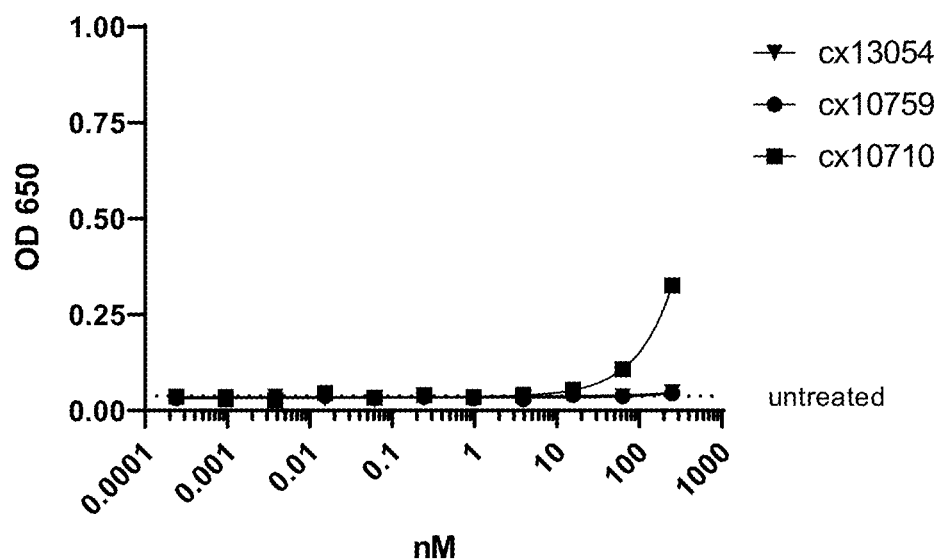

As shown in FIG. 3C and Table 4, all the B10 VHH based anti-IgE antibodies showed titratable binding to human IgE. As shown in FIGS. 3D and 3F-3H, the single-domain antibody comprising the hzB10v40 VHH (cx13032) showed no measurable affinity for human IgA, or IgM, or mouse or rat IgE. A small binding signal for human IgG2 was observed in some studies at high concentrations (see FIG. 3E). Similar results were observed for cx13054 (SEQ ID NO: 86), which also comprises the hzB10v40 VHH (data not shown). cx10710 had a small, but measurable binding signal for human IgA and IgM, and mouse and rat IgE. As shown in FIGS. 3I-3K, a single-domain antibody comprising the hzB10v40 VHH (cx13054) showed no measurable affinity for human IgD and dog IgE, with a very small binding signal for pig IgE at the highest concentrations. In contrast, cx10710 had a larger measurable binding signal for human IgD, pig and dog IgE. The affinity constants for binding to human IgE from this study are shown in Table 4.

TABLE 4

| Antibody | Apparent $K_d$ (nM); (95% Confidence Interval) | Bmax (OD 650 nm) | SEQ ID NO(s) |
|---|---|---|---|
| Human IgE | | | |
| hzB10v40-DSELF (cx13032) | 0.2662 (0.2118-0.3341) | 0.8732 (0.8317-0.9150) | 85 |
| cx10759, comprising IgG1 SELF Fc | 0.1760 (0.1196-0.2576) | 1.050 (0.9622-1.139) | 89 |
| cx10710, comprising IgG1 SELF Fc | 0.1270 (0.09197-0.1749) | 0.9458 (0.8823-1.009) | 87, 88 |

Example 3: Surface Plasmon Resonance IgE Binding and FCER1A Blocking Assays

Binding of a representative B10 VHH based anti-IgE sdAb, hzB10v14-IgG DSELF Fc (cx12739), to human IgE directly or to IgE pre-complexed to FCER1A, and the ability to block the binding of IgE to FCER1A was assessed by Surface Plasmon Resonance (SPR). The binding and blocking ability of one or both of the anti-IgE comparator molecules cx10759 and cx10710 were also examined in these studies. All experiments were done using a Biacore T200 instrument with a CM5 chip at 25° C., Flow Cell (FC) 1 was used as the reference for FC2, and FC3 for FC4.

To evaluate binding to immobilized IgE, IgE (Abcam ab65866) (3.2 µM stock) was used as a ligand to capture onto the chip, cx10759 (10 µM stock) and cx12739 (10 µM stock) were used as analytes to flow over the ligand immobilized surfaces (at 25° C.). Protein L (15 mg/mL) was diluted (1:50 dilution, 0.3 mg/mL diluted concentration) in 10 mM sodium acetate buffer at pH 4.5 and immobilized onto FCs 1 and 2 to a level of ~13000 RU, using the standard amine coupling chemistry. PBS-P (20 mM Phosphate buffer, pH 7.4, 137 mM NaCl, 2.7 mM KCl, 0.05% v/v surfactant P20) was used as the immobilization running buffer. IgE was diluted (1:250 dilution, ~12.8 μg/mL diluted concentration) in PBS-P captured onto FC2 to a level of ~75 RU. PBS-P was used as the capture running buffer. Overnight kinetics were performed for all analytes in the presence of PBS-P. The flow rate of all analyte solutions was maintained at 50 μL/min. The contact and dissociation times used were 120 seconds and 600 seconds, respectively. Glycine pH 2.0 was injected for 20 seconds for surface regeneration. This regeneration condition takes away all captured ligand. Therefore, fresh ligand solution was captured in the beginning of each injection cycle. Injected analyte concentrations are from 50 nM to 0.098 nM (two-fold dilutions). All analytes were injected in duplicate. Sensorgrams from the overnight kinetics were evaluated by using 1:1 kinetics model fitting. The binding constants are presented in Table 5.

TABLE 5

| Antibody | ka (1/Ms) | kd (1/s) | $K_D$ (nM) | Chi$^2$ | U-value |
|---|---|---|---|---|---|
| hzB10v14-DSELF (cx12739) | $3.593 \times 10^5$ | $2.88 \times 10^{-4}$ | 0.8 | 0.163 | 9 |
| cx10759 | $3.547 \times 10^6$ | $4.15 \times 10^{-4}$ | 0.1 | 0.821 | 5 |

As shown in Table 5 the B10 VHH based anti-IgE sdAb hzB10v14-IgG DSELF Fc (cx12739) binds to human IgE with subnanomolar affinity. Although the B10 VHH showed a lower binding affinity (as indicated by the $K_D$ value) compared to cx10759, it has a slower off-rate (kd value), potentially resulting in better pharmacokinetics.

To evaluate the ability to block IgE binding to FCER1A, recombinant FCER1A (ACRO FCA-H5228) (0.4 mg/ml stock) was used as ligand to capture onto the CM5 chip. IgE (3.2 μM stock), cx10759 (10 μM stock), cx10710 (10 μM stock), and cx12739 (10 μM stock) were used as analytes to flow over the ligand captured surfaces. Anti-His antibody (1 mg/ml stock) was diluted (1:100 dilution, 0.01 mg/ml diluted concentration) in 10 mM sodium acetate buffer at pH 4.5 and immobilized onto FCs 1 and 2 to a level of ~14000 RU, using the standard amine coupling chemistry. PBS-P (20 mM Phosphate buffer, pH 7.4, 137 mM NaCl, 2.7 mM KCl, 0.05% v/v surfactant P20) was used as the immobilization running buffer. FCER1A (0.4 mg/ml stock concentration) was diluted (1:250 dilution, ~0.004 mg/ml diluted concentration) in PBS-P captured onto FC2 to levels of ~130 RU. PBS-P was used as the capture running buffer. Overnight kinetics were performed for all analytes in the presence of PBS-P. The flow rate of all analyte solutions was maintained at 50 μL/min. The contact and dissociation times used were 120 seconds and 300 seconds, respectively. Glycine pH 1.5 was injected for 20 seconds for surface regeneration. This regeneration condition takes away all captured FCER1A. Therefore, fresh FCER1A was captured in the beginning of each injection cycle. 5 nM IgE alone and 200 nM to 0.39 nM (two-fold dilutions) of cx10759, cx10710, and cx12739 premixed with 5 nM IgE were injected. All analytes were injected in duplicate. After injection of all analytes, fresh FCER1A was recaptured and 200 nM of cx10759, cx10710, and cx12739 were manually injected, which did not result any meaningful binding of all cx10759, cx10710, and cx12739 to captured FCER1A. Sensorgrams from the overnight kinetics were plotted for further evaluation. The inhibition curves are presented in FIG. 4A-4C.

Figure 4A:
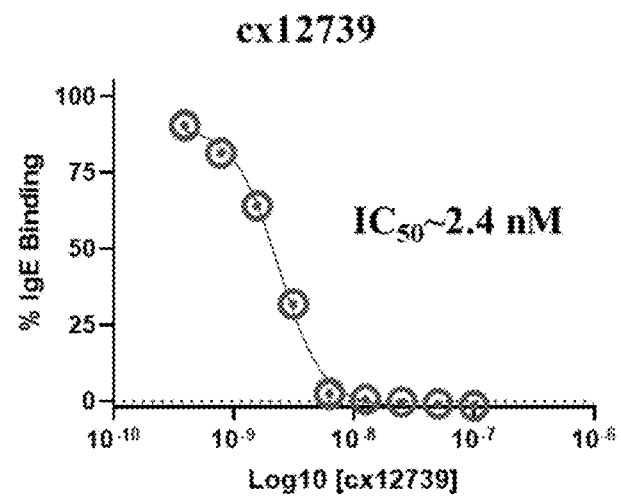
FIGS. 4A-4C show the inhibition curves as determined by Surface Plasmon Resonance (SPR) for the indicated anti-IgE antibodies blocking the binding of IgE to immobilized FCER1A as described in Example 3.
Figure 4B:
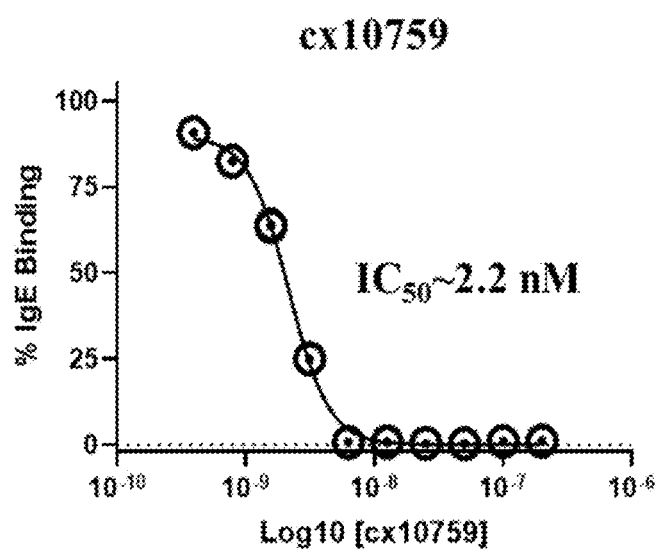
Figure 4C:
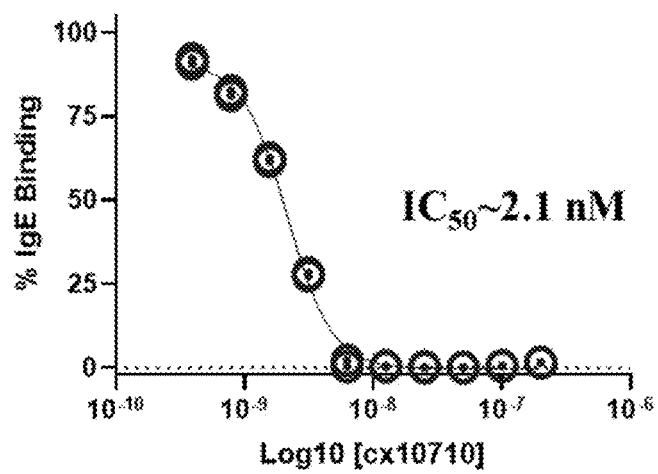

As shown in FIG. 4A the B10 VHH based anti-IgE sdAb (cx12739), blocks soluble IgE binding to FCER1A with a similar potency to the two comparator antibodies cx10759 and cx10710, FIGS. 4B and 4C, respectively.

To evaluate the binding to human IgE pre-complexed to FCER1A anti-His antibody (1 mg/ml stock concentration) was diluted (1:100 dilution, ~10 nM diluted concentration) in 10 mM sodium acetate buffer at pH 4.5 and immobilized onto FC1 and FC2 using standard amine coupling chemistry to a level of ~14000 RU. FCER1A (ACRO FCA-H5228) was diluted (1:175 dilution, ~100 nM diluted concentration) in HBS-P (10 mM Hepes pH 7.4, 150 mM NaCl, 0.05% v/v surfactant P20) and captured onto FC2 to a level of ~420 RU. FCER1A was crosslinked onto the anti-his antibody via 20 seconds injection of NHS-EDC followed by 20 seconds injection of ethanolamine. HBS-P was used as the capture running buffer.

FCER1A was diluted (1:175 dilution, ~100 nM diluted concentration) in 10 mM sodium acetate buffer at pH 5.5 and immobilized onto FC4 to a level of ~385 RU. HBS-P was used as the immobilization running buffer. 50 nM of IgE was injected over the ligand immobilized surfaces at a 2 μL/min flow rate in the presence of HBS-P to a level of a level of ~50 RU onto FC2 and ~75 RU onto FC4. cx12739, cx10710, and cx10759 were then injected over IgE captured surface for 1250 seconds followed by 600 seconds dissociation, in the presence of HBS-P, at a 8 μL/min flow rate. Two 15 seconds pulses of glycine pH 2.0 were finally injected for surface regeneration. This regeneration condition removes captured IgE. Therefore, fresh IgE solutions were captured in the beginning of each injection cycle. Injected analyte concentrations were 5000 nM, 1000 nM, 100 nM, and 10 nM. All analytes were injected only once. Representative sensorgrams from the amine coupled flow cells from 1000 nM, 100 nM and 10 nM analyte injections, with the blank subtracted are shown in FIGS. 5A-5C, respectively.

Figure 5A:
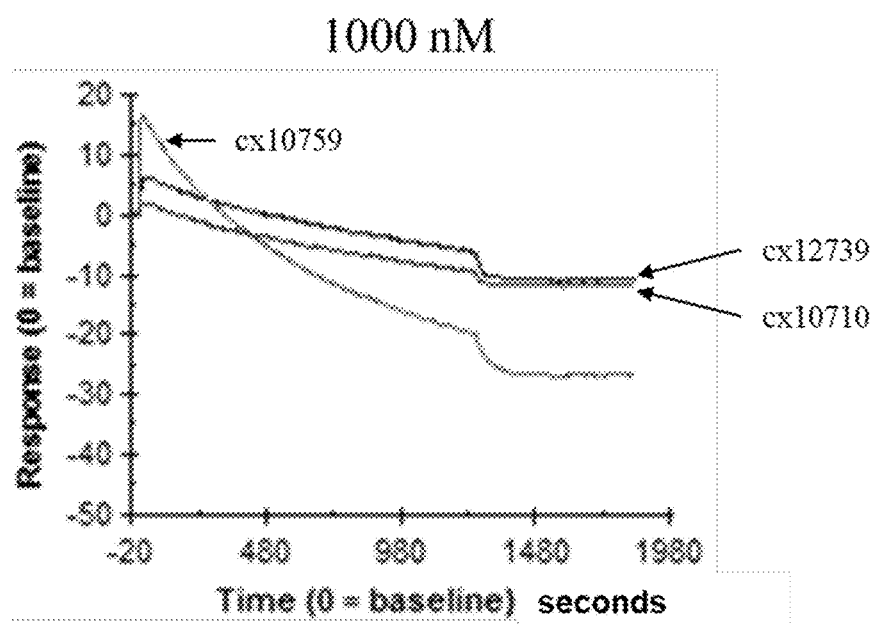
FIGS. 5A-5C show the sensorgrams of the binding of the indicated anti-IgE antibodies, injected at 1000 nM (FIG. 5A), 100 nM (FIG. 5B), and 10 nM (FIG. 5C), to human IgE pre-complexed to immobilized FCER1A as described in Example 3.
Figure 5B:
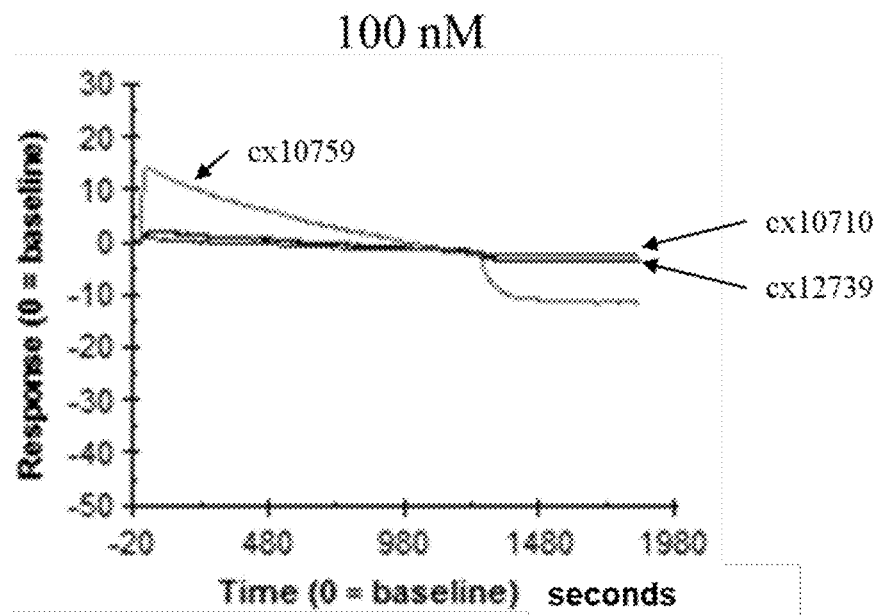
Figure 5C:
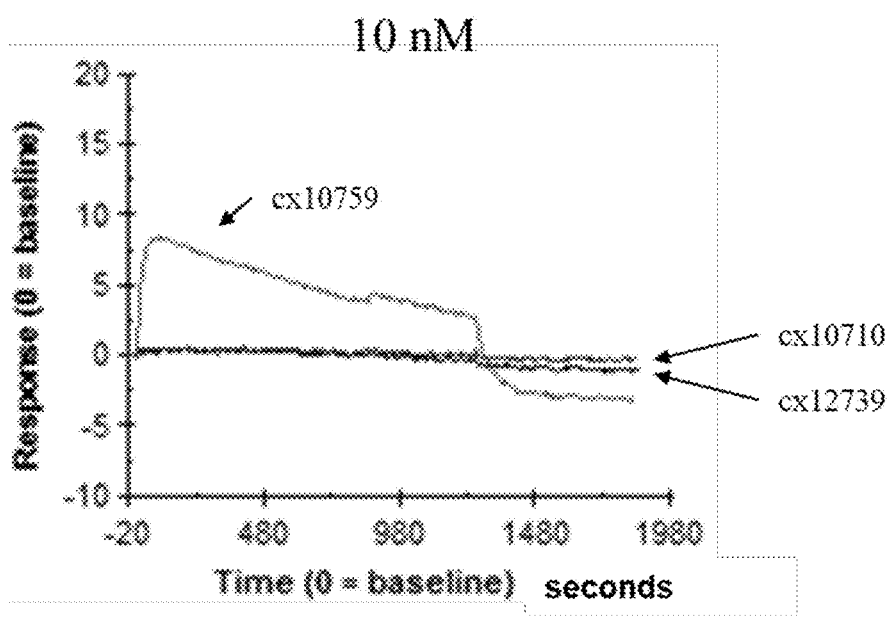

As shown in FIGS. 5A-5C the B10 VHH based anti-IgE sdAb, hzB10v14-IgG DSELF Fc (cx12739) and the conventional antibody comparator, cx10710, demonstrated little to no binding to IgE:FCER1A complexes at concentrations below 1 μM. In contrast, the 026 VHH based anti-IgE sdAb comparator (cx10759) showed appreciable binding as low as 10 nM indicating much higher affinity for IgE:FCER1A complexes. Such binding can result in direct, antigen-independent activation.

Example 4: ELISA IgE Binding and FCER1A Blocking Assays

Binding of a representative B10 VHH based anti-IgE sdAb, hzB10v40-IgG DSELF Fc (cx13032) to human IgE and the ability to block the binding of IgE to FCER1A was assessed by ELISA. The binding and blocking ability of the anti-IgE comparator molecules cx10759 and cx10710 were also examined in these studies.

Recombinant human FCER1A-His (ACRO FCA-H5228) or recombinant IgE (Abcam ab65866) were coated onto medisorp plates at 2 μg/mL and incubated at 4° C. overnight. The following day, plates were blocked with 1% BSA in PBS for 30 min-1 hour. For IgE binding, replicate eleven-point, three-fold dilutions in PBST of the antibodies were added to the IgE coated, BSA blocked plates and allowed to shake at 450 rpm at room temperature for 1 hour. Afterwards, the plates were PBST washed with the plate washer and detected with Peroxidase AffiniPure Donkey Anti-Human IgG, Fcγ fragment specific secondary detection antibody. Room temperature TMB was added and OD650 was measured using the Emax plate reader. For blocking IgE binding to FCER1A eleven point, four-fold dilutions of the antibodies were pre-complexed with IgE diluted in PBS-T and incubated at room temperature for 1.5 hours. 100 µL of the antibody:IgE mixture was added to FCER1A coated, BSA blocked plates. The final concentration of IgE was 5 nM and the test articles were titrated across 1:4 in duplicate with a starting concentration of 500 nM. The concentration of IgE was unchanged in the dilution. After a 1 hour incubation shaking at room temperature, the plates were PBST washed and detected with rabbit anti IgE, anti rabbit-HRP. Room temperature TMB was added and OD650 was measured using the Emax plate reader. The data was plotted and analyzed using GraphPad Prism analysis software. The apparent affinity of the observed binding interaction (Kd in nM) was determined using the One Site as described above, and the IC$_{50}$s were determined by the default curve fitting [Inhibitor] vs. response—Variable slope (four parameters) defined as Y=Bottom+ (Top−Bottom)/(1+(IC$_{50}$/X)^HillSlope).

Figure 6A:
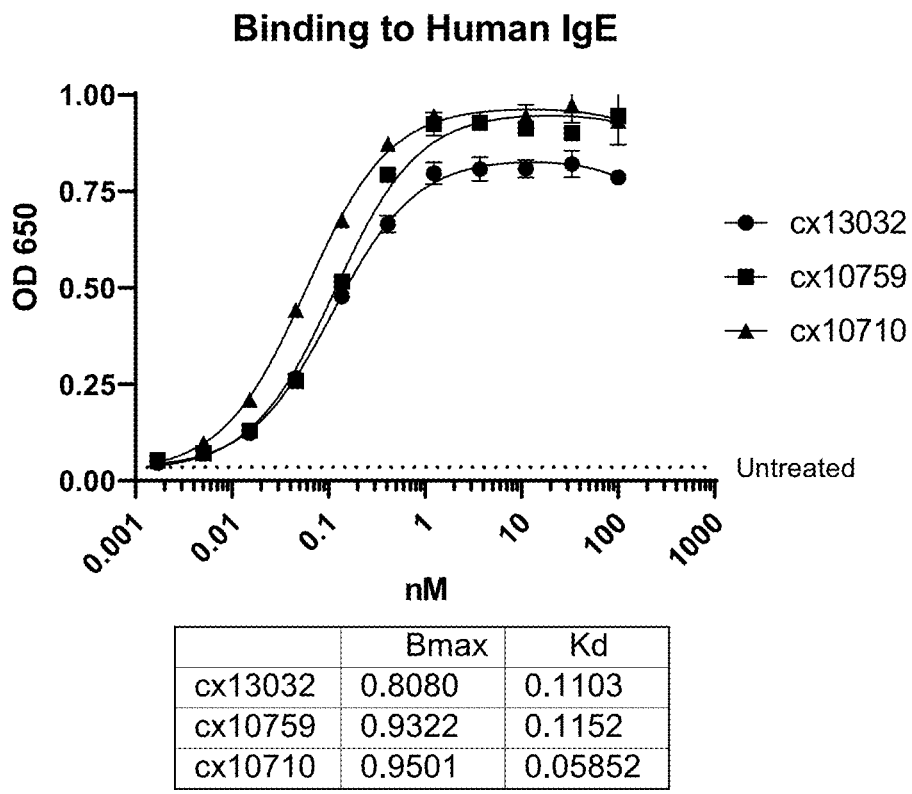
FIGS. 6A and 6C show the binding curves of the indicated anti-IgE antibodies binding to human IgE.
Figure 6B:
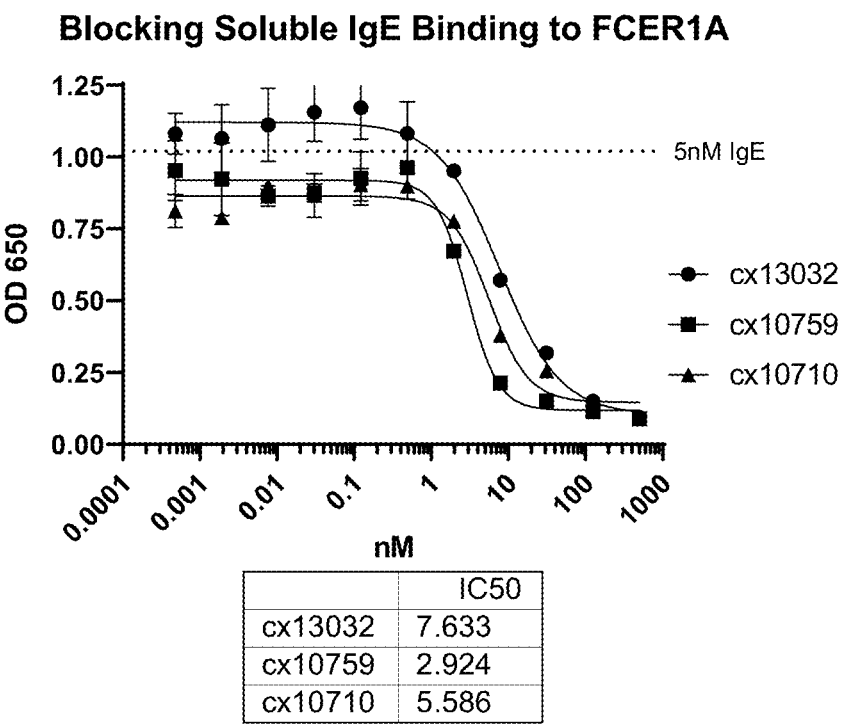
FIGS. 6B and 6D show the inhibition curves of the indicated antibodies blocking the binding of IgE to FCER1A.

As shown in FIG. 6A the B10 VHH based anti-IgE sdAb hzB10v40-IgG DSELF Fc (cx13032) also binds to human IgE with subnanomolar affinity. In addition, as shown in FIG. 6B, the B10 VHH based anti-IgE sdAb blocks soluble IgE binding to FCER1A with a similar potency to the two comparator antibodies.

In another study the binding of another representative B10 VHH based anti-IgE sdAb, hzB10v40-IgG SELF Fc (cx13054) to human IgE and the ability to block the binding of IgE to FCER1A or FCER2/CD23 (Acro CD3-H5249) was assessed by ELISA essentially as described above except the antibodies were titrated across 1:3 in duplicate with a starting concentration of 500 nM for the inhibition assays, and a starting concentration of 10 nM for the IgE binding assay. The binding and blocking ability of the anti-IgE comparator molecules cx10759 and cx10710 were also examined in these studies.

Figure 6C:
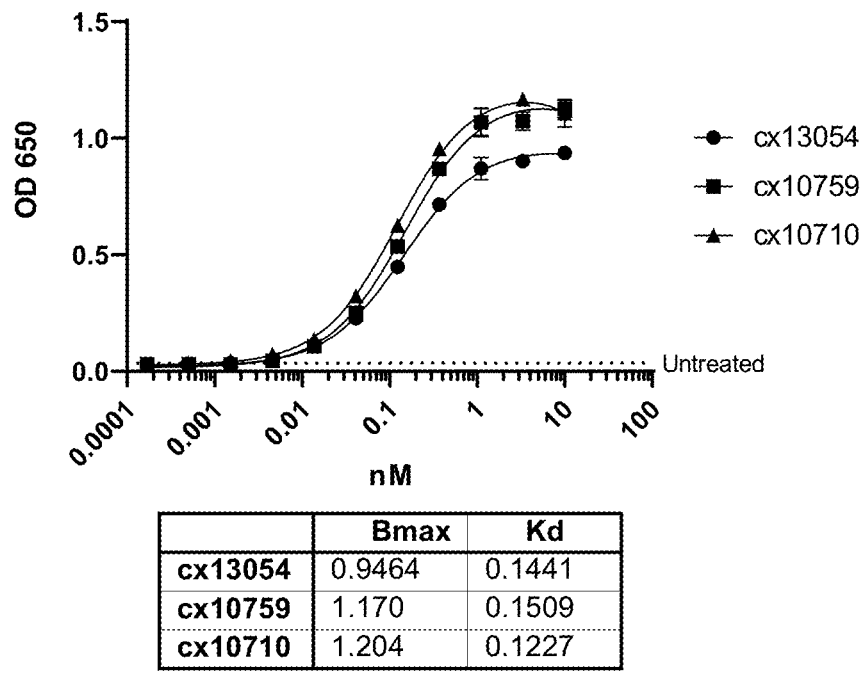
Figure 6D:
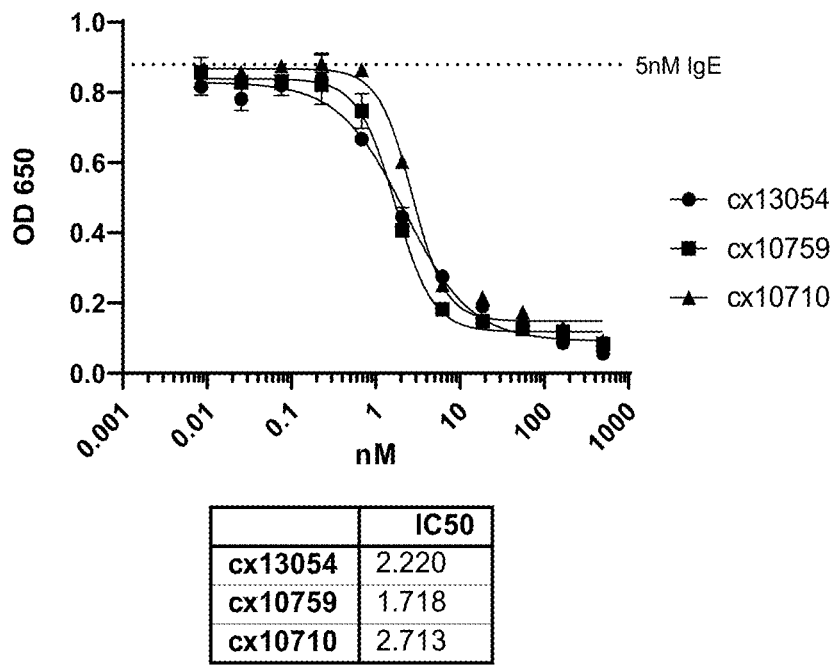
Figure 6E:
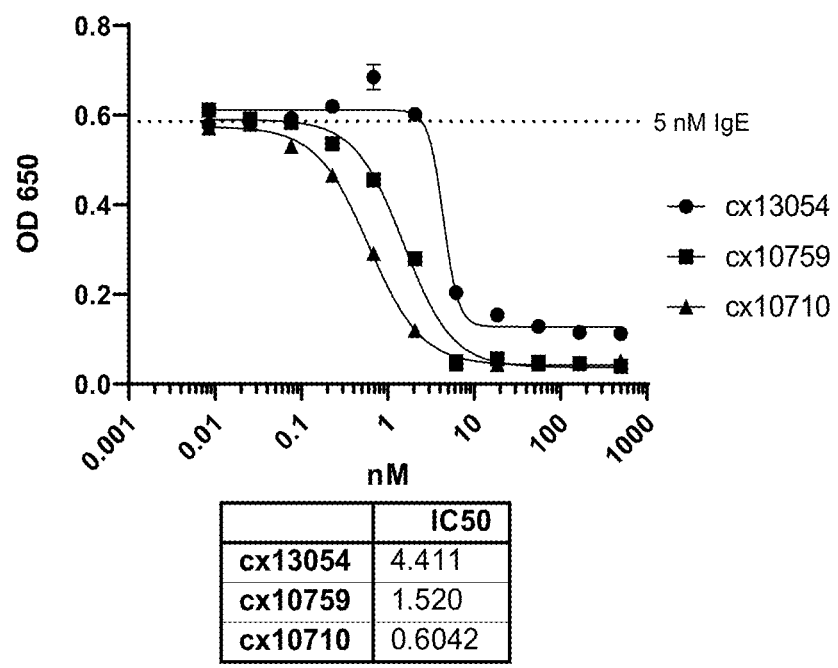
FIG. 6E shows inhibition curves of the indicated antibodies blocking the binding of IgE to FCER2 by ELISA as described in Example 4.

The B10 VHH based anti-IgE sdAb hzB10v40-IgG SELF Fc (cx13054) also binds to human IgE with subnanomolar affinity (FIG. 6C) and blocks soluble IgE binding to FCER1A with a similar potency to the two comparator antibodies (FIG. 6D). The B10 VHH based anti-IgE sdAb was seen to block IgE binding to FCER2 (CD23) at 2:1 ratio (antibody:IgE), but when B10 VHH was at a lower molar concentration than IgE, an increase in IgE bound to the surface was observed (FIG. 6E). Without being bound to any particular mechanism this may be due to the B10 based antibody forming larger complexes with IgE that can bind through a free CD23 binding site as there is not enough B10 to block both sides of the IgE polypeptide. CD23 binds to both sides of an IgE, so if B10 is not saturating, the B10:IgE complexes can associate with CD23.

In another study, a variant of hzB10v40, called hzB10v40.52, was generated with the sequence set forth in SEQ ID NO: 101. This variant was expected to have a lower likelihood of immunogenicity than hzB10v40, according to a computational algorithm. hzB10v40.52 was fused with an Fc domain that contains the SELF mutations, forming a polypeptide having the amino acid sequence of SEQ ID NO: 112 (hzB10v40.52-SELF). This construct was compared with hzB10v40-SELF in an IgE binding ELISA assay and an FCER1A blocking assay.

For the IgE binding ELISA assay, test articles were diluted in PBS-T and titrated (eleven-point) across the plate 1:3 in duplicate with a final, starting concentration of 100 nM. For the IgE blocking ELISA assay, test article dilutions were pre-complexed with Abcam IgE diluted in PBS-T and incubated at room temperature for 1-hour. 100 µL of this mixture of test article:IgE was added to the FCER1A coated, BSA blocked medisorp plates. The final concentration of IgE was 5 nM for all samples and the test articles were titrated (eleven-point) across 1:3 in duplicate with a final, starting concentration of 500 nM. Incubation, washes, and detection was performed similarly as described above in this Example 4. The apparent affinity of the observed binding interaction (Kd in nM) was determined using the One Site as described above, and the IC$_{50}$ values were determined by the default curve fitting as described above.

Figure 6F:
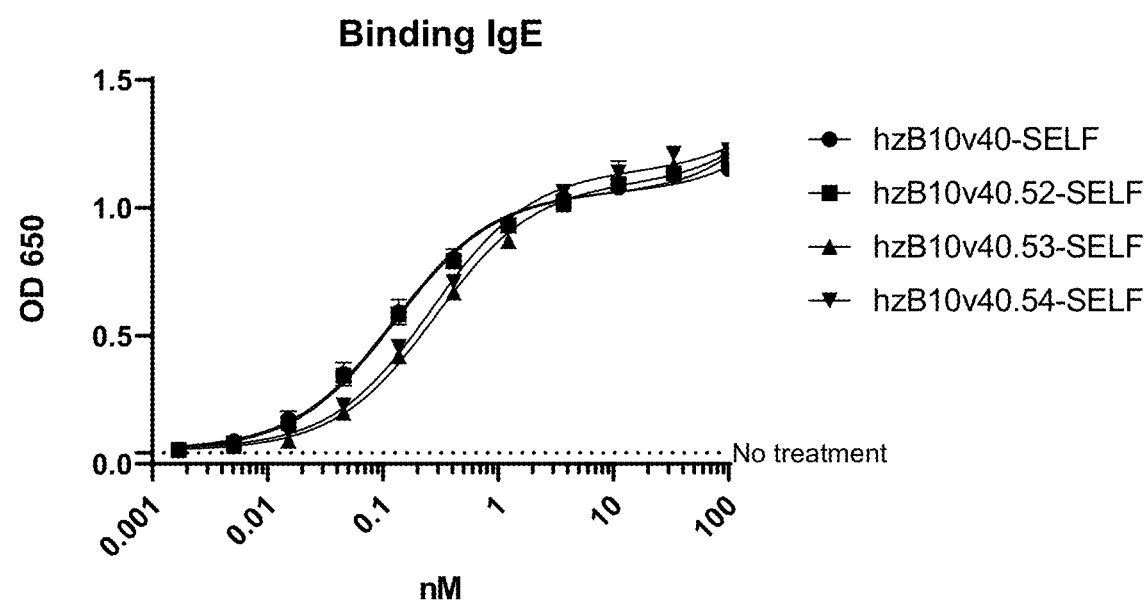
FIG. 6F shows binding curves of hzB10v40-SELF and hzB10v40.52-SELF to human IgE.
Figure 6G:
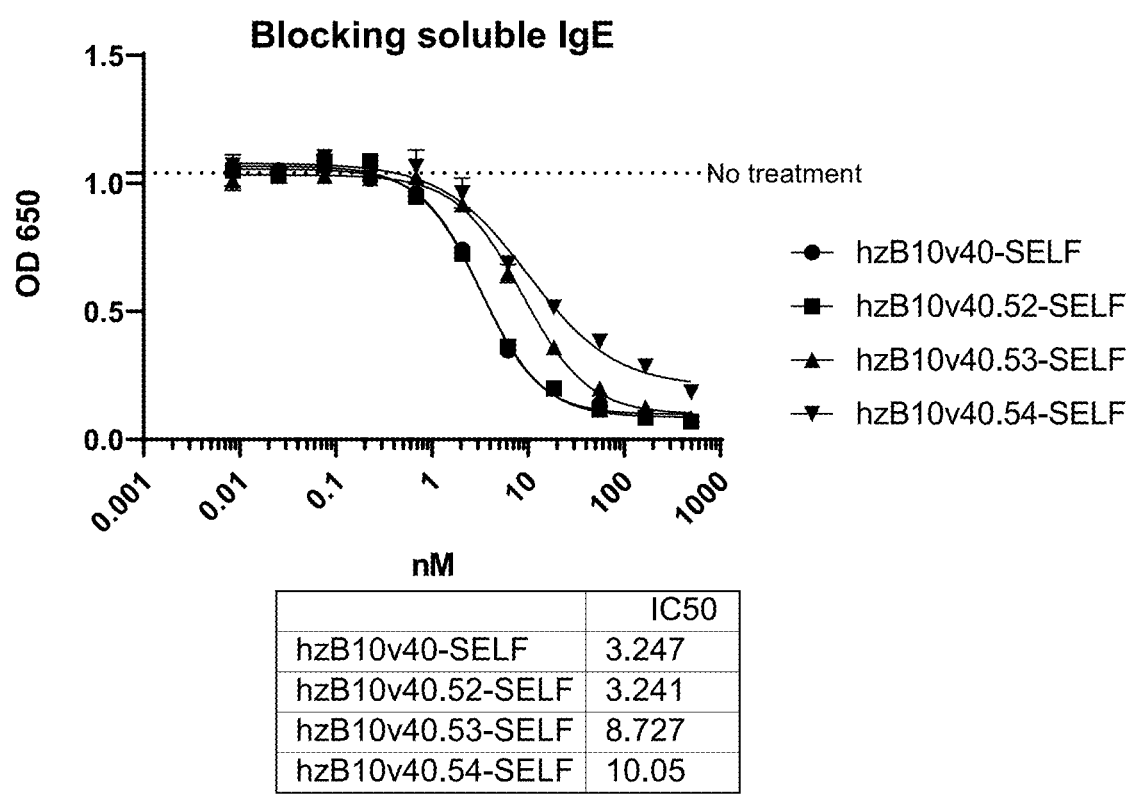
FIG. 6G shows inhibition curves of hzB10v40-SELF and hzB10v40.52-SELF to block the binding of IgE to FCER1A.

As shown in FIG. 6F, hzB10v40.52-SELF bound IgE with subnanomolar affinity, at a similar affinity as hzB10v40-SELF. In addition, as shown in FIG. 6G, hzB10v40.52-SELF blocked soluble IgE binding to FCER1A with a similar IC$_{50}$ as hzB10v40-SELF.

Example 5: Inhibition of IgE Binding to Mast Cells and Binding to IgE Pre-Complexed to FCER1A on Mast Cells Following a 10-week protocol described by Madeleine Radinger et. al, *Current Protocols in Immunology* 2010, (91:7.38.1-7.38.9), cryopreserved human mobilized peripheral blood CD34+ stem cell progenitors from two normal healthy donors (Stemexpress Cat #MLEG34005C) were thawed and differentiated in vitro into mast cells. First, the progenitor cells were stimulated with interleukin 3 (IL-3), interleukin 6 (IL-6), and recombinant human stem cell factor (rhSCF) for one week of culture in StemPro™-34 SFM media (Gibco Cat #10639011). After this period of time, the cells were expanded in volume with StemPro™ 34 SFM cell culture media that contained only IL-6 and rhSCF for a duration of 8 weeks. By week 10 at full differentiation, these cells expressed a combination of surface cell receptors that are distinct to human mast cells, including FCER1A. The in vitro derived mast cells are also capable of being activated and undergoing degranulation upon crosslinking of FCER1A.

Representative B10 VHH based anti-IgE sdAbs, hzB10v40-IgG DSELF Fc (cx13032) and a related construct hzB10v40-IgG SELF Fc comprising the same VHH linked to a human IgG1 SELF Fc region (cx13054, SEQ ID NO: 86), were tested for the ability to block soluble IgE from binding the in vitro derived mast cells described above. The hzB10v40 antibodies were pre-complexed with IgE (5 nM final, Abcam ab65866) and incubated in FACS buffer at room temperature for 30 minutes. Eleven point, four-fold dilutions (starting at 500 nM, in FACS buffer) of the complexed antibodies were added to the mast cells (25 k cells/well) and incubated for 60 minutes at room temperature. The cells were then washed and stained with secondary detection antibodies (IgE-APC and anti-FCER1A-FITC) and incubated for 30 minutes at room temperature. Next, the mast cells were washed twice, and bound antibodies were detected via flow cytometry (Novocyte). The data was plotted using GraphPad Prism analysis software. The IC$_{50}$s were determined by the default curve fitting [Inhibitor] vs. response as described above. Data from a representative donor is shown in FIG. 7A.

Figure 7A:
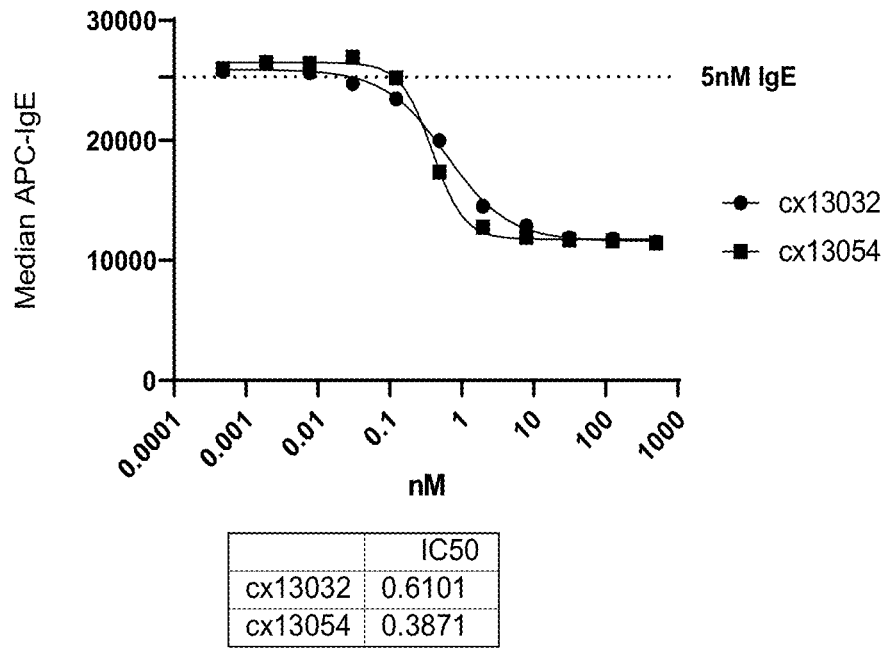
FIG. 7A shows the median fluorescence intensity inhibition curves of the indicated antibodies blocking the binding of IgE to FCER1A on the surface of human mast cells.

As shown in FIG. 7A the B10 VHH based anti-IgE sdAbs, hzB10v40-IgG DSELF Fc (cx13032), and hzB10v40-IgG SELF Fc (cx13054), block soluble IgE binding to FCER1A with a similar potency.

Binding of the B10 VHH based anti-IgE sdAbs, cx13032 and cx13054, to IgE pre-complexed to FCER1A on the surface of mast was also assessed. The binding of the anti-IgE comparator molecules cx10759 and cx10710 were also examined in this study. Mast cells (prepared as described above) pre-treated with 10 nM human IgE (Abcam) in StemPro™-34 media and incubated at 37° C. overnight. The next day, mast cells were washed and plated 25 k cells/well and incubated with titrated anti-IgE antibodies (eleven point, four-fold dilutions starting at 1000 nM in FACS buffer) for 60 minutes room temperature, washed then stained with secondary detection antibodies (anti-hFc-488, and anti-cKit-APC) and analyzed on the Novocyte 3000 flow cytometer. The data was plotted using GraphPad Prism analysis software. Data from a representative donor are presented in FIG. 7B.

Figure 7B:
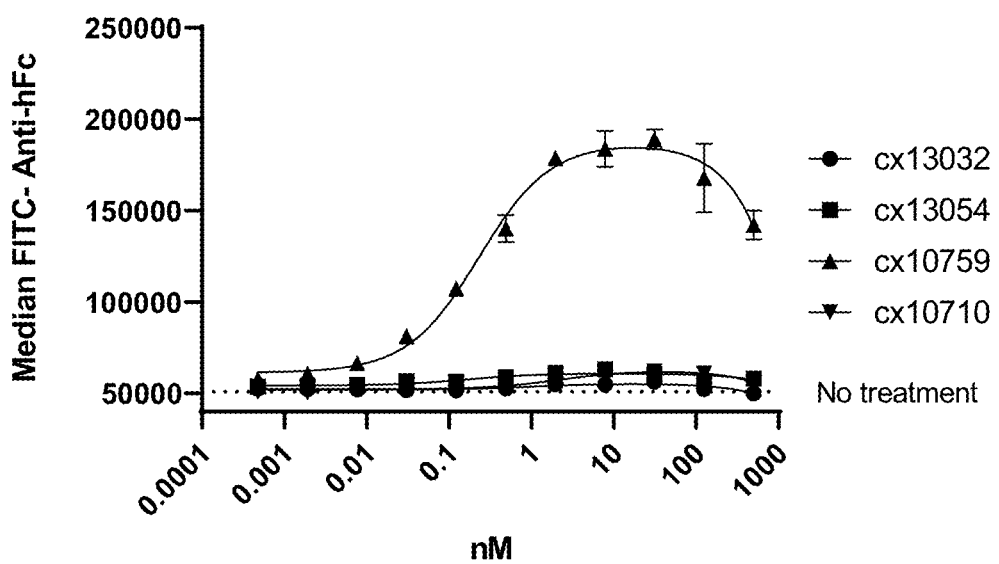
FIG. 7B shows the median fluorescence intensity binding curves of the indicated antibodies binding to human IgE pre-complexed to FCER1A on the surface of human mast cells determined by flow cytometry as described in Example 5.

As shown in FIG. 7B the B10 VHH based anti-IgE sdAbs (cx13032 and 13054), and the conventional antibody comparator, cx10710 do not bind to IgE bound to FCER1A on mast cells. In contrast, the 026 VHH based anti-IgE sdAb comparator, cx10759, showed appreciable binding, such binding can result in direct, antigen-independent activation.

Example 6: Evaluation of Mast Cell Activation

Representative B10 VHH based anti-IgE sdAbs, hzB10v40-IgG DSELF Fc (cx13032) and hzB10v40-IgG SELF Fc (cx13054) were tested for the ability to inhibit mast cell activation and stimulate direct antigen-independent activation of mast cells, using CD63 expression as a marker of mast cell activation. As noted above binding to IgE complexed to FCER1A can result in undesirable direct activation. The activity of one or both of the anti-IgE comparator molecules cx10759 and cx10710 were also examined in these studies.

A recombinant human anti-hapten dinitrophenol (DNP) IgE (rhIgE) capable of inducing activation of mast cells when exposed to a polyvalent DNP-human serum albumin ("DNP-HSA") conjugate was produced using the constant domain sequence of GenBank accession number AAB59424.1. In vitro derived mast cells, cultured as described above, were plated (30 k cells/well) in 96-well tissue culture plates. All incubations in this assay were carried out at 37° C., 5% $CO_2$ in a humidified, water jacketed incubator. For evaluation of inhibition of mast cell activation, the anti-IgE antibodies (cx13032, cx13054 and cx10710) were titrated (nine-point, four-fold dilutions) and equal volumes of 15 nM rhIgE were added to the diluted antibodies and buffer alone controls. The antibody/IgE mixtures were incubated for 30-60 minutes at 37° C., then 50 μL of the IgE/antibody mixture, or 5 nM IgE alone (as a positive control) was added to the mast cells in 50 μL Tyrode's buffer+0.1% BSA and incubated for 30-60 minutes. Supernatants were decanted, and the cells were washed twice in 200 μL Tyrode's buffer+0.1% BSA, then 100 μL DNP-HSA diluted to 50 ng/ml in Tyrode's buffer at 37° C. was added to all but the unstimulated control cells to stimulate activation for 1 hour. The supernatant was removed and the mast cells were stained for CD63 expression using anti-CD63-FITC (Biolegend, Cat #353006) and cKit-APC (Biolegend, Cat #375204). Mast cell activation was determined by assessing CD63 expression by flow cytometry (Novocyte).

For evaluation of direct (antigen-independent) activation, mast cells were plated as described above and incubated with 5 nM rhIgE overnight in StemPro™-34 media. The following day, mast cells were washed and incubated with nine-point, four-fold dilutions of the anti-IgE antibodies (cx13032, cx13054, cx10759 and cx10710) in 100 μL Tyrode's buffer, or buffer alone (positive control wells) for 1 hour. Positive control wells were treated with DNP-HSA. The supernatant was removed and mast cells were stained for CD63 expression as describe above. Mast cell activation was determined by assessing CD63 expression by flow cytometry (Novocyte). The data was plotted and analyzed using GraphPad Prism analysis software. The ICsos were determined by the default curve fitting [Inhibitor] vs. response as described above and are presented in Table 6. Data from a representative donor are presented in FIG. 8A-8B.

Figure 8A:
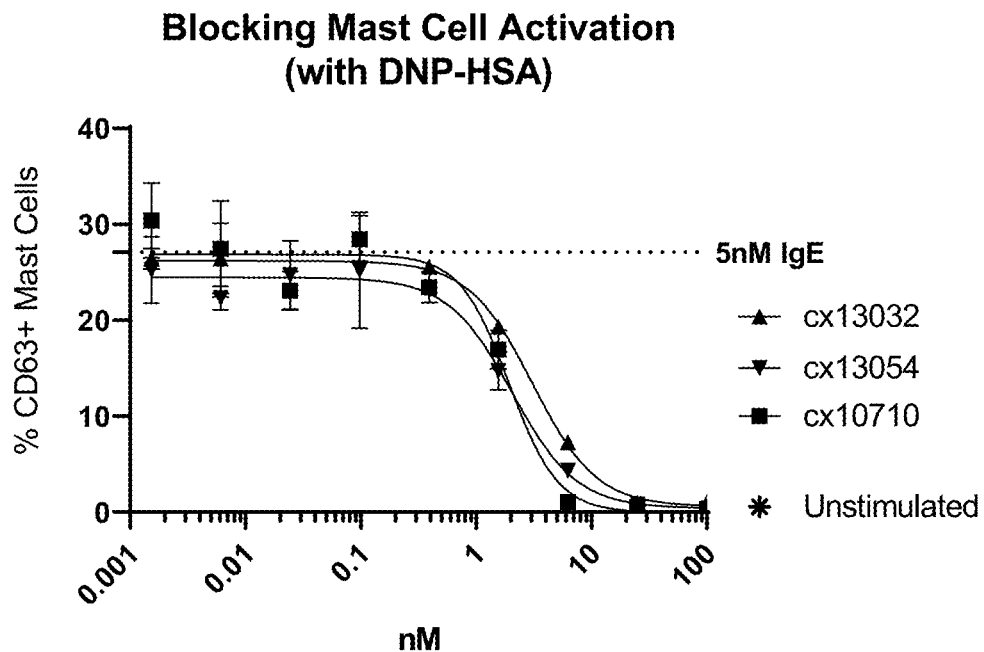
FIG. 8A shows the inhibition of mast cell activation by the indicated anti-IgE antibodies.
Figure 8B:
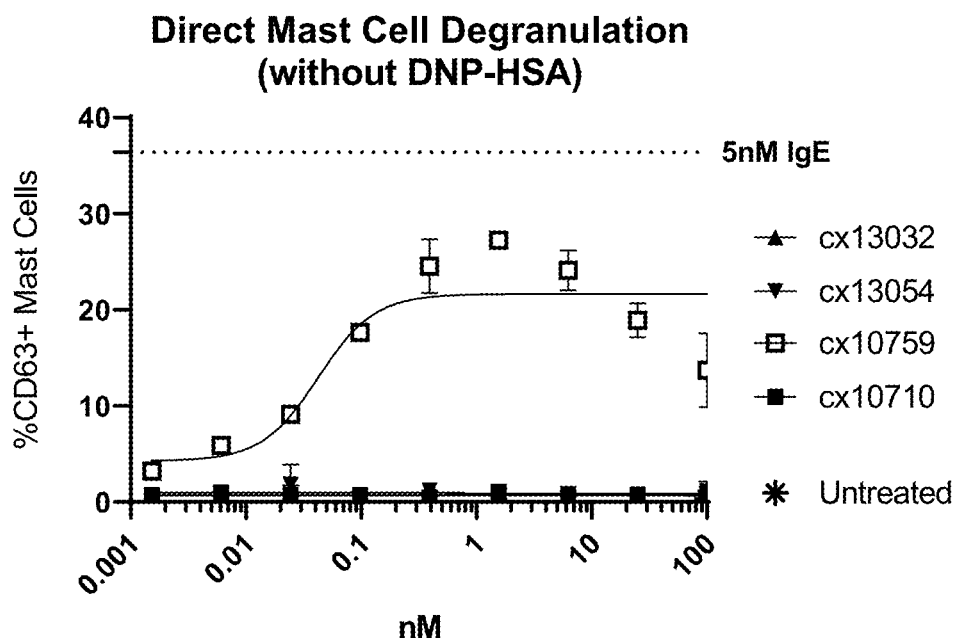
FIG. 8B shows the antigen-independent activation of mast cells by the indicated anti-IgE antibodies using flow cytometry to measure CD63 expression (plotted as % CD63+ mast cells) as described in Example 6.

As shown in FIG. 8A and Table 6, the B10 VHH based anti-IgE sdAbs (cx13032 and cx13054), inhibited antigen-dependent activation of the engineered cells with a similar ICso as cx10710. As shown in FIG. 8B, the B10 VHH based anti-IgE sdAbs (cx13032 and cx13054), did not lead to activation in the absence of DNP-HSA antigen, nor did the conventional antibody comparator, cx10710. In contrast, treatment with the 026 VHH based anti-IgE sdAb comparator, cx10759, led to activation in the absence of DNP-HSA antigen.

TABLE 6

Activation following co-incubation of IgE and antibodies

| Antibody | Activation $IC_{50}$ (nM) | SEQ ID NO(s) |
| --- | --- | --- |
| hzB10v40-IgG DSELF Fc (cx13032) | 3.086 | 85 |
| hzB10v40-IgG SELF Fc (cx13054) | 2.059 | 86 |
| cx10710, comprising IgG1 SELF Fc | 1.929 | 87, 88 |

Example 7: Surface Plasmon Resonance IgE Binding and FCER1A Blocking Assays

Binding of additional representative B10 VHH based anti-IgE sdAbs, hzB10v40-IgG DSELF Fc (cx13032) and hzB10v40-IgG SELF Fc (cx13054), to human IgE directly or to IgE pre-complexed to FCER1A, and the ability to block the binding of IgE to FCER1A was assessed by Surface Plasmon Resonance (SPR). The binding and blocking ability of the anti-IgE comparator molecules cx10759 or cx10710 were also examined in these studies. All experiments were done using a Biacore T200 instrument with a CM5 chip at 37° C. except immobilization of Protein L, which was done at 25° C.

To evaluate binding to IgE immobilized at three different densities, IgE (4.7 μM stock) was used and cx13032, cx13054, and cx10759 (each at 10 μM stock concentration) were used as analytes to flow over the ligand immobilized surfaces. For this study Flow Cell (FC) 1 was used as the reference for FC2, FC3 and FC4. Protein L (15 mg/ml stock concentration) was diluted (1:50 dilution, 0.3 mg/ml diluted concentration) in 10 mM sodium acetate buffer at pH 4.5 and immobilized onto all FCs to a level of ~14000 RU, using the standard amine coupling chemistry. HBS-P (10 mM Hepes, pH 7.4, 150 mM NaCl, 0.05% v/v surfactant P20) was used as the immobilization running buffer. IgE was diluted (1:3750 dilution, ~1.25 μg/ml diluted concentration, low density) in HBS-P captured onto FC2 to a level of ~14 RU (IgE-LD). IgE was diluted (1:375 dilution, ~12.5 μg/ml diluted concentration, medium density comparable to that used in Example 3) in HBS-P captured onto FC3 to a level of ~114 RU (IgE-MD). IgE was diluted (1:37.5 dilution, ~125 µg/ml diluted concentration, high density) in HBS-P captured onto FC4 to a level of ~1400 RU (IgE-HD). HBS-P was used as the capture running buffer. Overnight kinetics were performed for all analytes in the presence of HBS-P. The flow rate of all analyte solutions was maintained at 50 µL/min. The contact and dissociation times used were 120 seconds and 600 seconds, respectively. Glycine pH 1.5 was injected for 20 seconds for surface regeneration. This regeneration condition takes away all captured ligand. Therefore, fresh ligand solution was captured in the beginning of each injection cycle. Injected analyte concentrations are from 80 nM to 0.01953 nM (four-fold dilutions). All analytes were injected in duplicate. Sensorgrams from the overnight kinetics were evaluated by using 1:1 kinetics model fitting.

The binding constants for all the IgE densities are presented in Table 7 and demonstrate that the additional B10 VHH based anti-IgE sdAbs (cx13032 and cx13054) also bind to human IgE with subnanomolar affinity except at the highest IgE density where a very low nanomolar affinity was observed.

test (BAT) to determine whether they crosslink IgE and activate basophils through FCER1A in the absence of antigen. Crosslinking of FCER1A-bound IgE on basophils leads to basophil activation and release of allergy mediators. The capacity of cx13032, cx13054, and the comparator molecules cx10759, and cx10710 to induce antigen-independent signaling through IgE-bound to FcεR1A was determined using a basophil activation test (BAT) (Flow Contract Site Laboratories, Bothell, WA). A 3× working stocks of the anti-IgE antibodies (0.75, 3, and 9 µM) and two positive controls anti-FceR1 mAb (30 mg/mL; clone AER-37 (CRA1), Thermo Fisher) and fMLP (90 nM; Sigma) were prepared in dilution buffer (RPMI 1640 with IVIG (6 mg/ml final)). 50 µL of each 3× test article or dilution buffer alone was placed in duplicate tubes and 100 µl whole blood (collected from donors in sodium heparinized blood collection tubes) was added, and samples were incubated for 30-35 minutes at 37° C. in a water bath. The samples were then placed on ice and 5 µL of cold 3 mM EDTA was added to each tube, followed by 100 µL of 1:500 Zombie Aqua Viability Dye (BioLegend) and 18.5 µL of antibody cocktail

TABLE 7

| Antibody | ka (1/Ms) | kd (1/s) | KD (nM) | Chi² | U-value |
|---|---|---|---|---|---|
| IgE Low Density | | | | | |
| hzB10v40-DSELF (cx13032) | $4.216 \times 10^5$ | $4.495 \times 10^{-4}$ | 0.6 | 0.0199 | 5 |
| hzB10v40-SELF (cx13054) | $5.344 \times 10^5$ | $4.397 \times 10^{-4}$ | 0.8 | 0.0891 | 7 |
| cx10759 | $3.736 \times 10^6$ | $3.842 \times 10^{-4}$ | 0.1 | 0.221 | 9 |
| IgE Medium Density | | | | | |
| hzB10v40-DSELF (cx13032) | $3.726 \times 10^5$ | $2.067 \times 10^{-4}$ | 0.6 | 0.368 | 5 |
| hzB10v40-SELF (cx13054) | $4.150 \times 10^5$ | $2.592 \times 10^{-4}$ | 0.6 | 0.598 | 5 |
| cx10759 | $7.969 \times 10^6$ | $3.711 \times 10^{-4}$ | 0.05 | 1.20 | 5 |
| IgE High Density | | | | | |
| hzB10v40-DSELF (cx13032) | $2.424 \times 10^5$ | $2.583 \times 10^{-4}$ | 1.1 | 13.5 | 2 |
| hzB10v40-SELF (cx13054) | $2.531 \times 10^5$ | $2.498 \times 10^{-4}$ | 1.0 | 18.6 | 3 |
| cx10759 | $1.067 \times 10^6$ | $3.226 \times 10^{-4}$ | 0.3 | 63.7 | 3 |

To evaluate the ability to block IgE binding to FCER1A, FCER1A (His-tagged, 0.4 mg/mL stock) was used as ligand to capture onto the CM5 chip. IgE (5.3 µM stock), cx13054, cx13032 and cx10710 (each at 10 µM stock) were used as analytes to flow over the ligand captured surfaces essentially as described in Example 3 above, except HBS-P (10 mM Hepes, pH 7.4, 150 mM NaCl, 0.05% v/v surfactant P20) was used as the immobilization and capture running buffer, and for all the overnight kinetic runs. For these studies 5 nM IgE alone and 50 nM to 0.39 nM (two-fold dilutions) of cx13032, cx13054, and cx10710 premixed with 5 nM IgE were injected. Sensorgrams from the overnight kinetics were plotted for further evaluation. The inhibition curves are presented in FIG. 9A-9C.

Figure 9A:
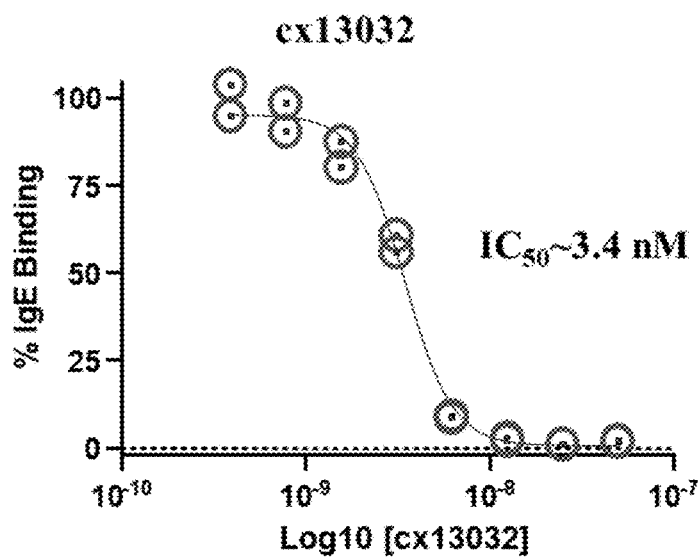
FIGS. 9A-9C show the inhibition curves as determined by Surface Plasmon Resonance (SPR) for the indicated anti-IgE antibodies blocking the binding of IgE to immobilized FCER1A as described in Example 7.
Figure 9B:
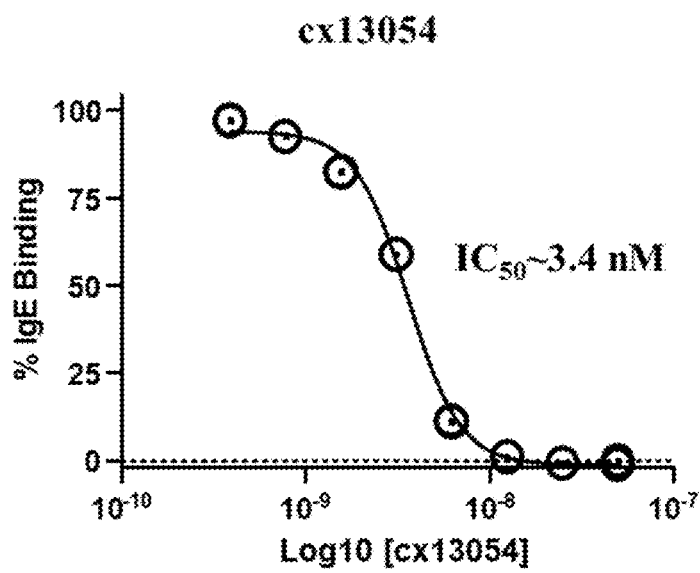
Figure 9C:
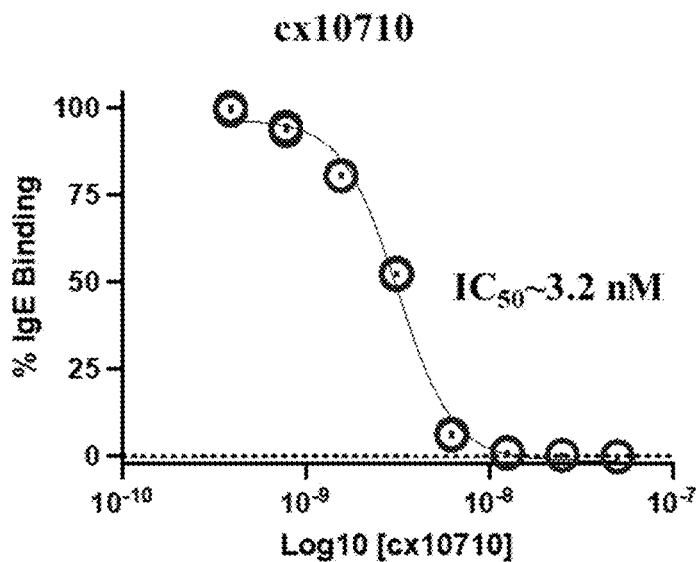

As shown in FIG. 9A-9B the B10 VHH based anti-IgE sdAbs cx13032 (FIG. 9A), and cx13054 (FIG. 9B) blocks soluble IgE binding to FCER1A with a similar potency to the comparator antibody cx10710 (FIG. 9C).

Example 8: Basophil Activation Test (BAT)

Certain IgE binding sdAbs were tested for the ability to activate basophils in whole blood in a basophil activation (CCR3 (5E8-V421); HLADR (L243-PE); CD63 (H5C6-APCCy7); CD203c (NP4D6-PECy7); CD123 (6H6-FITC); and BV510-aqua) and the samples were incubated for 30-35 minutes on ice in the dark. Following incubation, the cells were washed with 3 mL Wash Buffer (Stain Buffer BSA (Becton Dickinson) with 3 mM EDTA (in DPBS buffer)), the supernatant was removed and 4 mL of 1× Pharm Lyse was added, the tubes were vortexed and incubate at room temperature in the dark for 10-12 minutes. Samples were washed again with 3 mL washing buffer and resuspended in 150 µL washing buffer and cell populations were examined by flow cytometry (FACSCanto™ or FACSCanto™) and analyzed with BDFACSDiva™ software, by gating on CCR3 CD123 HLADR-basophils and reporting mean fluorescence intensities (MFI) for both CD63 and CD203c, which are well established markers for basophil activation. The % CD63 was determined using unstimulated controls to set the positive gate and the data for 12 donors treated with 250 nM, 1 µM, or 3 µM of the anti-IgE antibodies is shown FIG. 10A-10C.

Figure 10A:
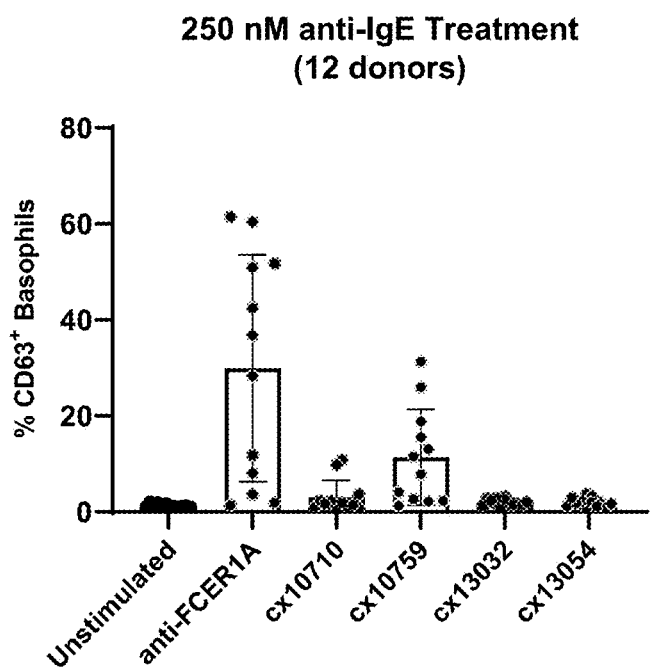
FIGS. 10A-10C show the antigen-independent activation by the indicated anti-IgE antibodies at 250 nM (FIG. 10A), 1 µM (FIG. 10B), or 3 µM (FIG. 10C), in a Basophil Activation Test (BAT) using flow cytometry to measure CD63 expression (plotted as % CD63+ basophils) from whole blood of 12 donors, as described in Example 8.
Figure 10B:
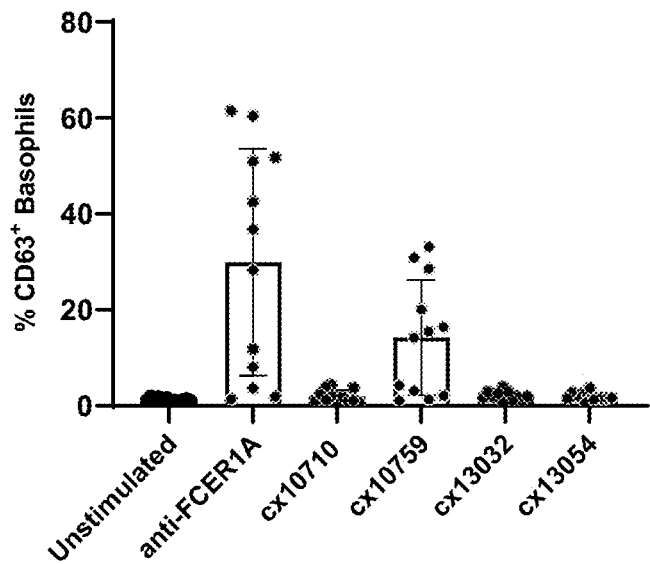
Figure 10C:
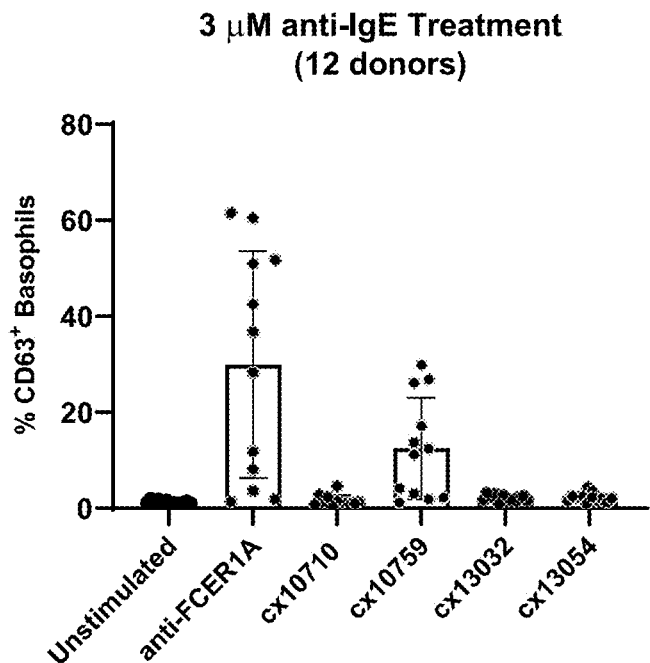
Figure 10D:
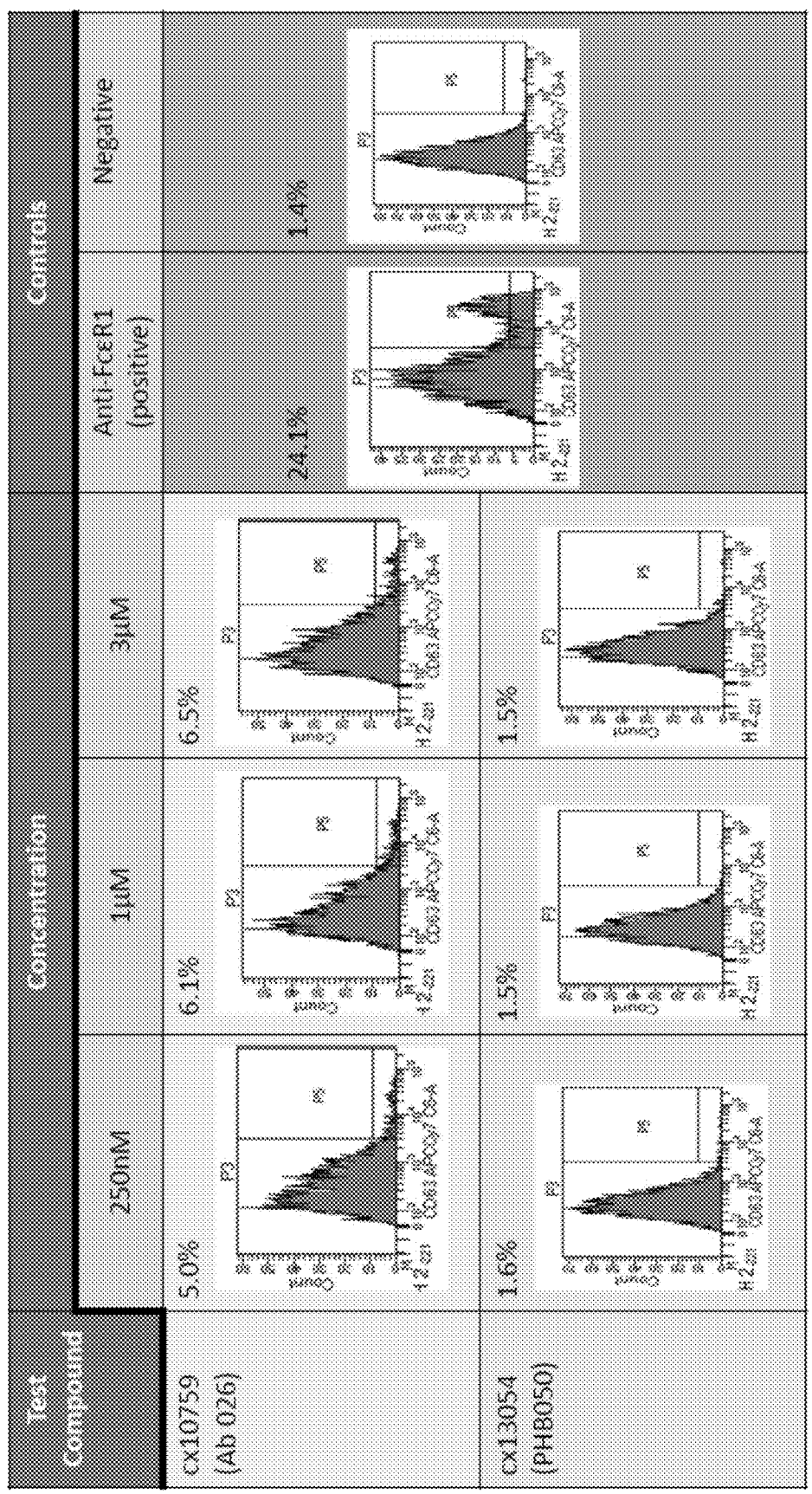
FIGS. 10D-10G show histograms of CD63 expression in a BAT assay using whole blood of four additional donors, as described in Example 8.
Figure 10E:
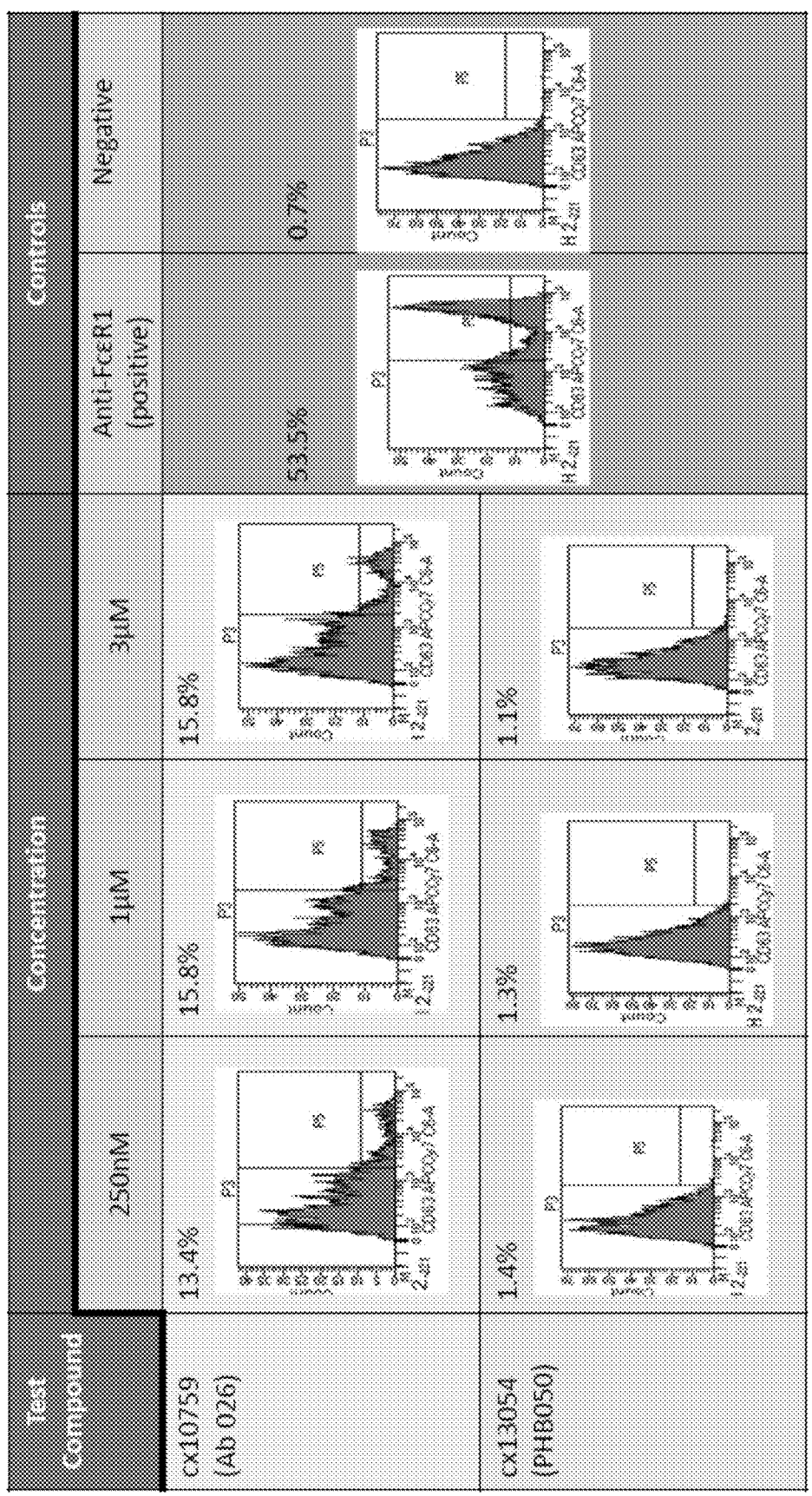
Figure 10F:
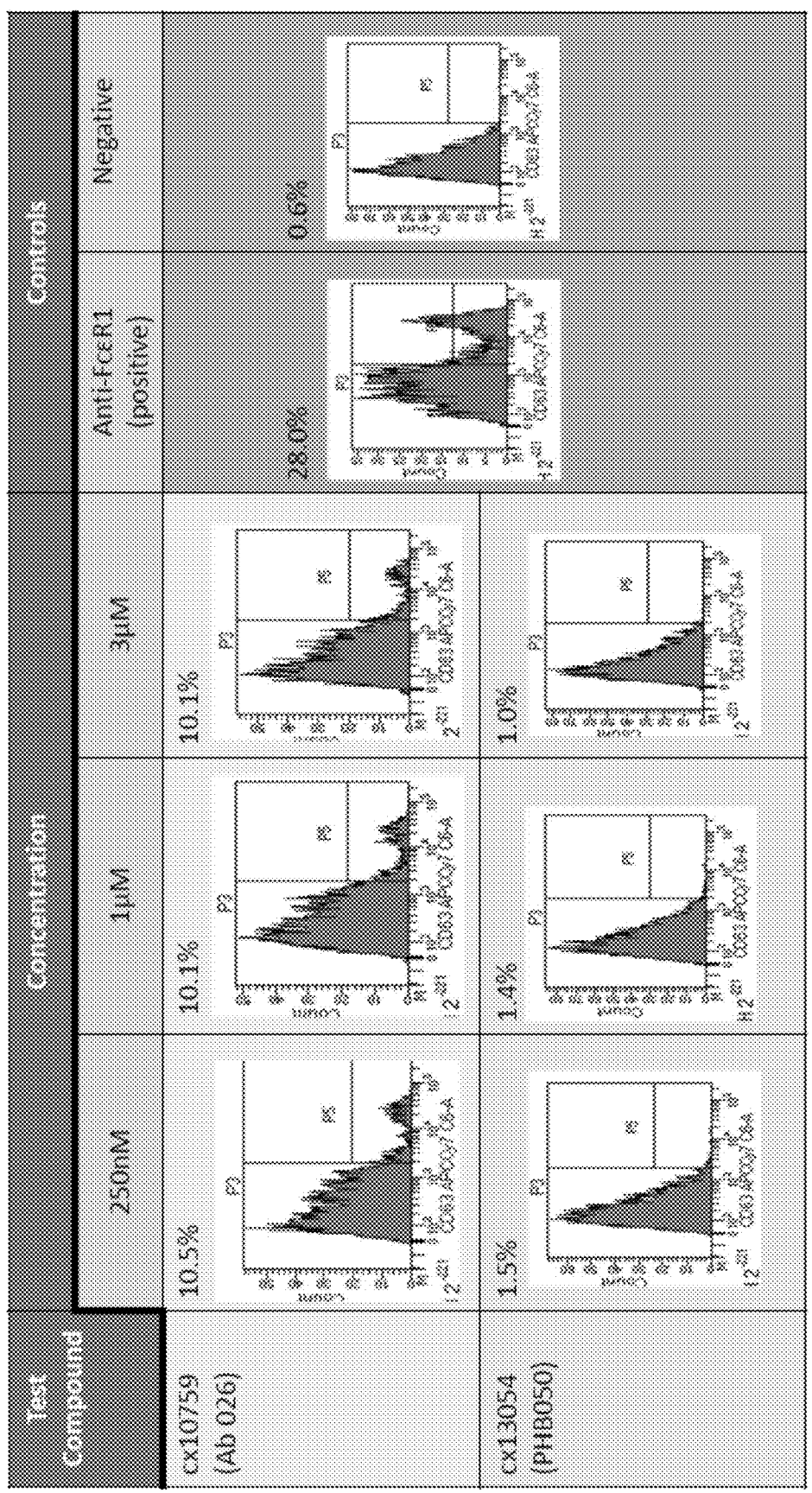
Figure 10G:
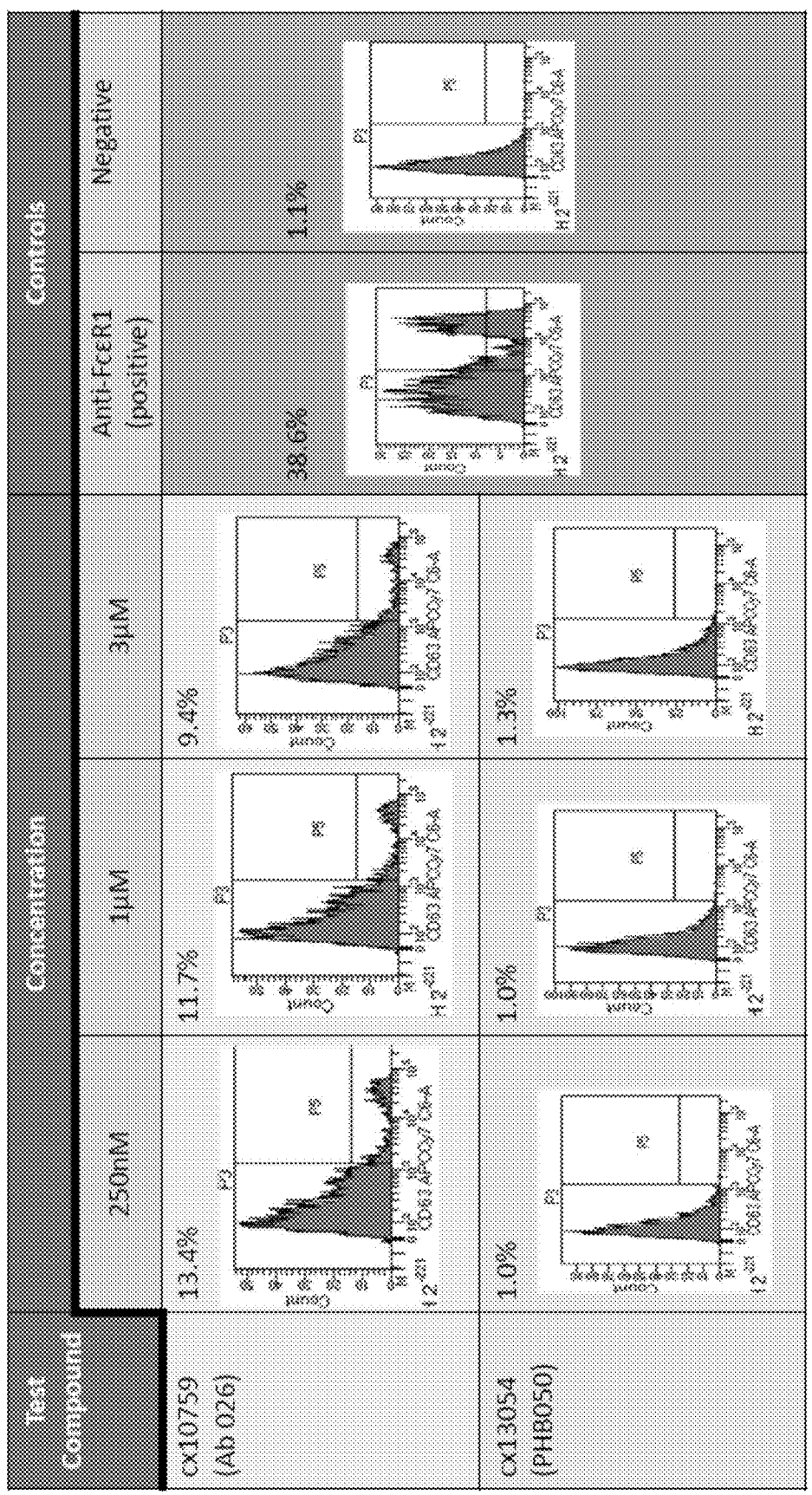

As shown in FIG. 10A-10C, no significant upregulation of CD63 was observed for basophils incubated with hzB10v40-

IgG1 DSELF Fc (cx13032) or hzB10v40-IgG1 SELF Fc (cx13054) for any of the donors examined indicating that the B10 derived antibodies did not induce antigen-independent basophil activation over a broad range of concentrations. While no significant upregulation was observed for the conventional antibody comparator (cx10710), the 026 based sdAb (cx10759) exhibited significant upregulation of CD63 over a broad range of concentrations and among many donors. The positive control, anti-FCER1A is plotted and induced a significant upregulation of the BAT markers.

The whole blood samples from the 12 donors in the study above have various level of sensitivity, due to heterogenicity in the human population. cx13054 and cx10759 were further compared in the basophil activation test (BAT) assay, using whole blood samples from four donors who were known to have higher sensitivity. Upregulation of CD63 in the samples treated with 250 nM, 1 µM, or 3 µM of cx13054 and cx10759 were plotted in histograms. As shown in FIGS. 10D-10G (one figure per donor), cx10759 exhibited significant upregulation of CD63 over a broad range of concentrations in all four donors. This is reflected by not only the induction of a new peak in the P5 gate, which generally corresponds to fully degranulated basophils, but the widening of the main peak that indicates partial degranulation in basophils.

Example 9: Interaction of FceRI:IgE with hzB10v40-IgG1

The ability of a representative B10 VHH based anti-IgE sdAb, hzB10v40-IgG1 SELF Fc (cx13054) to interact with human IgE that was pre-complexed to FceR1A was assessed by Surface Plasmon Resonance (SPR). The ability of an anti-IgE comparator molecule derived from Omalizumab ("cx-Oma") to interact with IgE was also examined in these studies.

Figure 11A:
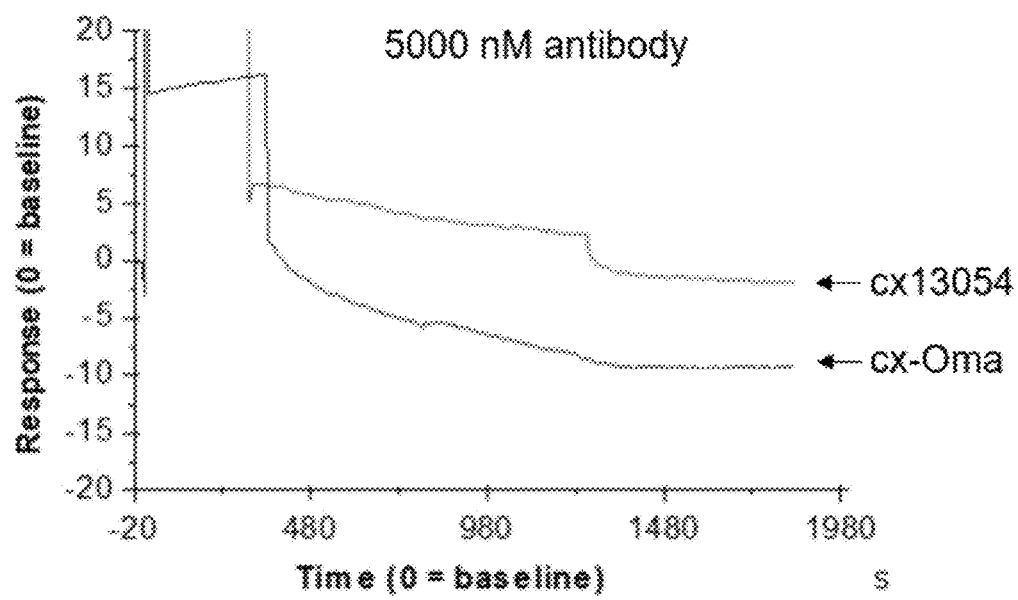
FIGS. 11A-11D show binding of the indicated anti-IgE antibodies to FceR1A:IgE complex by response values over time (seconds, s) as determined by surface plasmon resonance (SPR). Binding of each antibody was tested using analyte concentrations of 5000 nM (FIG. 11A), 1000 nM (FIG. 11B), 100 nM (FIG. 11C), and 10 nM (FIG. 11D).

To evaluate interaction with IgE in complex with FceR1A, the extracellular domain of FceR1A fused with a His tag was amine conjugated to the C1 chip. For each run, fresh IgE was loaded onto the FceR1A-conjugated chip. After formation of the FceR1A:IgE complex, cx13054 and cx-Oma analytes were injected over the ligand immobilized surfaces (at 37° C.) at concentrations of 5000 nM (FIG. 11A), 1000 nM (FIG. 11B), 100 nM (FIG. 11C), and 10 nM (FIG. 11D). The association and dissociation phases lasted 1250 seconds and 600 seconds, respectively. Sensorgrams from the were analyzed to determine displacement of IgE from the FceR1:IgE complex.

Figure 11B:
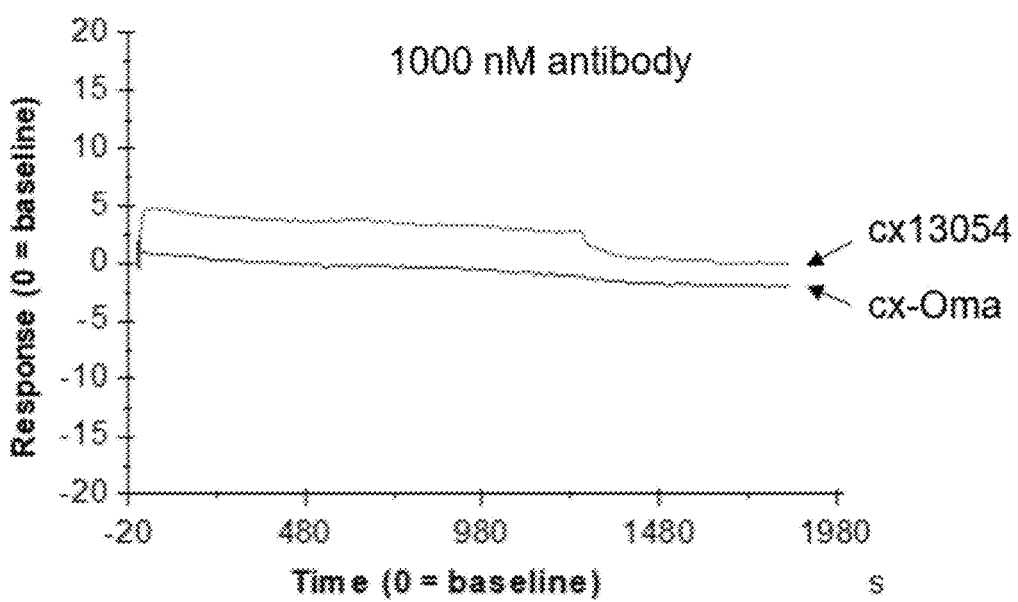
Figure 11C:
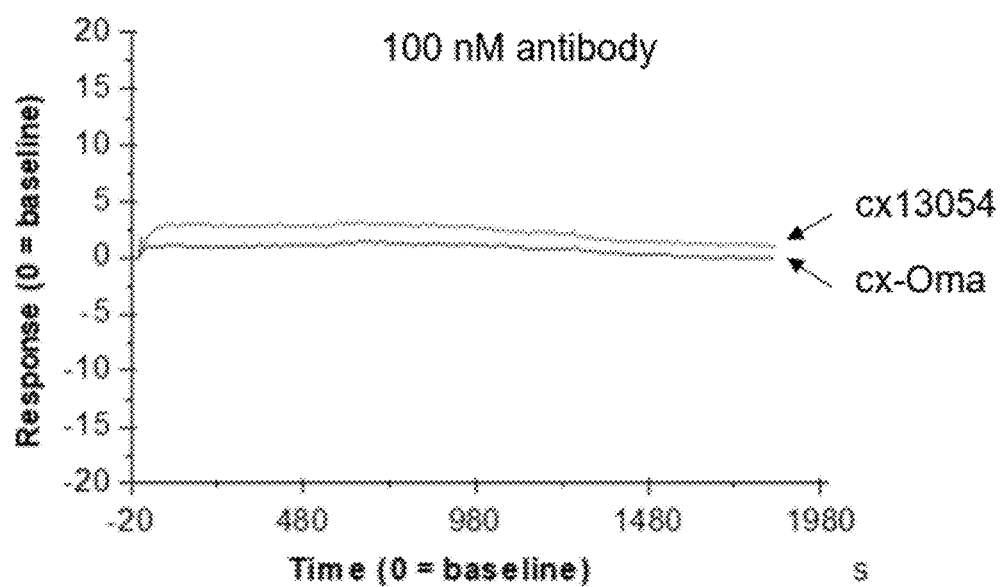
Figure 11D:
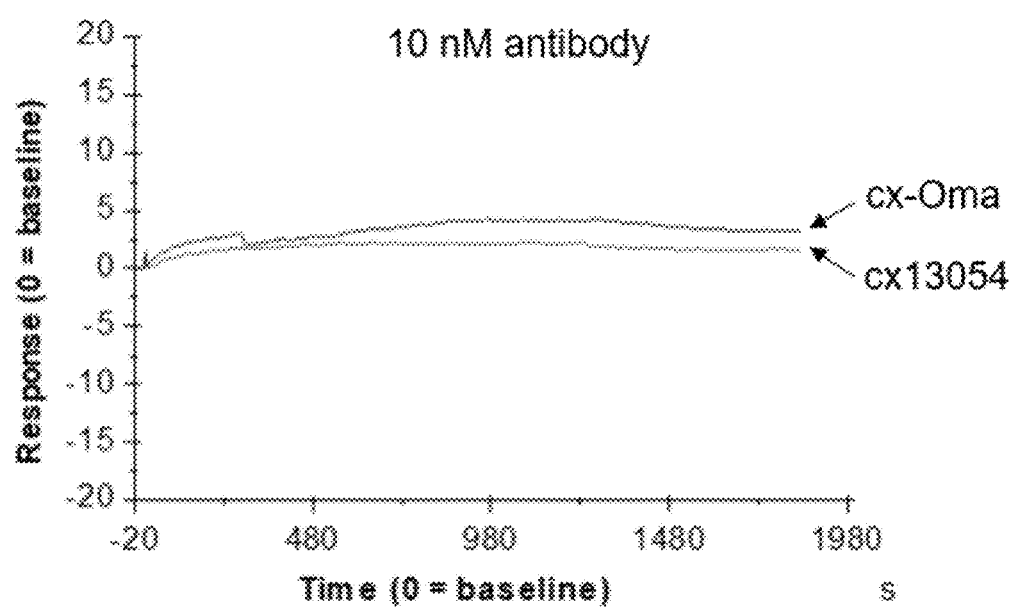

As shown in FIGS. 11B-11D, concentrations of cx13054 or cx-Oma up to 1000 nM had minimal to no interaction with the FceR1:IgE complex. As shown in FIG. 11A, at 5000 nM cx13054 minimally displaced IgE whereas cx-Oma demonstrated a greater relative ability to displace IgE.

Example 10: Competition of hzB10v40-IgG1 with Reference IgE Antibodies

To map a putative binding site of B10 VHH based anti-IgE sdAb, competition of the hzB10v14-IgG1-SELF ("739"; SEQ ID NO: 95) VHH, an analog of hzB10v40, for binding IgE with reference IgE antibodies was assessed by Surface Plasmon Resonance (SPR). The ability of anti-IgE reference antibodies 710 (a derivative of Omalizumab), single-chain Ligelizumab (sc-Ligelizumab) comprising the VH sequence of SEQ ID NO: 96 and the VL sequence of SEQ ID NO: 97, and single-chain 8D6 (sc8D6) comprising the VH sequence of SEQ ID NO: 98 and VL sequence of SEQ ID NO: 99 (also known as UB-221) to displace the 739 VHH from IgE was examined in these studies.

Figure 13A:
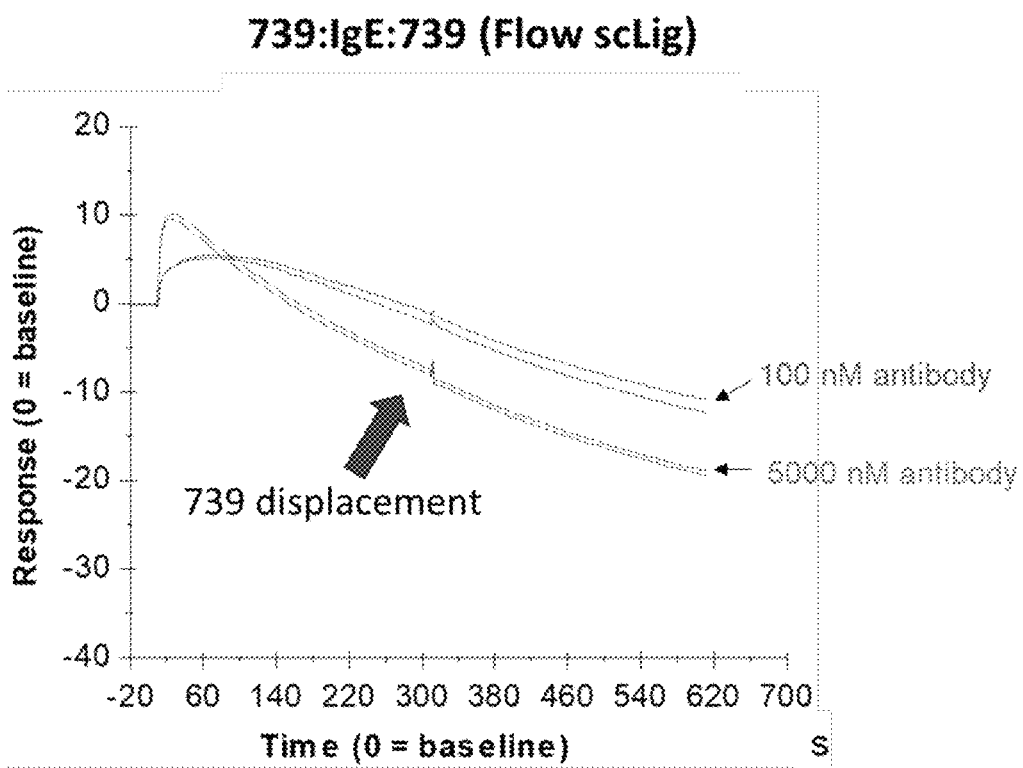
FIGS. 13A and 13B show binding of the indicated anti-IgE antibodies injected over SPR chips conjugated to the indicated antibody-IgE complexes. Response over time (seconds, s) is graphed. The antibody analytes injected over the chip were tested using analyte concentrations ranging from 5000 nM to 1 nM.
Figure 13B:
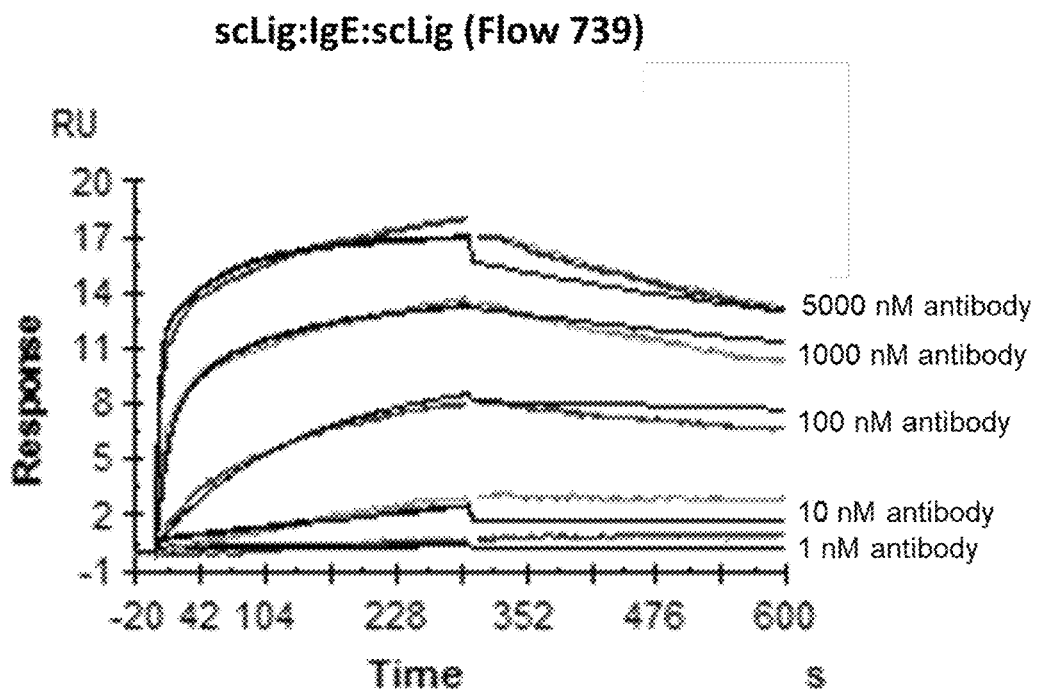
Figure 14A:
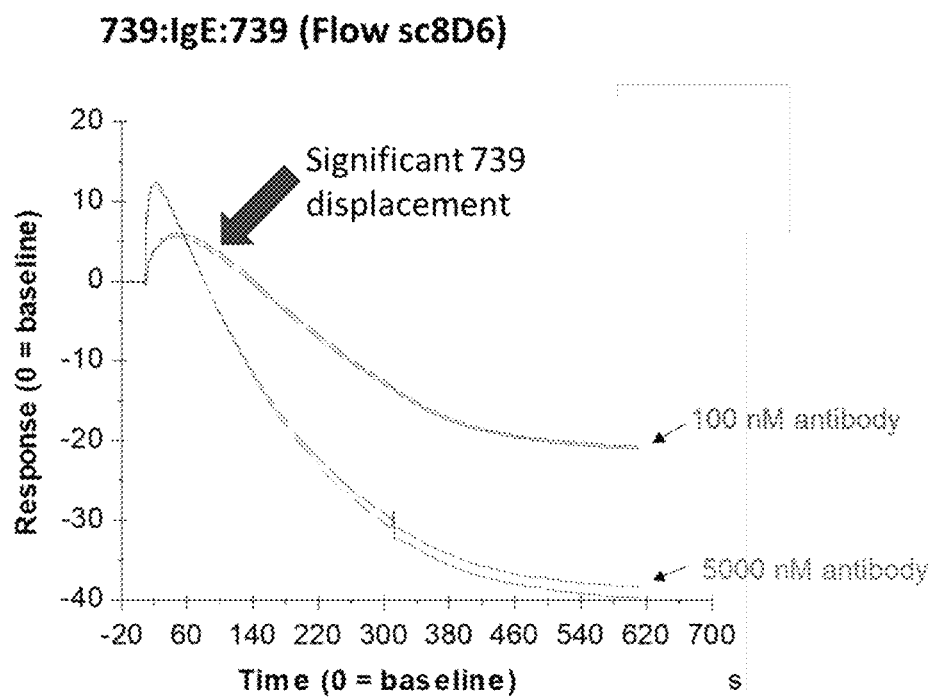
FIGS. 14A and 14B show binding of the indicated anti-IgE antibodies injected over SPR chips conjugated to the indicated antibody-IgE complexes. Response over time (seconds, s) is graphed. The antibody analytes injected over the chip were tested using analyte concentrations ranging from 5000 nM to 1 nM.

All experiments were performed using a Biacore T200 instrument with a CM5 chip. First, the 739 VHH (FIGS. 12A, 13A, and 14A), 710 (FIGS. 12B and 12C), sc-Ligelizumab (scLig) (FIG. 13B) or sc8D6 (FIG. 14B) was amine conjugated to a CM5 chip. The chip surface was then loaded with IgE and subsequently saturated with the same antibody as conjugated to the chip. The surface was then injected with an analyte pulse of the 739 VHH (FIGS. 12B, 12C, 13B, and 14B), 710 (FIG. 12A), sc-Ligelizumab (FIG. 13A), or sc8D6 (FIG. 14A). The analytes were run with about 300 s association and about 300 s dissociation phases. The concentrations of the analytes ranged from 5000 nM to 1 nM. All analytes were injected in duplicate. Sensorgrams were evaluated to determine co-binding to IgE or displacement of the antibody initially bound to IgE.

Figure 12A:
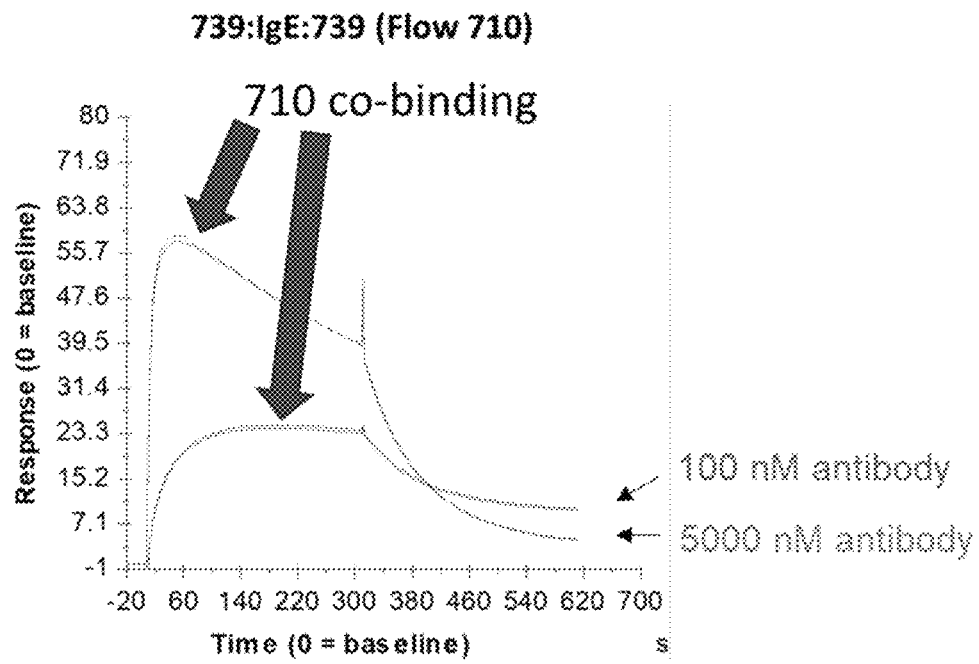
FIGS. 12A-12C show binding of the indicated anti-IgE antibodies injected over SPR chips conjugated to the indicated antibody-IgE complexes. Response over time (seconds, s) is graphed. The antibody analytes injected over the chip were tested using analyte concentrations ranging from 5000 nM to 1 nM.
Figure 12B:
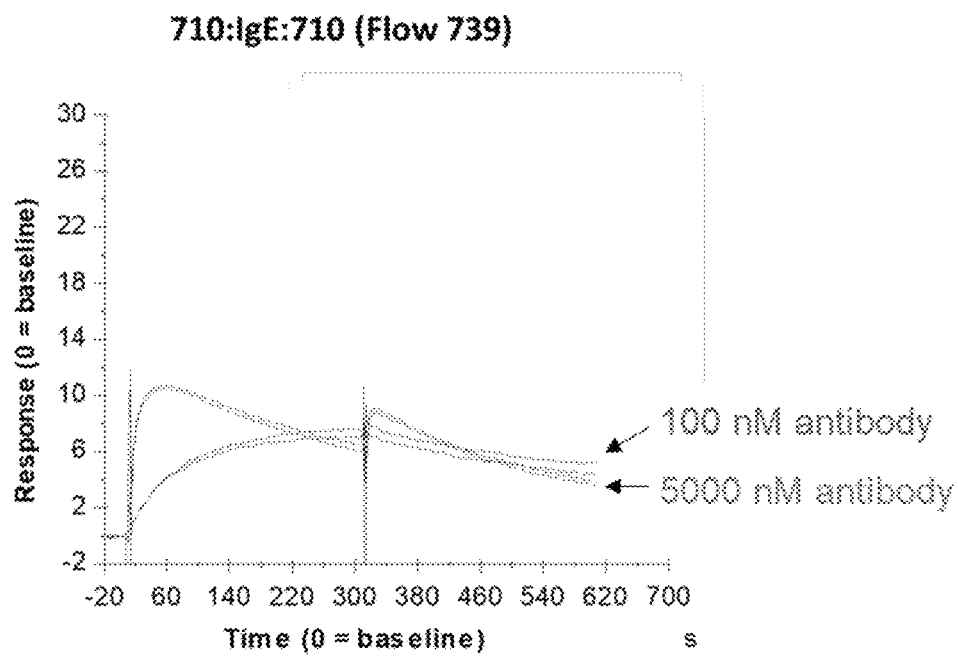
Figure 12C:
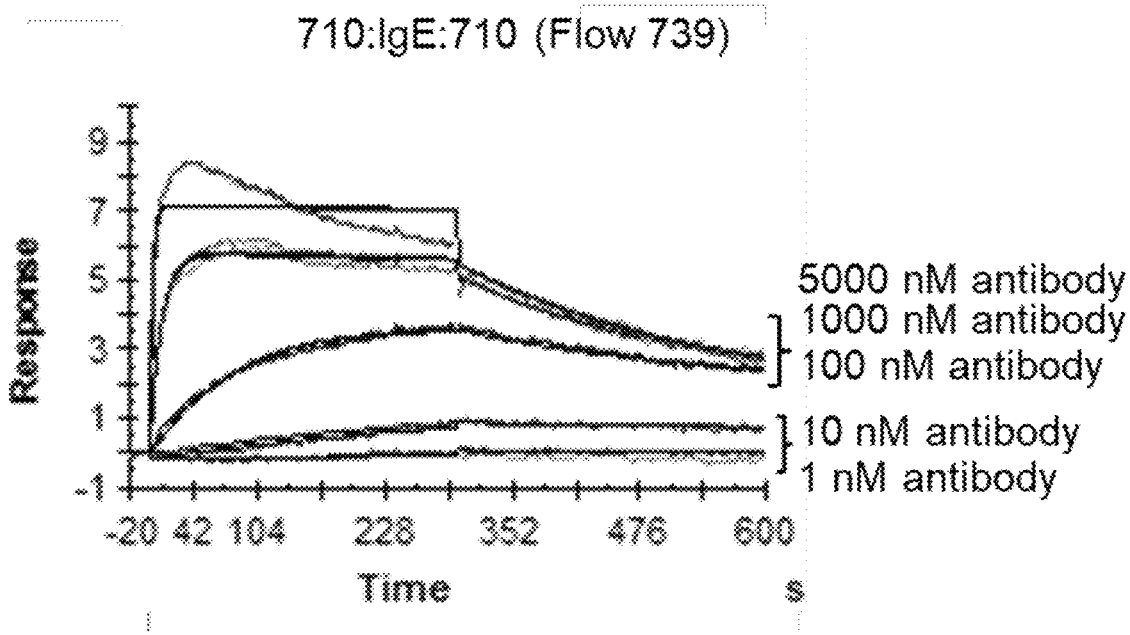
Figure 14B:
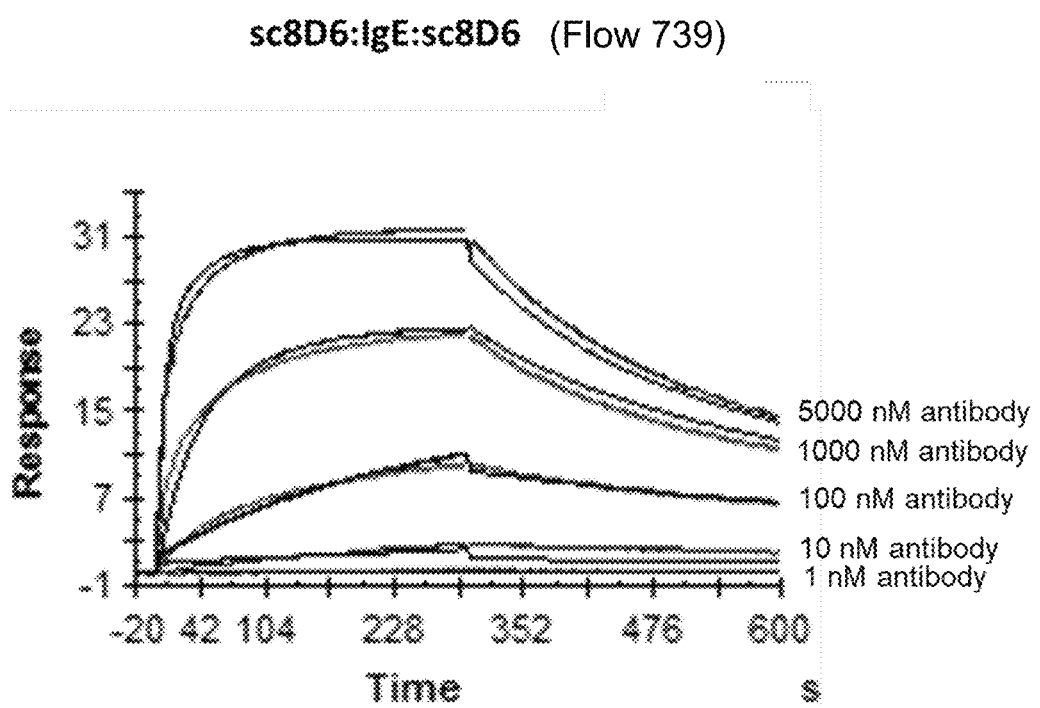
Figure 15A:
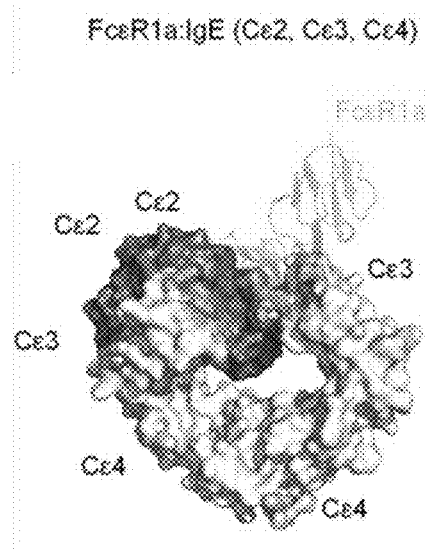
FIGS. 15A-15D show crystal structures of FceR1A (FIG. 15A), 8D6 (FIG. 15B), Ligelizumab (FIG. 15C) or Omalizumab (FIG. 15D) in complex with the indicated IgE Ce domains. The likely B10 antibody binding site is indicated by an arrow in FIG. 15B.
Figure 15B:
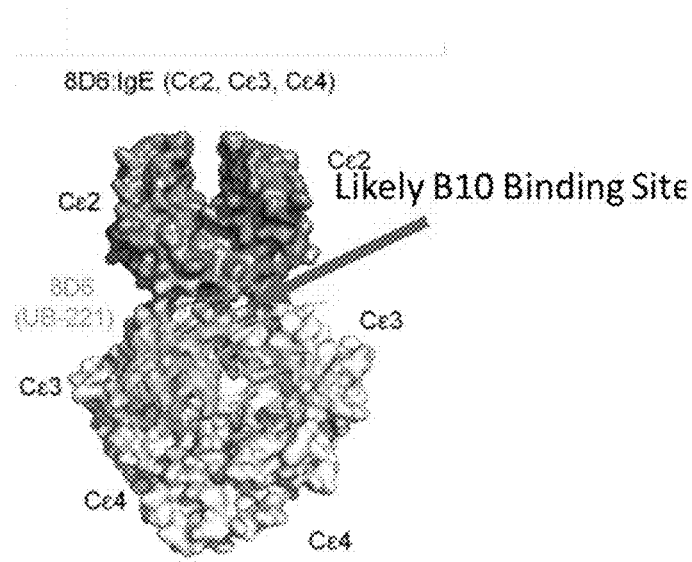
Figure 15C:
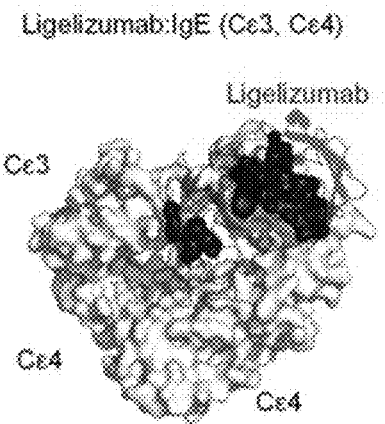
Figure 15D:
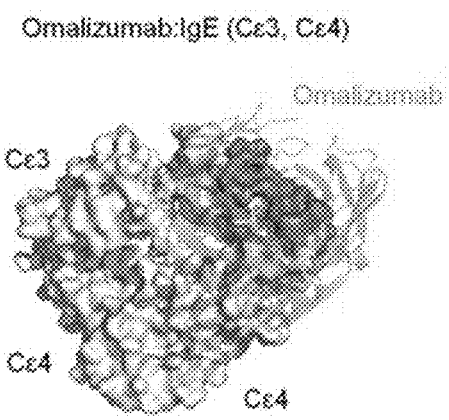

FIGS. 12A-12C show co-binding of the 739 VHH and 710 to IgE. When IgE was first saturated with the 739 VHH and then sc-Ligelizumab was pulsed over the chip, FIG. 13A shows displacement of the 739 VHH from IgE, indicating overlapping binding to IgE of the 739 VHH and sc-Ligelizumab. However, co-binding was observed under the inverse conditions (FIG. 13B). Displacement of the 739 VHH was observed when IgE was first saturated with the 739 VHH and then sc8D6 was pulsed over the chip (FIG. 14A), indicating overlapping binding to IgE of the 739 VHH and sc8D6. However, co-binding was observed under the inverse conditions (FIG. 14B).

FIGS. 15A-15D show the crystal structures of FceR1A (FIG. 15A), 8D6 (FIG. 15B), Ligelizumab (FIG. 15C) and Omalizumab (FIG. 15D) in complex with the indicated IgE CE domain. Based on the competition data, the likely binding site for the 739 VHH, which overlaps with that of ligelizumab and 8D6 but not Omalizumab, is indicated by the arrow in FIG. 15B.

Example 11: Parsimonious Mutagenesis Mapping of the B10 VHH Paratope

Figure 16A:
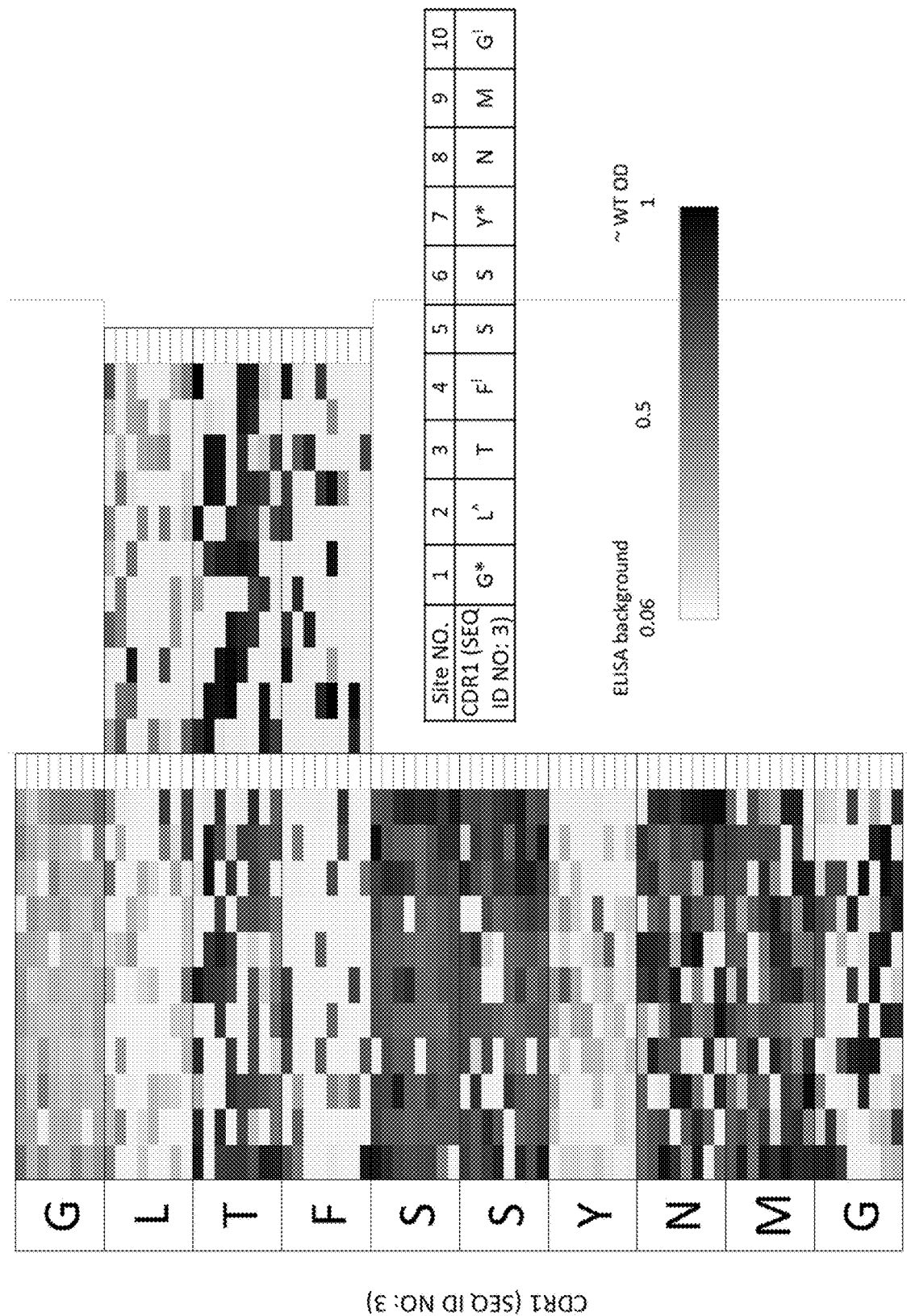
FIGS. 16A-16C show heat maps of OD values as determined by ELISA for hzB10v40 VHH variants randomly mutagenized individually in CDR1 (SEQ ID NO: 3.
Figure 16B:
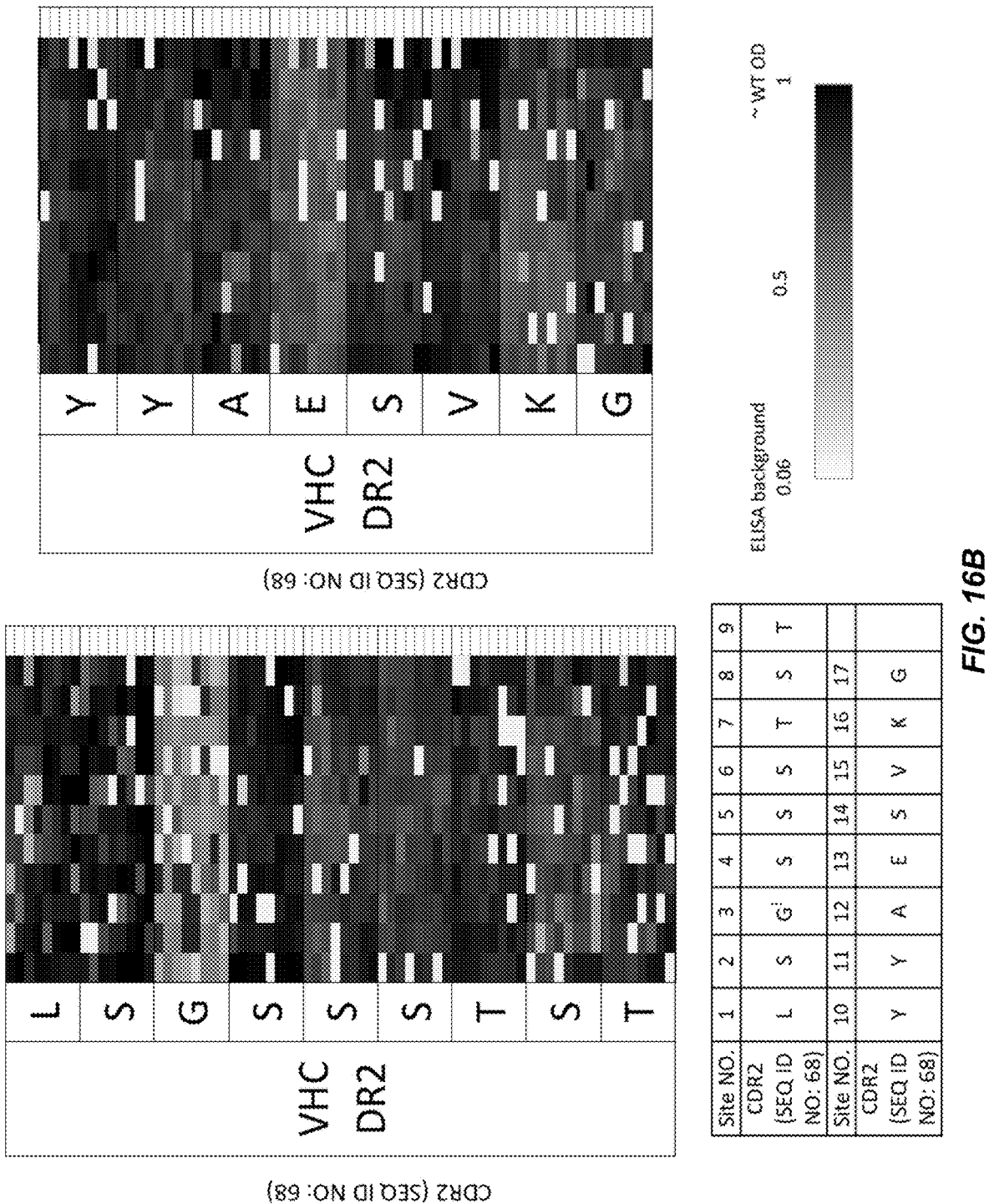
Figure 16C:
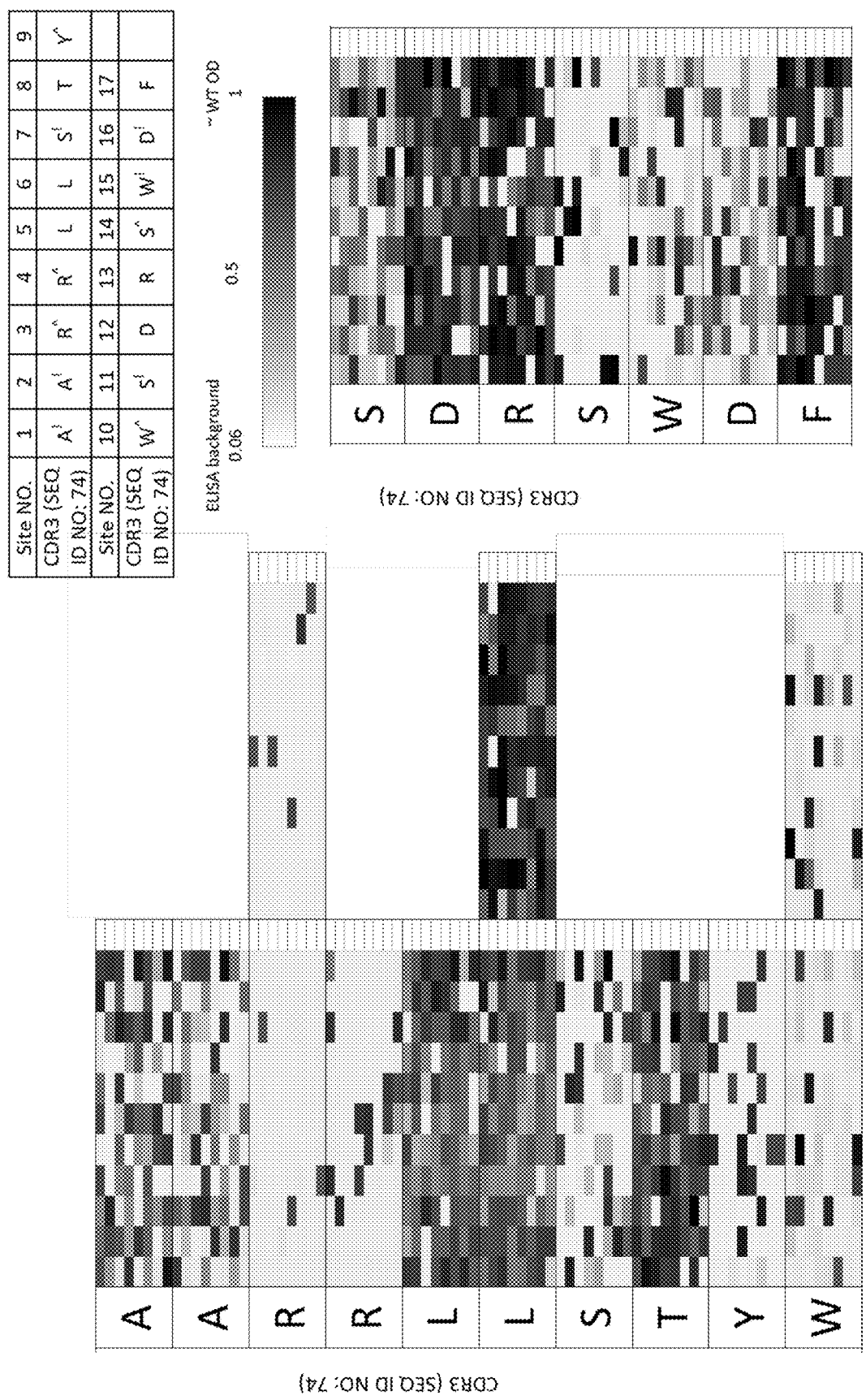
Figure 17A:
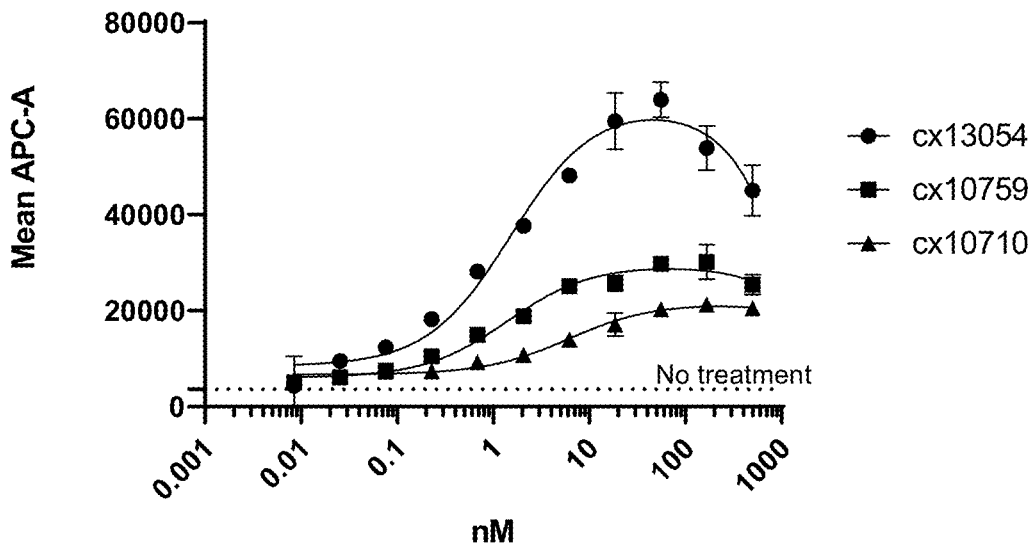
FIG. 17A shows binding curves of the indicated anti-IgE antibodies binding to human IgE complexed to FceRII on the surface of RPMI 8866 cells, as assessed by flow cytometry. Bmax and Kd values for the indicated anti-IgE antibodies are shown below the graph.
Figure 17B:
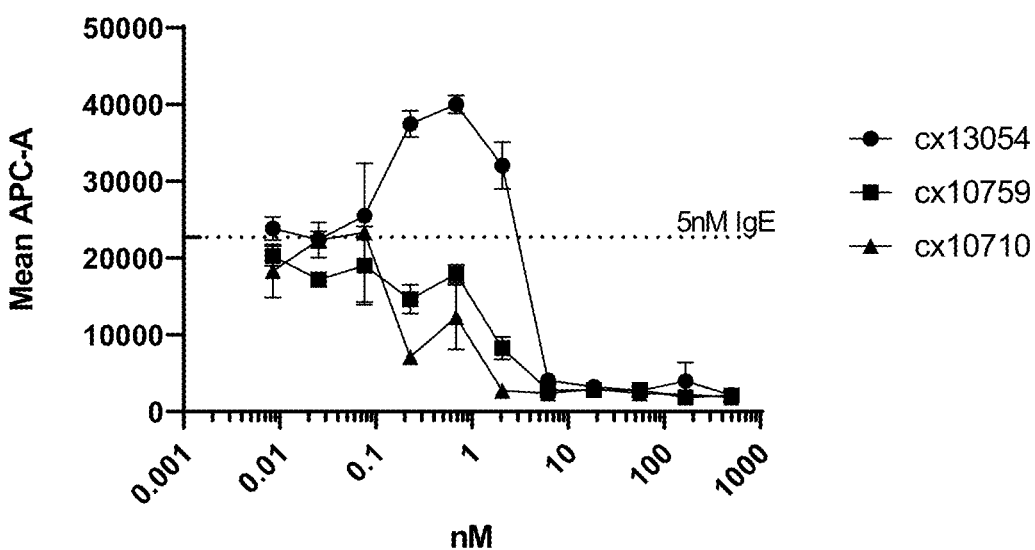
FIG. 17B shows binding curves of 5 nM of IgE, when pre-complexed with the indicated anti-IgE antibodies, to CD23 on the surface of RPMI 8866 cells, as assessed by flow cytometry.

To determine B10 VHH paratope residues important for binding IgE, exemplary CDRs were randomly mutagenized and evaluated for ability to bind IgE. Each amino acid in CDR1 (SEQ ID NO: 3), CDR2 (SEQ ID NO: 68), and CDR3 (SEQ ID NO: 74) was randomly replaced such that the 20 natural amino acids would likely all have been sampled at every position. The expression vector for the VHH containing the mutagenized CDRs was then transfected into *E. coli*, and at least 96 clones were randomly chosen for each position mutated in each CDR. This gives likely coverage of all potential mutations at each position since the probability to get any given amino acid at that position is 5%. Each clone was lysed and the lysate was tested for binding to the plate bound IgE by ELISA. The heat maps represent the relative binding for each clone determined by the range of OD values from the ELISA background to WT CDR binding (FIGS. 16A-16C). Site numbering for each residue tested is indicated by the inset tables in FIGS. 16A-16C. Positions where changes led to complete loss of binding are indicated with a "*", positions where changes led to almost complete loss of binding are indicated by "^", and positions where changes led to partial loss of binding are indicated by "!." Clones which had equal or greater binding relative to the parent B10 VHH CDRs were sequenced, and binding affinity was verified two more times.

Analysis of ELISA results for the CDR1 screen (FIG. 16A) demonstrated that changes to sites 1 and 7 of SEQ ID NO: 3 led to complete loss of binding to IgE, and a change to site 2 led to almost complete loss of binding to IgE. Altering residues 4 and 10 of SEQ ID NO:3 led to partial binding loss. Mutation of most residues of CDR2 had little effect on binding to IgE (FIG. 16B). However, altering site 3 of SEQ ID NO: 68 did lead to partial loss of binding with IgE. For CDR3 (SEQ ID NO: 74), changes to sites 3, 4, 9, 10, and 14 led to almost complete loss of binding to IgE (FIG. 16C). Partial loss of IgE binding was observed with alteration of sites 1, 2, 7, 11, 15, and 16 of SEQ ID NO: 74.

These data show that CDR2 has minimal to no interaction with IgE, since almost all of the amino acid changes were well tolerated. Therefore, hzB10v40 VHH binding to IgE is primarily dictated through residues in CDR1 and CDR3, in which mutation of certain residues lead to loss of IgE binding.

Selected mutations in CDR1 and CDR3 that retained VHH binding to IgE are shown in FIGS. 16D and 16E, respectively. Consensus CDR sequences were created based on these mutations, as set forth in Table 2D supra. Table 2D does not include CDR1 consensus sequences under Kabat, Chothia, or IMGT definition, given that the CDR1 sequences under these definitions do not include all the invariant position corresponding to site 1 of SEQ ID NO:

Example 12: Binding and Blocking of hzB10v40-IgG1 SELF with IgE and FCERII/CD23

The ability of a representative B10 VHH based anti-IgE sdAb, hzB10v40-IgG1 SELF Fc (cx13054), to interact with human IgE that was pre-complexed to the low-affinity FceRII/CD23 on the surface of RPMI 8866 cells was assessed by flow cytometry. In addition, the ability of the representative B10 VHH based anti-IgE sdAb, hzB10v40-IgG1 SELF Fc (cx13054) to block soluble IgE from binding to CD23 on the surface of RPMI 8866 cells was assessed by flow cytometry. RPMI 8866 cells are a B cell lymphoblastoid cell line that expresses FceRII on the cell surface but lack FCER1A and are a useful in vitro model to assess IgE interactions with CD23. The ability of anti-IgE comparator molecules cx10759 and cx10710 to interact with/block soluble IgE was also examined in these studies. To assess binding to IgE pre-complexed to CD23, ~10 million RPMI 8866 cells (ECACC Cat #95041316) were mixed with 10 nM human IgE (Abcam Cat #ab65866) and incubated overnight in complete media at 37° C., 5% CO2. The next day the cells were washed with FACS buffer (50 mM Tris-Cl, 150 mM NaCl, 1% Fetal Bovine Serum, 0.02% Sodium Azide, pH 7.6) to remove any remaining unbound, soluble IgE. The washed cells were diluted to $0.8\times10^6$ cells/mL. 50 μL of this cell suspension was then transferred to wells of a round-bottom 96-well assay plate (40 k cells/well). 50 μL of titrated test articles (diluted to 1 μM and titrated across 1:3 in FACS buffer) were added to the RPMI 8866 cells which produced a 2-fold dilution of the antibody concentrations from the titration series. The final starting concentration was 500 nM with a total of 11 points in the titration. After a 30 minute incubation with the test article titrations, the RPMI 8866 cells were washed in FACS buffer and stained with Alexa Fluor® 647 AffiniPure Donkey Anti-Human IgG, Fcγ fragment specific (Jackson Cat #709-605-098) diluted 1:6,000 in FACS buffer. The cells were incubated with secondary detection antibodies for 20 minutes then washed once, resuspended in 60 μL of FACS Buffer, and analyzed on a NovoCyte 3000 flow cytometer (ACEA Biosciences, Inc.). The mean fluorescence of 647 signal was calculated using Novoexpress onboard software gating on single RPMI8866 cells. The binding curves, Bmax, and Kd values were determined, using similar methods as described in Example 1. These data were not background-subtracted before subjecting to the curve-fitting analysis. The empirically derived background signal (No treatment) due to a secondary detection antibody binding is included in the plotted data (FIG. 17A) for reference.

As shown in FIG. 17A, cx13054 bound with high affinity to IgE in complex with CD23 on the surface of RPMI 8866 cells. The comparator antibodies cx10759 and cx10710 both demonstrated slightly reduced affinity and substantially lower Bmax values indicating decreased interaction with IgE: CD23 complexes. Without being bound by theory, the overall robust signal suggests that the B10 based antibody binds IgE outside of the CD23 binding site.

To assess blocking of soluble IgE from binding CD23 on the surface of RPMI 8866 cells, 5 nM human IgE (Abcam Cat #65866) was pre-incubated with a titration of cx13054 diluted (1:3 in duplicate with a final starting concentration of 500 nM) in FACS buffer. After a 1-hour room temperature incubation, 100 μL of the cx13054:IgE mixture was added in duplicate to the CD23-expressing B cell lymphoblastoid cell line, RPMI 8866. Following incubation for 1 hour, the RPMI 8866 cells were washed and IgE binding was determined using a rabbit anti-human IgE antibody (Invitrogen Cat #SA5-10201) followed by treatment with Alexa Fluor 647-conjugated goat anti-rabbit IgG (Jackson Cat #111-606-046). Mean IgE fluorescence intensity was calculated and graphed versus cx13054 concentration. The data was plotted using GraphPad Prism analysis software. These data were not background-subtracted before subjecting to the curve-fitting analysis. The average max signal from wells not treated with cx13054 is indicated as "5 nM IgE" in the plotted data (FIG. 17B) for reference.

As shown in FIG. 17B cx13054 was observed to block IgE binding at molar concentrations equal to and greater than that of IgE. At concentrations of cx13054 below a 1:1 molar ratio to IgE, a subsequent increase in IgE bound to the surface of RPMI 8866 cells was observed. This increase exceeded the level of IgE that was seen in the absence of cx13054 which indicated that additional IgE was being recruited to the cell surface in the presence of low levels of cx13054. This phenomenon was also observed when analyzing the ability of cx13054 to block IgE binding to recombinant CD23 (FIG. 6E and data not shown), suggesting that the trend is not due to interaction with Fc receptors expressed on the RPMI 8866 cells. Without being bound to any particular mechanism, it is possible that the B10 based antibody binds to soluble IgE to form oligomeric complexes that have the capacity to bind CD23 once the antibody concentration drops below a 2:1 molar ratio, which exposes a free CD23 binding site on IgE. The binding of such IgE complexes to CD23 may downregulate IgE through CD23-mediated negative feedback regulation of IgE synthesis on B cells.

Example 13: In Vitro Inhibition of B Cells

The ability of two B10 VHH based anti-IgE sdAb comprising the hzB10v40 VHH but having different Fc regions (cx13054, comprising the IgG1 SELF Fc region (SEQ ID NO: 79) and cx13055 comprising the IgG1 xELL Fc region (SEQ ID NO: 77)) to inhibit IgE production by B cells was evaluated in an in vitro assay. An omalizumab analog (Evidentic Cat. No. AVXS262503) was included as a comparator.

The experimental setup was adapted from Chu et al. (J. Allergy Clin. Immunol. (2012) 129 (4): 1102-15). Healthy normal blood donor PBMCs were thawed from liquid nitrogen storage and washed with CTL supplement (×2), then plated into 24-well plates at a density of 3 million live cells/well in 1 mL. IgE antibody production was stimulated by incubating B cells in RPMI-1640 media supplemented with 5 ng/ml recombinant human IL-4 (PeproTech AF-200-04) and 250 ng/mL anti-CD40 antibody (R&D Systems MAB6321-SP). A "no stimulation" control group was included on each assay plate. 10 μL of test articles were added for a final concentration of 10 nM, 1 nM, and 0.1 nM across all 3 plates in replicate and the assay plates were incubated at 37° C./$CO_2$ for 14 days until harvest. On day 15, the supernatants were collected and centrifuged to remove cells/debris, then frozen at −80° C. until analysis. For analysis, the MSD R-PLEX singleplex assay protocol 1, as provided in the product insert, was applied to the human IgE test kit (K1515AR-2) except that Polyclonal Goat anti-Human IgE Cross-Adsorbed antibody (Thermo Cat #A18801) was selected as the detection antibody because it did not compete for the same IgE epitope as the test articles in the experiment. This antibody was conjugated according to the MSD GOLD SULFO-TAG NHS-Ester Conjugation Pack (Cat #R31AA-1) protocol. Samples were tested at a 1:2 final dilution.

Figure 18:
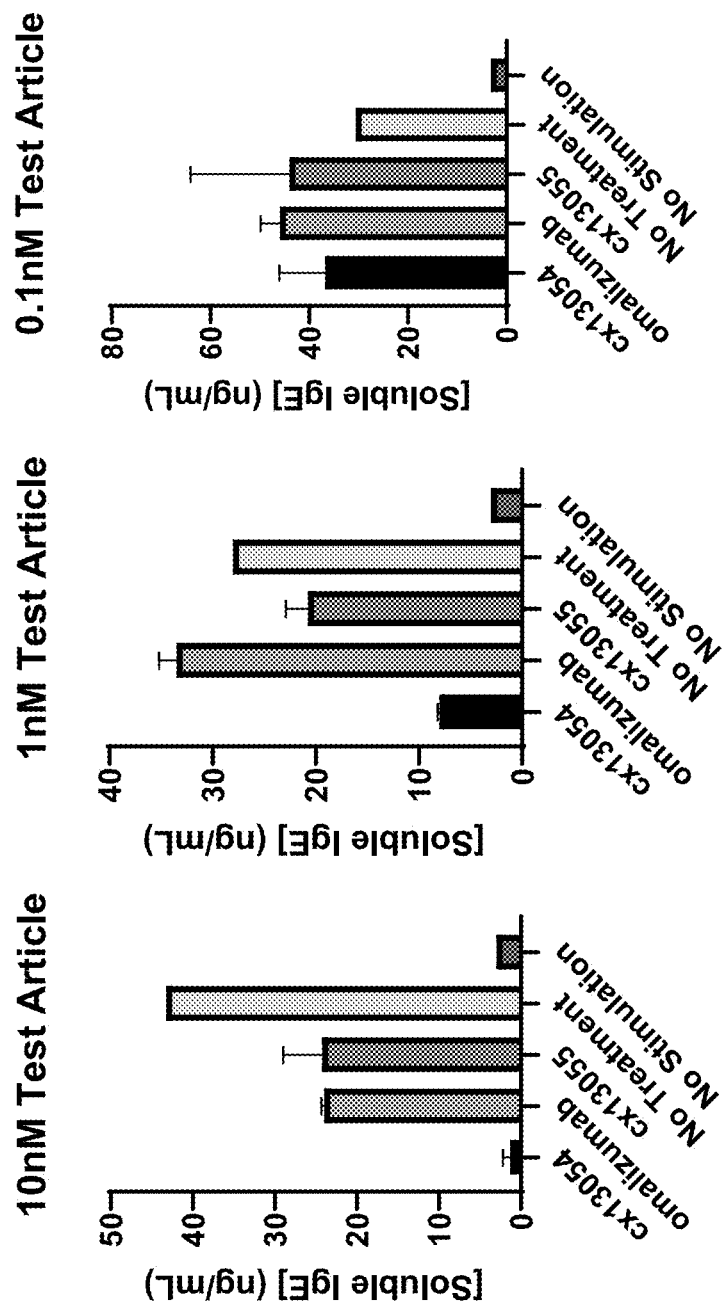
FIG. 18 shows the inhibition of IgE production by cx13054, cx13055, and omalizumab at three concentrations (10 nM, 1 nM, and 0.1 nM) in cultured human PBMCs as described in Example 13. IgE production was also measured with no antibody treatment or no stimulation as controls.

As show in FIG. 18, cx13054, which comprised the IgG1 SELF Fc region, inhibited IgE production in a dose dependent manner. In contrast, cx13055, which comprised the IgG1 xELL Fc region, and omalizumab, which comprised a wild type IgG1 Fc region, exhibited little to no inhibition. These data support the use of a B10 VHH based sdAb fused with the SELF Fc region for inhibiting IgE production from B cells. It was also observed that cx13054 did not inhibit production of other types of immunoglobulins, such as IgD, from a B cell culture (data not shown). This result demonstrates that cx13054 specifically targets IgE-producing B cells.

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

Table of Certain Sequences

| SEQ ID NO | Description | Sequence |
| --- | --- | --- |
| 1 | Human IgE, heavy chain, GenBank AAB59424.1 | MDWTWILFLVAAATRVHSQTQLVQSGAEVRKPGASVRVSCKASGYTF IDSYIHWIRQAPGHGLEWVGWINPNSGGTNYAPRFQGRVTMTRDASF STAYMDLRSLRSDDSAVFYCAKSDPFWSDYYNEDYSYTLDVWGQGTT VTVSSASTQSPSVFPLTRCCKNIPSNATSVTLGCLATGYFPEPVMVT WDTGSLNGTTMTLPATTLTLSGHYATISLLTVSGAWAKQMFTCRVAH TPSSTDWVDNKTFSVCSRDFTPPTVKILQSSCDGGGHFPPTIQLLCL VSGYTPGTINITWLEDGQVMDVDLSTASTTQEGELASTQSELTLSQK HWLSDRTYTCQVTYQGHTFEDSTKKCADSNPRGVSAYLSRPSPFDLF IRKSPTITCLVVDLAPSKGTVNLTWSRASGKPVNHSTRKEEKQRNGT LTVTSTLPVGTRDWIEGETYQCRVTHPHLPRALMRSTTKTSGPRAAP EVYAFATPEWPGSRDKRTLACLIQNEMPEDISVQWLHNEVQLPDARH STTQPRKTKGSGFFVESRLEVTRAEWEQKDEFICRAVHEAASPSQTV QRAVSVNPGK |
| 2 | B10 VHH | EVQLVQSGGELVQAGGSLRLSCVASGLTESSYNMGWLRQAPGKEREF VGMSGSSSTSTYYADSVKGRFTISRDNSKNTVYLQMNSLKPEDTAVY YCAARRMLSTYWSDRSWDFWGQGTQVTVKP |
| 3 | B10 CDR1 | GLTFSSYNMG |
| 4 | B10 CDR2 | MSGSSSTSTY |
| 5 | B10 CDR3 | RRMLSTYWSDRSWDF |
| 6 | hzB10v1 VHH | EVQLLESGGGLVQPGGSLRLSCVASGLTFSSYNMGWLRQAPGKEREF VGMSGSSSTSTYYADSVKGRFTISRDNSKNTVYLQMNSLKPEDTAVY YCAARRMLSTYWSDRSWDFWGQGTQVTVKP |
| 7 | hzB10v2 VHH | EVQLVQSGGELVQAGGSLRLSCVASGLTESSYNMGWVRQAPGKEREF VSMSGSSSTSTYYADSVKGRFTISRDNSKNTVYLQMNSLKPEDTAVY YCAARRMLSTYWSDRSWDFWGQGTQVTVKP |
| 8 | hzB10v3 VHH | EVQLVQSGGELVQAGGSLRLSCVASGLTFSSYNMGWVRQAPGKEREF VGMSGSSSTSTYYADSVKGRFTISRDNSKNTVYLQMNSLKPEDTAVY YCAARRMLSTYWSDRSWDFWGQGTQVTVKP |
| 9 | hzB10v4 VHH | EVQLVQSGGELVQAGGSLRLSCVASGLTFSSYNMGWLRQAPGKEREF VGMSGSSSTSTYYAESVKGRFTISRDNAKNTLYLQMSSLRAEDTAVY YCAARRMLSTYWSDRSWDFWGQGTQVTVKP |
| 10 | hzB10v5 VHH | EVQLVQSGGELVQAGGSLRLSCVASGLTFSSYNMGWLRQAPGKEREF VGMSGSSSTSTYYADSVKGRFTISRDNSKNTVYLQMNSLKPEDTAVY YCAARRMLSTYWSDRSWDFWGQGTQVTVEP |

Table of Certain Sequences

| SEQ ID NO | Description | Sequence |
|---|---|---|
| 11 | hzB10v6 VHH | EVQLVQSGGELVQAGGSLRLSCVASGLTFSSYNMGWLRQAPGKEREF VGMSGSSSTSTYYADSVKGRFTISRDNSKNTVYLQMNSLKPEDTAVY YCAARRMLSTYWSDRSWDFWGQGTQVTVRP |
| 12 | hzB10v7 VHH | EVQLVQSGGELVQAGGSLRLSCVASGLTESSYNMGWLRQAPGKEREF VGLSGSSSTSTYYADSVKGRFTISRDNSKNTVYLQMNSLKPEDTAVY YCAARRMLSTYWSDRSWDFWGQGTQVTVKP |
| 13 | hzB10v8 VHH | EVQLVQSGGELVQAGGSLRLSCVASGLTFSSYNMGWLRQAPGKEREF VGISGSSSTSTYYADSVKGRFTISRDNSKNTVYLQMNSLKPEDTAVY YCAARRMLSTYWSDRSWDFWGQGTQVTVKP |
| 14 | hzB10v9 VHH | EVQLVQSGGELVQAGGSLRLSCVASGLTFSSYNMGWLRQAPGKEREF VGVSGSSSTSTYYADSVKGRFTISRDNSKNTVYLQMNSLKPEDTAVY YCAARRMLSTYWSDRSWDFWGQGTQVTVKP |
| 15 | hzB10v10 VHH | EVQLVQSGGELVQAGGSLRLSCVASGLTFSSYNMGWLRQAPGKEREF VGMSGSSSTSTYYADSVKGRFTISRDNSKNTVYLQMNSLKPEDTAVY YCAARRLLSTYWSDRSWDFWGQGTQVTAKP |
| 16 | hzB10v11 VHH | EVQLVQSGGELVQAGGSLRLSCVASGLTFSSYNMGWLRQAPGKEREF VGMSGSSSTSTYYADSVKGRFTISRDNSKNTVYLQMNSLKPEDTAVY YCAARRILSTYWSDRSWDFWGQGTQVTVKP |
| 17 | hzB10v12 VHH | EVQLVQSGGELVQAGGSLRLSCVASGLTFSSYNMGWLRQAPGKEREF VGMSGSSSTSTYYADSVKGRFTISRDNSKNTVYLQMNSLKPEDTAVY YCAARRVLSTYWSDRSWDFWGQGTQVTVKP |
| 18 | hzB10v13 VHH | EVQLVQSGGELVQAGGSLRLSCVASGLTFSSYNMGWLRQAPGKEREF VGMSGSSSTSTYYAESVKGRFTISRDNAKNTVYLQMNSLKPEDTAVY YCAARRMLSTYWSDRSWDFWGQGTQVTAKP |
| 19 | hzB10v14 VHH | EVQLLESGGGEVQPGGSLRLSCVASGLTFSSYNMGWLRQAPGKEREF VGLSGSSSTSTYYADSVKGRFTISRDNSKNTVYLQMNSLKPEDTAVY YCAARRLLSTYWSDRSWDEWGQGTQVTVEP |
| 20 | hzB10v15 VHH | EVQLLESGGGEVQPGGSLRLSCVASGLTFSSYNMGWVRQAPGKEREF VSLSGSSSTSTYYADSVKGRFTISRDNSKNTVYLQMNSLKPEDTAVY YCAARRLLSTYWSDRSWDFWGQGTQVTVEP |
| 21 | hzB10v16 VHH | EVQLLESGGGEVQPGGSLRLSCVASGLTFSSYNMGWLRQAPGKEREF VGLSGSSSTSTYYAESVKGRFTISRDNSKNTVYLQMNSLKPEDTAVY YCAARRLLSTYWSDRSWDFWGQGTQVTVEP |
| 22 | hzB10v17 VHH | EVQLLESGGGEVQPGGSLRLSCVASGLTFSSYNMGWLRQAPGKEREF VGLSGSSSTSTYYADAVKGRFTISRDNSKNTVYLQMNSLKPEDTAVY YCAARRLLSTYWSDRSWDFWGQGTQVTVEP |
| 23 | hzB10v18 VHH | EVQLLESGGGEVQPGGSLRLSCVASGLTFSSYNMGWLRQAPGKEREF VGLSGSSSTSTYYADTVKGRFTISRDNSKNTVYLQMNSLKPEDTAVY YCAARRLLSTYWSDRSWDFWGQGTQVTVEP |
| 24 | hzB10v20 VHH | EVQLLESGGGEVQPGGSLRLSCVASGLTFSSYNMGWLRQAPGKEREF VGLSGSSSTSTYYADSVKGRFTISRDNSKNTLYLQMNSLKPEDTAVY YCAARRLLSTYWSDRSWDFWGQGTQVTVEP |
| 25 | hzB10v21 VHH | EVQLLESGGGEVQPGGSLRLSCVASGLTFSSYNMGWLRQAPGKEREF VGLSGSSSTSTYYADSVKGRFTISRDNSKNTVYLQMSSLKPEDTAVY YCAARRLLSTYWSDRSWDFWGQGTQVTVEP |
| 26 | hzB10v22 VHH | EVQLLESGGGEVQPGGSLRLSCVASGLTFSSYNMGWLRQAPGKEREF VGLSGSSSTSTYYADSVKGRFTISRDNSKNTVYLQMNSLRPEDTAVY YCAARRLLSTYWSDRSWDFWGQGTQVTVEP |
| 27 | hzB10v23 VHH | EVQLLESGGGEVQPGGSLRLSCVASGLTESSYNMGWLRQAPGKEREF VGLSGSSSTSTYYADSVKGRFTISRDNSKNTVYLQMNSLKAEDTAVY YCAARRLLSTYWSDRSWDFWGQGTQVTVEP |
| 28 | hzB10v24 VHH | EVQLLESGGGEVQPGGSLRLSCVASGLTFSSYNMGWVRQAPGKEREF VGLSGSSSTSTYYADSVKGRFTISRDNSKNTVYLQMNSLKPEDTAVY YCAARRLLSTYWSDRSWDFWGQGTQVTVEP |

Table of Certain Sequences

| SEQ ID NO | Description | Sequence |
|---|---|---|
| 29 | hzB10v25 VHH | EVQLLESGGGEVQPGGSLRLSCVASGLTFSSYNMGWLRQAPGKEREF VSLSGSSSTSTYYADSVKGRFTISRDNSKNTVYLQMNSLKPEDTAVY YCAARRLLSTYWSDRSWDFWGQGTQVTVEP |
| 30 | hzB10v26 VHH | EVQLLESGGGEVQPGGSLRLSCVASGLTFSSYNMGWLRQAPGKEREF VGMSGSSSTSTYYADSVKGRFTISRDNSKNTVYLQMNSLKPEDTAVY YCAARRMLSTYWSDRSWDFWGQGTQVTVKP |
| 31 | hzB10v27 VHH | EVQLLESGGGEVQPGGSLRLSCVASGLTFSSYNMGWLRQAPGKEREF VGLSGSSSTSTYYAESVKGRFTISRDNSKNTVYLQMNSLRAEDTAVY YCAARRLLSTYWSDRSWDFWGQGTQVTVEP |
| 32 | hzB10v28 VHH | EVQLLESGGGEVQPGGSLRLSCVASGLTESSYNMGWLRQAPGKEREF VGLSGSSSTSTYYAESVKGRFTISRDNSKNTVYLQMSSLRAEDTAVY YCAARRLLSTYWSDRSWDEWGQGTQVTVEP |
| 33 | hzB10v29 VHH | EVQLLESGGGEVQPGGSLRLSCVASGLTFSSYNMGWLRQAPGKEREF VGLSGSSSTSTYYAESVKGRFTISRDNSKNTVYLQMQSLRAEDTAVY YCAARRLLSTYWSDRSWDFWGQGTQVTVEP |
| 34 | hzB10v30 VHH | EVQLLESGGGEVQPGGSLRLSCVASGLTFSSYNMGWLRQAPGKEREF VGLSGSSSTSTYYAESVKGRFTISRDNSKNTVYLQMTSLRAEDTAVY YCAARRLLSTYWSDRSWDFWGQGTQVTVEP |
| 35 | hzB10v31 VHH | EVQLLESGGGEVQPGGSLRLSCVASGLTESSYNMGWLRQAPGKEREF VGLSGSSSTSTYYAESVKGRFTISRDNSKNTVYLQMNTLRAEDTAVY YCAARRLLSTYWSDRSWDFWGQGTQVTVEP |
| 36 | hzB10v32 VHH | EVQLLESGGGEVQPGGSLRLSCVASGLTFSSYNMGWVRQAPGKEREF VGLSGSSSTSTYYAESVKGRFTISRDNSKNTVYLQMNSLRAEDTAVY YCAARRLLSTYWSDRSWDFWGQGTQVTVEP |
| 37 | hzB10v33 VHH | EVQLLESGGGEVQPGGSLRLSCVASGLTFSSYNMGWLRQAPGKEREF VSLSGSSSTSTYYAESVKGRFTISRDNSKNTVYLQMNSLRAEDTAVY YCAARRLLSTYWSDRSWDFWGQGTQVTVEP |
| 38 | hzB10v34 VHH | EVQLLESGGGEVQPGGSLRLSCVASGLTFSSYNMGWVRQAPGKEREF VSLSGSSSTSTYYAESVKGRFTISRDNSKNTVYLQMNSLRAEDTAVY YCAARRLLSTYWSDRSWDFWGQGTQVTVEP |
| 39 | hzB10v37 VHH | EVQLLESGGGEVQPGGSLRLSCVASGLTESSYNMGWLRQAPGKEREF VGLSGSSSTSTYYAESVKGRFTISRDNSKNTVYLQMTSLKAEDTAVY YCAARRLLSTYWSDRSWDFWGQGTLVTVEP |
| 40 | hzB10v38 VHH | EVQLLESGGGEVQPGGSLRLSCVASGLTESSYNMGWLRQAPGKEREF VGLSGSSSTSTYYAESVKGRFTISRDNSKNTVYLQMTSLRPEDTAVY YCAARRLLSTYWSDRSWDFWGQGTLVTVEP |
| 41 | hzB10v39 VHH | EVQLLESGGGEVQPGGSLRLSCVASGLTFSSYNMGWLRQAPGKEREF VGLSGSSSTSTYYAESVKGRFTISRDNSKNTVYLQMTSLRAEDTAVY YCAARRLLSTYWSDRSWDFWGQGTLVTVEP |
| 42 | hzB10v40 VHH | EVQLLESGGGEVQPGGSLRLSCVASGLTFSSYNMGWLRQAPGKEREF VGLSGSSSTSTYYAESVKGRFTISRDNAKNTVYLQMTSLRAEDTAVY YCAARRLLSTYWSDRSWDEWGQGTLVTVEP |
| 43 | hzB10v41 VHH | EVQLLESGGGEVQPGGSLRLSCVASGLTFSSYNMGWLRQAPGKEREF VGLSGSSSTSTYYAESVKGRFTISRDQSKNTVYLQMTSLRAEDTAVY YCAARRLLSTYWSDRSWDFWGQGTLVTVEP |
| 44 | hzB10v42 VHH | EVQLLESGGGEVQPGGSLRLSCVASGLTFSSYNMGWLRQAPGKEREF VGLSGSSSTSTYYAESVKGRFTISRDSSKNTVYLQMTSLRAEDTAVY YCAARRLLSTYWSDRSWDFWGQGTLVTVEP |
| 45 | hzB10v43 VHH | EVQLLESGGGEVQPGGSLRLSCVASGLTFSSYNMGWLRQAPGKEREF VGLSGSSSTSTYYAESVKGRFTISRDTSKNTVYLQMTSLRAEDTAVY YCAARRLLSTYWSDRSWDFWGQGTLVTVEP |
| 46 | hzB10v44 VHH | EVQLLESGGGEVQPGGSLRLSCVASGLTFSSYNMGWLRQAPGKEREF VGLSGSSSTSTYYAESVKGRFTISRDNTKNTVYLQMTSLRAEDTAVY YCAARRLLSTYWSDRSWDFWGQGTLVTVEP |

Table of Certain Sequences

| SEQ ID NO | Description | Sequence |
|---|---|---|
| 47 | hzB10con VHH | EVQL$X_1$$X_2$SGG$X_3$$X_4$VQ$X_5$GGSLRLSCVASGLTFSSYNMGW$X_6$RQAPGK EREFV$X_7$$X_8$SGSSSTSTYYA$X_9$$X_{10}$VKGRFTISRD$X_{11}$$X_{12}$KNT$X_{13}$YLQM $X_{14}$$X_{15}$L$X_{16}$$X_{17}$EDTAVYYCARR$X_{18}$LSTYWSDRSWDFWGQGT$X_{19}$VT$X_{20}$$X_{21}$P<br>wherein:<br>$X_1$ is L or V    $X_8$ is L, I, V, or M    $X_{15}$ is S or T<br>$X_2$ is E or Q    $X_9$ is E or D    $X_{16}$ is R or K<br>$X_3$ is G or E    $X_{10}$ is S, A, or T    $X_{17}$ is A or P<br>$X_4$ is E or L    $X_{11}$ is N, Q, S, or T    $X_{18}$ is L, I, V, or M<br>$X_5$ is P or A    $X_{12}$ is S, A, or T    $X_{19}$ is L or Q<br>$X_6$ is L or V    $X_{13}$ is V or L    $X_{20}$ is V or A<br>$X_7$ is G or S    $X_{14}$ is T, N, S, or Q    $X_{21}$ is E, K, or R |
| 48 | hzB10v7, v14-v18, v20-v25, v27-v34, and v37-v44 CDR2 | LSGSSSTSTY |
| 49 | hzB10v8 CDR2 | ISGSSSTSTY |
| 50 | hzB10v9 CDR2 | VSGSSSTSTY |
| 51 | hzB10v10, v14-v18, v20-v25, v27-v34, and v37-v44 CDR3 | RRLLSTYWSDRSWDF |
| 52 | hzB10v11 CDR3 | RRILSTYWSDRSWDF |
| 53 | hzB10v12 CDR3 | RRVLSTYWSDRSWDF |
| 54 | hzB10con CDR1 Chothia | GLTFSSY |
| 55 | hzB10con CDR1 Kabat | SYNMG |
| 56 | hzB10con CDR1 Contact | SSYNMG |
| 57 | hzB10con CDR1 IMGT | LTFSSYN |
| 58 | hzB10con CDR2 Abm | XSGSSSTSTY<br>wherein: X is L, I, V, or M |
| 59 | hzB10con CDR2 Chothia | GSSSTS |
| 60 | hzB10con CDR2 Kabat | $X_1$SGSSSTSTYYA$X_2$$X_3$VKG<br>wherein: $X_1$ is L, I, V, or M; $X_2$ is E or D; and $X_3$ is: S, A, or T |
| 61 | hzB10con CDR2 Contact | FV$X_1$$X_2$SGSSSTSTY<br>wherein: $X_1$ is G or S; and $X_2$ is L, I, V, or M |
| 62 | hzB10con CDR2 IMGT | SGSSSTST |
| 63 | hzB10con CDR3 Abm | RRXLSTYWSDRSWDF<br>wherein: X is L, I, V, or M |
| 64 | hzB10con CDR3 Chothia | RRXLSTYWSDRSWDF<br>wherein: X is L, I, V, or M |
| 65 | hzB10con CDR3 Kabat | RRXLSTYWSDRSWDF<br>wherein: X is L, I, V, or M |
| 66 | hzB10con CDR3 Contact | AARRXLSTYWSDRSWD<br>wherein: X is L, I, V, or M |
| 67 | hzB10con CDR3 IMGT | AARRXLSTYWSDRSWDF<br>wherein: X is L, I, V, or M |

-continued

| Table of Certain Sequences | | |
|---|---|---|
| SEQ ID NO | Description | Sequence |
| 68 | hzB10v37-v44 CDR2 Kabat | LSGSSSTSTYYAESVKG |
| 69 | hzB10v37-v44 CDR2 Contact | FVGLSGSSSTSTY |
| 70 | hzB10v37-v44 CDR2 IMGT | SGSSSTST |
| 71 | hzB10v37-v44 CDR3 Chothia | RRLLSTYWSDRSWDF |
| 72 | hzB10v37-v44 CDR3 Kabat | RRLISTYWSDRSWDF |
| 73 | hzB10v37-v44 CDR3 Contact | AARRILSTYWSDRSWD |
| 74 | hzB10v37-v44 CDR3 IMGT | AARRLISTYWSDRSWDF |
| 75 | Human IgG1 Fc region | DKTHTCPPCPAPELLGGPSVFLFPPKPKDTLMISRTPEVTCVVVDVS HEDPEVKFNWYVDGVEVHNAKTKPREEQYNSTYRVVSVLTVLHQDWL NGKEYKCKVSNKALPAPIEKTISKAKGQPREPQVYTLPPSREEMTKN QVSLTCLVKGFYPSDIAVEWESNGQPENNYKTTPPVLDSDGSFFLYS KLTVDKSRWQQGNVFSCSVMHEALHNHYTQKSLSLSPGK |
| 76 | Human IgG1 Fc region (without terminal lysine) | DKTHTCPPCPAPELLGGPSVFLFPPKPKDTLMISRTPEVTCVVVDVS HEDPEVKENWYVDGVEVHNAKTKPREEQYNSTYRVVSVLTVLHQDWL NGKEYKCKVSNKALPAPIEKTISKAKGQPREPQVYTLPPSREEMTKN QVSLTCLVKGFYPSDIAVEWESNGQPENNYKTTPPVLDSDGSFFLYS KLTVDKSRWQQGNVFSCSVMHEALHNHYTQKSLSLSPG |
| 77 | human IgG1 Fc xELL | DKTHTCPPCPAPGGPSVFLFPPKPKDTLMISRTPEVTCVVVDVSHED PEVKFNWYVDGVEVHNAKTKPREEQYNSTYRVVSVLTVLHQDWLNGK EYKCKVSNKALPAPIEKTISKAKGQPREPQVYTLPPSRDELTKNQVS LTCLVKGFYPSDIAVEWESNGQPENNYKTTPPVLDSDGSFFLYSKLT VDKSRWQQGNVFSCSVMHEALHNHYTQKSLSLSPGK |
| 78 | human IgG1 Fc xELL (without terminal lysine) | DKTHTCPPCPAPGGPSVFLFPPKPKDTLMISRTPEVTCVVVDVSHED PEVKFNWYVDGVEVHNAKTKPREEQYNSTYRVVSVLTVLHQDWLNGK EYKCKVSNKALPAPIEKTISKAKGQPREPQVYTLPPSRDELTKNQVS LTCLVKGFYPSDIAVEWESNGQPENNYKTTPPVLDSDGSFFLYSKLT VDKSRWQQGNVFSCSVMHEALHNHYTQKSLSLSPG |
| 79 | Human IgG1 SELF Fc region (S267E/L328F) | DKTHTCPPCPAPELLGGPSVFLFPPKPKDTLMISRTPEVTCVVVDVE HEDPEVKFNWYVDGVEVHNAKTKPREEQYNSTYRVVSVLTVLHQDWL NGKEYKCKVSNKAFPAPIEKTISKAKGQPREPQVYTLPPSREEMTKN QVSLTCLVKGFYPSDIAVEWESNGQPENNYKTTPPVLDSDGSFFLYS KLTVDKSRWQQGNVFSCSVMHEALHNHYTQKSLSLSPGK |
| 80 | Human IgG1 SELF Fc region (S267E/L328F) (without terminal lysine) | DKTHTCPPCPAPELLGGPSVELFPPKPKDTLMISRTPEVTCVVVDVE HEDPEVKFNWYVDGVEVHNAKTKPREEQYNSTYRVVSVLTVLHQDWL NGKEYKCKVSNKAFPAPIEKTISKAKGQPREPQVYTLPPSREEMTKN QVSLTCLVKGFYPSDIAVEWESNGQPENNYKTTPPVLDSDGSFFLYS KLTVDKSRWQQGNVFSCSVMHEALHNHYTQKSLSLSPG |
| 81 | Human IgG1 DSELF Fc region (G236D/S267E/ L328F) | DKTHTCPPCPAPELLDGPSVFLFPPKPKDTLMISRTPEVTCVVVDVE HEDPEVKFNWYVDGVEVHNAKTKPREEQYNSTYRVVSVLTVLHQDWL NGKEYKCKVSNKAFPAPIEKTISKAKGQPREPQVYTLPPSREEMTKN QVSLTCLVKGFYPSDIAVEWESNGQPENNYKTTPPVLDSDGSFFLYS KLTVDKSRWQQGNVFSCSVMHEALHNHYTQKSLSLSPGK |
| 82 | Human IgG1 DSELF Fc region (G236D/S267E/ L328F) (without terminal lysine) | DKTHTCPPCPAPELLDGPSVFLFPPKPKDTLMISRTPEVTCVVVDVE HEDPEVKENWYVDGVEVHNAKTKPREEQYNSTYRVVSVLTVLHQDWL NGKEYKCKVSNKAFPAPIEKTISKAKGQPREPQVYTLPPSREEMTKN QVSLTCLVKGFYPSDIAVEWESNGQPENNYKTTPPVLDSDGSFFLYS KLTVDKSRWQQGNVFSCSVMHEALHNHYTQKSLSLSPG |

Table of Certain Sequences

| SEQ ID NO | Description | Sequence |
|---|---|---|
| 83 | Human IgG1 NNT Fc | GGPSVFLFPPKPKDTLMISRTPEVTCVVVDVSHEDPEVKENWYVDGV EVHNAKTKPREEQYNSTYRVVSVLTVLHQDWLNGKEYKCKVSNKALP APIEKTISKAKGQPREPQVYTLPPSRDELTKNQVNLTCLVKGFYPSD IAVEWESNGQPENNYKTTPPVLDSDGSFFLNSTLTVDKSRWQQGNVF SCSVMHEALHNHYTQKSLSLSPGK |
| 84 | hzB10v14-IgG1 DSELF Fc region (cx12739) | EVQLLESGGGEVQPGGSLRLSCVASGLTFSSYNMGWLRQAPGKEREF VGLSGSSSTSTYYADSVKGRFTISRDNSKNTVYLQMNSLKPEDTAVY YCAARRLLSTYWSDRSWDFWGQGTQVTVEPGGGGDKTHTCPPCPAPE LLDGPSVFLFPPKPKDTLMISRTPEVTCVVVDVEHEDPEVKENWYVD GVEVHNAKTKPREEQYNSTYRVVSVLTVLHQDWLNGKEYKCKVSNKA FPAPIEKTISKAKGQPREPQVYTLPPSREEMTKNQVSLTCLVKGFYP SDIAVEWESNGQPENNYKTTPPVLDSDGSFFLYSKLTVDKSRWQQGN VFSCSVMHEALHNHYTQKSLSLSPGK |
| 85 | hzB10v40-IgG1 DSELF Fc region (cx13032) | EVQLLESGGGEVQPGGSLRLSCVASGLTFSSYNMGWLRQAPGKEREF VGLSGSSSTSTYYAESVKGRFTISRDNAKNTVYLQMTSLRAEDTAVY YCAARRLLSTYWSDRSWDFWGQGTLVTVEPGGGGDKTHTCPPCPAPE LLDGPSVFLFPPKPKDTLMISRTPEVTCVVVDVEHEDPEVKENWYVD GVEVHNAKTKPREEQYNSTYRVVSVLTVLHQDWLNGKEYKCKVSNKA FPAPIEKTISKAKGQPREPQVYTLPPSREEMTKNQVSLTCLVKGFYP SDIAVEWESNGQPENNYKTTPPVLDSDGSFFLYSKLTVDKSRWQQGN VFSCSVMHEALHNHYTQKSLSLSPGK |
| 86 | hzB10v40-IgG1 SELF Fc region (cx13054) | EVQLLESGGGEVQPGGSLRLSCVASGLTFSSYNMGWLRQAPGKEREF VGLSGSSSTSTYYAESVKGRFTISRDNAKNTVYLQMTSLRAEDTAVY YCAARRLLSTYWSDRSWDFWGQGTLVTVEPGGGGDKTHTCPPCPAPE LLGGPSVFLFPPKPKDTLMISRTPEVTCVVVDVEHEDPEVKENWYVD GVEVHNAKTKPREEQYNSTYRVVSVLTVLHQDWLNGKEYKCKVSNKA FPAPIEKTISKAKGQPREPQVYTLPPSREEMTKNQVSLTCLVKGFYP SDIAVEWESNGQPENNYKTTPPVLDSDGSFFLYSKLTVDKSRWQQGN VFSCSVMHEALHNHYTQKSLSLSPGK |
| 87 | cx10710 Heavy Chain | QVQLQESGPGLVKPSETLSLTCAVSGYSITSGYSWNWIRQPPGKKLE WIGSITYDGSSNYNPSLKSRVTISRDTSKNQFSLKLSSVTAADTAVY YCARGSHYFGHWHFAVWGAGTLVTVSSASTKGPSVFPLAPSSKSTSG GTAALGCLVKDYFPEPVTVSWNSGALTSGVHTFPAVLQSSGLYSLSS VVTVPSSSLGTQTYICNVNHKPSNTKVDKKVEPKSCDKTHTCPPCPA PELLGGPSVELFPPKPKDTLMISRTPEVTCVVVDVEHEDPEVKENWY VDGVEVHNAKTKPREEQYNSTYRVVSVLTVLHQDWLNGKEYKCKVSN KAFPAPIEKTISKAKGQPREPQVYTLPPSREEMTKNQVSLTCLVKGF YPSDIAVEWESNGQPENNYKTTPPVLDSDGSFFLYSKLTVDKSRWQQ GNVFSCSVMHEALHNHYTQKSLSLSPGK |
| 88 | cx10710 Light Chain | DIQLTQSPSSLSASVGDRVTITCRASQSVDYDGDSYMNWYQQKPGQP PKLLIYAASYLGSEIPARFSGSGSGTDFTLTISSLQPEDFATYYCQQ SHEDPYTFGAGTKLEIKRTVAAPSVFIFPPSDEQLKSGTASVVCLLN NFYPREAKVQWKVDNALQSGNSQESVTEQDSKDSTYSLSSTLTLSKA DYEKHKVYACEVTHQGLSSPVTKSENRGEC |
| 89 | cx10759 (humanized IgE026-IgG SELF Fc) | EVQLLESGGGEVQPGGSLRLSCAASGFTFGNYDMAWVRQAPGKRPEW VSSIDTGGGSTYYAESVKGRFTISRDNAKNTLYLQMSSLRAEDTAVY WCATDEEYALGPNEFDYYGQGTLVTVKPGGGGDKTHTCPPCPAPELL GGPSVFLFPPKPKDTLMISRTPEVTCVVVDVEHEDPEVKENWYVDGV EVHNAKTKPREEQYNSTYRVVSVLTVLHQDWLNGKEYKCKVSNKAFP APIEKTISKAKGQPREPQVYTLPPSREEMTKNQVSLTCLVKGFYPSD IAVEWESNGQPENNYKTTPPVLDSDGSFFLYSKLTVDKSRWQQGNVF SCSVMHEALHNHYTQKSLSLSPGK |
| 90 | Human FCER1A (mature) | VPQKPKVSLNPPWNRIFKGENVTLTCNGNNFFEVSSTKWFHNGSLSEETNSS LNIVNAKFEDSGEYKCQHQQVNESEPVYLEVFSDWLLLQASAEVVMEGQPLF LRCHGWRNWDVYKVIYYKDGEALKYWYENHNISITNATVEDSGTYYCTGKVW QLDYESEPLNITVIKAPREKYWLQFFIPLLVVILFAVDTGLFISTQQQVTFL LKIKRTRKGFRLLNPHPKPNPKNN |
| 91 | Linker | GGGG |
| 92 | hzB10v40-IgG1 DSELF Fc region (cx13032) (without C-terminal lysine) | EVQLLESGGGEVQPGGSLRLSCVASGLTFSSYNMGWLRQAPGKEREF VGLSGSSSTSTYYAESVKGRFTISRDNAKNTVYLQMTSLRAEDTAVY YCAARRLLSTYWSDRSWDFWGQGTLVTVEPGGGGDKTHTCPPCPAPE LLDGPSVFLFPPKPKDTLMISRTPEVTCVVVDVEHEDPEVKENWYVD GVEVHNAKTKPREEQYNSTYRVVSVLTVLHQDWLNGKEYKCKVSNKA FPAPIEKTISKAKGQPREPQVYTLPPSREEMTKNQVSLTCLVKGFYP |

| SEQ ID NO | Description | Sequence |
|---|---|---|
|  |  | SDIAVEWESNGQPENNYKTTPPVLDSDGSFFLYSKLTVDKSRWQQGN VFSCSVMHEALHNHYTQKSLSLSPG |
| 93 | hzB10v40-IgG1 SELF Fc region (cx13054) (without C-terminal lysine) | EVQLLESGGGEVQPGGSLRLSCVASGLTESSYNMGWLRQAPGKEREF VGLSGSSSTSTYYAESVKGRFTISRDNAKNTVYLQMTSLRAEDTAVY YCAARRLLSTYWSDRSWDFWGQGTLVTVEPGGGGDKTHTCPPCPAPE LLGGPSVFLPPKPKDTLMISRTPEVTCVVVDVEHEDPEVKENWYVD GVEVHNAKTKPREEQYNSTYRVVSVLTVLHQDWLNGKEYKCKVSNKA FPAPIEKTISKAKGQPREPQVYTLPPSREEMTKNQVSLTCLVKGFYP SDIAVEWESNGQPENNYKTTPPVLDSDGSFFLYSKLTVDKSRWQQGN VFSCSVMHEALHNHYTQKSLSLSPG |
| 94 | Human germline sequence VH3-23 | EVQLLESGGGEVQPGGSLRLSCAASGFTFSSYAMSWVRQAPGKGLEW VSAISGSGGSTYYAESVKGRETISRDNAKNTLYLQMSSLRAEDTAVY YC |
| 95 | hzB10v14-IgG1 SELF Fc region ("739") | EVQLLESGGGEVQPGGSLRLSCVASGLTFSSYNMGWLRQAPGKEREF VGLSGSSSTSTYYADSVKGRFTISRDNSKNTVYLQMNSLKPEDTAVY YCAARRLLSTYWSDRSWDFWGQGTQVTVEPGGGGDKTHTCPPCPAPE LLGGPSVFLPPKPKDTLMISRTPEVTCVVVDVEHEDPEVKENWYVD GVEVHNAKTKPREEQYNSTYRVVSVLTVLHQDWLNGKEYKCKVSNKA FPAPIEKTISKAKGQPREPQVYTLPPSREEMTKNQVSLTCLVKGFYP SDIAVEWESNGQPENNYKTTPPVLDSDGSFFLYSKLTVDKSRWQQGN VFSCSVMHEALHNHYTQKSLSLSPGK |
| 96 | Ligelizumab VH | QVQLVQSGAEVMKPGSSVKVSCKASGYTFSWYWLEWVRQAPGHGLEW MGEIDPGTFTTNYNEKFKARVTFTADTSTSTAYMELSSLRSEDTAVY YCARFSHFSGSNYDYFDYWGQGTLVTVSS |
| 97 | Ligelizumab VL | EIVMTQSPATLSVSPGERATLSCRASQSIGTNIHWYQQKPGQAPRLL IYYASESISGIPARFSGSGSGTEFTLTISSLQSEDFAVYYCQQSWSW PTTFGGGTKVEIK |
| 98 | 8D6 VH | QVQLVQSGAEVKKPGSSVKVSCKASGYTFNGYWMHWVRQAPGQGLEW IGYINPTTGHTEYNQKFKDKATITADESTNTAYMELSSLRSEDTAVY YCARQEYRHSWFAYWGQGTLVTVSS |
| 99 | 8D6 VL | DIQLTQSPSSLSASVGDRVTITCRASQSVDYDGDTYMNWYQQKPGKA PKLLIYAASNLDSGVPSRESGSGSGTDETLTISSLQPEDFATYYCQQ TNEDPWTFGQGTKVEIK |
| 100 | hzB10v40-IgG1 xELL Fc region (cx13055) | EVQLLESGGGEVQPGGSLRLSCVASGLTFSSYNMGWLRQAPGKEREF VGLSGSSSTSTYYAESVKGRFTISRDNAKNTVYLQMTSLRAEDTAVY YCAARRLLSTYWSDRSWDFWGQGTLVTVEPGGGGDKTHTCPPCPAPG GPSVFLPPKPKDTLMISRTPEVTCVVVDVSHEDPEVKENWYVDGVE VHNAKTKPREEQYNSTYRVVSVLTVLHQDWLNGKEYKCKVSNKALPA PIEKTISKAKGQPREPQVYTLPPSRDELTKNQVSLTCLVKGFYPSDI AVEWESNGQPENNYKTTPPVLDSDGSFFLYSKLTVDKSRWQQGNVFS CSVMHEALHNHYTQKSLSLSPGK |
| 101 | hzB10v40.52 | EVQLLESGGGEVQPGGSLRLSCVASGLTFSSYNMGWLRQAPGKEREF VGLSGVSSTSTYYAESVKGRFTISRDNAKNTGYLQMNSLRAEDTAVY YCAARRLLSTYWSHRSWDFWGQGTLVTVEP |
| 102 | hzB10v40.52 CDR2 (AbM) | LSGVSSTSTY |
| 103 | hzB10v40.52 CDR3 AbM | RRLLSTYWSHRSWDF |
| 104 | hzB10con-1 CDR2 AbM | X$_1$SGX$_2$SSTSTY<br>wherein: X$_1$ is L, I, V, or M; and X$_2$ is S or V |
| 105 | hzB10con-1 CDR2 Chothia | GXSSTS<br>wherein: X is S or V |
| 106 | hzB10con-1 CDR2 Kabat | X$_1$SGX$_2$SSTSTYYAX$_3$X$_4$VKG<br>wherein: X$_1$ is L, I, V, or M; X$_2$ is S or V; X$_3$ is E or D; and X$_4$ is: S, A, or T |
| 107 | hzB10con-1 CDR2 Contact | FVX$_1$X$_2$SGX$_3$SSTSTY<br>wherein: X$_1$ is G or S; X$_2$ is L, I, V, or M; and X$_3$ is S or V |

| SEQ ID NO | Description | Sequence |
|---|---|---|
| 108 | hzB10con-1 CDR2 IMGT | $X_1SGX_2SSTSTY$<br>wherein: $X_1$ is L, I, V, or M; and $X_2$ is S or V |
| 109 | hzB10con-1 CDR3 AbM, Chothia, Kabat | $RRX_1LSTYWSX_2RSWDF$<br>wherein: $X_1$ is L, I, V, or M; and $X_2$ is D or H |
| 110 | hzB10con-1 CDR3 Contact | $AARRX_1LSTYWSX_2RSWD$<br>wherein: $X_1$ is L, I, V, or M; and $X_2$ is D or H |
| 111 | hzB10con-1 CDR3 IMGT | $AARRX_1LSTYWSX_2RSWDF$<br>wherein: $X_1$ is L, I, V, or M; and $X_2$ is D or H |
| 112 | hzB10v40.52-IgG1-SELF (cx13784) | EVQLLESGGGEVQPGGSLRLSCVASGLTFSSYNMGWLRQAPGKEREF VGLSGVSSTSTYYAESVKGRFTISRDNAKNTYLQMNSLRAEDTAVY YCAARRLLSTYWSHRSWDFWGQGTLVTVEPGGGGDKTHTCPPCPAPE LLGGPSVFLFPPKPKDTLMISRTPEVTCVVVDVEHEDPEVKENWYVD GVEVHNAKTKPREEQYNSTYRVVSVLTVLHQDWLNGKEYKCKVSNKA FPAPIEKTISKAKGQPREPQVYTLPPSREEMTKNQVSLTCLVKGFYP SDIAVEWESNGQPENNYKTTPPVLDSDGSFFLYSKLTVDKSRWQQGN VFSCSVMHEALHNHYTQKSLSLSPGK |
| 113 | hzB10v40.52-IgG1-SELF (cx13784) (without C-terminal lysine) | EVQLLESGGGEVQPGGSLRLSCVASGLTFSSYNMGWLRQAPGKEREF VGLSGVSSTSTYYAESVKGRFTISRDNAKNTYLQMNSLRAEDTAVY YCAARRLLSTYWSHRSWDFWGQGTLVTVEPGGGGDKTHTCPPCPAPE LLGGPSVFLFPPKPKDTLMISRTPEVTCVVVDVEHEDPEVKENWYVD GVEVHNAKTKPREEQYNSTYRVVSVLTVLHQDWLNGKEYKCKVSNKA FPAPIEKTISKAKGQPREPQVYTLPPSREEMTKNQVSLTCLVKGFYP SDIAVEWESNGQPENNYKTTPPVLDSDGSFFLYSKLTVDKSRWQQGN VFSCSVMHEALHNHYTQKSLSLSPG |
| 114 | hzB10v40 variants consensus CDR1 AbM | $GX_1X_2X_3X_4X_5YX_6X_7X_8$<br>wherein $X_1$ is L, I, or V; $X_2$ is T, V, N, K, or I; $X_3$ is F, Y, P, or G; $X_4$ is S, K, A, D, or R; $X_5$ is S, E, Q, T, R, A, or P; $X_6$ is N, T, S, or R; $X_7$ is M, V, I, L, S, T, or F; and $X_8$ is G, S, or A |
| 115 | hzB10v40 variants consensus CDR1 Chothia | $GX_1X_2X_3X_4X_5Y$<br>wherein $X_1$ is L, I, or V; $X_2$ is T, V, N, K, or I; $X_3$ is F, Y, P, or G; $X_4$ is S, K, A, D, or R; and $X_5$ is S, E, Q, T, R, A, or P |
| 116 | hzB10v40 variants consensus CDR3 AbM, Kabat, Chothia | $RRX_1X_2SX_3YWSX_4RSWDX_5$<br>wherein $X_1$ is L or R; $X_2$ is L, K, F, or H; $X_3$ is T or R; $X_4$ is D, M, or H; and $X_5$ is F, K, or M |
| 117 | hzB10v40 variants consensus CDR3 IMGT | $X_1ARRX_2X_3SX_4YWSX_5RSWDX_6$<br>wherein $X_1$ is A or S; $X_2$ is L or R; $X_3$ is L, K, F, or H; $X_4$ is T or R; $X_5$ is D, M, or H; and $X_6$ is F, K, or M |
| 118 | hzB10v40 variants consensus CDR3 Contact | $X_1ARRX_2X_3SX_4YWSX_5RSWD$<br>wherein $X_1$ is A or S; $X_2$ is L or R; $X_3$ is L, K, F, or H; $X_4$ is T or R; and $X_5$ is D, M, or H |
| 119 | hzB10con1 VHH | $EVQLX_1X_2SGGX_3X_4VQX_5GGSLRLSCVASGLTFSSYNMGWX_6RQAPGK$ $EREFVX_7X_8SGX_9SSTSTYYAX_{10}X_{11}VKGRFTISRDX_{12}X_{13}KNTX_{14}YLQ$ $MX_{15}X_{16}LX_{17}X_{18}EDTAVYYCAARRX_{19}LSTYWSX_{20}RSWDFWGQGTX_{21}V$ $TX_{22}X_{23}P$<br>wherein:<br>$X_1$ is L or V; $X_2$ is E or Q; $X_3$ is G or E; $X_4$ is E or L; $X_5$ is P or A; $X_6$ is L or V; $X_7$ is G or S; $X_8$ is L, I, V, or M; $X_9$ is S or V; $X_{10}$ is E or D; $X_{11}$ is S, A, or T; $X_{12}$ is N, Q, S, or T; $X_{13}$ is S, A, or T; $X_{14}$ is V, G, or L; $X_{15}$ is T, N, S, or Q; $X_{16}$ is S or T; $X_{17}$ is R or K; $X_{18}$ is A or P; $X_{19}$ is L, I, V, or M; $X_{20}$ is D or H; $X_{21}$ is L or Q; $X_{22}$ is V or A; and $X_{23}$ is E, K, or R |

SEQUENCE LISTING

```
Sequence total quantity: 119
SEQ ID NO: 1               moltype = AA   length = 574
FEATURE                    Location/Qualifiers
source                     1..574
                           mol_type = protein
                           organism = Homo sapiens
SEQUENCE: 1
MDWTWILFLV AAATRVHSQT QLVQSGAEVR KPGASVRVSC KASGYTFIDS YIHWIRQAPG    60
HGLEWVGWIN PNSGGTNYAP RFQGRVTMTR DASFSTAYMD LRSLRSDDSA VFYCAKSDPF   120
WSDYYNFDYS YTLDVWGQGT TVTVSSASTQ SPSVFPLTRC CKNIPSNATS VTLGCLATGY   180
FPEPVMVTWD TGSLNGTTMT LPATTLTLSG HYATISLLTV SGAWAKQMFT CRVAHTPSST   240
DWVDNKTFSV CSRDFTPPTV KILQSSCDGG GHFPPTIQLL CLVSGYTPGT INITWLEDGQ   300
VMDVDLSTAS TTQEGELAST QSELTLSQKH WLSDRTYTCQ VTYQGHTFED STKKCADSNP   360
RGVSAYLSRP SPFDLFIRKS PTITCLVVDL APSKGTVNLT WSRASGKPVN HSTRKEEKQR   420
NGTLTVTSTL PVGTRDWIEG ETYQCRVTHP HLPRALMRST TKTSGPRAAP EVYAFATPEW   480
PGSRDKRTLA CLIQNFMPED ISVQWLHNEV QLPDARHSTT QPRKTKGSGF FVFSRLEVTR   540
AEWEQKDEFI CRAVHEAASP SQTVQRAVSV NPGK                              574

SEQ ID NO: 2               moltype = AA   length = 124
FEATURE                    Location/Qualifiers
source                     1..124
                           mol_type = protein
                           organism = synthetic construct
SEQUENCE: 2
EVQLVQSGGE LVQAGGSLRL SCVASGLTFS SYNMGWLRQA PGKEREFVGM SGSSSTSTYY    60
ADSVKGRFTI SRDNSKNTVY LQMNSLKPED TAVYYCAARR MLSTYWSDRS WDFWGQGTQV   120
TVKP                                                               124

SEQ ID NO: 3               moltype = AA   length = 10
FEATURE                    Location/Qualifiers
source                     1..10
                           mol_type = protein
                           organism = synthetic construct
SEQUENCE: 3
GLTFSSYNMG                                                          10

SEQ ID NO: 4               moltype = AA   length = 10
FEATURE                    Location/Qualifiers
source                     1..10
                           mol_type = protein
                           organism = synthetic construct
SEQUENCE: 4
MSGSSSTSTY                                                          10

SEQ ID NO: 5               moltype = AA   length = 15
FEATURE                    Location/Qualifiers
source                     1..15
                           mol_type = protein
                           organism = synthetic construct
SEQUENCE: 5
RRMLSTYWSD RSWDF                                                    15

SEQ ID NO: 6               moltype = AA   length = 124
FEATURE                    Location/Qualifiers
source                     1..124
                           mol_type = protein
                           organism = synthetic construct
SEQUENCE: 6
EVQLLESGGG LVQPGGSLRL SCVASGLTFS SYNMGWLRQA PGKEREFVGM SGSSSTSTYY    60
ADSVKGRFTI SRDNSKNTVY LQMNSLKPED TAVYYCAARR MLSTYWSDRS WDFWGQGTQV   120
TVKP                                                               124

SEQ ID NO: 7               moltype = AA   length = 124
FEATURE                    Location/Qualifiers
source                     1..124
                           mol_type = protein
                           organism = synthetic construct
SEQUENCE: 7
EVQLVQSGGE LVQAGGSLRL SCVASGLTFS SYNMGWVRQA PGKEREFVSM SGSSSTSTYY    60
ADSVKGRFTI SRDNSKNTVY LQMNSLKPED TAVYYCAARR MLSTYWSDRS WDFWGQGTQV   120
TVKP                                                               124

SEQ ID NO: 8               moltype = AA   length = 124
FEATURE                    Location/Qualifiers
source                     1..124
                           mol_type = protein
                           organism = synthetic construct
SEQUENCE: 8
```

```
EVQLVQSGGE LVQAGGSLRL SCVASGLTFS SYNMGWVRQA PGKEREFVGM SGSSSTSTYY    60
ADSVKGRFTI SRDNSKNTVY LQMNSLKPED TAVYYCAARR MLSTYWSDRS WDFWGQGTQV   120
TVKP                                                               124

SEQ ID NO: 9              moltype = AA   length = 124
FEATURE                   Location/Qualifiers
source                    1..124
                          mol_type = protein
                          organism = synthetic construct
SEQUENCE: 9
EVQLVQSGGE LVQAGGSLRL SCVASGLTFS SYNMGWLRQA PGKEREFVGM SGSSSTSTYY    60
AESVKGRFTI SRDNAKNTLY LQMSSLRAED TAVYYCAARR MLSTYWSDRS WDFWGQGTQV   120
TVKP                                                               124

SEQ ID NO: 10             moltype = AA   length = 124
FEATURE                   Location/Qualifiers
source                    1..124
                          mol_type = protein
                          organism = synthetic construct
SEQUENCE: 10
EVQLVQSGGE LVQAGGSLRL SCVASGLTFS SYNMGWLRQA PGKEREFVGM SGSSSTSTYY    60
ADSVKGRFTI SRDNSKNTVY LQMNSLKPED TAVYYCAARR MLSTYWSDRS WDFWGQGTQV   120
TVEP                                                               124

SEQ ID NO: 11             moltype = AA   length = 124
FEATURE                   Location/Qualifiers
source                    1..124
                          mol_type = protein
                          organism = synthetic construct
SEQUENCE: 11
EVQLVQSGGE LVQAGGSLRL SCVASGLTFS SYNMGWLRQA PGKEREFVGM SGSSSTSTYY    60
ADSVKGRFTI SRDNSKNTVY LQMNSLKPED TAVYYCAARR MLSTYWSDRS WDFWGQGTQV   120
TVRP                                                               124

SEQ ID NO: 12             moltype = AA   length = 124
FEATURE                   Location/Qualifiers
source                    1..124
                          mol_type = protein
                          organism = synthetic construct
SEQUENCE: 12
EVQLVQSGGE LVQAGGSLRL SCVASGLTFS SYNMGWLRQA PGKEREFVGL SGSSSTSTYY    60
ADSVKGRFTI SRDNSKNTVY LQMNSLKPED TAVYYCAARR MLSTYWSDRS WDFWGQGTQV   120
TVKP                                                               124

SEQ ID NO: 13             moltype = AA   length = 124
FEATURE                   Location/Qualifiers
source                    1..124
                          mol_type = protein
                          organism = synthetic construct
SEQUENCE: 13
EVQLVQSGGE LVQAGGSLRL SCVASGLTFS SYNMGWLRQA PGKEREFVGI SGSSSTSTYY    60
ADSVKGRFTI SRDNSKNTVY LQMNSLKPED TAVYYCAARR MLSTYWSDRS WDFWGQGTQV   120
TVKP                                                               124

SEQ ID NO: 14             moltype = AA   length = 124
FEATURE                   Location/Qualifiers
source                    1..124
                          mol_type = protein
                          organism = synthetic construct
SEQUENCE: 14
EVQLVQSGGE LVQAGGSLRL SCVASGLTFS SYNMGWLRQA PGKEREFVGV SGSSSTSTYY    60
ADSVKGRFTI SRDNSKNTVY LQMNSLKPED TAVYYCAARR MLSTYWSDRS WDFWGQGTQV   120
TVKP                                                               124

SEQ ID NO: 15             moltype = AA   length = 124
FEATURE                   Location/Qualifiers
source                    1..124
                          mol_type = protein
                          organism = synthetic construct
SEQUENCE: 15
EVQLVQSGGE LVQAGGSLRL SCVASGLTFS SYNMGWLRQA PGKEREFVGM SGSSSTSTYY    60
ADSVKGRFTI SRDNSKNTVY LQMNSLKPED TAVYYCAARR LLSTYWSDRS WDFWGQGTQV   120
TAKP                                                               124

SEQ ID NO: 16             moltype = AA   length = 124
FEATURE                   Location/Qualifiers
source                    1..124
                          mol_type = protein
                          organism = synthetic construct
```

```
SEQUENCE: 16
EVQLVQSGGE LVQAGGSLRL SCVASGLTFS SYNMGWLRQA PGKEREFVGM SGSSSTSTYY    60
ADSVKGRFTI SRDNSKNTVY LQMNSLKPED TAVYYCAARR ILSTYWSDRS WDFWGQGTQV   120
TVKP                                                               124

SEQ ID NO: 17           moltype = AA   length = 124
FEATURE                 Location/Qualifiers
source                  1..124
                        mol_type = protein
                        organism = synthetic construct
SEQUENCE: 17
EVQLVQSGGE LVQAGGSLRL SCVASGLTFS SYNMGWLRQA PGKEREFVGM SGSSSTSTYY    60
ADSVKGRFTI SRDNSKNTVY LQMNSLKPED TAVYYCAARR VLSTYWSDRS WDFWGQGTQV   120
TVKP                                                               124

SEQ ID NO: 18           moltype = AA   length = 124
FEATURE                 Location/Qualifiers
source                  1..124
                        mol_type = protein
                        organism = synthetic construct
SEQUENCE: 18
EVQLVQSGGE LVQAGGSLRL SCVASGLTFS SYNMGWLRQA PGKEREFVGM SGSSSTSTYY    60
AESVKGRFTI SRDNAKNTVY LQMNSLKPED TAVYYCAARR MLSTYWSDRS WDFWGQGTQV   120
TAKP                                                               124

SEQ ID NO: 19           moltype = AA   length = 124
FEATURE                 Location/Qualifiers
source                  1..124
                        mol_type = protein
                        organism = synthetic construct
SEQUENCE: 19
EVQLLESGGG EVQPGGSLRL SCVASGLTFS SYNMGWLRQA PGKEREFVGL SGSSSTSTYY    60
ADSVKGRFTI SRDNSKNTVY LQMNSLKPED TAVYYCAARR LLSTYWSDRS WDFWGQGTQV   120
TVEP                                                               124

SEQ ID NO: 20           moltype = AA   length = 124
FEATURE                 Location/Qualifiers
source                  1..124
                        mol_type = protein
                        organism = synthetic construct
SEQUENCE: 20
EVQLLESGGG EVQPGGSLRL SCVASGLTFS SYNMGWVRQA PGKEREFVSL SGSSSTSTYY    60
ADSVKGRFTI SRDNSKNTVY LQMNSLKPED TAVYYCAARR LLSTYWSDRS WDFWGQGTQV   120
TVEP                                                               124

SEQ ID NO: 21           moltype = AA   length = 124
FEATURE                 Location/Qualifiers
source                  1..124
                        mol_type = protein
                        organism = synthetic construct
SEQUENCE: 21
EVQLLESGGG EVQPGGSLRL SCVASGLTFS SYNMGWLRQA PGKEREFVGL SGSSSTSTYY    60
AESVKGRFTI SRDNSKNTVY LQMNSLKPED TAVYYCAARR LLSTYWSDRS WDFWGQGTQV   120
TVEP                                                               124

SEQ ID NO: 22           moltype = AA   length = 124
FEATURE                 Location/Qualifiers
source                  1..124
                        mol_type = protein
                        organism = synthetic construct
SEQUENCE: 22
EVQLLESGGG EVQPGGSLRL SCVASGLTFS SYNMGWLRQA PGKEREFVGL SGSSSTSTYY    60
ADAVKGRFTI SRDNSKNTVY LQMNSLKPED TAVYYCAARR LLSTYWSDRS WDFWGQGTQV   120
TVEP                                                               124

SEQ ID NO: 23           moltype = AA   length = 124
FEATURE                 Location/Qualifiers
source                  1..124
                        mol_type = protein
                        organism = synthetic construct
SEQUENCE: 23
EVQLLESGGG EVQPGGSLRL SCVASGLTFS SYNMGWLRQA PGKEREFVGL SGSSSTSTYY    60
ADTVKGRFTI SRDNSKNTVY LQMNSLKPED TAVYYCAARR LLSTYWSDRS WDFWGQGTQV   120
TVEP                                                               124

SEQ ID NO: 24           moltype = AA   length = 124
FEATURE                 Location/Qualifiers
source                  1..124
                        mol_type = protein
```

```
                                     -continued
                             organism = synthetic construct
SEQUENCE: 24
EVQLLESGGG EVQPGGSLRL SCVASGLTFS SYNMGWLRQA PGKEREFVGL SGSSSTSTYY    60
ADSVKGRFTI SRDNSKNTLY LQMNSLKPED TAVYYCAARR LLSTYWSDRS WDFWGQGTQV   120
TVEP                                                                124

SEQ ID NO: 25           moltype = AA  length = 124
FEATURE                 Location/Qualifiers
source                  1..124
                        mol_type = protein
                        organism = synthetic construct
SEQUENCE: 25
EVQLLESGGG EVQPGGSLRL SCVASGLTFS SYNMGWLRQA PGKEREFVGL SGSSSTSTYY    60
ADSVKGRFTI SRDNSKNTVY LQMSSLKPED TAVYYCAARR LLSTYWSDRS WDFWGQGTQV   120
TVEP                                                                124

SEQ ID NO: 26           moltype = AA  length = 124
FEATURE                 Location/Qualifiers
source                  1..124
                        mol_type = protein
                        organism = synthetic construct
SEQUENCE: 26
EVQLLESGGG EVQPGGSLRL SCVASGLTFS SYNMGWLRQA PGKEREFVGL SGSSSTSTYY    60
ADSVKGRFTI SRDNSKNTVY LQMNSLRPED TAVYYCAARR LLSTYWSDRS WDFWGQGTQV   120
TVEP                                                                124

SEQ ID NO: 27           moltype = AA  length = 124
FEATURE                 Location/Qualifiers
source                  1..124
                        mol_type = protein
                        organism = synthetic construct
SEQUENCE: 27
EVQLLESGGG EVQPGGSLRL SCVASGLTFS SYNMGWLRQA PGKEREFVGL SGSSSTSTYY    60
ADSVKGRFTI SRDNSKNTVY LQMNSLKAED TAVYYCAARR LLSTYWSDRS WDFWGQGTQV   120
TVEP                                                                124

SEQ ID NO: 28           moltype = AA  length = 124
FEATURE                 Location/Qualifiers
source                  1..124
                        mol_type = protein
                        organism = synthetic construct
SEQUENCE: 28
EVQLLESGGG EVQPGGSLRL SCVASGLTFS SYNMGWVRQA PGKEREFVGL SGSSSTSTYY    60
ADSVKGRFTI SRDNSKNTVY LQMNSLKPED TAVYYCAARR LLSTYWSDRS WDFWGQGTQV   120
TVEP                                                                124

SEQ ID NO: 29           moltype = AA  length = 124
FEATURE                 Location/Qualifiers
source                  1..124
                        mol_type = protein
                        organism = synthetic construct
SEQUENCE: 29
EVQLLESGGG EVQPGGSLRL SCVASGLTFS SYNMGWLRQA PGKEREFVSL SGSSSTSTYY    60
ADSVKGRFTI SRDNSKNTVY LQMNSLKPED TAVYYCAARR LLSTYWSDRS WDFWGQGTQV   120
TVEP                                                                124

SEQ ID NO: 30           moltype = AA  length = 124
FEATURE                 Location/Qualifiers
source                  1..124
                        mol_type = protein
                        organism = synthetic construct
SEQUENCE: 30
EVQLLESGGG EVQPGGSLRL SCVASGLTFS SYNMGWLRQA PGKEREFVGM SGSSSTSTYY    60
ADSVKGRFTI SRDNSKNTVY LQMNSLKPED TAVYYCAARR MLSTYWSDRS WDFWGQGTQV   120
TVKP                                                                124

SEQ ID NO: 31           moltype = AA  length = 124
FEATURE                 Location/Qualifiers
source                  1..124
                        mol_type = protein
                        organism = synthetic construct
SEQUENCE: 31
EVQLLESGGG EVQPGGSLRL SCVASGLTFS SYNMGWLRQA PGKEREFVGL SGSSSTSTYY    60
AESVKGRFTI SRDNSKNTVY LQMNSLRAED TAVYYCAARR LLSTYWSDRS WDFWGQGTQV   120
TVEP                                                                124

SEQ ID NO: 32           moltype = AA  length = 124
FEATURE                 Location/Qualifiers
source                  1..124
```

```
                        mol_type = protein
                        organism = synthetic construct
SEQUENCE: 32
EVQLLESGGG EVQPGGSLRL SCVASGLTFS SYNMGWLRQA PGKEREFVGL SGSSSTSTYY    60
AESVKGRFTI SRDNSKNTVY LQMSSLRAED TAVYYCAARR LLSTYWSDRS WDFWGQGTQV   120
TVEP                                                                124

SEQ ID NO: 33           moltype = AA   length = 124
FEATURE                 Location/Qualifiers
source                  1..124
                        mol_type = protein
                        organism = synthetic construct
SEQUENCE: 33
EVQLLESGGG EVQPGGSLRL SCVASGLTFS SYNMGWLRQA PGKEREFVGL SGSSSTSTYY    60
AESVKGRFTI SRDNSKNTVY LQMQSLRAED TAVYYCAARR LLSTYWSDRS WDFWGQGTQV   120
TVEP                                                                124

SEQ ID NO: 34           moltype = AA   length = 124
FEATURE                 Location/Qualifiers
source                  1..124
                        mol_type = protein
                        organism = synthetic construct
SEQUENCE: 34
EVQLLESGGG EVQPGGSLRL SCVASGLTFS SYNMGWLRQA PGKEREFVGL SGSSSTSTYY    60
AESVKGRFTI SRDNSKNTVY LQMTSLRAED TAVYYCAARR LLSTYWSDRS WDFWGQGTQV   120
TVEP                                                                124

SEQ ID NO: 35           moltype = AA   length = 124
FEATURE                 Location/Qualifiers
source                  1..124
                        mol_type = protein
                        organism = synthetic construct
SEQUENCE: 35
EVQLLESGGG EVQPGGSLRL SCVASGLTFS SYNMGWLRQA PGKEREFVGL SGSSSTSTYY    60
AESVKGRFTI SRDNSKNTVY LQMNTLRAED TAVYYCAARR LLSTYWSDRS WDFWGQGTQV   120
TVEP                                                                124

SEQ ID NO: 36           moltype = AA   length = 124
FEATURE                 Location/Qualifiers
source                  1..124
                        mol_type = protein
                        organism = synthetic construct
SEQUENCE: 36
EVQLLESGGG EVQPGGSLRL SCVASGLTFS SYNMGWVRQA PGKEREFVGL SGSSSTSTYY    60
AESVKGRFTI SRDNSKNTVY LQMNSLRAED TAVYYCAARR LLSTYWSDRS WDFWGQGTQV   120
TVEP                                                                124

SEQ ID NO: 37           moltype = AA   length = 124
FEATURE                 Location/Qualifiers
source                  1..124
                        mol_type = protein
                        organism = synthetic construct
SEQUENCE: 37
EVQLLESGGG EVQPGGSLRL SCVASGLTFS SYNMGWLRQA PGKEREFVSL SGSSSTSTYY    60
AESVKGRFTI SRDNSKNTVY LQMNSLRAED TAVYYCAARR LLSTYWSDRS WDFWGQGTQV   120
TVEP                                                                124

SEQ ID NO: 38           moltype = AA   length = 124
FEATURE                 Location/Qualifiers
source                  1..124
                        mol_type = protein
                        organism = synthetic construct
SEQUENCE: 38
EVQLLESGGG EVQPGGSLRL SCVASGLTFS SYNMGWVRQA PGKEREFVSL SGSSSTSTYY    60
AESVKGRFTI SRDNSKNTVY LQMNSLRAED TAVYYCAARR LLSTYWSDRS WDFWGQGTQV   120
TVEP                                                                124

SEQ ID NO: 39           moltype = AA   length = 124
FEATURE                 Location/Qualifiers
source                  1..124
                        mol_type = protein
                        organism = synthetic construct
SEQUENCE: 39
EVQLLESGGG EVQPGGSLRL SCVASGLTFS SYNMGWLRQA PGKEREFVGL SGSSSTSTYY    60
AESVKGRFTI SRDNSKNTVY LQMTSLKAED TAVYYCAARR LLSTYWSDRS WDFWGQGTLV   120
TVEP                                                                124

SEQ ID NO: 40           moltype = AA   length = 124
FEATURE                 Location/Qualifiers
```

```
source                  1..124
                        mol_type = protein
                        organism = synthetic construct
SEQUENCE: 40
EVQLLESGGG EVQPGGSLRL SCVASGLTFS SYNMGWLRQA PGKEREFVGL SGSSSTSTYY    60
AESVKGRFTI SRDNSKNTVY LQMTSLRPED TAVYYCAARR LLSTYWSDRS WDFWGQGTLV   120
TVEP                                                                124

SEQ ID NO: 41           moltype = AA   length = 124
FEATURE                 Location/Qualifiers
source                  1..124
                        mol_type = protein
                        organism = synthetic construct
SEQUENCE: 41
EVQLLESGGG EVQPGGSLRL SCVASGLTFS SYNMGWLRQA PGKEREFVGL SGSSSTSTYY    60
AESVKGRFTI SRDNSKNTVY LQMTSLRAED TAVYYCAARR LLSTYWSDRS WDFWGQGTLV   120
TVEP                                                                124

SEQ ID NO: 42           moltype = AA   length = 124
FEATURE                 Location/Qualifiers
source                  1..124
                        mol_type = protein
                        organism = synthetic construct
SEQUENCE: 42
EVQLLESGGG EVQPGGSLRL SCVASGLTFS SYNMGWLRQA PGKEREFVGL SGSSSTSTYY    60
AESVKGRFTI SRDNAKNTVY LQMTSLRAED TAVYYCAARR LLSTYWSDRS WDFWGQGTLV   120
TVEP                                                                124

SEQ ID NO: 43           moltype = AA   length = 124
FEATURE                 Location/Qualifiers
source                  1..124
                        mol_type = protein
                        organism = synthetic construct
SEQUENCE: 43
EVQLLESGGG EVQPGGSLRL SCVASGLTFS SYNMGWLRQA PGKEREFVGL SGSSSTSTYY    60
AESVKGRFTI SRDQSKNTVY LQMTSLRAED TAVYYCAARR LLSTYWSDRS WDFWGQGTLV   120
TVEP                                                                124

SEQ ID NO: 44           moltype = AA   length = 124
FEATURE                 Location/Qualifiers
source                  1..124
                        mol_type = protein
                        organism = synthetic construct
SEQUENCE: 44
EVQLLESGGG EVQPGGSLRL SCVASGLTFS SYNMGWLRQA PGKEREFVGL SGSSSTSTYY    60
AESVKGRFTI SRDSSKNTVY LQMTSLRAED TAVYYCAARR LLSTYWSDRS WDFWGQGTLV   120
TVEP                                                                124

SEQ ID NO: 45           moltype = AA   length = 124
FEATURE                 Location/Qualifiers
source                  1..124
                        mol_type = protein
                        organism = synthetic construct
SEQUENCE: 45
EVQLLESGGG EVQPGGSLRL SCVASGLTFS SYNMGWLRQA PGKEREFVGL SGSSSTSTYY    60
AESVKGRFTI SRDTSKNTVY LQMTSLRAED TAVYYCAARR LLSTYWSDRS WDFWGQGTLV   120
TVEP                                                                124

SEQ ID NO: 46           moltype = AA   length = 124
FEATURE                 Location/Qualifiers
source                  1..124
                        mol_type = protein
                        organism = synthetic construct
SEQUENCE: 46
EVQLLESGGG EVQPGGSLRL SCVASGLTFS SYNMGWLRQA PGKEREFVGL SGSSSTSTYY    60
AESVKGRFTI SRDNTKNTVY LQMTSLRAED TAVYYCAARR LLSTYWSDRS WDFWGQGTLV   120
TVEP                                                                124

SEQ ID NO: 47           moltype = AA   length = 124
FEATURE                 Location/Qualifiers
source                  1..124
                        mol_type = protein
                        organism = synthetic construct
VARIANT                 5
                        note = L or V
VARIANT                 6
                        note = E or Q
VARIANT                 10
                        note = G or E
```

```
VARIANT              11
                     note = E or L
VARIANT              14
                     note = P or A
VARIANT              37
                     note = L or V
VARIANT              49
                     note = G or S
VARIANT              50
                     note = L, I, V or M
VARIANT              62
                     note = E or D
VARIANT              63
                     note = S, A, or T
VARIANT              74
                     note = N, Q, S, or T
VARIANT              75
                     note = S, A, or T
VARIANT              79
                     note = V or L
VARIANT              84
                     note = T, N, S, or Q
VARIANT              85
                     note = S or T
VARIANT              87
                     note = R or K
VARIANT              88
                     note = A or P
VARIANT              101
                     note = L, I, V or M
VARIANT              119
                     note = L or Q
VARIANT              122
                     note = V or A
VARIANT              123
                     note = E, K, or R
SEQUENCE: 47
EVQLXXSGGX XVQXGGSLRL SCVASGLTFS SYNMGWXRQA PGKEREFVXX SGSSSTSTYY    60
AXXVKGRFTI SRDXXKNTXY LQMXXLXXED TAVYYCAARR XLSTYWSDRS WDFWGQGTXV   120
TXXP                                                                124

SEQ ID NO: 48           moltype = AA   length = 10
FEATURE                 Location/Qualifiers
source                  1..10
                        mol_type = protein
                        organism = synthetic construct
SEQUENCE: 48
LSGSSSTSTY                                                           10

SEQ ID NO: 49           moltype = AA   length = 10
FEATURE                 Location/Qualifiers
source                  1..10
                        mol_type = protein
                        organism = synthetic construct
SEQUENCE: 49
ISGSSSTSTY                                                           10

SEQ ID NO: 50           moltype = AA   length = 10
FEATURE                 Location/Qualifiers
source                  1..10
                        mol_type = protein
                        organism = synthetic construct
SEQUENCE: 50
VSGSSSTSTY                                                           10

SEQ ID NO: 51           moltype = AA   length = 15
FEATURE                 Location/Qualifiers
source                  1..15
                        mol_type = protein
                        organism = synthetic construct
SEQUENCE: 51
RRLLSTYWSD RSWDF                                                     15

SEQ ID NO: 52           moltype = AA   length = 15
FEATURE                 Location/Qualifiers
source                  1..15
                        mol_type = protein
                        organism = synthetic construct
SEQUENCE: 52
```

```
RRILSTYWSD RSWDF                                                               15

SEQ ID NO: 53           moltype = AA   length = 15
FEATURE                 Location/Qualifiers
source                  1..15
                        mol_type = protein
                        organism = synthetic construct SEQUENCE: 53
RRVLSTYWSD RSWDF                                                               15

SEQ ID NO: 54           moltype = AA   length = 7
FEATURE                 Location/Qualifiers
source                  1..7
                        mol_type = protein
                        organism = synthetic construct SEQUENCE: 54
GLTFSSY                                                                         7

SEQ ID NO: 55           moltype = AA   length = 5
FEATURE                 Location/Qualifiers
source                  1..5
                        mol_type = protein
                        organism = synthetic construct SEQUENCE: 55
SYNMG                                                                           5

SEQ ID NO: 56           moltype = AA   length = 6
FEATURE                 Location/Qualifiers
source                  1..6
                        mol_type = protein
                        organism = synthetic construct SEQUENCE: 56
SSYNMG                                                                          6

SEQ ID NO: 57           moltype = AA   length = 7
FEATURE                 Location/Qualifiers
source                  1..7
                        mol_type = protein
                        organism = synthetic construct SEQUENCE: 57
LTFSSYN                                                                         7

SEQ ID NO: 58           moltype = AA   length = 10
FEATURE                 Location/Qualifiers
source                  1..10
                        mol_type = protein
                        organism = synthetic construct
VARIANT                 1
                        note = L, I, V or M SEQUENCE: 58
XSGSSSTSTY                                                                     10

SEQ ID NO: 59           moltype = AA   length = 6
FEATURE                 Location/Qualifiers
source                  1..6
                        mol_type = protein
                        organism = synthetic construct SEQUENCE: 59
GSSSTS                                                                          6

SEQ ID NO: 60           moltype = AA   length = 17
FEATURE                 Location/Qualifiers
source                  1..17
                        mol_type = protein
                        organism = synthetic construct
VARIANT                 1
                        note = L, I, V or M
VARIANT                 13
                        note = E or D
VARIANT                 14
                        note = S, A, or T SEQUENCE: 60
XSGSSSTSTY YAXXVKG                                                             17

SEQ ID NO: 61           moltype = AA   length = 13
FEATURE                 Location/Qualifiers
source                  1..13
                        mol_type = protein
                        organism = synthetic construct
```

```
VARIANT                  3
                         note = G or S
VARIANT                  4
                         note = L, I, V or M
SEQUENCE: 61
FVXXSGSSST STY                                                                    13

SEQ ID NO: 62            moltype = AA  length = 8
FEATURE                  Location/Qualifiers
source                   1..8
                         mol_type = protein
                         organism = synthetic construct
SEQUENCE: 62
SGSSSTST                                                                          8

SEQ ID NO: 63            moltype = AA  length = 15
FEATURE                  Location/Qualifiers
source                   1..15
                         mol_type = protein
                         organism = synthetic construct
VARIANT                  3
                         note = L, I, V or M
SEQUENCE: 63
RRXLSTYWSD RSWDF                                                                  15

SEQ ID NO: 64            moltype = AA  length = 15
FEATURE                  Location/Qualifiers
source                   1..15
                         mol_type = protein
                         organism = synthetic construct
VARIANT                  3
                         note = L, I, V or M
SEQUENCE: 64
RRXLSTYWSD RSWDF                                                                  15

SEQ ID NO: 65            moltype = AA  length = 15
FEATURE                  Location/Qualifiers
source                   1..15
                         mol_type = protein
                         organism = synthetic construct
VARIANT                  3
                         note = L, I, V or M
SEQUENCE: 65
RRXLSTYWSD RSWDF                                                                  15

SEQ ID NO: 66            moltype = AA  length = 16
FEATURE                  Location/Qualifiers
source                   1..16
                         mol_type = protein
                         organism = synthetic construct
VARIANT                  5
                         note = L, I, V or M
SEQUENCE: 66
AARRXLSTYW SDRSWD                                                                 16

SEQ ID NO: 67            moltype = AA  length = 17
FEATURE                  Location/Qualifiers
source                   1..17
                         mol_type = protein
                         organism = synthetic construct
VARIANT                  5
                         note = L, I, V or M
SEQUENCE: 67
AARRXLSTYW SDRSWDF                                                                17

SEQ ID NO: 68            moltype = AA  length = 17
FEATURE                  Location/Qualifiers
source                   1..17
                         mol_type = protein
                         organism = synthetic construct
SEQUENCE: 68
LSGSSSTSTY YAESVKG                                                                17

SEQ ID NO: 69            moltype = AA  length = 13
FEATURE                  Location/Qualifiers
source                   1..13
                         mol_type = protein
                         organism = synthetic construct
SEQUENCE: 69
```

```
FVGLSGSSST STY                                                             13

SEQ ID NO: 70           moltype = AA  length = 8
FEATURE                 Location/Qualifiers
source                  1..8
                        mol_type = protein
                        organism = synthetic construct
SEQUENCE: 70
SGSSSTST                                                                    8

SEQ ID NO: 71           moltype = AA  length = 15
FEATURE                 Location/Qualifiers
source                  1..15
                        mol_type = protein
                        organism = synthetic construct
SEQUENCE: 71
RRLLSTYWSD RSWDF                                                           15

SEQ ID NO: 72           moltype = AA  length = 15
FEATURE                 Location/Qualifiers
source                  1..15
                        mol_type = protein
                        organism = synthetic construct
SEQUENCE: 72
RRLLSTYWSD RSWDF                                                           15

SEQ ID NO: 73           moltype = AA  length = 16
FEATURE                 Location/Qualifiers
source                  1..16
                        mol_type = protein
                        organism = synthetic construct
SEQUENCE: 73
AARRLLSTYW SDRSWD                                                          16

SEQ ID NO: 74           moltype = AA  length = 17
FEATURE                 Location/Qualifiers
source                  1..17
                        mol_type = protein
                        organism = synthetic construct
SEQUENCE: 74
AARRLLSTYW SDRSWDF                                                         17

SEQ ID NO: 75           moltype = AA  length = 227
FEATURE                 Location/Qualifiers
source                  1..227
                        mol_type = protein
                        organism = Homo sapiens
SEQUENCE: 75
DKTHTCPPCP APELLGGPSV FLFPPKPKDT LMISRTPEVT CVVVDVSHED PEVKFNWYVD           60
GVEVHNAKTK PREEQYNSTY RVVSVLTVLH QDWLNGKEYK CKVSNKALPA PIEKTISKAK          120
GQPREPQVYT LPPSREEMTK NQVSLTCLVK GFYPSDIAVE WESNGQPENN YKTTPPVLDS          180
DGSFFLYSKL TVDKSRWQQG NVFSCSVMHE ALHNHYTQKS LSLSPGK                        227

SEQ ID NO: 76           moltype = AA  length = 226
FEATURE                 Location/Qualifiers
source                  1..226
                        mol_type = protein
                        organism = Homo sapiens
SEQUENCE: 76
DKTHTCPPCP APELLGGPSV FLFPPKPKDT LMISRTPEVT CVVVDVSHED PEVKFNWYVD           60
GVEVHNAKTK PREEQYNSTY RVVSVLTVLH QDWLNGKEYK CKVSNKALPA PIEKTISKAK          120
GQPREPQVYT LPPSREEMTK NQVSLTCLVK GFYPSDIAVE WESNGQPENN YKTTPPVLDS          180
DGSFFLYSKL TVDKSRWQQG NVFSCSVMHE ALHNHYTQKS LSLSPG                         226

SEQ ID NO: 77           moltype = AA  length = 224
FEATURE                 Location/Qualifiers
source                  1..224
                        mol_type = protein
                        organism = Homo sapiens
SEQUENCE: 77
DKTHTCPPCP APGGPSVFLF PPKPKDTLMI SRTPEVTCVV VDVSHEDPEV KFNWYVDGVE           60
VHNAKTKPRE EQYNSTYRVV SVLTVLHQDW LNGKEYKCKV SNKALPAPIE KTISKAKGQP          120
REPQVYTLPP SRDELTKNQV SLTCLVKGFY PSDIAVEWES NGQPENNYKT TPPVLDSDGS          180
FFLYSKLTVD KSRWQQGNVF SCSVMHEALH NHYTQKSLSL SPGK                           224

SEQ ID NO: 78           moltype = AA  length = 223
FEATURE                 Location/Qualifiers
source                  1..223
                        mol_type = protein
```

```
                                    organism = Homo sapiens
SEQUENCE: 78
DKTHTCPPCP APGGPSVFLF PPKPKDTLMI SRTPEVTCVV VDVSHEDPEV KFNWYVDGVE    60
VHNAKTKPRE EQYNSTYRVV SVLTVLHQDW LNGKEYKCKV SNKALPAPIE KTISKAKGQP   120
REPQVYTLPP SRDELTKNQV SLTCLVKGFY PSDIAVEWES NGQPENNYKT TPPVLDSDGS   180
FFLYSKLTVD KSRWQQGNVF SCSVMHEALH NHYTQKSLSL SPG                     223

SEQ ID NO: 79           moltype = AA  length = 227
FEATURE                 Location/Qualifiers
source                  1..227
                        mol_type = protein
                        organism = Homo sapiens
SEQUENCE: 79
DKTHTCPPCP APELLGGPSV FLFPPKPKDT LMISRTPEVT CVVVDVEHED PEVKFNWYVD    60
GVEVHNAKTK PREEQYNSTY RVVSVLTVLH QDWLNGKEYK CKVSNKAFPA PIEKTISKAK   120
GQPREPQVYT LPPSREEMTK NQVSLTCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 80           moltype = AA  length = 226
FEATURE                 Location/Qualifiers
source                  1..226
                        mol_type = protein
                        organism = Homo sapiens
SEQUENCE: 80
DKTHTCPPCP APELLGGPSV FLFPPKPKDT LMISRTPEVT CVVVDVEHED PEVKFNWYVD    60
GVEVHNAKTK PREEQYNSTY RVVSVLTVLH QDWLNGKEYK CKVSNKAFPA PIEKTISKAK   120
GQPREPQVYT LPPSREEMTK NQVSLTCLVK GFYPSDIAVE WESNGQPENN YKTTPPVLDS   180
DGSFFLYSKL TVDKSRWQQG NVFSCSVMHE ALHNHYTQKS LSLSPG                  226

SEQ ID NO: 81           moltype = AA  length = 227
FEATURE                 Location/Qualifiers
source                  1..227
                        mol_type = protein
                        organism = synthetic construct
SEQUENCE: 81
DKTHTCPPCP APELLDGPSV FLFPPKPKDT LMISRTPEVT CVVVDVEHED PEVKFNWYVD    60
GVEVHNAKTK PREEQYNSTY RVVSVLTVLH QDWLNGKEYK CKVSNKAFPA PIEKTISKAK   120
GQPREPQVYT LPPSREEMTK NQVSLTCLVK GFYPSDIAVE WESNGQPENN YKTTPPVLDS   180
DGSFFLYSKL TVDKSRWQQG NVFSCSVMHE ALHNHYTQKS LSLSPGK                 227

SEQ ID NO: 82           moltype = AA  length = 226
FEATURE                 Location/Qualifiers
source                  1..226
                        mol_type = protein
                        organism = Homo sapiens
SEQUENCE: 82
DKTHTCPPCP APELLDGPSV FLFPPKPKDT LMISRTPEVT CVVVDVEHED PEVKFNWYVD    60
GVEVHNAKTK PREEQYNSTY RVVSVLTVLH QDWLNGKEYK CKVSNKAFPA PIEKTISKAK   120
GQPREPQVYT LPPSREEMTK NQVSLTCLVK GFYPSDIAVE WESNGQPENN YKTTPPVLDS   180
DGSFFLYSKL TVDKSRWQQG NVFSCSVMHE ALHNHYTQKS LSLSPG                  226

SEQ ID NO: 83           moltype = AA  length = 212
FEATURE                 Location/Qualifiers
source                  1..212
                        mol_type = protein
                        organism = Homo sapiens
SEQUENCE: 83
GGPSVFLFPP KPKDTLMISR TPEVTCVVVD VSHEDPEVKF NWYVDGVEVH NAKTKPREEQ    60
YNSTYRVVSV LTVLHQDWLN GKEYKCKVSN KALPAPIEKT ISKAKGQPRE PQVYTLPPSR   120
DELTKNQVNL TCLVKGFYPS DIAVEWESNG QPENNYKTTP PVLDSDGSFF LNSTLTVDKS   180
RWQQGNVFSC SVMHEALHNH YTQKSLSLSP GK                                 212

SEQ ID NO: 84           moltype = AA  length = 355
FEATURE                 Location/Qualifiers
source                  1..355
                        mol_type = protein
                        organism = synthetic construct
SEQUENCE: 84
EVQLLESGGG EVQPGGSLRL SCVASGLTFS SYNMGWLRQA PGKEREFVGL SGSSSTSTYY    60
ADSVKGRFTI SRDNSKNTVY LQMNSLKPED TAVYYCAARR LLSTYWSDRS WDFWGQGTQV   120
TVEPGGGGDK THTCPPCPAP ELLDGPSVFL FPPKPKDTLM ISRTPEVTCV VVDVEHEDPE   180
VKFNWYVDGV EVHNAKTKPR EEQYNSTYRV VSVLTVLHQD WLNGKEYKCK VSNKAFPAPI   240
EKTISKAKGQ PREPQVYTLP PSREEMTKNQ VSLTCLVKGF YPSDIAVEWE SNGQPENNYK   300
TTPPVLDSDG SFFLYSKLTV DKSRWQQGNV FSCSVMHEAL HNHYTQKSLS LSPGK        355

SEQ ID NO: 85           moltype = AA  length = 355
FEATURE                 Location/Qualifiers
source                  1..355
                        mol_type = protein
```

```
                    organism = synthetic construct
SEQUENCE: 85
EVQLLESGGG EVQPGGSLRL SCVASGLTFS SYNMGWLRQA PGKEREFVGL SGSSSTSTYY    60
AESVKGRFTI SRDNAKNTVY LQMTSLRAED TAVYYCAARR LLSTYWSDRS WDFWGQGTLV   120
TVEPGGGGDK THTCPPCPAP ELLDGPSVFL FPPKPKDTLM ISRTPEVTCV VVDVEHEDPE   180
VKFNWYVDGV EVHNAKTKPR EEQYNSTYRV VSVLTVLHQD WLNGKEYKCK VSNKAFPAPI   240
EKTISKAKGQ PREPQVYTLP PSREEMTKNQ VSLTCLVKGF YPSDIAVEWE SNGQPENNYK   300
TTPPVLDSDG SFFLYSKLTV DKSRWQQGNV FSCSVMHEAL HNHYTQKSLS LSPGK        355

SEQ ID NO: 86           moltype = AA  length = 355
FEATURE                 Location/Qualifiers
source                  1..355
                        mol_type = protein
                        organism = synthetic construct
SEQUENCE: 86
EVQLLESGGG EVQPGGSLRL SCVASGLTFS SYNMGWLRQA PGKEREFVGL SGSSSTSTYY    60
AESVKGRFTI SRDNAKNTVY LQMTSLRAED TAVYYCAARR LLSTYWSDRS WDFWGQGTLV   120
TVEPGGGGDK THTCPPCPAP ELLGGPSVFL FPPKPKDTLM ISRTPEVTCV VVDVEHEDPE   180
VKFNWYVDGV EVHNAKTKPR EEQYNSTYRV VSVLTVLHQD WLNGKEYKCK VSNKAFPAPI   240
EKTISKAKGQ PREPQVYTLP PSREEMTKNQ VSLTCLVKGF YPSDIAVEWE SNGQPENNYK   300
TTPPVLDSDG SFFLYSKLTV DKSRWQQGNV FSCSVMHEAL HNHYTQKSLS LSPGK        355

SEQ ID NO: 87           moltype = AA  length = 451
FEATURE                 Location/Qualifiers
source                  1..451
                        mol_type = protein
                        organism = synthetic construct
SEQUENCE: 87
QVQLQESGPG LVKPSETLSL TCAVSGYSIT SGYSWNWIRQ PPGKKLEWIG SITYDGSSNY    60
NPSLKSRVTI SRDTSKNQFS LKLSSVTAAD TAVYYCARGS HYFGHWHFAV WGAGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV EHEDPEVKFN WYVDGVEVHN AKTKPREEQY   300
NSTYRVVSVL TVLHQDWLNG KEYKCKVSNK AFPAPIEKTI SKAKGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                  451

SEQ ID NO: 88           moltype = AA  length = 218
FEATURE                 Location/Qualifiers
source                  1..218
                        mol_type = protein
                        organism = synthetic construct
SEQUENCE: 88
DIQLTQSPSS LSASVGDRVT ITCRASQSVD YDGDSYMNWY QQKPGQPPKL LIYAASYLGS    60
EIPARFSGSG SGTDFTLTIS SLQPEDFATY YCQQSHEDPY TFGAGTKLEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 89           moltype = AA  length = 353
FEATURE                 Location/Qualifiers
source                  1..353
                        mol_type = protein
                        organism = synthetic construct
SEQUENCE: 89
EVQLLESGGG EVQPGGSLRL SCAASGFTFG NYDMAWVRQA PGKRPEWVSS IDTGGGSTYY    60
AESVKGRFTI SRDNAKNTLY LQMSSLRAED TAVYWCATDE EYALGPNEFD YYGQGTLVTV   120
KPGGGGDKTH TCPPCPAPEL LGGPSVFLPP PKPKDTLMIS RTPEVTCVVV DVEHEDPEVK   180
FNWYVDGVEV HNAKTKPREE QYNSTYRVVS VLTVLHQDWL NGKEYKCKVS NKAFPAPIEK   240
TISKAKGQPR EPQVYTLPPS REEMTKNQVS LTCLVKGFYP SDIAVEWESN GQPENNYKTT   300
PPVLDSDGSF FLYSKLTVDK SRWQQGNVFS CSVMHEALHN HYTQKSLSLS PGK          353

SEQ ID NO: 90           moltype = AA  length = 232
FEATURE                 Location/Qualifiers
source                  1..232
                        mol_type = protein
                        organism = Homo sapiens
SEQUENCE: 90
VPQKPKVSLN PPWNRIFKGE NVTLTCNGNN FFEVSSTKWF HNGSLSEETN SSLNIVNAKF    60
EDSGEYKCQH QQVNESEPVY LEVFSDWLLL QASAEVVMEG QPLFLRCHGW RNWDVYKVIY   120
YKDGEALKYW YENHNISITN ATVEDSGTYY CTGKVWQLDY ESEPLNITVI KAPREKYWLQ   180
FFIPLLVVIL FAVDTGLFIS TQQQVTFLLK IKRTRKGFRL LNPHPKPNPK NN           232

SEQ ID NO: 91           moltype = AA  length = 4
FEATURE                 Location/Qualifiers
source                  1..4
                        mol_type = protein
                        organism = synthetic construct
SEQUENCE: 91
GGGG                                                                  4
```

```
SEQ ID NO: 92            moltype = AA  length = 354
FEATURE                  Location/Qualifiers
source                   1..354
                         mol_type = protein
                         organism = synthetic construct
SEQUENCE: 92
EVQLLESGGG EVQPGGSLRL SCVASGLTFS SYNMGWLRQA PGKEREFVGL SGSSSTSTYY    60
AESVKGRFTI SRDNAKNTVY LQMTSLRAED TAVYYCAARR LLSTYWSDRS WDFWGQGTLV   120
TVEPGGGGDK THTCPPCPAP ELLDGPSVFL FPPKPKDTLM ISRTPEVTCV VVDVEHEDPE   180
VKFNWYVDGV EVHNAKTKPR EEQYNSTYRV VSVLTVLHQD WLNGKEYKCK VSNKAFPAPI   240
EKTISKAKGQ PREPQVYTLP PSREEMTKNQ VSLTCLVKGF YPSDIAVEWE SNGQPENNYK   300
TTPPVLDSDG SFFLYSKLTV DKSRWQQGNV FSCSVMHEAL HNHYTQKSLS LSPG         354

SEQ ID NO: 93            moltype = AA  length = 354
FEATURE                  Location/Qualifiers
source                   1..354
                         mol_type = protein
                         organism = synthetic construct
SEQUENCE: 93
EVQLLESGGG EVQPGGSLRL SCVASGLTFS SYNMGWLRQA PGKEREFVGL SGSSSTSTYY    60
AESVKGRFTI SRDNAKNTVY LQMTSLRAED TAVYYCAARR LLSTYWSDRS WDFWGQGTLV   120
TVEPGGGGDK THTCPPCPAP ELLGGPSVFL FPPKPKDTLM ISRTPEVTCV VVDVEHEDPE   180
VKFNWYVDGV EVHNAKTKPR EEQYNSTYRV VSVLTVLHQD WLNGKEYKCK VSNKAFPAPI   240
EKTISKAKGQ PREPQVYTLP PSREEMTKNQ VSLTCLVKGF YPSDIAVEWE SNGQPENNYK   300
TTPPVLDSDG SFFLYSKLTV DKSRWQQGNV FSCSVMHEAL HNHYTQKSLS LSPG         354

SEQ ID NO: 94            moltype = AA  length = 96
FEATURE                  Location/Qualifiers
source                   1..96
                         mol_type = protein
                         organism = Homo sapiens
SEQUENCE: 94
EVQLLESGGG EVQPGGSLRL SCAASGFTFS SYAMSWVRQA PGKGLEWVSA ISGSGGSTYY    60
AESVKGRFTI SRDNAKNTLY LQMSSLRAED TAVYYC                              96

SEQ ID NO: 95            moltype = AA  length = 355
FEATURE                  Location/Qualifiers
source                   1..355
                         mol_type = protein
                         organism = synthetic construct
SEQUENCE: 95
EVQLLESGGG EVQPGGSLRL SCVASGLTFS SYNMGWLRQA PGKEREFVGL SGSSSTSTYY    60
ADSVKGRFTI SRDNSKNTVY LQMNSLKPED TAVYYCAARR LLSTYWSDRS WDFWGQGTQV   120
TVEPGGGGDK THTCPPCPAP ELLGGPSVFL FPPKPKDTLM ISRTPEVTCV VVDVEHEDPE   180
VKFNWYVDGV EVHNAKTKPR EEQYNSTYRV VSVLTVLHQD WLNGKEYKCK VSNKAFPAPI   240
EKTISKAKGQ PREPQVYTLP PSREEMTKNQ VSLTCLVKGF YPSDIAVEWE SNGQPENNYK   300
TTPPVLDSDG SFFLYSKLTV DKSRWQQGNV FSCSVMHEAL HNHYTQKSLS LSPGK        355

SEQ ID NO: 96            moltype = AA  length = 123
FEATURE                  Location/Qualifiers
source                   1..123
                         mol_type = protein
                         organism = synthetic construct
SEQUENCE: 96
QVQLVQSGAE VMKPGSSVKV SCKASGYTFS WYWLEWVRQA PGHGLEWMGE IDPGTFTTNY    60
NEKFKARVTF TADTSTSTAY MELSSLRSED TAVYYCARFS HFSGSNYDYF DYWGQGTLVT   120
VSS                                                                 123

SEQ ID NO: 97            moltype = AA  length = 107
FEATURE                  Location/Qualifiers
source                   1..107
                         mol_type = protein
                         organism = synthetic construct
SEQUENCE: 97
EIVMTQSPAT LSVSPGERAT LSCRASQSIG TNIHWYQQKP GQAPRLLIYY ASESISGIPA    60
RFSGSGSGTE FTLTISSLQS EDFAVYYCQQ SWSWPTTFGG GTKVEIK                 107

SEQ ID NO: 98            moltype = AA  length = 119
FEATURE                  Location/Qualifiers
source                   1..119
                         mol_type = protein
                         organism = synthetic construct
SEQUENCE: 98
QVQLVQSGAE VKKPGSSVKV SCKASGYTFN GYWMHWVRQA PGQGLEWIGY INPTTGHTEY    60
NQKFKDKATI TADESTNTAY MELSSLRSED TAVYYCARQE YRHSWFAYWG QGTLVTVSS    119

SEQ ID NO: 99            moltype = AA  length = 111
FEATURE                  Location/Qualifiers
```

```
source                  1..111
                        mol_type = protein
                        organism = synthetic construct
SEQUENCE: 99
DIQLTQSPSS LSASVGDRVT ITCRASQSVD YDGDTYMNWY QQKPGKAPKL LIYAASNLDS    60
GVPSRFSGSG SGTDFTLTIS SLQPEDFATY YCQQTNEDPW TFGQGTKVEI K            111

SEQ ID NO: 100          moltype = AA   length = 352
FEATURE                 Location/Qualifiers
source                  1..352
                        mol_type = protein
                        organism = synthetic construct
SEQUENCE: 100
EVQLLESGGG EVQPGGSLRL SCVASGLTFS SYNMGWLRQA PGKEREFVGL SGSSSTSTYY    60
AESVKGRFTI SRDNAKNTVY LQMTSLRAED TAVYYCAARR LLSTYWSDRS WDFWGQGTLV    120
TVEPGGGGDK THTCPPCPAP GGPSVFLFPP KPKDTLMISR TPEVTCVVVD VSHEDPEVKF    180
NWYVDGVEVH NAKTKPREEQ YNSTYRVVSV LTVLHQDWLN GKEYKCKVSN KALPAPIEKT    240
ISKAKGQPRE PQVYTLPPSR DELTKNQVSL TCLVKGFYPS DIAVEWESNG QPENNYKTTP    300
PVLDSDGSFF LYSKLTVDKS RWQQGNVFSC SVMHEALHNH YTQKSLSLSP GK            352

SEQ ID NO: 101          moltype = AA   length = 124
FEATURE                 Location/Qualifiers
source                  1..124
                        mol_type = protein
                        organism = synthetic construct
SEQUENCE: 101
EVQLLESGGG EVQPGGSLRL SCVASGLTFS SYNMGWLRQA PGKEREFVGL SGVSSTSTYY    60
AESVKGRFTI SRDNAKNTGY LQMNSLRAED TAVYYCAARR LLSTYWSHRS WDFWGQGTLV    120
TVEP                                                                124

SEQ ID NO: 102          moltype = AA   length = 10
FEATURE                 Location/Qualifiers
source                  1..10
                        mol_type = protein
                        organism = synthetic construct
SEQUENCE: 102
LSGVSSTSTY                                                          10

SEQ ID NO: 103          moltype = AA   length = 15
FEATURE                 Location/Qualifiers
source                  1..15
                        mol_type = protein
                        organism = synthetic construct
SEQUENCE: 103
RRLLSTYWSH RSWDF                                                    15

SEQ ID NO: 104          moltype = AA   length = 10
FEATURE                 Location/Qualifiers
source                  1..10
                        mol_type = protein
                        organism = synthetic construct
VARIANT                 1
                        note = L, I, V or M
VARIANT                 4
                        note = S or V
SEQUENCE: 104
XSGXSSTSTY                                                          10

SEQ ID NO: 105          moltype = AA   length = 6
FEATURE                 Location/Qualifiers
source                  1..6
                        mol_type = protein
                        organism = synthetic construct
VARIANT                 2
                        note = S or V
SEQUENCE: 105
GXSSTS                                                              6

SEQ ID NO: 106          moltype = AA   length = 17
FEATURE                 Location/Qualifiers
source                  1..17
                        mol_type = protein
                        organism = synthetic construct
VARIANT                 1
                        note = L, I, V, or M
VARIANT                 4
                        note = S or V
VARIANT                 13
                        note = E or D
```

```
VARIANT                      14
                             note = S, A, or T
SEQUENCE: 106
XSGXSSTSTY YAXXVKG                                                                    17

SEQ ID NO: 107               moltype = AA  length = 13
FEATURE                      Location/Qualifiers
source                       1..13
                             mol_type = protein
                             organism = synthetic construct
VARIANT                      3
                             note = G or S
VARIANT                      4
                             note = L, I, V, or M
VARIANT                      7
                             note = S or V
SEQUENCE: 107
FVXXSGXSST STY                                                                        13

SEQ ID NO: 108               moltype = AA  length = 10
FEATURE                      Location/Qualifiers
source                       1..10
                             mol_type = protein
                             organism = synthetic construct
VARIANT                      1
                             note = L, I, V, or M
VARIANT                      4
                             note = S or V
SEQUENCE: 108
XSGXSSTSTY                                                                            10

SEQ ID NO: 109               moltype = AA  length = 15
FEATURE                      Location/Qualifiers
source                       1..15
                             mol_type = protein
                             organism = synthetic construct
VARIANT                      3
                             note = L, I, V, or M
VARIANT                      10
                             note = D or H
SEQUENCE: 109
RRXLSTYWSX RSWDF                                                                      15

SEQ ID NO: 110               moltype = AA  length = 16
FEATURE                      Location/Qualifiers
source                       1..16
                             mol_type = protein
                             organism = synthetic construct
VARIANT                      5
                             note = L, I, V, or M
VARIANT                      12
                             note = D or H
SEQUENCE: 110
AARRXLSTYW SXRSWD                                                                     16

SEQ ID NO: 111               moltype = AA  length = 17
FEATURE                      Location/Qualifiers
source                       1..17
                             mol_type = protein
                             organism = synthetic construct
VARIANT                      5
                             note = L, I, V, or M
VARIANT                      12
                             note = D or H
SEQUENCE: 111
AARRXLSTYW SXRSWDF                                                                    17

SEQ ID NO: 112               moltype = AA  length = 355
FEATURE                      Location/Qualifiers
source                       1..355
                             mol_type = protein
                             organism = synthetic construct
SEQUENCE: 112
EVQLLESGGG EVQPGGSLRL SCVASGLTFS SYNMGWLRQA PGKEREFVGL SGVSSTSTYY    60
AESVKGRFTI SRDNAKNTGY LQMNSLRAED TAVYYCAARR LLSTYWSHRS WDFWGQGTLV   120
TVEPGGGGDK THTCPPCPAP ELLGGPSVFL FPPKPKDTLM ISRTPEVTCV VVDVEHEDPE   180
VKFNWYVDGV EVHNAKTKPR EEQYNSTYRV VSVLTVLHQD WLNGKEYKCK VSNKAFPAPI   240
EKTISKAKGQ PREPQVYTLP PSREEMTKNQ VSLTCLVKGF YPSDIAVEWE SNGQPENNYK   300
TTPPVLDSDG SFFLYSKLTV DKSRWQQGNV FSCSVMHEAL HNHYTQKSLS LSPGK       355
```

```
SEQ ID NO: 113           moltype = AA  length = 354
FEATURE                  Location/Qualifiers
source                   1..354
                         mol_type = protein
                         organism = synthetic construct
SEQUENCE: 113
EVQLLESGGG EVQPGGSLRL SCVASGLTFS SYNMGWLRQA PGKEREFVGL SGVSSTSTYY   60
AESVKGRFTI SRDNAKNTGY LQMNSLRAED TAVYYCAARR LLSTYWSHRS WDFWGQGTLV  120
TVEPGGGGDK THTCPPCPAP ELLGGPSVFL FPPKPKDTLM ISRTPEVTCV VVDVEHEDPE  180
VKFNWYVDGV EVHNAKTKPR EEQYNSTYRV VSVLTVLHQD WLNGKEYKCK VSNKAFPAPI  240
EKTISKAKGQ PREPQVYTLP PSREEMTKNQ VSLTCLVKGF YPSDIAVEWE SNGQPENNYK  300
TTPPVLDSDG SFFLYSKLTV DKSRWQQGNV FSCSVMHEAL HNHYTQKSLS LSPG        354

SEQ ID NO: 114           moltype =     length =
SEQUENCE: 114
000

SEQ ID NO: 115           moltype =     length =
SEQUENCE: 115
000

SEQ ID NO: 116           moltype = AA  length = 15
FEATURE                  Location/Qualifiers
source                   1..15
                         mol_type = protein
                         organism = synthetic construct
VARIANT                  3
                         note = L or R
VARIANT                  4
                         note = L, K, F, or H
VARIANT                  6
                         note = T or R
VARIANT                  10
                         note = D, M, or H
VARIANT                  15
                         note = F, K, or M
SEQUENCE: 116
RRXXSXYWSX RSWDX                                                    15

SEQ ID NO: 117           moltype = AA  length = 17
FEATURE                  Location/Qualifiers
source                   1..17
                         mol_type = protein
                         organism = synthetic construct
VARIANT                  1
                         note = A or S
VARIANT                  5
                         note = L or R
VARIANT                  6
                         note = L, K, F, or H
VARIANT                  8
                         note = T or R
VARIANT                  12
                         note = D, M, or H
VARIANT                  17
                         note = F, K, or M
SEQUENCE: 117
XARRXXSXYW SXRSWDX                                                  17

SEQ ID NO: 118           moltype = AA  length = 16
FEATURE                  Location/Qualifiers
source                   1..16
                         mol_type = protein
                         organism = synthetic construct
VARIANT                  1
                         note = A or S
VARIANT                  5
                         note = L or R
VARIANT                  6
                         note = L, K, F, or H
VARIANT                  8
                         note = T or R
VARIANT                  12
                         note = D, M, or H
SEQUENCE: 118
XARRXXSXYW SXRSWD                                                   16

SEQ ID NO: 119           moltype = AA  length = 124
```

-continued

```
FEATURE                  Location/Qualifiers
source                   1..124
                         mol_type = protein
                         organism = synthetic construct
VARIANT                  5
                         note = L or V
VARIANT                  6
                         note = E or Q
VARIANT                  10
                         note = G or E
VARIANT                  11
                         note = E or L
VARIANT                  14
                         note = P or A
VARIANT                  37
                         note = L or V
VARIANT                  49
                         note = G or S
VARIANT                  50
                         note = L, I, V, or M
VARIANT                  53
                         note = S or V
VARIANT                  62
                         note = E or D
VARIANT                  63
                         note = S, A, or T
VARIANT                  74
                         note = N, Q, S, or T
VARIANT                  75
                         note = S, A, or T
VARIANT                  79
                         note = V, G, or L
VARIANT                  84
                         note = T, N, S, or Q
VARIANT                  85
                         note = S or T
VARIANT                  87
                         note = R or K
VARIANT                  88
                         note = A or P
VARIANT                  101
                         note = L, I, V, or M
VARIANT                  108
                         note = D or H
VARIANT                  119
                         note = L or Q
VARIANT                  122
                         note = V or A
VARIANT                  123
                         note = E, K, or R
SEQUENCE: 119
EVQLXXSGGX XVQXGGSLRL SCVASGLTFS SYNMGWXRQA PGKEREFVXX SGXSSTSTYY  60
AXXVKGRFTI SRDXXKNTXY LQMXXLXXED TAVYYCAARR XLSTYWSXRS WDFWGQGTXV  120
TXXP                                                               124
```

What is claimed is:

1. A VHH domain that binds IgE, comprising a complementarity determining region 1 (CDR1), a complementarity determining region 2 (CDR2), and a complementarity determining region 3 (CDR3) of a VHH that comprises the amino acid sequence of SEQ ID NO: 42.

2. The VHH domain of claim 1, wherein the CDR1 comprises the amino acid sequence of SEQ ID NO: 3, the CDR2 comprises the amino acid sequence of SEQ ID NO: 48, and the CDR3 comprises the amino acid sequence of SEQ ID NO: 51, under the AbM definition.

3. The VHH domain of claim 1, wherein the CDR1 comprises the amino acid sequence of SEQ ID NO: 54, the CDR2 comprises the amino acid sequence of SEQ ID NO: 59, and the CDR3 comprises the amino acid sequence of SEQ ID NO: 71, under the Chothia definition.

4. The VHH domain of claim 1, wherein the CDR1 comprises the amino acid sequence of SEQ ID NO: 55, the CDR2 comprises the amino acid sequence of SEQ ID NO: 68, and the CDR3 comprises the amino acid sequence of SEQ ID NO: 72, under the Kabat definition.

5. The VHH domain of claim 1, wherein the CDR1 comprises the amino acid sequence of SEQ ID NO: 56, the CDR2 comprises the amino acid sequence of SEQ ID NO: 69, and the CDR3 comprises the amino acid sequence of SEQ ID NO: 73, under the Contact definition.

6. The VHH domain of claim 1, wherein the CDR1 comprises the amino acid sequence of SEQ ID NO: 57, the CDR2 comprises the amino acid sequence of SEQ ID NO: 70, and the CDR3 comprises the amino acid sequence of SEQ ID NO: 74, under the IMGT definition.

7. The VHH domain of claim 1, comprising:

(a) a framework 1 region, wherein the framework 1 region comprises glutamate (E), aspartate (D), lysine (K), or arginine (R) at position 11 according to Kabat numbering, and/or (b) a framework 4 region, wherein the framework 4 region comprises:
  (i) glutamate (E), arginine (R), or aspartate (D) at position 112 according to Kabat numbering, and/or
  (ii) leucine (L) at position 108 according to Kabat numbering.

8. The VHH domain of claim 1, wherein the VHH domain is humanized.

9. The VHH domain of claim 1, comprising an amino acid sequence at least 90% identical to the amino acid sequence of SEQ ID NO: 42.

10. The VHH domain of claim 1, comprising the amino acid sequence of SEQ ID NO: 42.

11. A polypeptide comprising the VHH domain of claim 1.

12. The polypeptide of claim 11, further comprising an Fc region.

13. The polypeptide of claim 12, wherein the Fc region is a human IgG1 Fc region.

14. The polypeptide of claim 11, comprising the amino acid sequence of SEQ ID NO: 86.

15. A composition comprising two or more multimerized polypeptides of claim 11.

16. A pharmaceutical composition comprising:
  (a) the polypeptide of claim 11; and
  (b) a pharmaceutically acceptable carrier.

17. The polypeptide of claim 11, comprising the amino acid sequence of SEQ ID NO: 93.

18. The polypeptide of claim 12, wherein the Fc region is a human IgG1 Fc region comprising substitutions S267E and L328F, numbered according to the EU index as in Kabat.

19. A polypeptide comprising the VHH domain of claim 10 and an Fc region.

20. The polypeptide of claim 19, wherein the Fc region is a human IgG1 Fc region comprising substitutions S267E and L328F, numbered according to the EU index as in Kabat.

21. A composition comprising two dimerized polypeptides of claim 12.

22. A composition comprising two dimerized polypeptides of claim 14.

23. A pharmaceutical composition comprising the polypeptide of claim 14 and a pharmaceutically acceptable carrier.

24. A pharmaceutical composition comprising the polypeptide of claim 17 and a pharmaceutically acceptable carrier.

25. A polypeptide comprising:
  (a) a VHH domain comprising the amino acid sequence of SEQ ID NO: 42;
  (b) a human IgG1 Fc region comprising substitutions S267E and L328F, numbered according to the EU index as in Kabat; and
  (c) a polypeptide linker,
  wherein the VHH domain is linked to the human IgG1 Fc region via the polypeptide linker.

26. A polypeptide consisting of the amino acid sequence of SEQ ID NO: 86.

27. A pharmaceutical composition comprising the polypeptide of claim 26 and a pharmaceutically acceptable carrier.

28. The pharmaceutical composition of claim 27, the pharmaceutical composition further comprising a polypeptide consisting of the amino acid sequence of SEQ ID NO: 93.

29. A polypeptide consisting of the amino acid sequence of SEQ ID NO: 93.

30. A pharmaceutical composition comprising the polypeptide of claim 29 and a pharmaceutically acceptable carrier.

* * * * *